US011952591B2

(12) United States Patent
Rieck et al.

(10) Patent No.: US 11,952,591 B2
(45) Date of Patent: *Apr. 9, 2024

(54) GENERATION OF HUMAN PLURIPOTENT STEM CELL DERIVED FUNCTIONAL BETA CELLS SHOWING A GLUCOSE-DEPENDENT MITOCHONDRIAL RESPIRATION AND TWO-PHASE INSULIN SECRETION RESPONSE

(71) Applicant: Janssen Biotech, Inc., Horsham, PA (US)

(72) Inventors: Sebastian Rieck, San Diego, CA (US); Alireza Rezania, Wellesley, MA (US)

(73) Assignee: Janssen Biotech, Inc., Horsham, PA (US)

( * ) Notice: Subject to any disclaimer, the term of this patent is extended or adjusted under 35 U.S.C. 154(b) by 716 days.

This patent is subject to a terminal disclaimer.

(21) Appl. No.: 16/817,413

(22) Filed: Mar. 12, 2020

(65) Prior Publication Data

US 2020/0208116 A1 Jul. 2, 2020

Related U.S. Application Data

(63) Continuation of application No. 15/622,931, filed on Jun. 14, 2017, now Pat. No. 10,633,635.

(60) Provisional application No. 62/352,968, filed on Jun. 21, 2016.

(51) Int. Cl.
| | |
|---|---|
| *C12N 5/071* | (2010.01) |
| *A61K 35/39* | (2015.01) |
| *C07K 14/72* | (2006.01) |
| *C12Q 1/6806* | (2018.01) |

(52) U.S. Cl.
CPC ........... *C12N 5/0678* (2013.01); *A61K 35/39* (2013.01); *C07K 14/72* (2013.01); *C12N 5/0677* (2013.01); *C12N 5/068* (2013.01); *C12Q 1/6806* (2013.01); *C12N 2500/25* (2013.01); *C12N 2500/32* (2013.01); *C12N 2500/34* (2013.01); *C12N 2500/38* (2013.01); *C12N 2501/105* (2013.01); *C12N 2501/115* (2013.01); *C12N 2501/117* (2013.01); *C12N 2501/119* (2013.01); *C12N 2501/15* (2013.01); *C12N 2501/335* (2013.01); *C12N 2501/345* (2013.01); *C12N 2501/375* (2013.01); *C12N 2501/415* (2013.01); *C12N 2501/727* (2013.01); *C12N 2506/02* (2013.01); *C12N 2533/90* (2013.01)

(58) Field of Classification Search
CPC .................................................. C12N 5/0678
See application file for complete search history.

(56) References Cited

U.S. PATENT DOCUMENTS

| | | | |
|---|---|---|---|
| 10,006,006 B2 * | 6/2018 | Rezania | ............ A61P 1/18 |
| 2009/0220959 A1 * | 9/2009 | D'Amour | ............ C12N 5/0603 |
| | | | 435/378 |
| 2009/0263896 A1 | 10/2009 | Kelly et al. | |
| 2009/0269313 A1 | 10/2009 | Nadler | |
| 2010/0112693 A1 | 5/2010 | Rezania et al. | |
| 2011/0008887 A1 | 1/2011 | Tsang et al. | |
| 2011/0151560 A1 | 6/2011 | Xu | |
| 2013/0189777 A1 | 7/2013 | Rezania | |
| 2014/0329704 A1 * | 11/2014 | Melton | ............ C12Q 1/6881 |
| | | | 435/6.12 |
| 2015/0329828 A1 | 11/2015 | Rezania | |

FOREIGN PATENT DOCUMENTS

| | | |
|---|---|---|
| EP | 2604685 A1 | 6/2013 |
| WO | 2006105152 A3 | 6/2009 |
| WO | 2009132083 A2 | 10/2009 |
| WO | 2013095953 A1 | 6/2013 |
| WO | 2014033322 A1 | 3/2014 |
| WO | 2014105543 A1 | 7/2014 |
| WO | 2014105546 A1 | 7/2014 |
| WO | WO 2014/104403 A1 | 7/2014 |
| WO | 2015002724 A4 | 3/2015 |
| WO | WO 2017/144695 A1 | 8/2017 |

OTHER PUBLICATIONS

Xu et al. (2014, Embo J., vol. 33, pp. 2157-2170). (Year: 2014).*
Chareyron et al. (2020, Diabetologia, vol. 63, pp. 2628-2640) (Year: 2020).*
Henquin et al. (2006, Diabetes, vol. 55, pp. 441-451) (Year: 2006).*
Altirriba, et al. "The Role of Transmembrane Protein 27 (TMEM27) in islet physiology and its potential use as a beta cell mass biomarker." Diabetologia (2010): 53: 1406-1414.
Banerjee and Otonkoski, "A simple two-step protocol for the purification of human pancreatic beta cells." Diabetologia (2009) 52: 621-625.
Brewer, et al. "Optimized Survivial of Hippocampal Neurons in B27-Supplemented Neurobasal, a New Serum-free Medium Combination." Journal of Neuroscience Research 35: 567-576 (1993).
Cheng, et al. "Self-Renewing Endodermnal Progenitor Lines Generated From Human Pluripotent Stem Cells." Cell Stem Cell, vol. 10, No. 4, Apr. 1, 2012, pp. 371-384.
Cho, et al. "Inhibition of Activin/Nodal Signalling is necessary for pancreatic differentiatoin of human pluripotent stem cells." Diabetologia (2012) 55: 3284-3295.
Cuny, et al. Structure-activity relationship study of bone morpogenetic protein (BMP) signlaing inhibitors. Bioorg Med Chem Lett. Aug. 1, 2008; 18(15): 4388-4392.

(Continued)

*Primary Examiner* — Anoop K Singh
*Assistant Examiner* — David A Montanari
(74) *Attorney, Agent, or Firm* — Klarquist Sparkman, LLP; Susan Alpert Siegel; Sheree Lynn Rybak

(57) ABSTRACT

The invention provides for methods of differentiating pancreatic endocrine cells into pancreatic beta cells expressing PDX1, NKX6.1, MAFA, UCN3 and SLC2A. These pancreatic beta cells may be obtained by step-wise differentiation of pluripotent stem cells. The pancreatic beta cells exhibit glucose-dependent mitochondrial respiration and glucose-stimulated insulin secretion similar to islet cells.

19 Claims, 106 Drawing Sheets

(56) References Cited

OTHER PUBLICATIONS

Declaration of Maria Cristina Nostro, Ph.D. dated Jul. 22, 201 in Toronto, Canada.
Fraker, et al. "Enhanced Oxygenation Promotes B-Cell Differentiation in Vitro." Stem Cells 2007; 25: 3155-3164.
Guillemain, et al., Glucose Is Necessary For Embryonic Pancreatic Endocrine Cell Differentiation*, The Journal Of Biological Chemistry, May 18, 2007, pp. 15228-15237, vol. 282 Issue 20.
Hald, et al."Pancreatic Islet and Progenitor Cell Surface Markers with Cell Sorting Potential". Diabetologia (2012) 55: 154-165.
Heinis, et al., Oxygen Tension Regulates Pancreatic Beta-Cell Differentiation Through Hypoxia-Inducible Factor 1x, Diabetes, 2010, pp. 662-669, vol. 59.
Iype, et al. The Transcriptional Repressor Nkx6.1 Also Functions as Deoxyribonucleic Acid Context-Dependent Transcriptional Activator During Pancreatic B-cell Differntiation: Evidence for Feedback Acitivation of the nkx6.1.
Korytnikov, et al. "Generation of Polyhormonal and Multipotent pancreatic progenitor lineages form human pluripotent stem cells." Methods, vol. 101, May 15, 2016, pp. 56-64.
Leontovyc, et al. The Effect of Epigenetic Factors on Differentiation of Pancreatic Progenitor Cells into Insulin-Producing Cells. Transplant. Proc., 2011, vol. 43, pp. 3212-3216.
Mfopou, et al. "Noggin, Retinoids, and Fibroblast Growth Factor Regulate Hepatic or Pancreatic Fate of Human Embryonic Stem Cells." Gastroenterology 2010; 138:2233-2245.
Micallef, et al. "INSGFP/W Human Emryonic Stem Cells Facilitate Isolation of in vitro derived insulin-producing cells." Diabetologia (2012) 55: 694-706.
Stassi, et al. "Expression of Apotosis-Inducing CD95 (Fas/Apo-1) on Human B-Cells Sorted by Flow-Cytometry and Cultured in Vitro." Transplantation Proceedings, vol. 27, No. 6 Dec. 1995: 3271-3275.
Thermofisher Scientific, B-27 Serum-Free Supplement 50x Liquid, Technical Resources, 2016, URL:https://www.thermofisher.com/nl/en/home/technical-resources/media-formulation.250.html, retrieved from the internet.
Falzacappa, V. et al., 3,5,3'-Triiodothyronine (T3) is a Survival Factor for Pancreatic Beta-Cells Undergoing Apoptosis, Journal of Cell Physiology, Feb. 2006, pp. 309-321, vol. 206, No. 2.
Fomina -Yadlin, et al., Small-molecule inducers of insulin expression in pancreatic α-cells, PNAS, Aug. 24, 2010, pp. 15099-15104, vol. 107 Issue 34.
Inman, et al., SB-431542 is a Potent and Specific Inhibitor of Transforming Growth Factor-B Superfamily Type I Activing Receptor-Like Kinase (ALK) Receptors Alf.4, Alf.5, and ALK7, Molecular Pharmacology, 2002, pp. 65-74, vol. 62, No. 1.
Ku et al., Committing Embryonic Stem Cells to Early Endocrine Pancreas In Vitro, Stem Cells, 2004, vol. 22, pp. 1205-1217, AlphaMed Press.
Kunisada, et al., Small molecules induce efficient differentiation into insulin-producing cells from human induced pluripotent stem cells, Stem Cell Research, Oct. 11, 2011, pp. 274-284, vol. 8.
Murtaugh, et al., Notch Signaling Controls Multiple Steps of Pancreatic Differentiation, 2003, PNAS, vol. 100, No. 25, pp. 14928-14925.
Nishimura et al., A Switch from MafB to MafA Expression Accompanies Differentiation to B-Cells, Developmental Biology, 2006, vol. 293, pp. 526-539.
Pagliuca et al., How to Make a Functional Beta-Cell, Development, 2013, pp. 2472-2483, vol. 140, No. 2.
Sui, et al. Stem Cell Therapy for Diabetes: A Call for Efficient Differentiation of Pancreatic Progenitors, J. Regenerative Medicine 2013, vol. 2, No. 1.
Zorn, et al., Vertebrate Endoderm Development and Organ Formation, Annual Review Cell Development Biology, Aug. 12, 2009, pp. 221-251, vol. 25.
Aslam et al., "Histone methyltransferase DOT1L controls state-specific identity during B cell differentiation," *EMBO Reports* 22: e51184, 21 pages (e-Pub Jan. 7, 2021).
Fujiwara et al., "3-deazaneplanocin A (DZNep), an inhibitor of s-adenosylmethionine-dependent methyltransferase, promotes erythroid differentiation," *J. Biol. Chem.* 289(12): 8121-8134 (Mar. 21, 2014).
Pinometostat (Synonyms: EPZ-5676), *MCE* https://www.medchemexpress.com/EPZ-5676.html?src=google-product&gclid=EAIaIQobChMI8Jr27Kyf-QIVhCCtBh1x-AveEAAYASAAEgKBVfD_BwE.pdf, 4 pages (downloaded Aug. 18, 2022).
De Vos et al., "Human and rat beta cells differ in glucose transporter but not in glucokinase gene expression," *J Clin Invest.* 96(5):2489-2495 (1995).
Kubicek et al., "Chromatin-targeting small molecules cause class-specific transcriptional changes in pancreatic endocrine cells," *Proc. National. Acad. Sci.* 109(14): 5364-5369 (Apr. 3, 2012).
Ma and Zhu "Chemical strategies for pancreatic [beta] cell differentiation, reprogramming, and regeneration," *Acta Biochim Biophys Sin (Shanghai)* 49(4): 289-301 (Feb. 22, 2017).
Pagliuca et al., "Generation of functional human pancreatic β cells in vitro," *Cell* 159(2): 428-439 (Oct. 9, 2014).

* cited by examiner

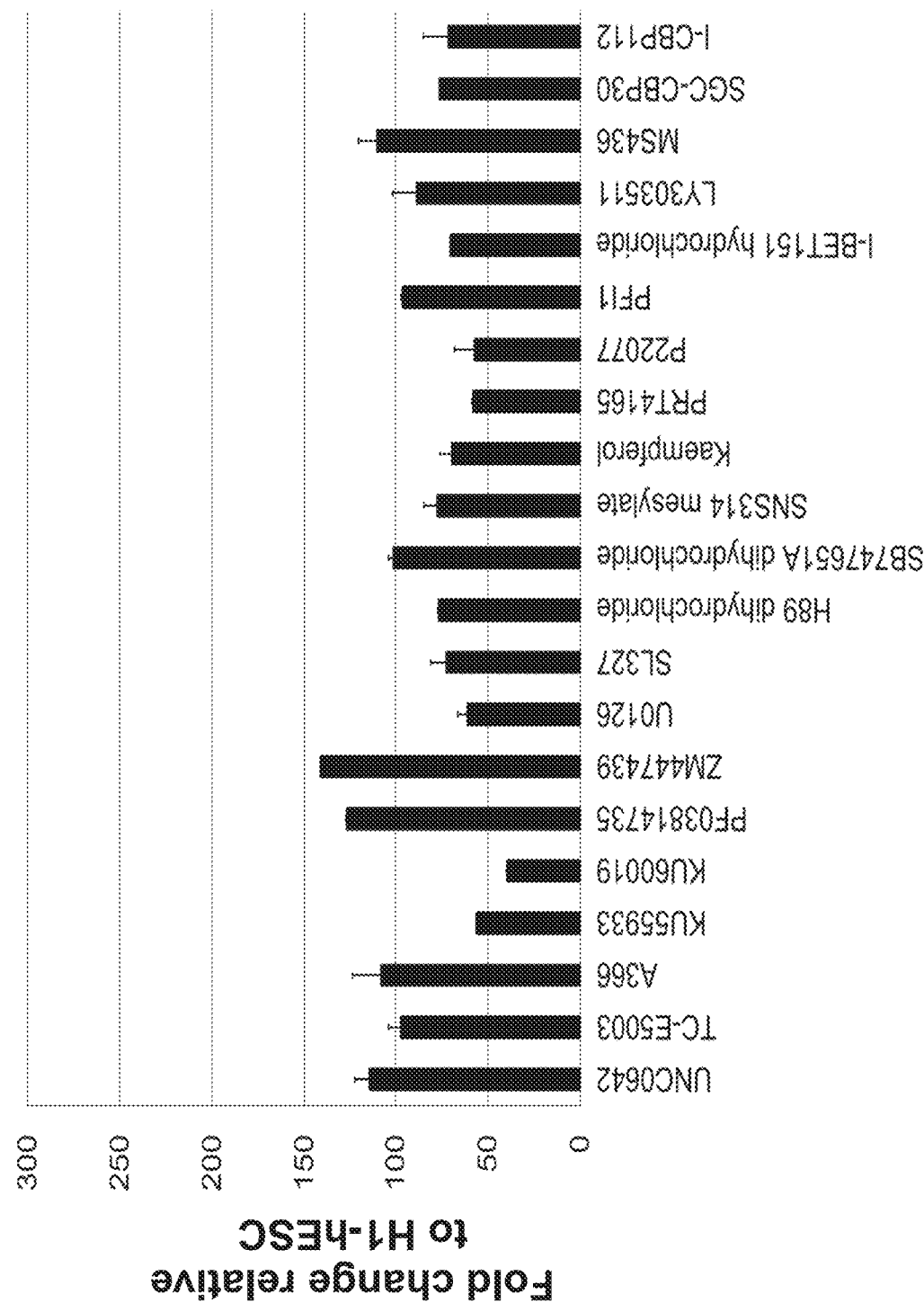

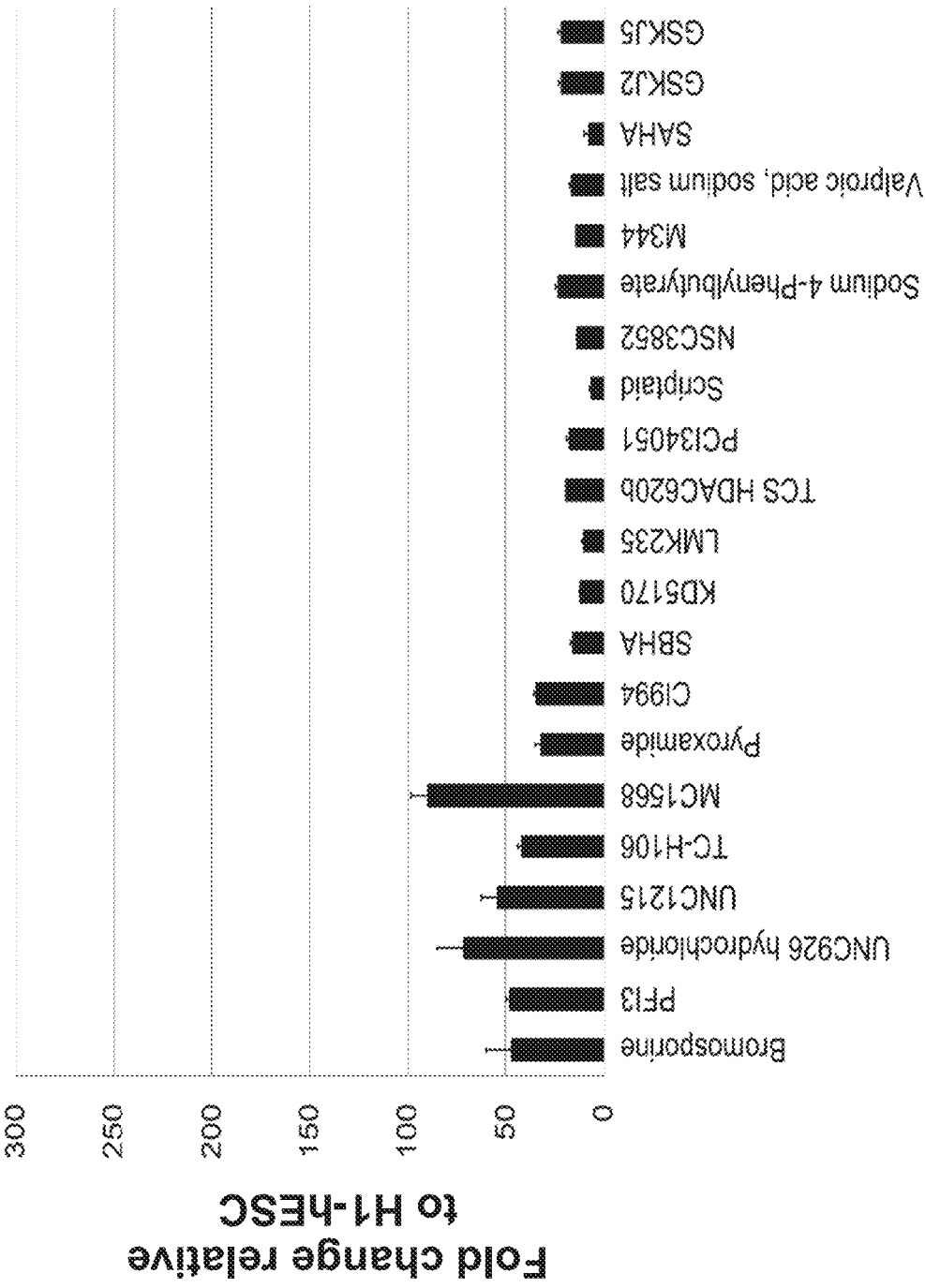

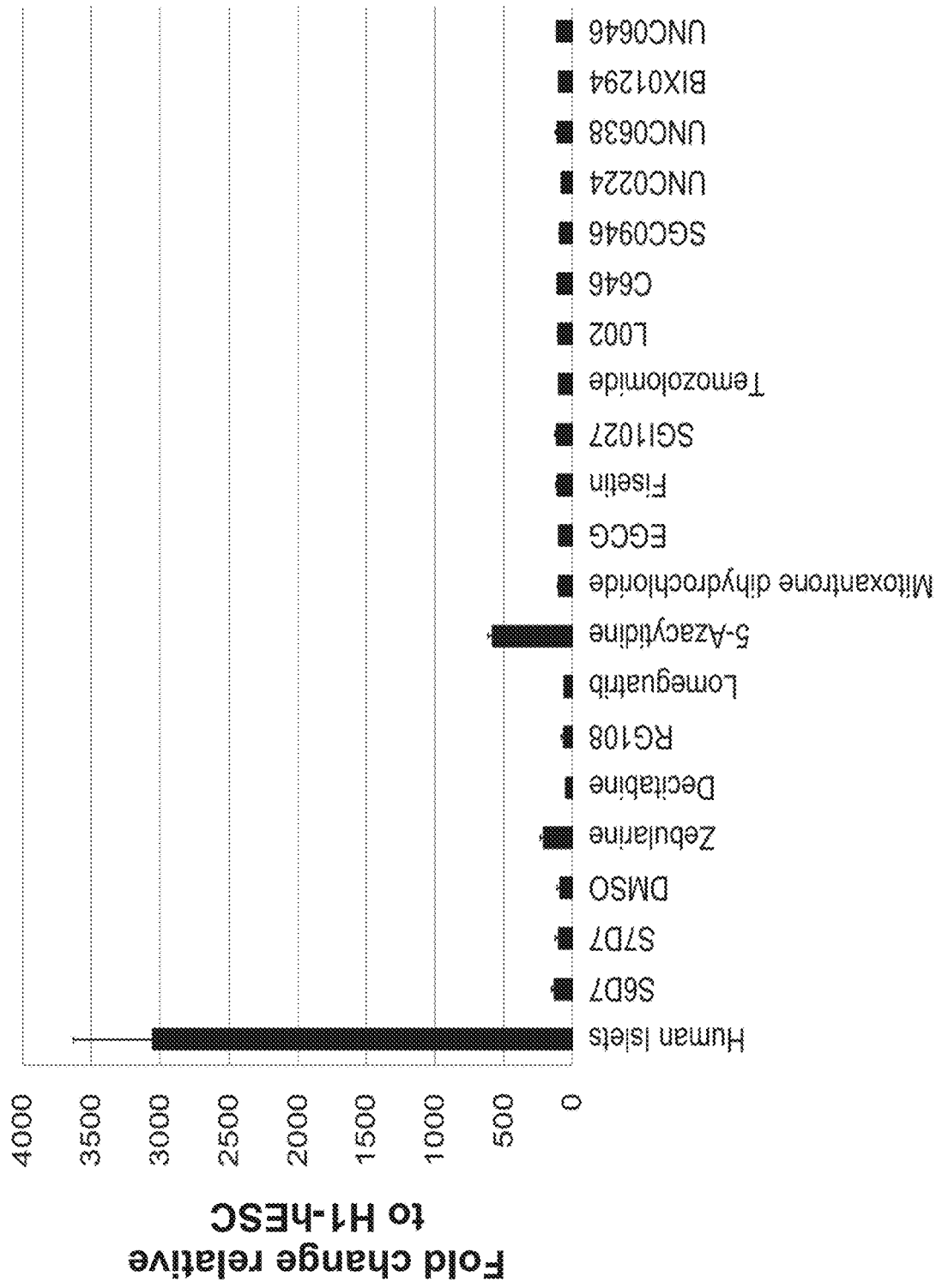

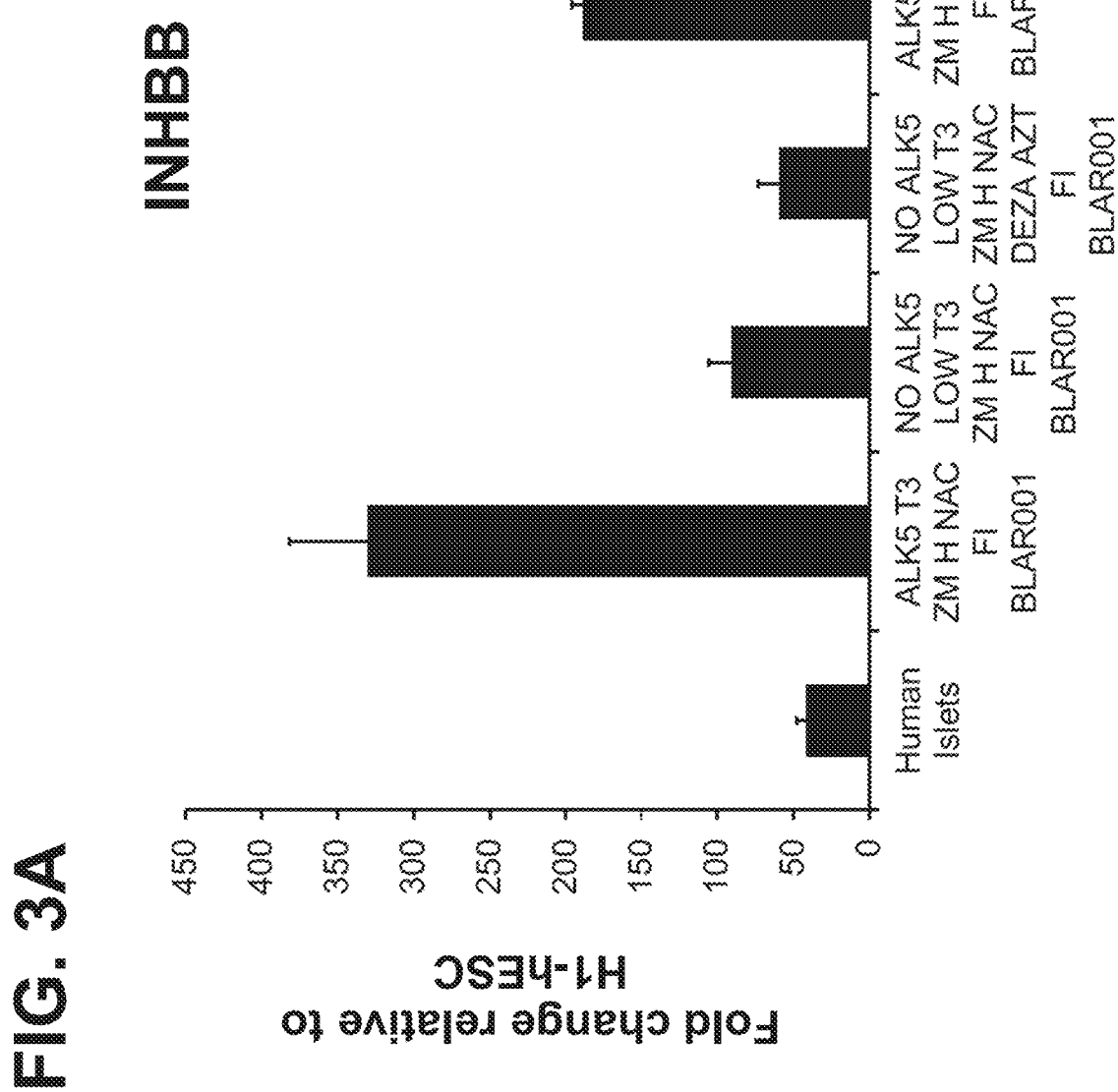

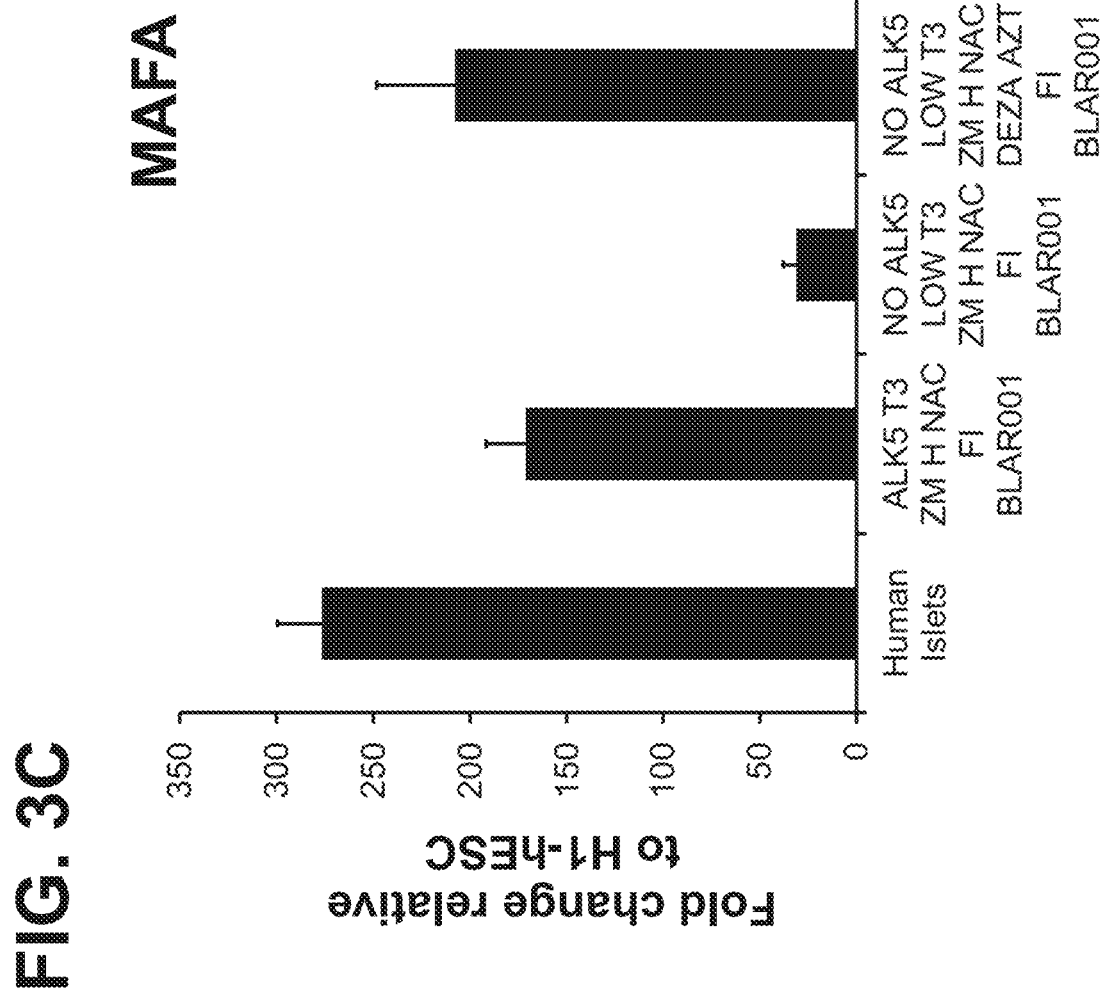

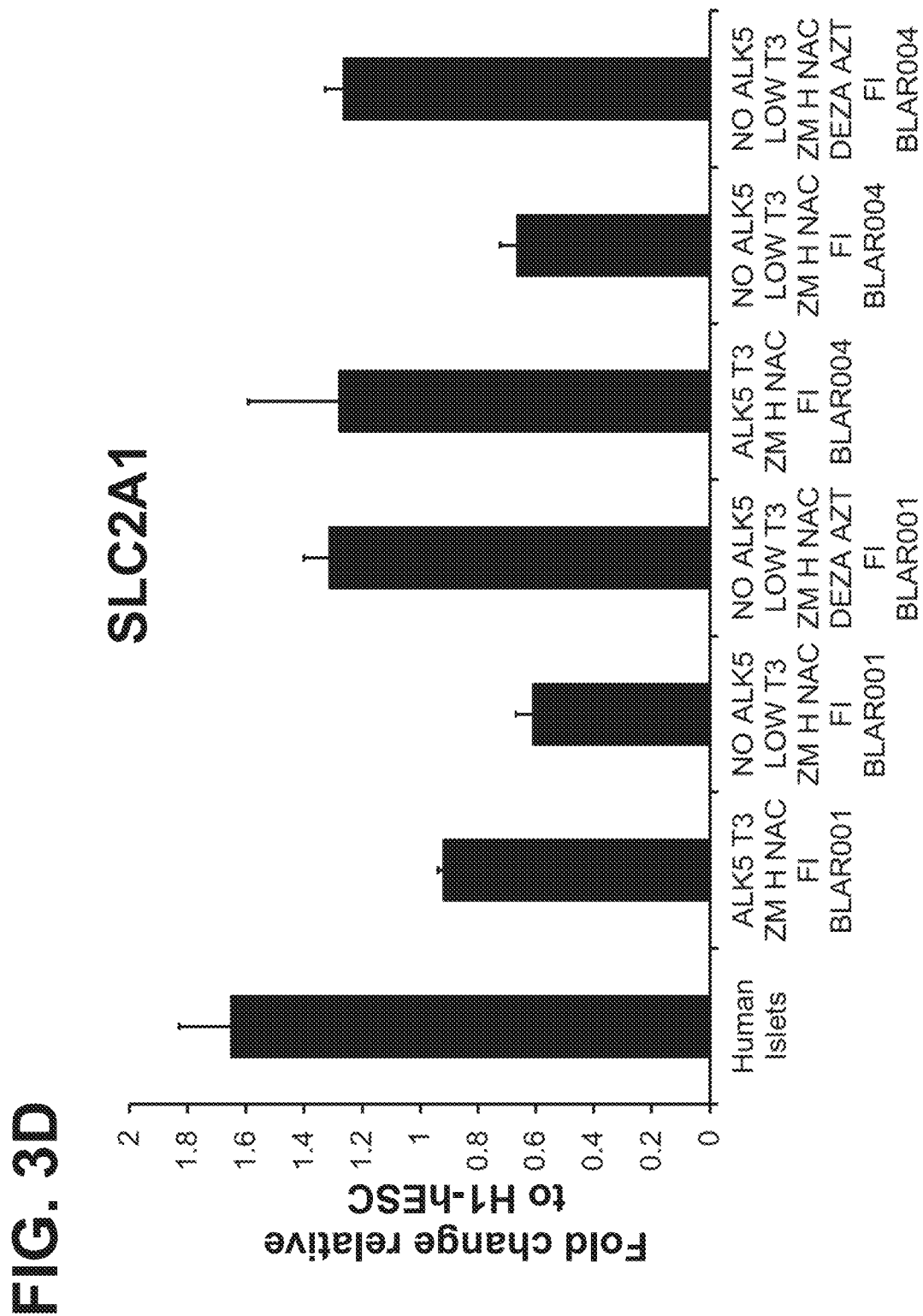

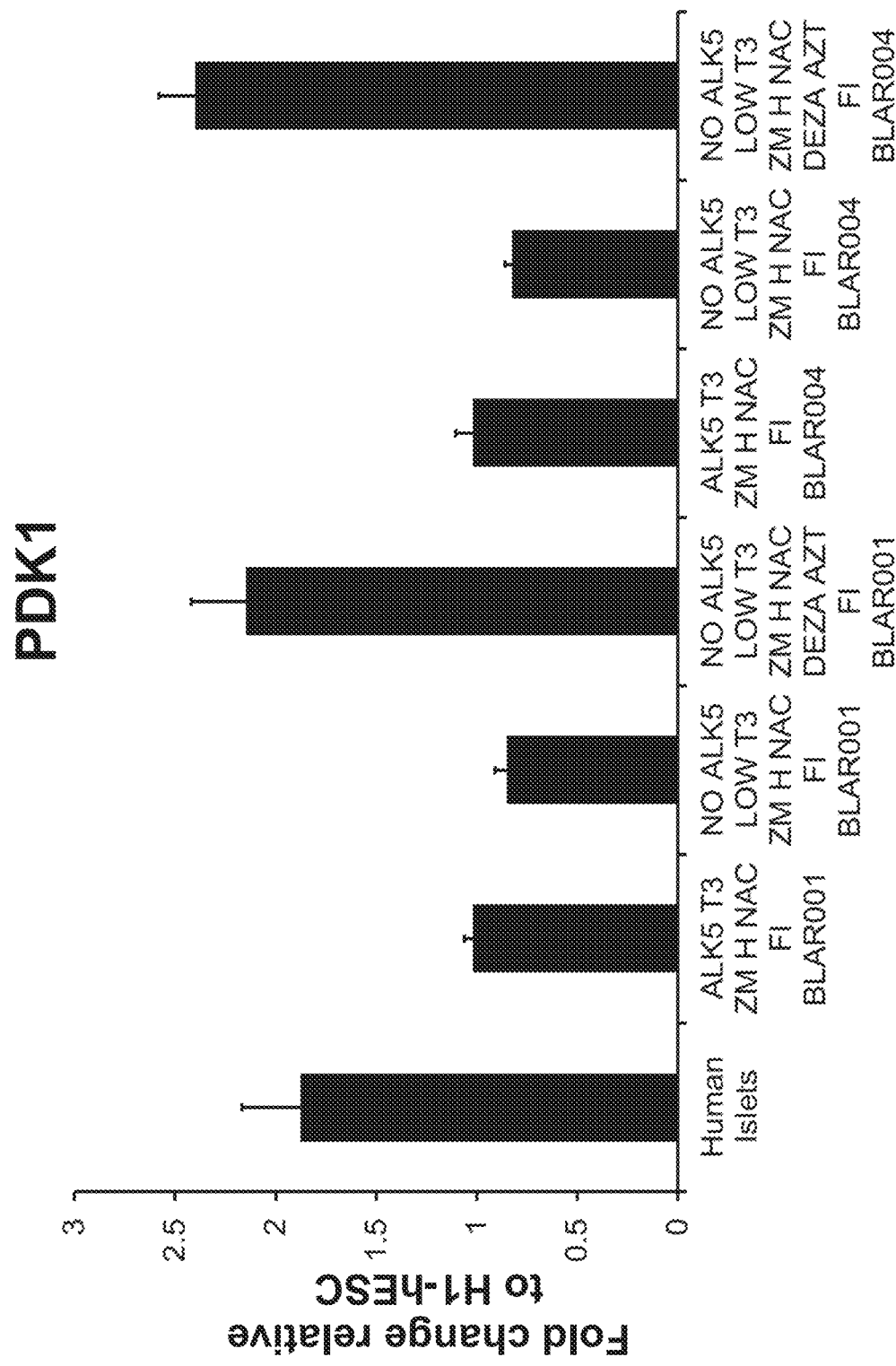

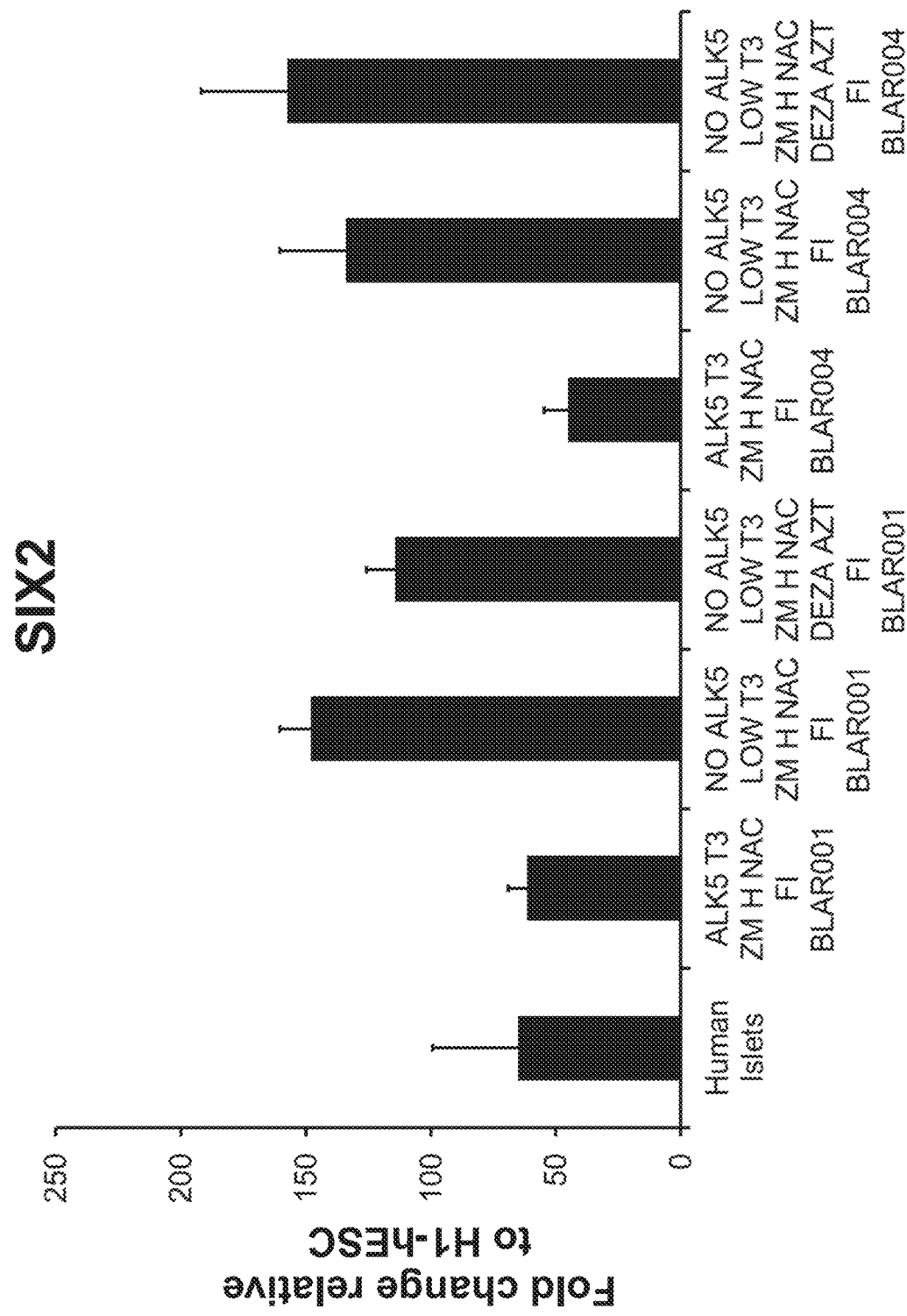

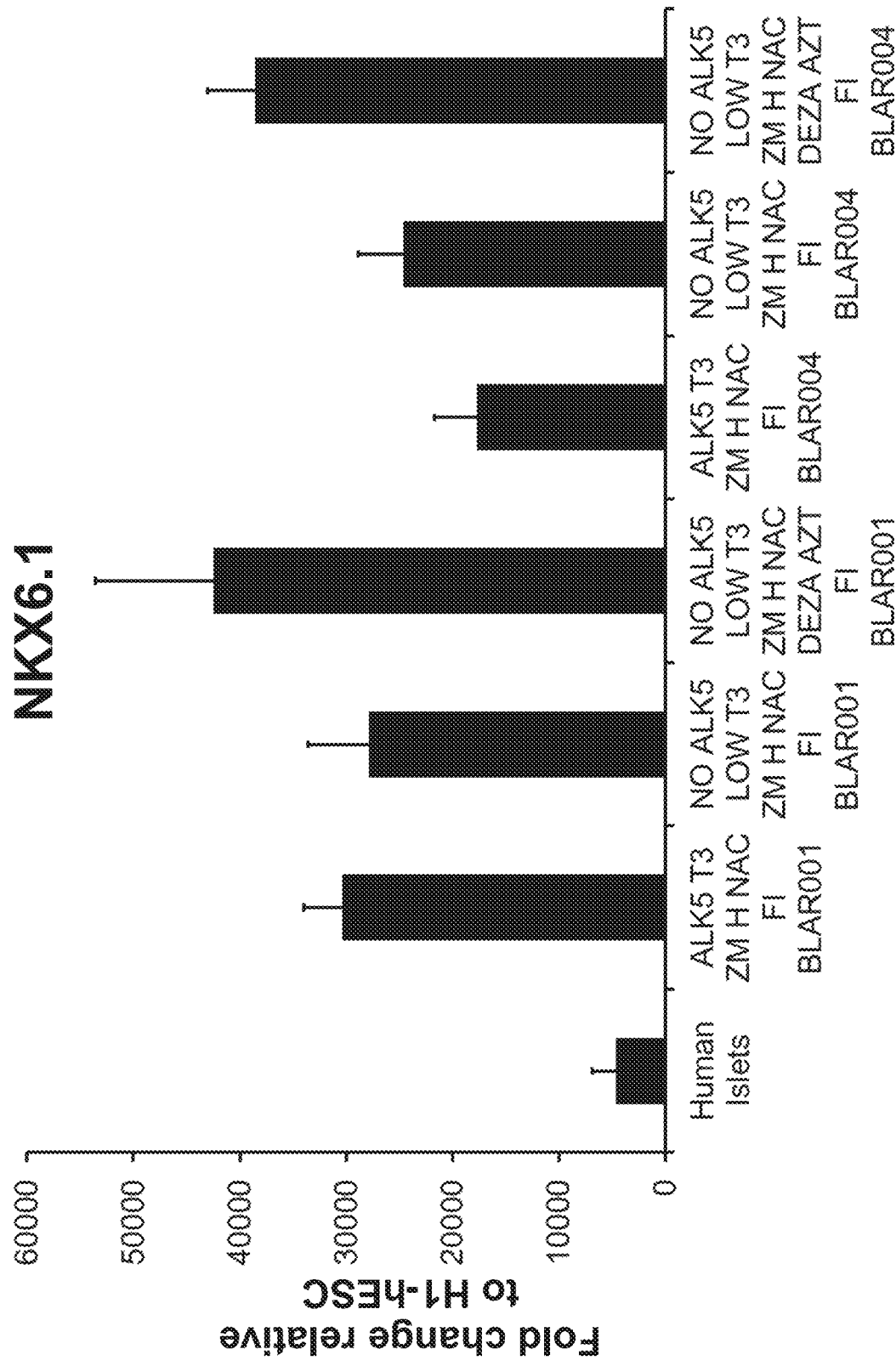

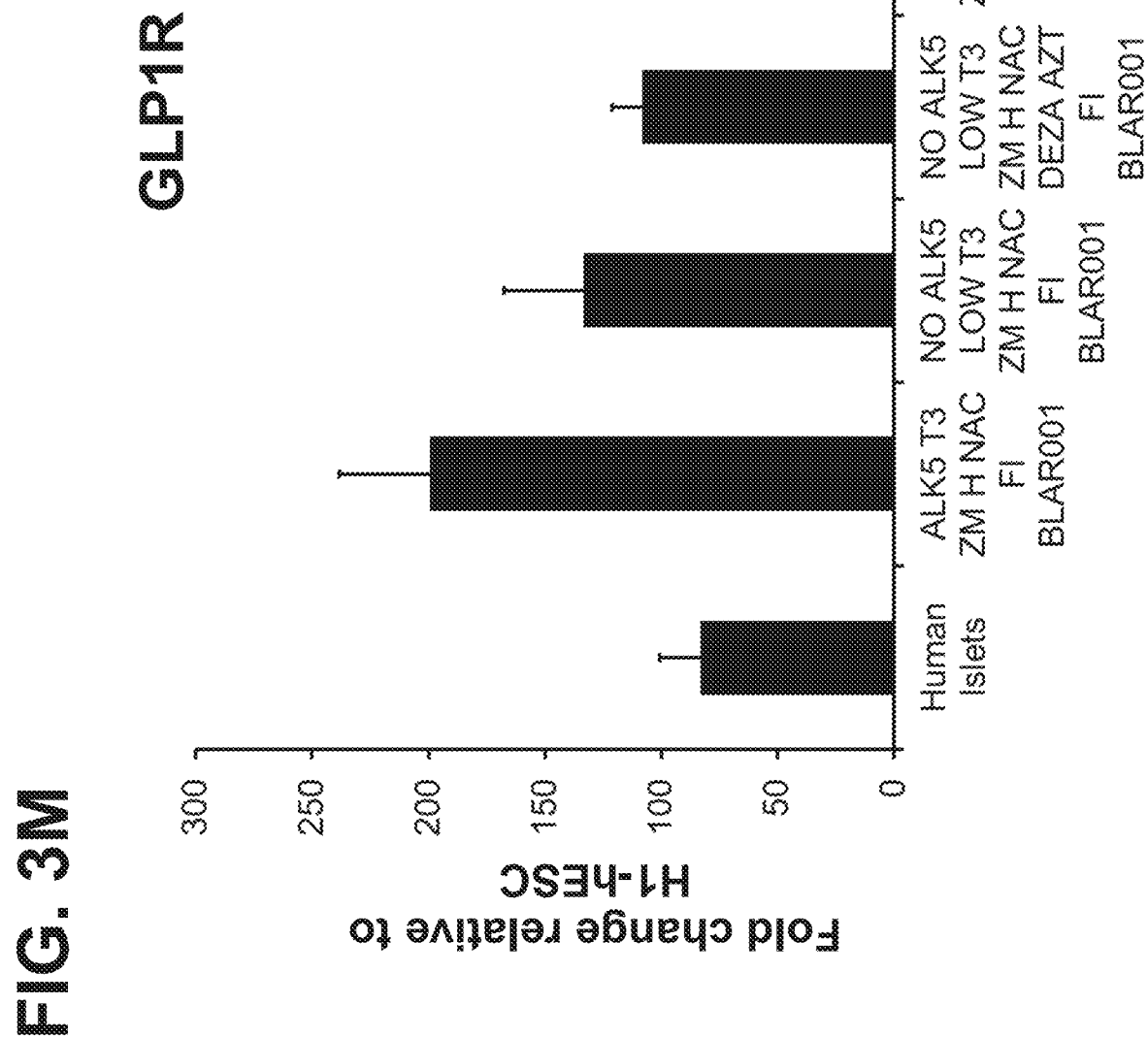

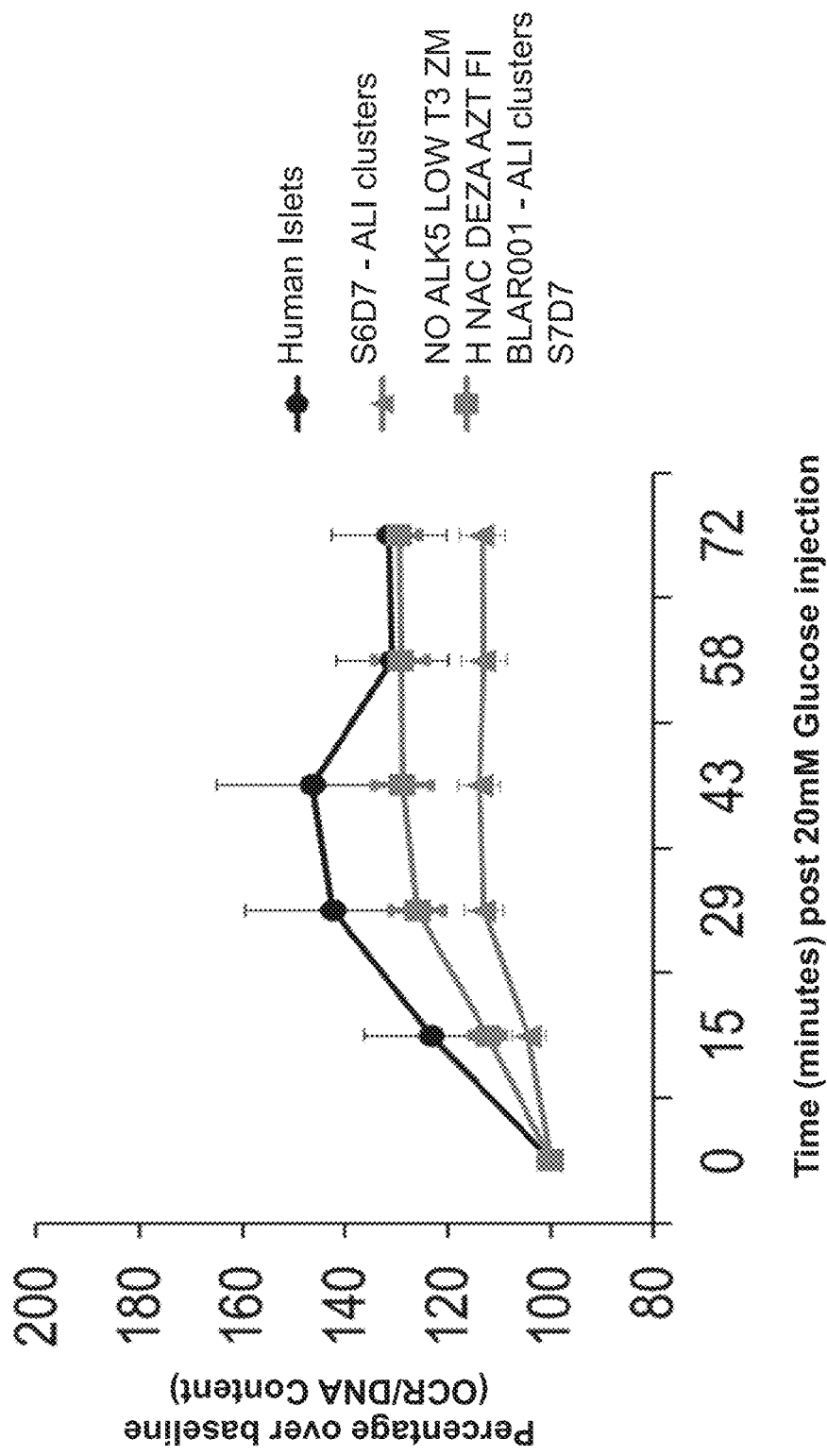

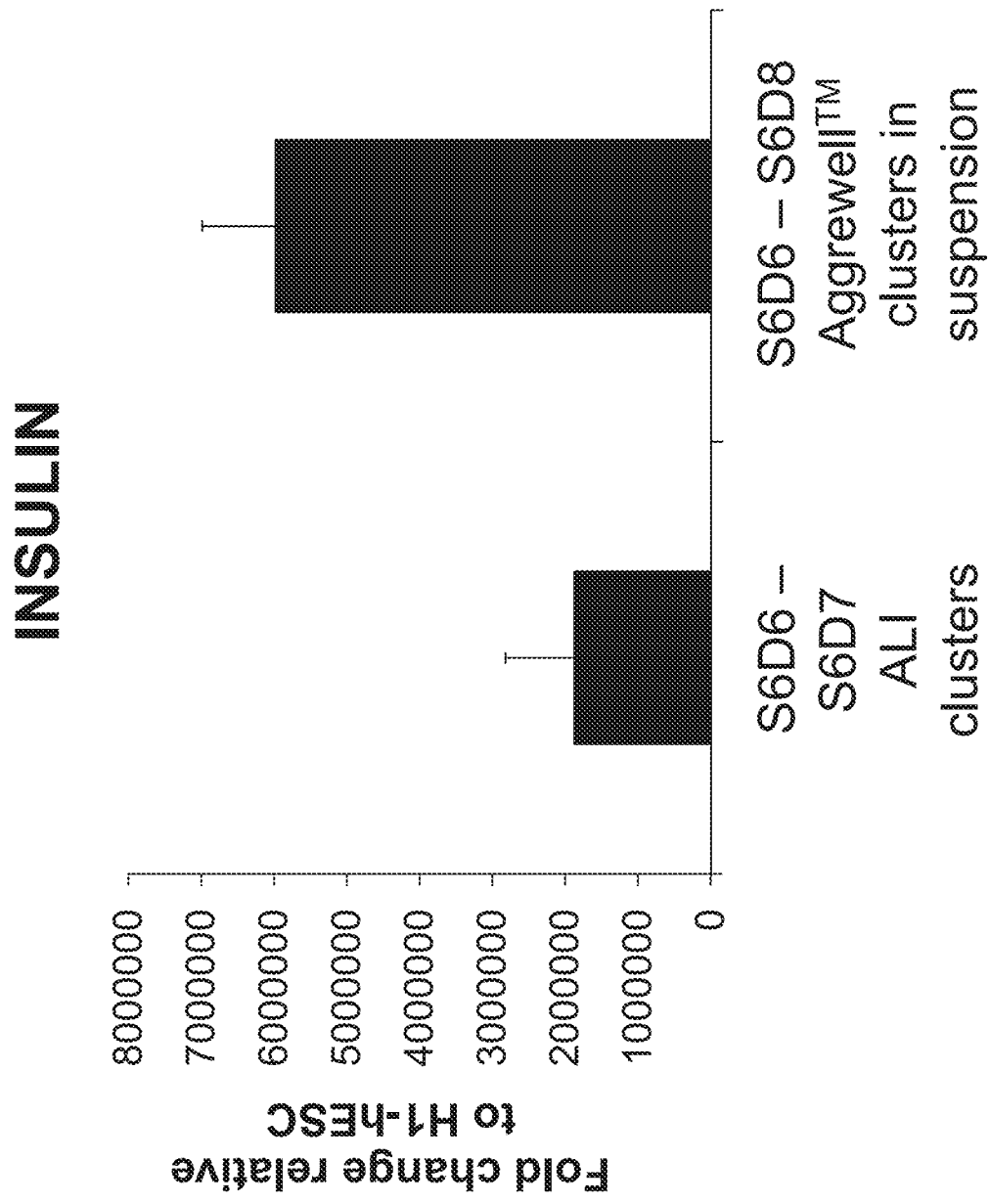

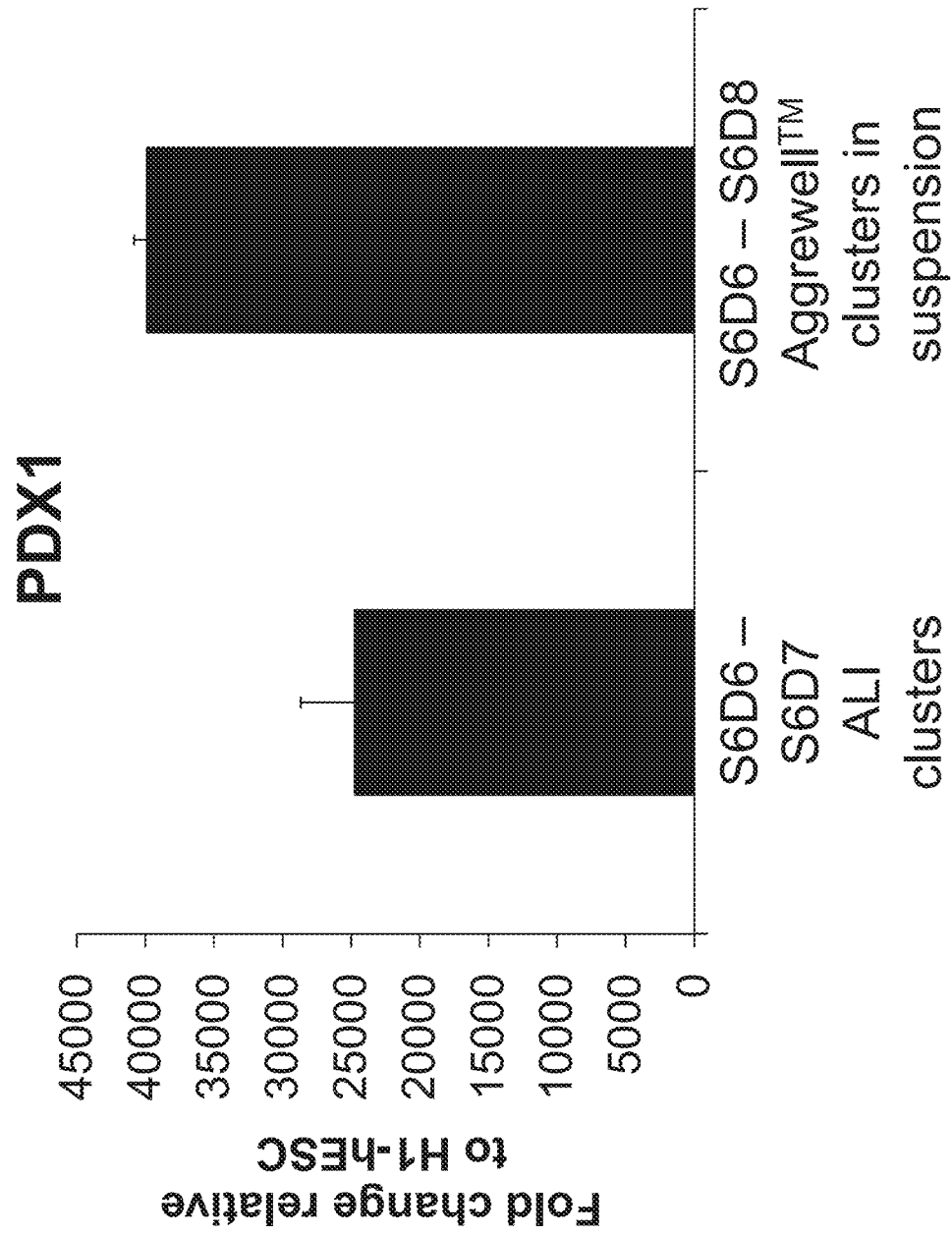

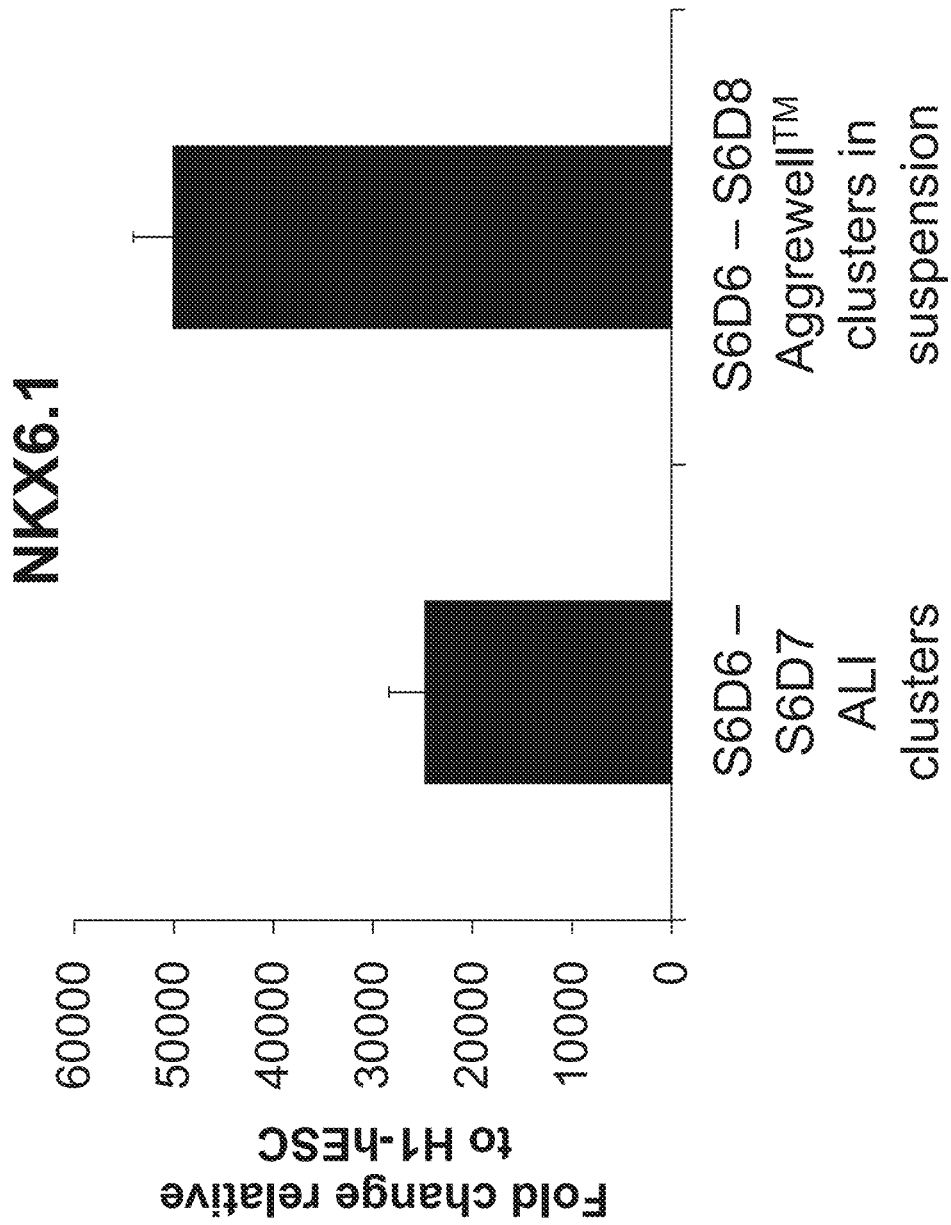

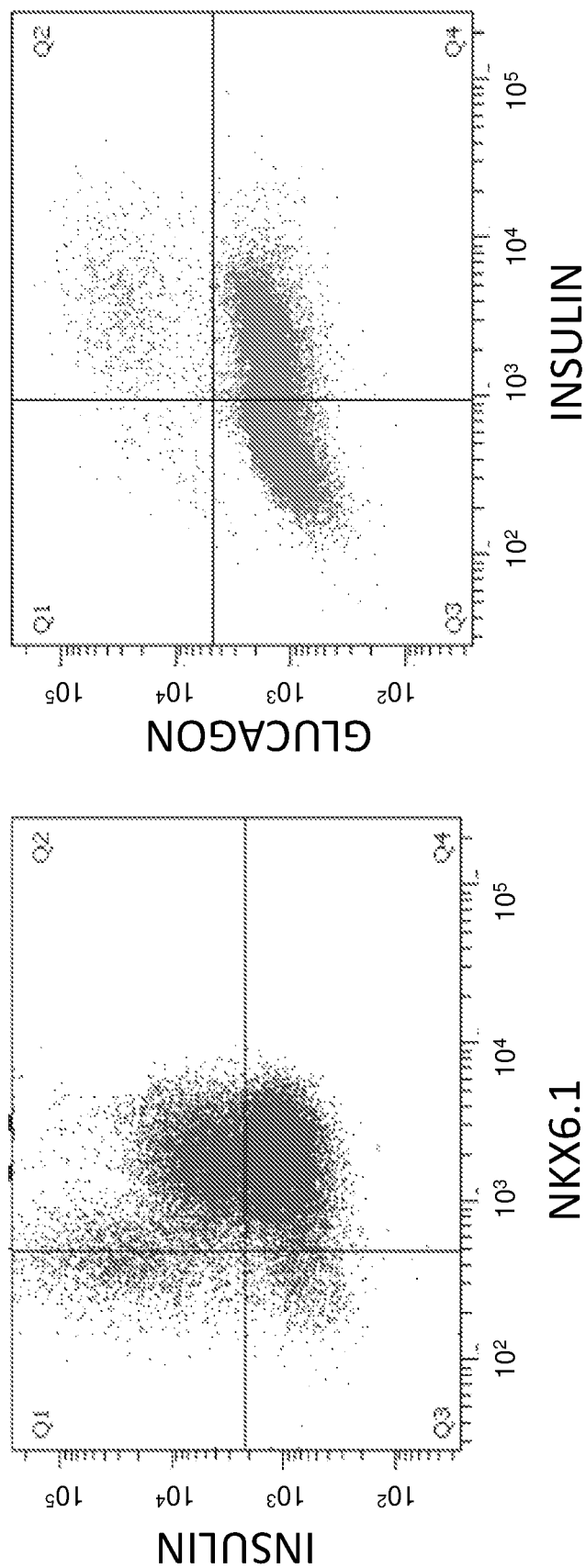

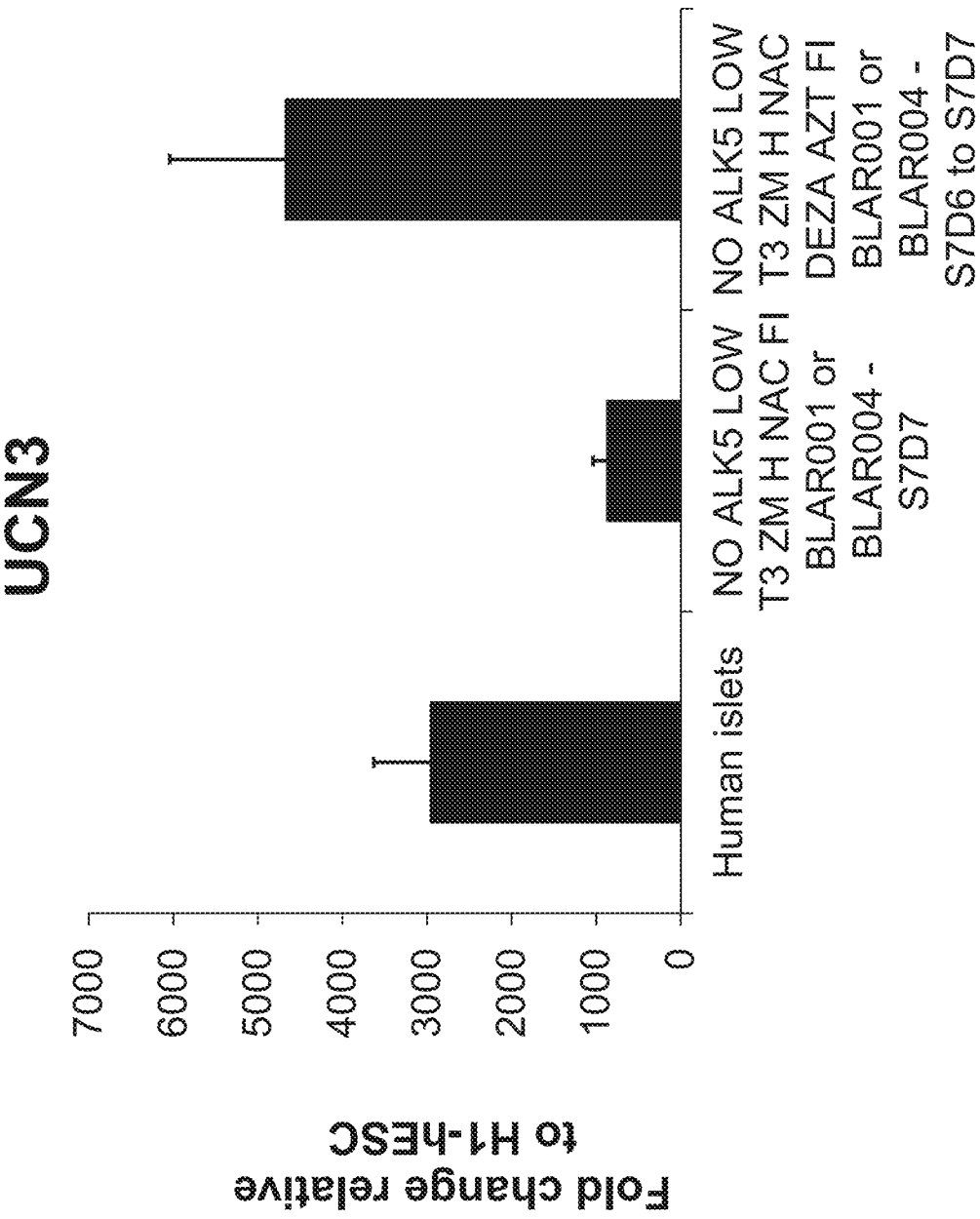

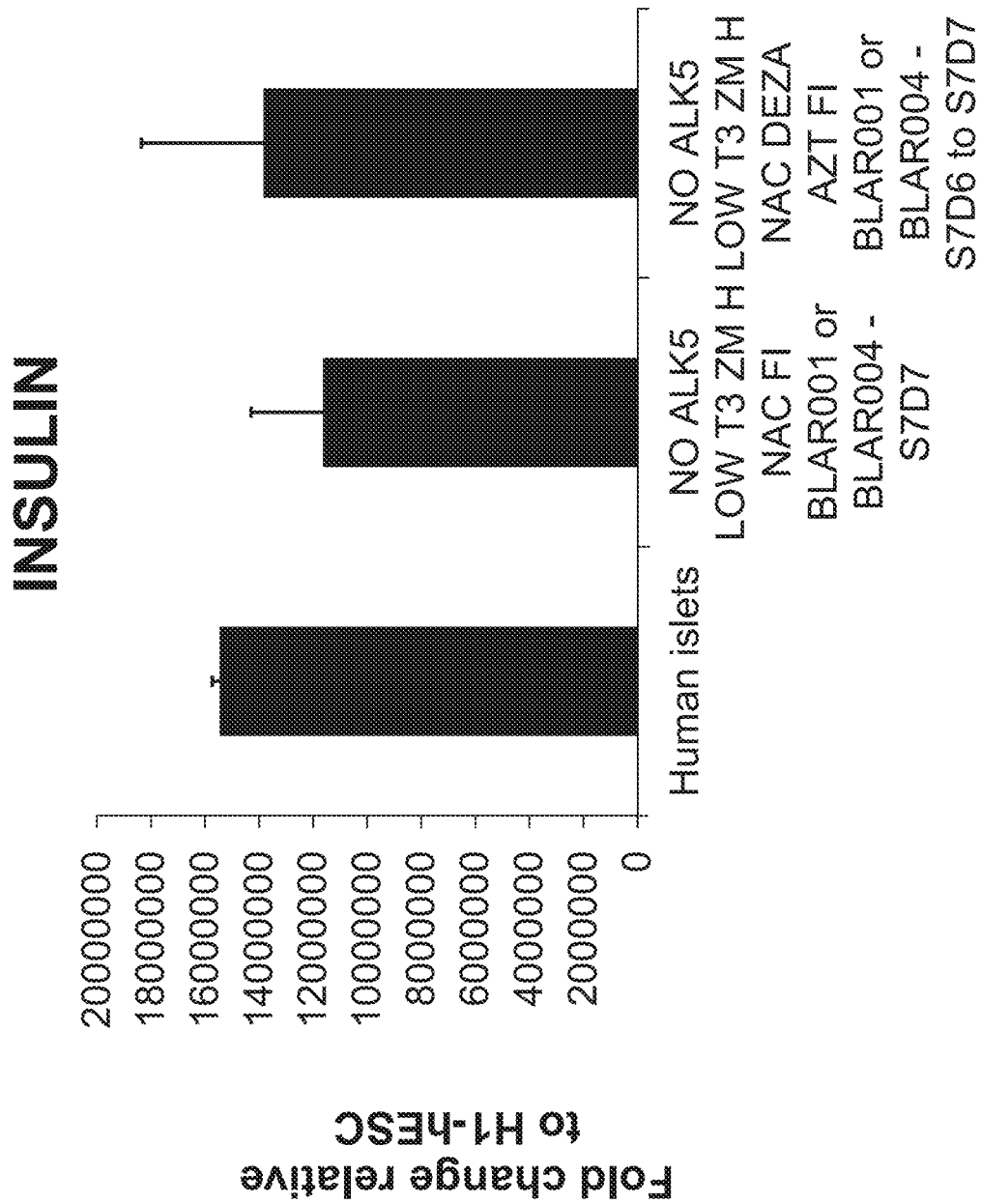

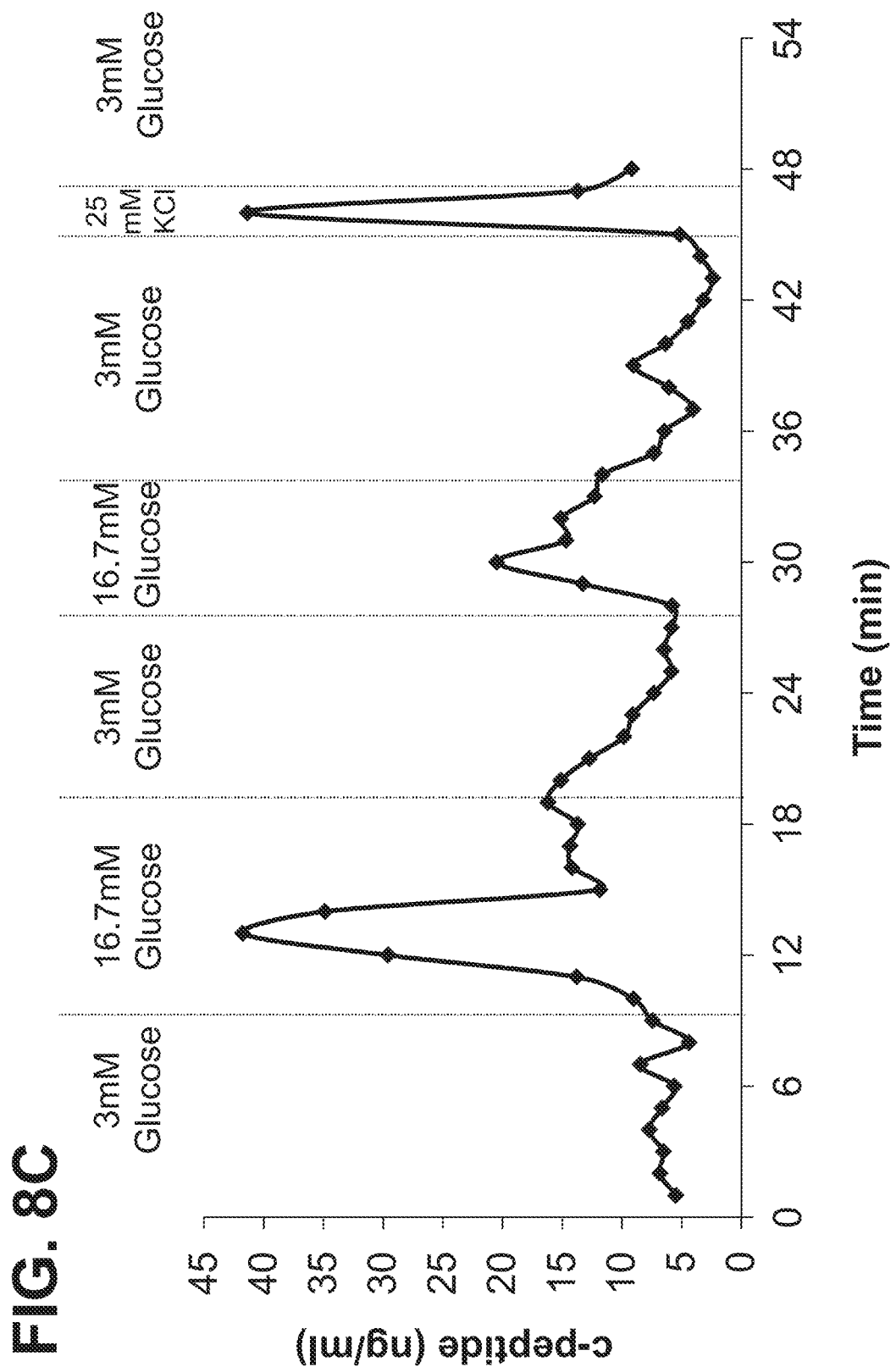

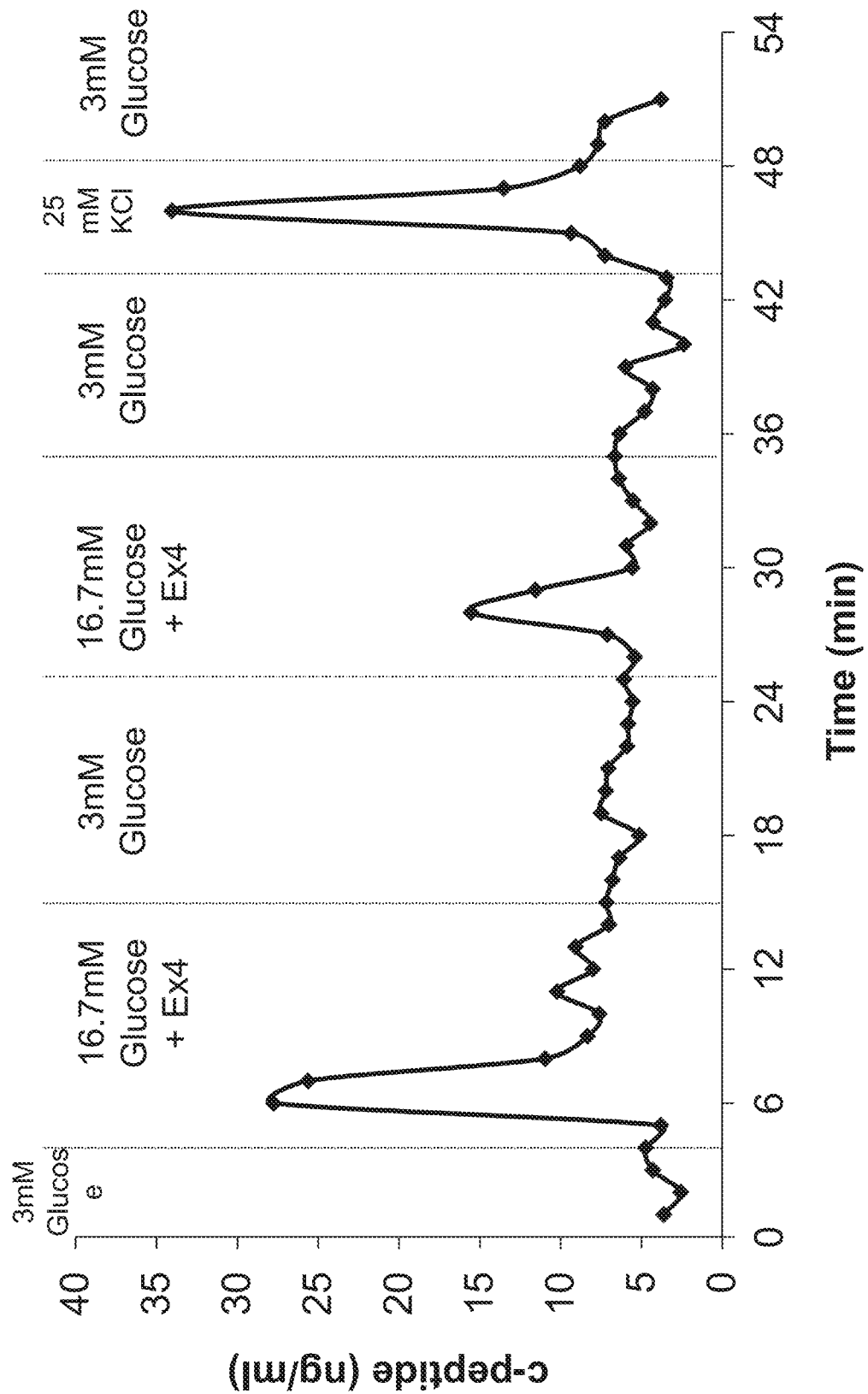

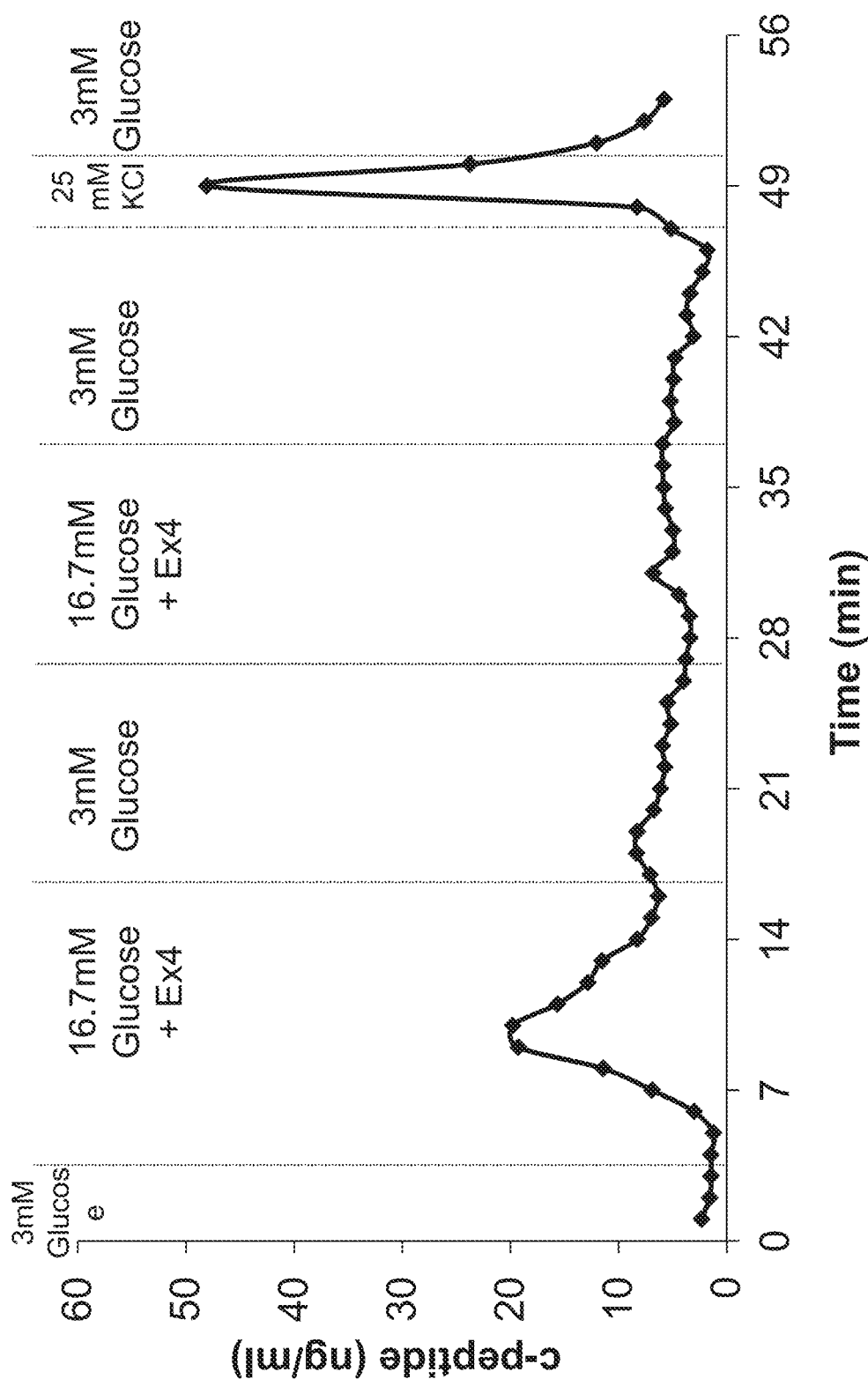

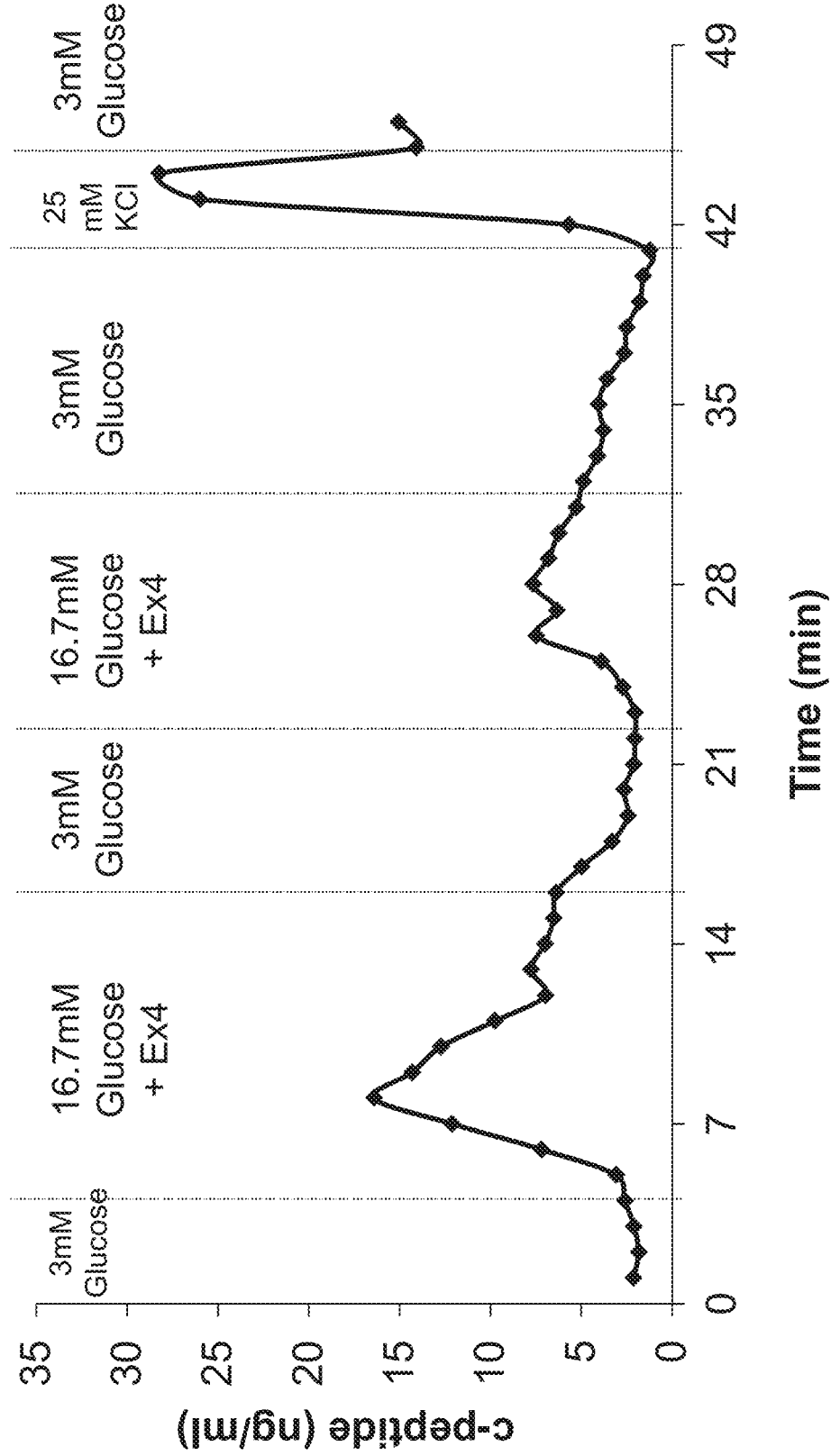

FIG. 9A

Human ES Cell – CyT49 hESC

| Definitive Endoderm Stage 1 (2 days) | Primitive Gut Tube Stage 2 – (3 days) | Foregut endoderm Stage 3 – (2 days) | Pancreatic endoderm Stage 4 – (3 days) |
|---|---|---|---|
| MCDB131 0.5% FAF-BSA | MCDB131 0.5% FAF-BSA | BLAR001 0.25% FAF-BSA | BLAR001 0.25% FAF-BSA |
| Activin A Wnt3A ITSX | Fgf7 | Fgf7 SANT TPPB RA | Fgf7 SANT TPPB RA |

FOXA2 — FOXA2 — FOXA2 PDX1 — FOXA2 PDX1 NKX6.1

FIG. 9B

| Type | hESC Input [million cells per mL] | S4D3 [million cells per mL] | S4D3 :: hESC Input |
|---|---|---|---|
| Roller Bottle | 0.181 ± 0.019 | 0.780 ± 0.216 | 4.30 ± 0.782 |
| 0.1 PBS Mini | 0.324 ± 0.003 | 1.06 ± 0.179 | 3.27 ± 0.585 |
| 0.5 PBS Mini | 0.301 ± 0.025 | 1.21 ± 0.246 | 4.08 ± 0.854 |

| Type | PEC-01 d12 :: hESC Input |
|---|---|
| PEC-01 d12 | 2.23 ± 0.090 |

FIG. 9C

| Type | S4D3 Yield [millions of cells] |
|---|---|
| 0.1 PBS Mini | 106.0 ± 17.9 |
| 0.5 PBS Mini | 606.2 ± 122.9 |

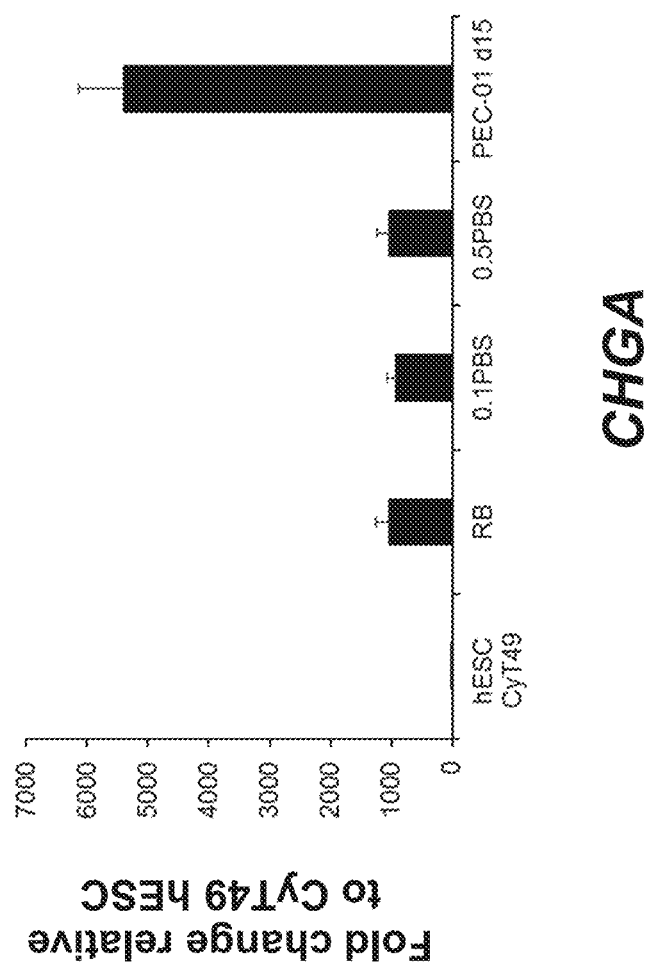

| Type | hESC Input [million cells per mL] | S6D7 [million cells per mL] | S6D7 :: hESC Input |
|---|---|---|---|
| Roller Bottle | 0.253 ± 0.088 | 0.240 ± 0.059 | 0.95 ± 0.31 |
| 0.1 PBS Mini | 0.324 ± 0.003 | 0.299 ± 0.079 | 0.92 ± 0.23 |
| 0.5 PBS Mini | 0.301 ± 0.025 | 0.746 ± 0.154 | 2.4 ± 0.169 |

| Type | S6D7 Yield [millions of cells] |
|---|---|
| 0.1 PBS Mini | 29.90 ± 7.90 |
| 0.5 PBS Mini | 223.8 ± 46.2 |

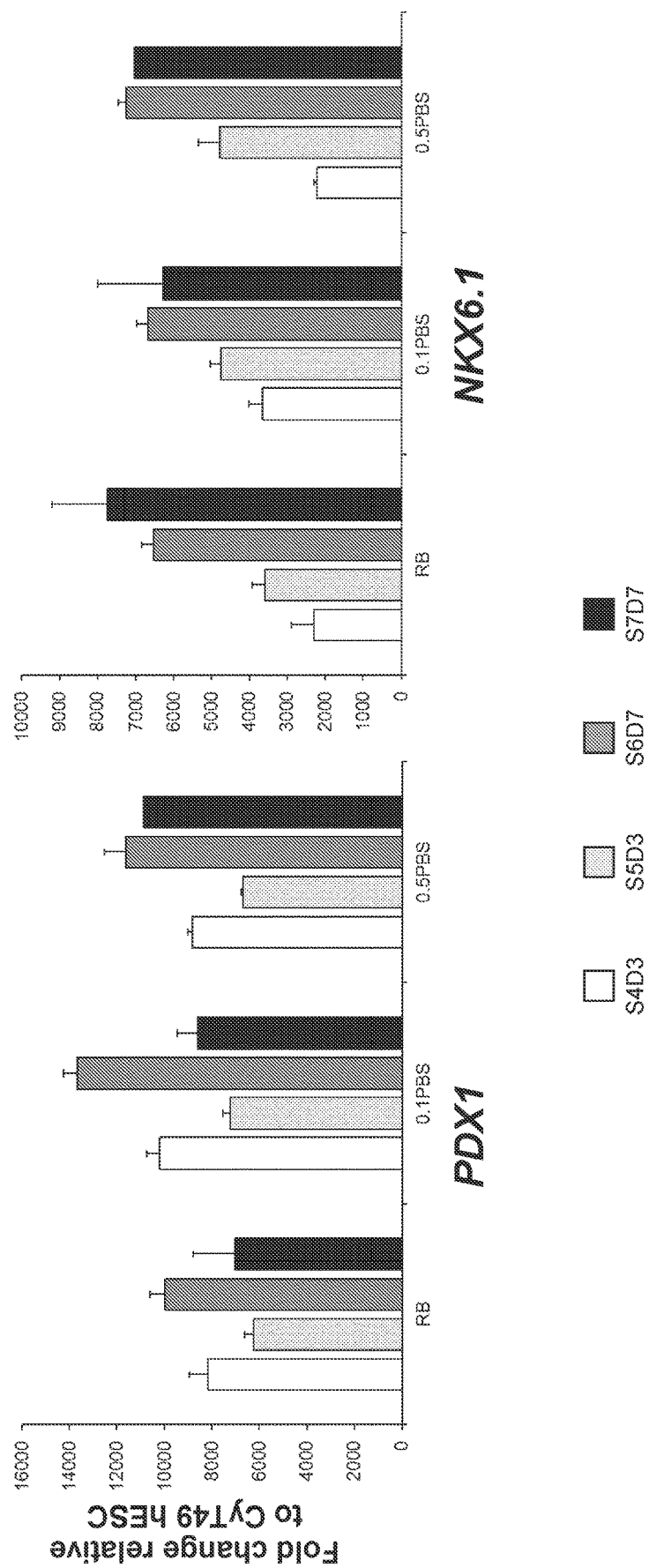

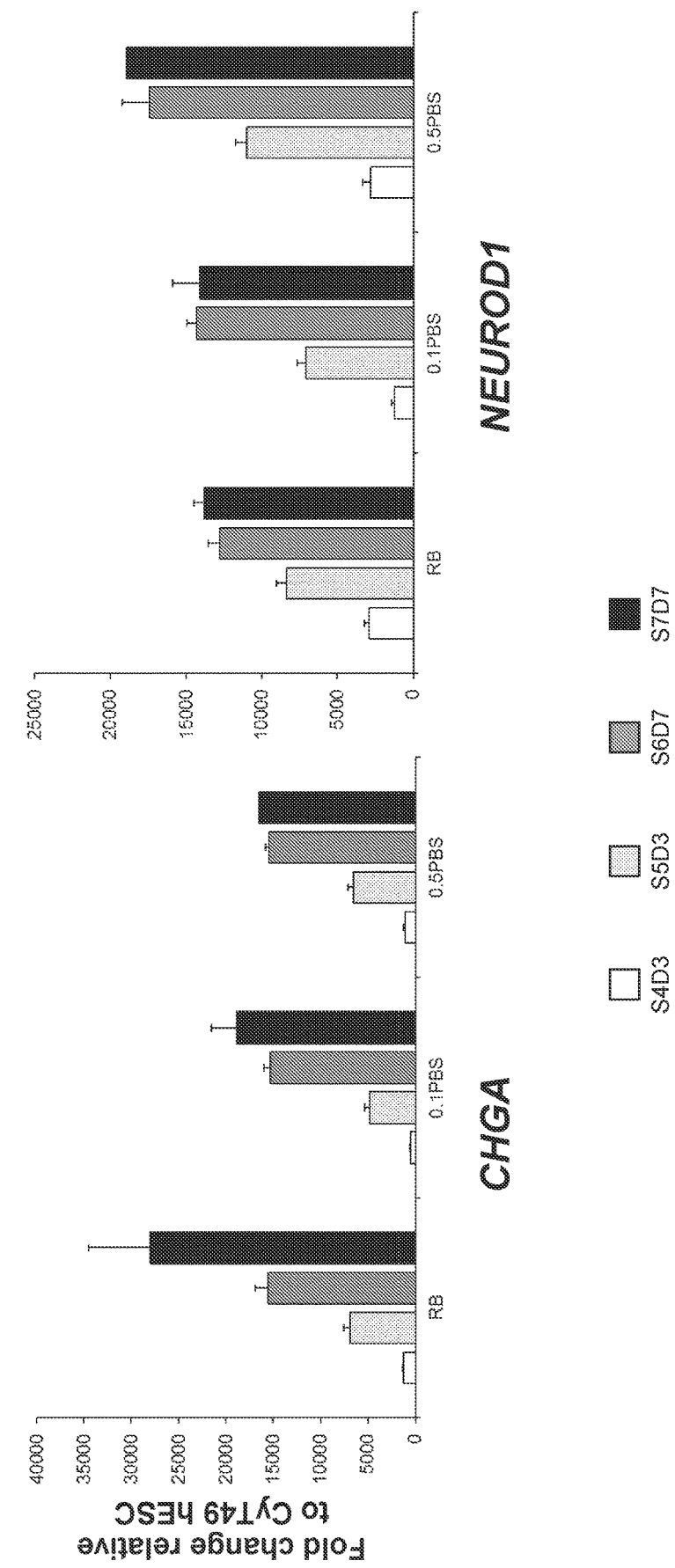

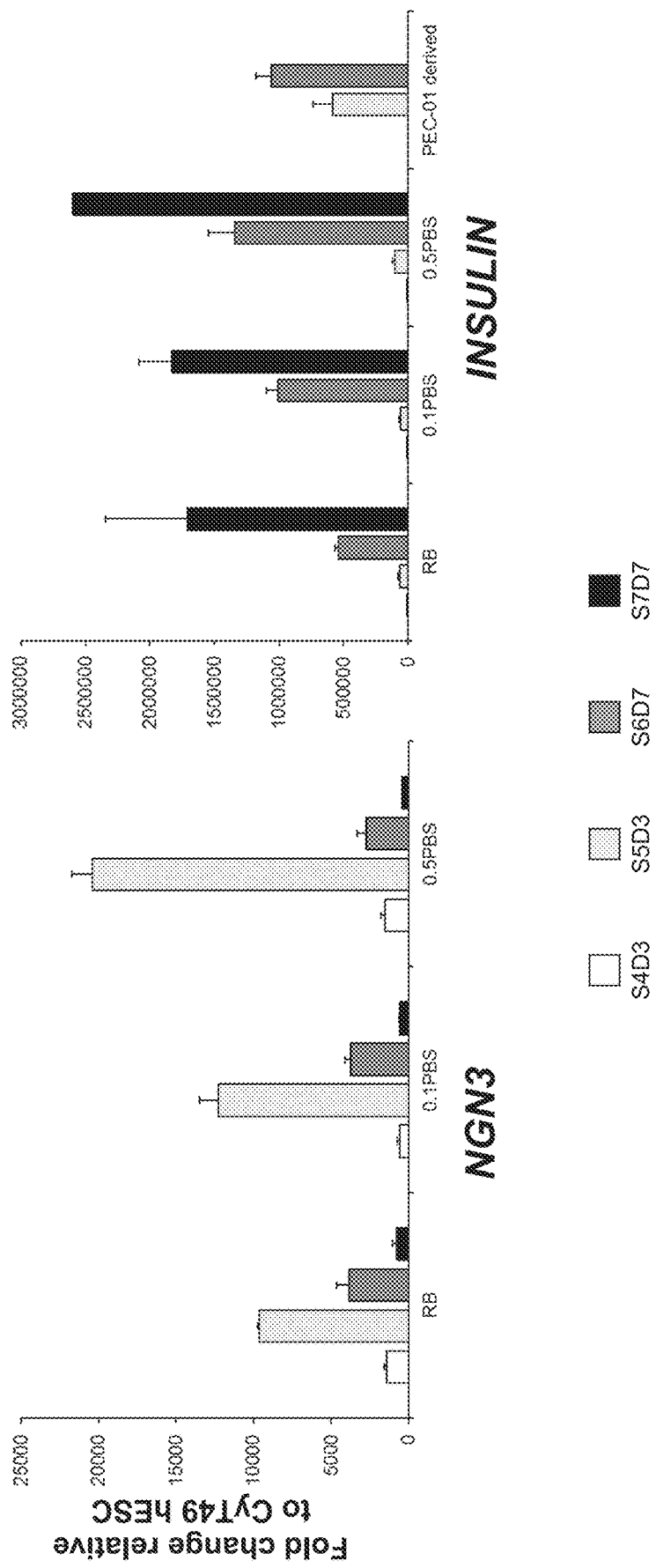

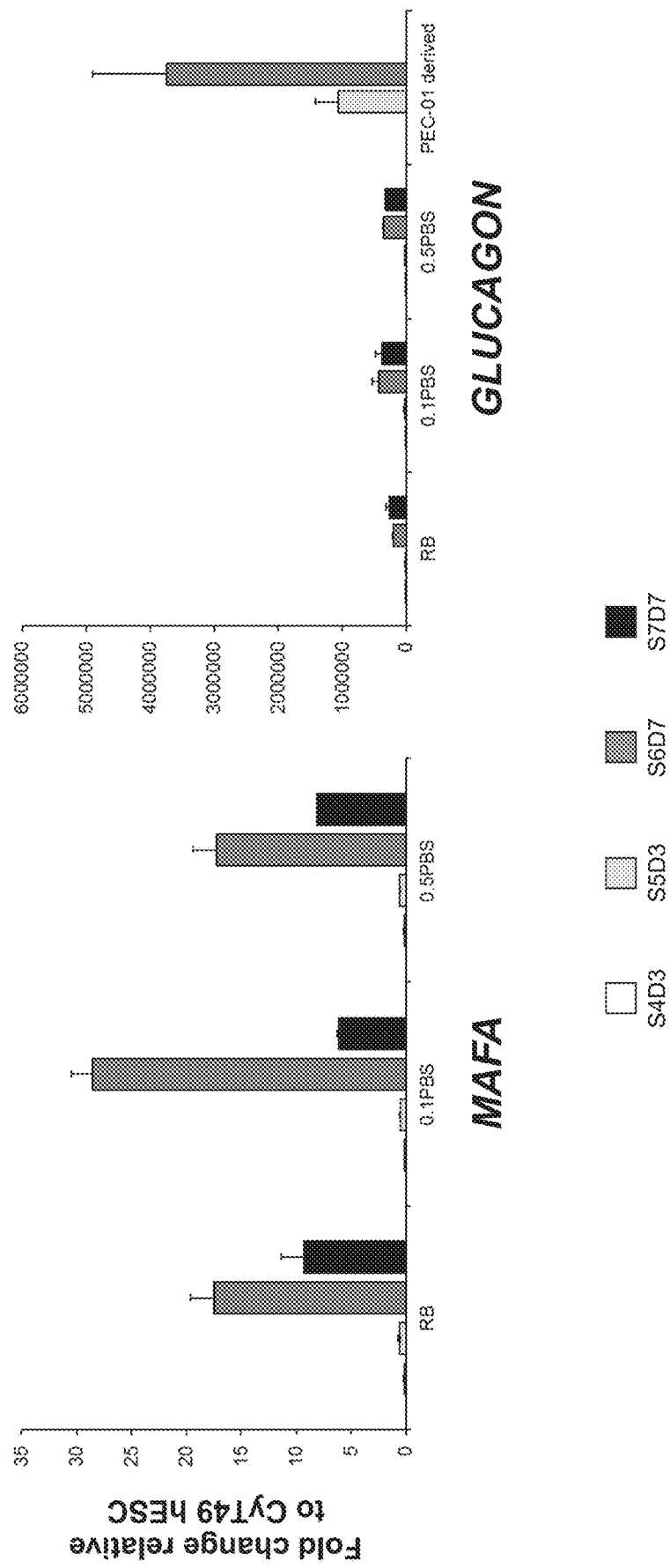

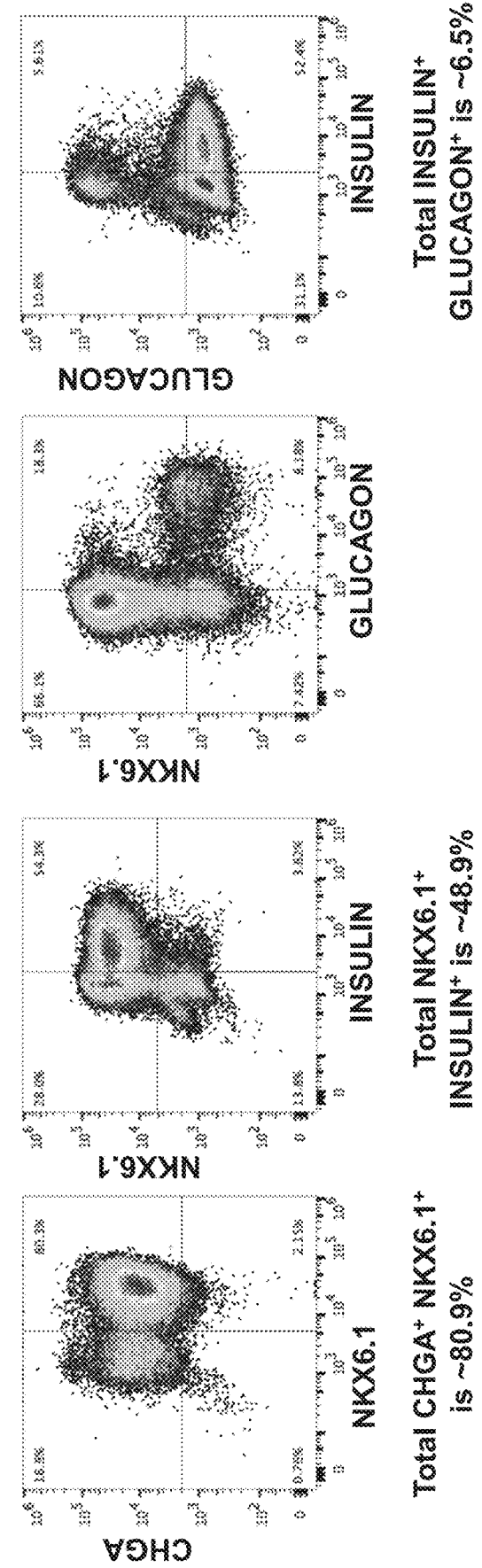

Roller bottle – S7D13

0.1 PBS Mini – S7D14

Roller bottle – PEC-01-derived S6D7

GENERATION OF HUMAN PLURIPOTENT STEM CELL DERIVED FUNCTIONAL BETA CELLS SHOWING A GLUCOSE-DEPENDENT MITOCHONDRIAL RESPIRATION AND TWO-PHASE INSULIN SECRETION RESPONSE

CROSS-REFERENCE TO RELATED APPLICATIONS

This is a continuation of U.S. patent application Ser. No. 15/622,931, filed on Jun. 14, 2017, which claims the benefit of U.S. Provisional Application 62/352,968, filed on Jun. 21, 2016. The prior applications are incorporated herein by reference in their entirety.

FIELD OF THE INVENTION

The present invention relates to methods for producing in vitro functional pancreatic beta cells, and populations resulting from, the differentiation of pluripotent stem cells. In particular, the invention relates to beta cells or a population of beta cells that exhibit mitochondrial respiration/activity response and a two-phase insulin secretion response.

BACKGROUND OF THE INVENTION

Advances in cell-replacement therapy for Type I diabetes mellitus and a shortage of transplantable islets of Langerhans have focused interest on developing sources of insulin-producing cells, or beta (β) cells, appropriate for engraftment. One approach is the generation of functional beta cells from pluripotent stem cells, such as, embryonic stem cells or induced pluripotent cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver will develop from the endoderm via an intermediate stage.

D'Amour et al. described the production of enriched cultures of human embryonic stem cell-derived definitive endoderm in the presence of a high concentration of activin and low serum (*Nature Biotechnology* 2005, 23:1534-1541; U.S. Pat. No. 7,704,738). Transplantation of these cells under the kidney capsule of mice resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF-10 and retinoic acid (U.S. Patent App. Pub. No. 2005/0266554). Subsequent transplantation of these pancreatic precursor cells in the fat pad of immune deficient mice resulted in the formation of functional pancreatic endocrine cells following a 3-4 month maturation phase (U.S. Pat. Nos. 7,534,608 and 7,993,920).

Small molecule inhibitors have been used for induction of pancreatic endocrine precursor cells. For example, small molecule inhibitors of TGF-β receptor and BMP receptors (Development 2011, 138:861-871; *Diabetes* 2011, 60:239-247) have been used to enhance the number of pancreatic endocrine cells. In addition, small molecule activators have also been used to generate definitive endoderm cells or pancreatic endoderm cells (*Curr. Opin. Cell Biol.* 2009, 21:727-732; *Nature Chem. Biol.* 2009, 5:258-265).

In general, the process of differentiating progenitor cells to functional beta cells progresses through various stages and strides have been made in improving protocols to generate pancreatic cells from progenitor cells, such as human pluripotent stem cells. Despite these advances in research, each step in the process of differentiating progenitor cells presents a unique challenge. As such, there is still a need for further differentiation protocol development for the purpose of producing functional pancreatic endocrine cells and, in particular, functional beta cells. In particular, it is desirable to provide for in vitro generation of glucose responsive insulin-producing cells capable of the rapid and regulated glucose-stimulated insulin secretion ("GSIS") observed with functional beta-cells. Specifically, it is desirable to provide a method of producing in vitro functional beta-cells exhibiting an increase in mitochondrial respiration/activity followed by the first phase and second phase of insulin secretion.

GSIS begins by the import of glucose into the beta-cell via a glucose transporter (solute carrier family 2 member 1; SLC2A1; or commonly referred to as glucose transporter 1; GLUT1 for human beta cells), and the metabolism of glucose to pyruvate, through a process named glycolysis. The import of pyruvate into the mitochondria, its metabolism through the TCA (tricarboxylic acid, and subsequent activation of the electron transport chain ("ETC" and referred to here as "mitochondrial activity" or "mitochondrial respiration") cycle is tightly coupled with insulin exocytosis to ensure the rapid and correct quantity of insulin release.

Functional beta cells within an islet have been shown to secrete insulin upon a sudden increase in glucose concentration in two sequential phases (Henquin et al. *Diabetologia* (2009) 52(5):739-751). The amplitude and duration of both phases is regulated by the kinetics of the intracellular $Ca^{2+}$ signal or additive secretion coupling factors. First phase ($1^{st}$) insulin secretion represents the exocytosis of a small pool of bound and readily releasable insulin granules. The second phase ($2^{nd}$) of insulin secretion, lower in amplitude but longer in duration, represents the translocation of granules from a reserve pool of granules, and their docking/priming for release. Biphasic GSIS, a key marker of maturation in beta cells, is not detected until the postnatal phase of human development, and is in contrast to the monophasic GSIS seen in immature beta-cells (Otonkoski et al. *Diabetes* (1988) 37:286-291).

In type 2 diabetics, the $1^{st}$ phase of GSIS is absent; and the $2^{nd}$ phase of GSIS is also reduced. Type 1 diabetics, whose beta-cell number is severely reduced via autoimmune attack, are reported to lack a robust biphasic GSIS (Krogvold et al. *Diabetes* (2015) 64: 2506-2512).

BRIEF SUMMARY OF THE INVENTION

As embodied and fully described, the invention provides methods for producing in vitro functional beta-cells (functional pancreatic beta-cells), and populations of cells resulting from, the differentiation of pluripotent stem cells. In particular, the invention relates to generating functional pancreatic beta-cells (insulin producing cells) or a population of functional beta-cells that exhibit mitochondrial respiration/activity response and a two-phase insulin secretion response.

One aspect of the invention is a method of differentiating pluripotent stem cells into functional beta-cells. A particular aspect of the invention is a method of differentiating pancreatic endoderm cells into functional beta-cells expressing PDX1, NKX6.1, MAFA, UCN3 and SLC2A1. In embodiments, the method comprises culturing pancreatic endocrine cells in a culture medium supplemented with one or more small molecules of UNC0638, UNC0642, UCN0646, TC-E5003, A366, PF03814735, ZM447439, SB747651A, PFI1, LY303511, MS436, AZT, DEZA, pyroxamide, CI994 or MC1568.

An embodiment of the invention is in vitro population of functional pancreatic beta-cells expressing single hormonal insulin, PDX1, NKX6.1 and MAFA obtained by in vitro differentiation of pancreatic endocrine cells. In some embodiments, the population of functional beta-cells also co-express UCN3 and SLC2A1. In embodiments, MAFA expression is increased as compared to immature beta-cells. In embodiments, the in vitro population of functional beta cells is obtained by culturing pancreatic endocrine cells in a medium supplemented with one or more small molecules of UNC0638, UNC0642, UCN0646, TC-E5003, A366, PF03814735, ZM447439, SB747651A, PFI1, LY303511, MS436, AZT, DEZA, pyroxamide, CI994 or MC1568.

A further embodiment of the invention is a method of differentiating pluripotent stem cells into functional beta cells expressing PDX1, NKX6.1, MAFA, UCN3 and SLC2A comprising the steps of differentiating pluripotent stem cells into pancreatic endocrine cells; and differentiating the pancreatic endocrine cells into functional beta cells expressing PDX1, NKX6.1, MAFA, UCN3 and SLC2A1. In embodiments, MAFA expression is increased as compared to immature beta-cells. In embodiments, the method comprises culturing pancreatic endocrine cells in a culture medium supplemented with one or more small molecules of UNC0638, UNC0642, UCN0646, TC-E5003, A366, PF03814735, ZM447439, SB747651A, PFI1, LY303511, MS436, AZT, DEZA, pyroxamide, CI994 or MC1568.

In each of the embodiments as described above, the culture medium is further supplemented with one or more of ZM447439, heparin, N-Acetyl Cysteine, and Formulation I. In embodiments above, the culture medium is further supplemented with one or more of T3, T4 and analogue thereof. In embodiments above, the culture medium is supplemented with an ALK5 inhibitor. In some embodiments above, the culture medium lacks an ALK5 inhibitor. In embodiments of the invention above, the culture medium is supplemented with AZT or DEZA. In some embodiments above, the culture medium is supplemented with both AZT and DEZA.

In the embodiments of the invention described above, the medium is further supplemented with a gamma secretase inhibitor. In some of the embodiments above, the culture medium is supplemented with T3. In some of the embodiments, the T3 is in the range of 1 nM to 1 In particular embodiments, the T3 is in the range of 1 nM to 100 nM.

Further in embodiments of the invention described above, the functional beta-cells are obtained by step-wise differentiation of one or more of cells selected from the group: cells expressing markers characteristic of the definitive endoderm; cells expressing markers characteristic of primitive gut tube cells; cells expressing markers characteristic of foregut endoderm cells; cells expressing markers characteristic of pancreatic endoderm cells; pancreatic endocrine precursor cells; and cells expressing markers characteristic of immature beta cells (pancreatic endocrine cells).

In each of the embodiments described above, the method comprises culturing the cells at the air-liquid interface. In some embodiments described above, the method comprises culturing the cells in suspension, for example cell clusters in suspension.

In the embodiments above, the differentiated functional beta-cell expresses MAFA at a higher level than an immature beta-cell. In embodiments, the differentiated functional beta-cell expresses UCN3 at a higher level than an immature beta-cell. In some embodiments above, expression of MAFA and UCN3 are increased compared to expression in an immature beta-cell.

In the embodiments of the invention above, the population of functional beta-cells exhibits glucose-stimulated insulin secretion and glucose-dependent mitochondrial respiration. In embodiments described above, the glucose-stimulated insulin secretion and glucose-dependent mitochondrial respiration is similar to that of human islet cells. In embodiments of the invention described above, the functional beta-cells secrete insulin in multiple phases.

In the embodiments described above, the glucose-dependent mitochondrial respiration has a maximum oxygen consumption rate response following glucose stimulation in the range of about 20% to about 80% over basal oxygen consumption rate. In embodiments, the oxygen consumption rate response occurred at least 15 minutes following glucose stimulation.

In the embodiments above, the glucose-stimulated insulin secretion comprises a rapid, bi-phasic insulin secretion in response to glucose stimulation. In embodiments, a first phase of the bi-phasic insulin secretion has at least a four-fold increase to at least an eight-fold increase over baseline secretion, and a second phase of the bi-phasic insulin secretion has at least a two-fold to at least a four-fold increase over baseline secretion. In embodiments, the insulin secretion occurs at least five minutes to at least ten minutes following the glucose stimulation.

In some embodiments, the method of differentiating pluripotent stem cells comprises the steps of: differentiating the pluripotent stem cells into cells expressing markers characteristic of the definitive endoderm ("Stage 1 cells"); differentiating the Stage 1 cells into cells expressing markers characteristic of primitive gut tube cells ("Stage 2 cells"); differentiating the Stage 2 cells into cells expressing markers characteristic of foregut endoderm cells ("Stage 3 cells"); differentiating the Stage 3 cells into cells expressing markers characteristic of pancreatic endoderm cells ("Stage 4 cells"); differentiating the Stage 4 cells into pancreatic endoderm/endocrine precursor cells (cells expressing markers characteristic of one or both of pancreatic endoderm cells and pancreatic endocrine precursor cells; "Stage 5"); differentiating the Stage 5 cells into immature beta-cells (pancreatic endocrine cells; "Stage 6"); and differentiating the Stage 6 cells into functional beta-cells (pancreatic endocrine cells; "Stage 7").

In embodiments, the method of differentiating comprises differentiating pluripotent stem cells into Stage 1 cells by culturing the pluripotent stem cells in a medium supplemented with MCX compound and GDF-8.

In embodiments, the method comprises differentiating the Stage 1 cells into Stage 2 cells by culturing the Stage 1 cells in a medium supplemented with FGF7 and ascorbic acid.

In embodiments, the method comprises differentiating the Stage 2 cells into Stage 3 cells by culturing the Stage 2 cells in a medium supplemented with FGF7, retinoic acid, SANT-1, a PKC activator, a BMP inhibitor and ascorbic acid.

In embodiments, the method comprises differentiating the Stage 3 cells into Stage 4 cells by culturing the Stage 3 cells in a medium supplemented with FGF7, retinoic acid, SANT-1, a PKC activator, a BMP inhibitor and ascorbic acid.

In embodiments, the method comprises differentiating the Stage 4 cells into Stage 5 cells by culturing the Stage 4 cells in a medium supplemented with SANT-1, a PKC activator, a BMP inhibitor, ascorbic acid. In embodiments, the medium is further supplemented with one or more of T3, T4 or analogue thereof. In some embodiments, the medium is further supplemented with an ALK5 inhibitor.

In embodiments, the method comprises culturing the Stage 5 cells into pancreatic endocrine cells by culturing the Stage 5 cells in a medium supplemented with a BMP inhibitor, ascorbic acid, one or more of T3, T4 or analogue thereof. In embodiments, the medium is supplemented with T3. In some embodiments, the T3 is in the range of 1 nM to 1 In certain embodiments, the T3 is in the range of 1 nM to 100 nM. In some embodiments, the medium is further supplemented with an ALK 5 inhibitor. In other embodiments, the culture medium is not supplemented with an ALK5 inhibitor. In some embodiments, the medium is further supplemented with a gamma secretase inhibitor. In certain embodiments, the medium is supplemented with one or more of ZM447439, heparin, N-Acetyl Cysteine, and Formulation I. In embodiments, the culture medium is supplemented with AZT or DEZA. In some embodiments, the culture medium is supplemented with both AZT and DEZA. In the embodiments, the method comprises culturing the cells at the air-liquid interface. In some embodiments, the method comprises culturing the cells in suspension, for example cell clusters in suspension.

In each of the embodiments of the method of differentiation described above, the pancreatic endocrine cells ("Stage 4 cells") may be cryopreserved. In some embodiments, the method of differentiating pancreatic endocrine cells into pancreatic endocrine precursor cells comprises culturing cryopreserved cells.

In each of the embodiments described above, the pluripotent stem cells may be human pluripotent stem cells such as human embryonic stem cells. In one embodiment, the pluripotent stem cells may be human H1 or H9 cells.

Another embodiment of the invention is a method of differentiating pluripotent stem cells into functional beta cells expressing PDX1, NKX6.1, MAFA, UCN3 and SLC2A comprising: (a) differentiating pluripotent stem cells into cells expressing markers characteristic of the definitive endoderm obtained by culturing pluripotent stem cells in a medium supplemented with activin A and WNT3A; (b) differentiating the cells expressing markers characteristic of the definitive endoderm into immature beta-cells; and (c) differentiating the immature beta-cells into functional beta-cells expressing PDX1, NKX6.1, MAFA, UCN3 and SLC2A1 by culturing immature beta-cells in a medium supplemented with one or more of UNC0638, UNC0642, UCN0646, TC-E5003, A366, PF03814735, ZM447439, SB747651A, PFI1, LY303511, MS436, AZT, DEZA, pyroxamide, CI994 or MC1568. The pluripotent stem cells used in this method may be human pluripotent stem cells, such as human embryonic stem cells. In one embodiment, the pluripotent stem cells are human CyT49 cells.

These functional beta cells may have glucose-dependent mitochondrial respiration or glucose-stimulated insulin secretion similar to human islet cells. The functional beta cells may also secrete insulin in multiple phases.

In certain embodiments of this method, the culture medium lacks an ALK5 inhibitor. In some embodiments, the culture medium is further supplemented with heparin, N-Acetyl Cysteine, Formulation I and one or more of T3, T4 or an analogue thereof. In other embodiments, the culture medium is supplemented with T3. In alternate embodiments, the medium is supplemented with ZM447439, heparin, N-Acetyl Cysteine and one or more of T3, T4 or an analogue thereof and contains no ALK5 inhibitor. The medium may be supplemented with T3, AZT or DEZA.

The method may include culturing the immature beta cells at the air-liquid interface, in suspension clusters, in roller bottles or on microcarriers. In one embodiment, the method includes culturing the immature beta cells in roller bottles. In another embodiment, the method includes culturing the immature beta cells in roller bottles on microcarriers.

The differentiating of the pluripotent stem cells into immature beta-cells in the method may comprise: (a) differentiating the pluripotent stem cells into cells expressing markers characteristic of the definitive endoderm ("Stage 1 cells") by culturing the pluripotent stem cells in a medium supplemented with activin A and WNT3A; (b) differentiating the Stage 1 cells into cells expressing markers characteristic of primitive gut tube cells ("Stage 2 cells"); (c) differentiating the Stage 2 cells into cells expressing markers characteristic of foregut endoderm cells ("Stage 3 cells"); (d) differentiating the Stage 3 cells into cells expressing markers characteristic of pancreatic endoderm cells ("Stage 4 cells"); (e) differentiating the Stage 4 cells into pancreatic endocrine precursor cells ("Stage 5"); and (f) differentiating the Stage 5 cells into the immature beta-cells. In certain embodiments, steps e. and f. include culturing at the air-liquid interface, in suspension clusters, in roller bottles or on micocarriers. In other embodiments, steps e. and f. comprise culturing the cells in roller bottles. In yet other embodiments, the steps e. and f. include culturing the immature beta cells in roller bottles on microcarriers.

In certain embodiments, the method includes differentiating the Stage 1 cells into Stage 2 cells by culturing the Stage 1 cells in a medium supplemented with FGF7 and ascorbic acid. In other embodiments, the method also includes differentiating the Stage 2 cells into Stage 3 cells by culturing the Stage 2 cells in a medium supplemented with FGF7, retinoic acid, SANT-1, a PKC activator and ascorbic acid. In certain embodiments, the medium lacks a BMP inhibitor. In yet another embodiment, the method comprises differentiating the Stage 3 cells into Stage 4 cells by culturing the Stage 3 cells in a medium supplemented with FGF7, retinoic acid, SANT-1, a PKC activator and ascorbic acid. Again, in certain embodiments, the medium lacks a BMP inhibitor.

In another embodiment, the method comprises differentiating the Stage 4 cells into Stage 5 cells by culturing the Stage 4 cells in a medium supplemented with SANT-1, a PKC activator, a BMP inhibitor, and ascorbic acid. The medium may be further supplemented one or more of T3, T4 or analogue thereof.

In an alternate embodiment, the method comprises culturing the Stage 5 cells into immature beta-cells by culturing the Stage 5 cells in a medium supplemented with a BMP inhibitor, ascorbic acid, one or more of T3, T4 or analogue thereof. The medium may be further supplemented with an ALK 5 inhibitor or a gamma secretase inhibitor. The method may also include differentiating the immature beta-cells into functional beta cells expressing PDX1, NKX6.1, MAFA, UCN3 and SLC2A by culturing immature beta-cells in a medium lacking an ALK5 inhibitor and supplemented with ZM447439, AZT, N-acetyl cysteine, DEZA, Formulation I and one or more of T3, T4 or analogue thereof.

In each of the embodiments of the method of differentiation described above, the culture may be a suspension culture or a cell aggregate suspension culture. In certain embodiments, the culturing may be carried out in roller bottles, on microcarriers or on microcarriers in roller bottles.

BRIEF DESCRIPTION OF THE DRAWINGS

FIGS. 1A-1H show results of screening for small molecules that upregulate MAFA or UCN3 expression at Stage 7. FIGS. 1A to 1D demonstrate that the Stage 7 expression of MAFA was significantly upregulated as compared to S6D7, or untreated or DMSO treated cultures at Stage 7 after treatment with UNC0638 (selective G9a and GLP histone lysine methyltransferase inhibitor), UNC0646 (potent and selective G9a/GLP inhibitor), UNC0642 (potent and selective G9a and GLP histone lysine methyltransferase inhibitor), TC-E5003 (selective PRMT1 arginine methyltransferase inhibitor), A366 (potent and selective G9a/GLP histone lysine methyltransferase inhibitor), PF03814735 (Aurora kinase A and B inhibitor), ZM447439 (Inhibits Aurora kinase B), SB747651A dihydrochloride (Potent MSK1 inhibitor; also inhibits other AGC group kinases), PFI1 (BET bromodomain inhibitor), LY303511 (BRD2, BRD3 and BRD4 inhibitor), MS436 (Potent and selective BRD4 bromodomain inhibitor), and MC1568 (selectively inhibits HDAC class II (Ha)). FIG. 1E to 1H demonstrate that the Stage 7 expression of UCN3 increased as compared to S6D7, or untreated or DMSO treated cultures at Stage 7 after the addition of 5-Azacytidine ("AZT") (DNA methyltransferase inhibitor), Pyroxamide (Histone deacetylase inhibitor), and CI994 (Histone deacetylase inhibitor). All conditions S7D7; ALI clusters.

FIGS. 3A-3M demonstrate an increase in gene expression, after seven days of improved Stage 7 conditioning, of a set of maturation markers in ALI cell clusters to levels observed in human islets. Improvements utilized during Stage 7 differentiation include: (i) removal of ALK5 inhibitor II; (ii) lowering of T3 concentration; (iii) addition of DEZA; (iv) addition of AZT; (v) addition of ZM; (vi) lowering glucose concentration to 5.56 mM; and (vii) the addition of a defined cocktail of vitamins, non-essential amino acids, lipids, sodium pyruvate, and trace elements (Formulation I Table XII). FIG. 3A shows that INHBB was enriched above the expression seen in human islets in conditions utilizing ALK5 inhibitor II, and the removal of ALK5 inhibitor in the absence or presence of AZT/DEZA decreased INHBB to levels seen in human islets. FIG. 3B shows that INHA expression was increased to human islet levels in ALI clusters by the removal of ALK5 inhibitor II. While MAFA and SLC2A1 expression, shown in FIGS. 3C and 3D respectively, are decreased by the removal of ALK5 inhibitor II, the addition of AZT/DEZA rescues MAFA and SLC2A1 expression to human islet levels. UCN3 (FIG. 3E), G6PC2 (Glucose-6-phosphatase catalytic subunit 2; FIG. 3F), and PDK1 (Pyruvate dehydrogenase kinase 1; FIG. 3G) expression was increased to levels at or above human islets by the addition of AZT/DEZA and removal of ALK5 inhibitor II in ALI clusters. The expression of INS (Insulin; FIG. 3H), GJD2 (Gap junction protein, delta 2; also CX36/connexin 36; FIG. 3I), SIX2 (SIX homeobox 2; FIG. 3J), and PDX1 (FIG. 3K) increased in a gradual step-wise manner, first by removal of ALK5 inhibitor II and second by the addition of AZT/DEZA. The expression of NKX6.1 (FIG. 3L), and GLP1R (Glucagon like peptide 1 receptor; FIG. 3M) did not significantly change across conditions, but their expression in ALI clusters were consistently at or above levels observed in human islets. All conditions S7D7; ALI clusters.

FIGS. 5A-5F demonstrate the generation of C-PEPTIDE cells at S7D7 that exhibit human-islet-similar glucose-dependent mitochondrial respiration kinetics on ALI, specifically by Stage 7 specific 'No ALK5, low T3, ZM, H, NAC, AZT, DEZA, FI, BLAR001' conditioning. FIG. 5A shows that human islets rapidly responded to high D-glucose, demonstrated by an OCR 123.3%±12.92 over baseline after 15 min post-injection ("ip"), and maintained a high OCR over time (131.5%±11.32; 72 min ip). Conversely, S6D7 ALI clusters, which were enriched for immature C-PEPTIDE positive cells, lacked a rapid OCR response to high D-glucose (104.4%±3.37; 15 min ip) and exhibit a relatively weak OCR response over time (113.3%±4.51; 72 min ip). FIG. 5D demonstrates that within the S7D7 ALI cluster group only the 'No ALK5, low T3, ZM, H, NAC, AZT/DEZA, FI, BLAR001' condition exhibited human-islet-similar glucose-dependent mitochondrial respiration kinetics (112.4%±3.25—15 min ip; 129.5%±3.78 min ip). S7D7 ALI cluster conditions that exhibit a glucose-dependent mitochondrial kinetics indistinguishable from immature S6D7 ALI clusters: 'ALK5, T3, ZM, H, NAC, FI, BLAR001' (100.3%±4.04—15 min ip; 107.8%±6.51—72 min ip) (FIG. 5B); 'No ALK5, low T3, ZM, H, NAC, FI, BLAR001' (96.9%±3.06—15 min ip; 109.0%±4.58—72 min ip) (FIG. 5C); 'No ALK5, low T3, ZM, H, NAC, FI, BLAR004' (103.4%±4.76—15 min ip; 113.6%±6.72—72 min ip) (FIG. 5E); and 'No ALK5, low T3, ZM, H, NAC, AZT/DEZA, FI, BLAR004' (102.1%±4.04—15 min ip; 112.7%±3.38—72 min ip) (FIG. 5F).

FIGS. 6A-6L demonstrate AGGREWELL™ cell clusters differentiated in suspension culture to immature pancreatic beta cells. FIG. 6A depicts the procedure through which a (i) fresh S4D3 monolayer or S4D3 cryopreserved cells was assembled (ii) via the AGGREWELL™ method into (iii) cell clusters. FIG. 6B shows that high protein presence of pancreatic endoderm TF PDX1 (top, left), and NKX6.1 (top, middle), but low protein presence of endocrine TF NEUROD1 (top, right); alternate non-pancreatic endoderm lineage allocating TF SOX2 (bottom, middle), and CDX2 (bottom, right) was detected in S4D5 AGGREWELL™ clusters. In FIG. 6C, FACS analysis shows that 99.3±0.1% of the cells were PDX1$^+$ (left), 84.4±0.1% NKX6.1$^+$ (middle), but 2.2±0.4% NKX6.1$^+$ NEUROD1$^+$ (right) or 1.35±0.55% NKX6.1$^+$ CHGA$^+$ (middle) (S4D5 AGGREWELL™ clusters). FIG. 6D shows that the robust pancreatic endoderm characteristics were maintained in S4D4 AGGREWELL™ clusters derived from S4D3 cryopreserved cells, as the high gene expression of PDX1 (top, left), NKX6.1 (top, right), and low expression of NEUROD1 (bottom, left), and CHGA (bottom, right) was maintained as compared to a S4D3 monolayer. FIG. 6E depicts the procedure through which a (i) fresh S4D3 monolayer or S4D3 cryopreserved cells was assembled (ii) via the AGGREWELL™ method into cell clusters, and (iii) differentiated in suspension culture to (iv) immature beta-cells by S6D6. FACS analysis of S6D6 AGGREWELL™ clusters shows a robust immature beta-cell protein profile, as 78.5±1.87% of cells were NKX6.1±CHGA$^+$ (left, FIG. 6F), 73.6±4.34% NKX6.1±NEUROD1$^+$ (right, FIG. 6F), and 38.4±5.96% NKX6.1$^+$ INSULIN$^+$ (left, FIG. 6G). The majority of the INSULIN-positive population (50.2±6.92% of total cells were INSULIN$^+$) was NKX6.1$^+$ (left, FIG. 6G) and not GLUCAGON-positive (7.43±1.49% INSULIN$^+$ GLUCAGON$^+$; (right, FIG. 6G). FIG. 6H shows by IF that at S6D6 the majority of C-PEPTIDE-positive cells in AGGREWELL™ clusters were both PDX1+(left) and NKX6.1±(middle). FIG. 6I shows that the protein presence of the maturation gatekeeper TF MAFA (right) was already easily detected at S6D6, and was expressed at a higher level than previous ALI clusters at S6D6-S6D7 (*Nature Biotechnology*, 2014 (32) 11, 1121-1133) (see also FIG. 3C for ALI S7D7 comparison). The expression of INSULIN (FIG. 6J), PDX1 (FIG. 6K), and NKX6.1 (FIG. 6L) was higher than previous ALI clusters at S6D6-S6D7.

FIGS. 7A-7M demonstrate generation of S7D7 AGGREWELL™ clusters by suspension culture to mature pancreatic beta cells. FIG. 7A depicts the procedure through which a (i) fresh S4D3 monolayer or S4D3 cryopreserved cells were assembled into AGGREWELL™ clusters, conditioned by suspension culture through (ii & iii) Stages 5, 6 and 7 to generate (iv) S7D7 AGGREWELL™ clusters. S7D7 AGGREWELL™ clusters cultured by 'NO ALK5 LOW T3 ZM H NAC DEZA AZT FI BLAR001' during Stage 7 maintained a baseline beta-cell protein profile (FIG. 7B-7C). 89% of cells were NKX6.1$^+$ CHGA$^+$ (left, FIG. 7B), 77.7% NKX6.1$^+$ NEUROD1$^+$ (right, FIG. 7B), and 40.8% NKX6.1$^+$ INSULIN$^+$ (left, FIG. 7C). The majority of the INSULIN-positive population (46.4% of total cells were INSULIN$^+$) was NKX6.1±(left, FIG. 7C) and not GLUCAGON-positive (3.9% INSULIN$^+$ GLUCAGON$^+$; (right, FIG. 7C). The gene expression of maturation markers MAFA (FIG. 7D), UCN3 (FIG. 7E), SLC2A1 (FIG. 7F), G6PC2 (FIG. 7G), INSULIN (FIG. 7H), and NKX6.1 (FIG. 7I), were at or above human islet levels in Stage 7 'NO ALK5 LOW T3 ZM H NAC DEZA AZT FI BLAR001 or BLAR004' conditioned S7D7 AGGREWELL™ clusters. The expression levels S7D7 of maturation marker such as MAFA (FIG. 3C), G2PC2 (FIG. 3F), INSULIN (FIG. 3H), and NKX6.1 (FIG. 3L) are much greater in AGGREWELL™ (NO ALK5 LOW T3 ZM H NAC DEZA AZT FI BLAR001 or BLAR004') than in ALI clusters. FIGS. 7J-7M demonstrate that the addition of DEZA and AZT to 'NO ALK5 LOW T3 ZM H NAC FI BLAR004' Stage 7 conditioning, generated a significant number of non-GLUCAGON (FIG. 7J; bottom, right)C-PEPTIDE cells that co-expressed at S7D7, in terms of protein presence, PDX1 (FIG. 7J; bottom, left), NKX6.1 (FIG. 7J; bottom, middle), MAFA (FIG. 7K; bottom, left), UCN3 (FIG. 7K; bottom, middle), and SLC2A1 (FIG. 7K; bottom, right). FIGS. 7L-7M demonstrate the generation, by 'NO ALK5 LOW T3 ZM H NAC FI BLAR004'-specific Stage 7 conditioning, of C-PEPTIDE cells that co-expressed, in terms of protein presence, by S7D7 maturation markers: PDX1 (FIG. 7L; bottom, left), NKX6.1 (FIG. 7L; bottom, middle), MAFA (FIG. 7M; bottom, left), SLC2A1 (FIG. 7M; bottom, right), but not GLUCAGON (FIG. 7L; bottom, right) or UCN3 (FIG. 7M; bottom, middle).

FIGS. 8A-8I demonstrate generation of pluripotent stem-cell derived mature pancreatic beta cells by suspension culture with human islet-similar glucose-dependent mitochondrial respiration and GSIS kinetics. FIGS. 8A-8B both show that human islet cells rapidly responded to high D-glucose, demonstrated by an OCR 123.3%±12.92 over baseline after 15 min ip and maintained a high OCR over time (131.5%±11.32; 72 min ip). S6D7 ALI clusters, which were enriched for immature C-PEPTIDE positive cells, lacked a rapid OCR response to high D-glucose (104.4%±3.37; 15 min ip) and exhibit a relatively weak OCR response over time (113.3%±4.51; 72 min ip). Human islet similar glucose-dependent mitochondrial respiration kinetics were observed in the 'No ALK5, low T3, ZM, H, NAC, FI, BLAR004' condition at S7D13 in the context of AGGREWELL™ clusters in suspension (110.7%±2.46—15 min ip; 125.9%±2.27—72 min ip) (FIG. 8A). 'No ALK5, low T3, ZM, H, NAC, AZT, DEZA, FI, BLAR004' AGGREWELL™ clusters in suspension consumed oxygen in response to high glucose stimulation above human islet levels (162.0%±11.51—15 min ip; 177.1%±0.99—72 min ip) (FIG. 8B). FIG. 8C shows that matured beta cells within human islets exhibited the ability for multiple rounds of rapid bi-phasic insulin secretion in response to glucose stimuli. Human islets demonstrated the ability for multiple rounds of "on-off" switching of insulin secretion. All conditions tested exhibited a strong insulin secretion response to KCl (FIGS. 8C-8I). The addition of Exendin-4 did not increase the amplitude of the GSIS response in human islets shown, but was included for comparison to ALI or AGGREWELL™ GSIS profiles (FIG. 8D). S7D21—ALI clusters conditioned during Stage 7 in 'No ALK5, low T3, ZM, H, NAC FI,' whether in BLAR001 (FIG. 8E) or BLAR004 (FIG. 8F), did show a first (~4-10 fold first phase of first GSIS response), but not a second, and a relatively slow, bi-phasic GSIS response. ALI clusters did not have the ability to shut off the second phase of insulin secretion upon re-perifusion of 3 mM D-glucose after stimulus. S7D14 AGGREWELL™ clusters conditioned during Stage 7 in 'No ALK5, low T3, ZM, H, NAC, FI BLAR004,' exhibited a strong first bi-phasic GSIS (~5 fold first phase of first GSIS response) followed by an ability to completely shut-down GSIS, and a weak second mono-phasic response (FIG. 8G). With the addition of DEZA and AZT to 'No ALK5, low T3, ZM, H, NAC, FI BLAR004' conditioning, S7D14 AGGREWELL™ clusters exhibited multiple rounds of human-islet-similar bi-phasic GSIS (~5-7 fold first phase of first GSIS response), and the ability to completely shut-down GSIS in between high glucose pulses (FIGS. 8H-8I).

FIG. 9A depicts the step-wise differentiation protocol to generate CyT49 hESC-derived pancreatic endoderm. Important transcription factors ("TF") are indicated for each stage. FIG. 9C demonstrates an approximately 6-fold increase in S4D3 total cell yield (in millions of cells) when scaled up from 100 ml (0.1 PBS) to 500 ml (0.5 PBS) media volume. FIG. 9F-9L demonstrates the robust induction of the pancreatic endoderm gene program, while limiting the expression of alternative endoderm lineages and early pancreatic endocrine differentiation, relative to PEC-01 d15 (prior art).

FIG. 10A depicts the disclosed stepwise differentiation protocol to generate CyT49 hESC-derived non-functional insulin-producing cells. Important transcription factors ("TF") are indicated for each stage, beginning with S4D3 CyT49 hESC-derived cells input into Stage 5 conditioning. FIG. 10B shows the number of S6D7 cells generated relative to hESC input in millions of cells per ml. For example, for the 0.5 PBS suspension culture format utilizing the new protocol generated 2.4±0.169 S6D7 cells per one hESC cell. FIG. 10C shows the S6D7 yield of 0.1 PBS and 0.5 PBS cultures. FIG. 10C demonstrates an approximately 7.5-fold increase in S6D7 total cell yield (in millions of cells) when scaled up from 100 ml (0.1 PBS) to 500 ml (0.5 PBS) media volume. FIG. 10G-10N show the gene expressions at S4D3, S5D3, S6D7 and S7D7. FIG. 10G-10N demonstrate that all suspension culture methods using the new protocol induced a robust pancreatic mono-hormonal insulin-producing cell gene signature; 2-liter roller bottle, 0.1PBS and 0.5 PBS suspension methods relatively equally induced the expression of PDX1 (FIG. 10G), NKX6.1 (FIG. 10H), CHGA (FIG. 10I), NEUROD1 (FIG. 10J), NGN3 (FIG. 10K), INSULIN (FIG. 10L), MAFA (FIG. 10M), and GLUCAGON (FIG. 10N). FIG. 10O-10T shows the step-wise formation of protein co-localization of insulin-producing cell markers such as CHGA, NKX6.1, INSULIN, but not GLUCAGON, at S5D3 in 0.5 PBS (FIG. 10O-10P), at S6D7 in 2-liter roller bottle (FIG. 10Q), at S6D7 in 0.1 PBS (FIG. 10R), at S7D13 in 2-liter roller bottle (FIG. 10S), and at S7D14 in 0.1 PBS (FIG. 10T). FIG. 10U shows high prevalence of poly-hormonal insulin-producing cells, and thus low numbers of mono-hormonal insulin-positive cells, for PEC-01 derived S6D7 aggregates in 2-liter roller bottle. FIG. 10V demonstrates that all INSULIN$^+$ GLUCAGON$^+$ cells are negative for NKX6.1 presence in all conditions tested (PEC-01-derived S6D7; 0.1PBS S7D14 and RB S7D13 utilizing new protocol). FIG. 10W-10AB shows the protein co-localization of insulin-producing cell markers such as SYNAPTOPHYSIN (pan-endocrine marker), NKX6.1, INSULIN, and MAFA at S6D7 in 0.1 PBS (FIG. 10W-10X), at S7D16 in 0.1 PBS (FIG. 10Y-10Z), and at S7D23 in 2-liter roller bottle (FIG. 10AA-10AB). By Stage 7, a robust protein co-localization between SYNAPTOPHYSIN, NKX6.1, INSULIN, and MAFA, indicative of non-functional mono-hormonal insulin-producing cells, was observed.

DETAILED DESCRIPTION OF THE INVENTION

Figure 1A:
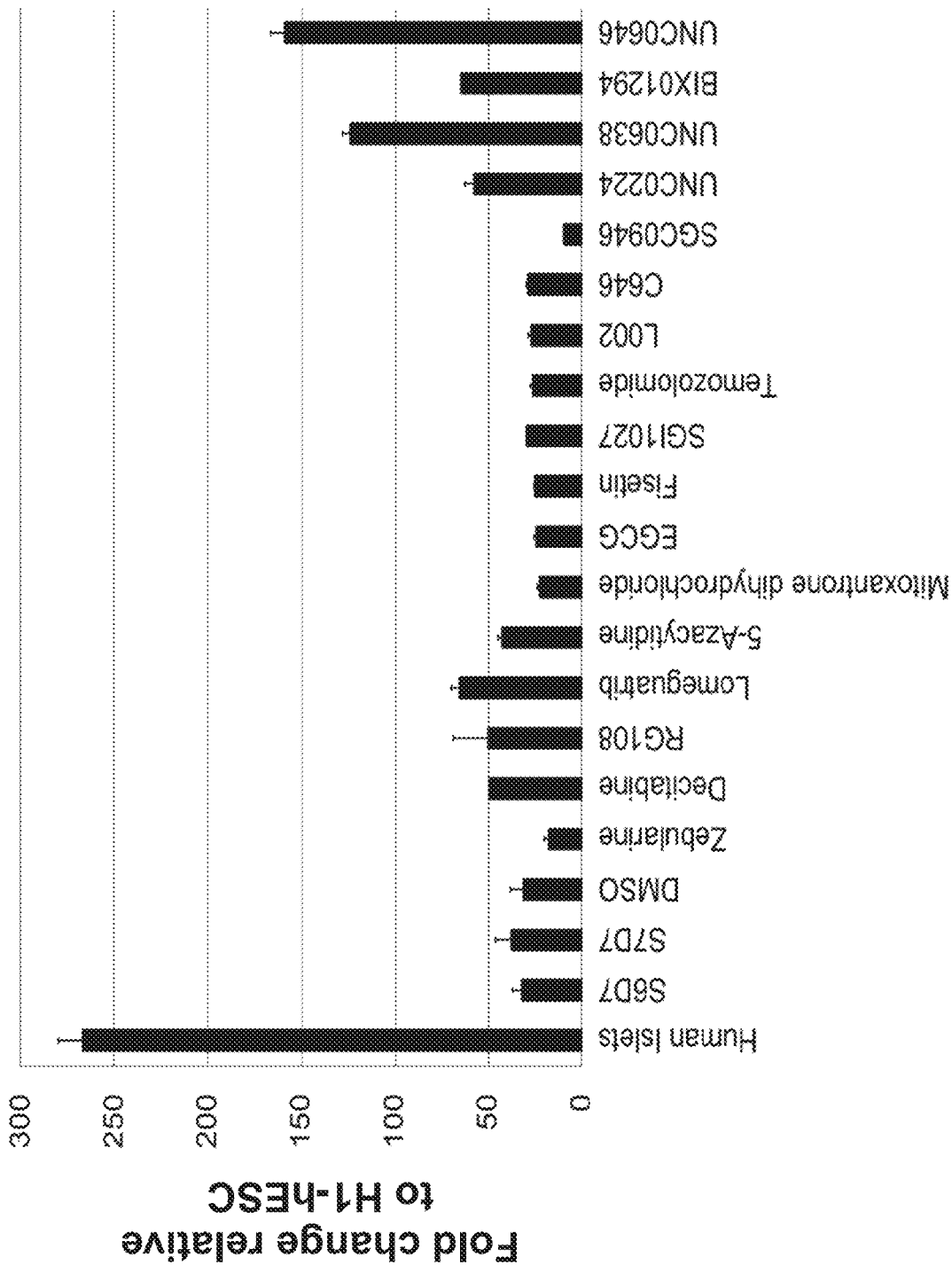
Figure 1D:
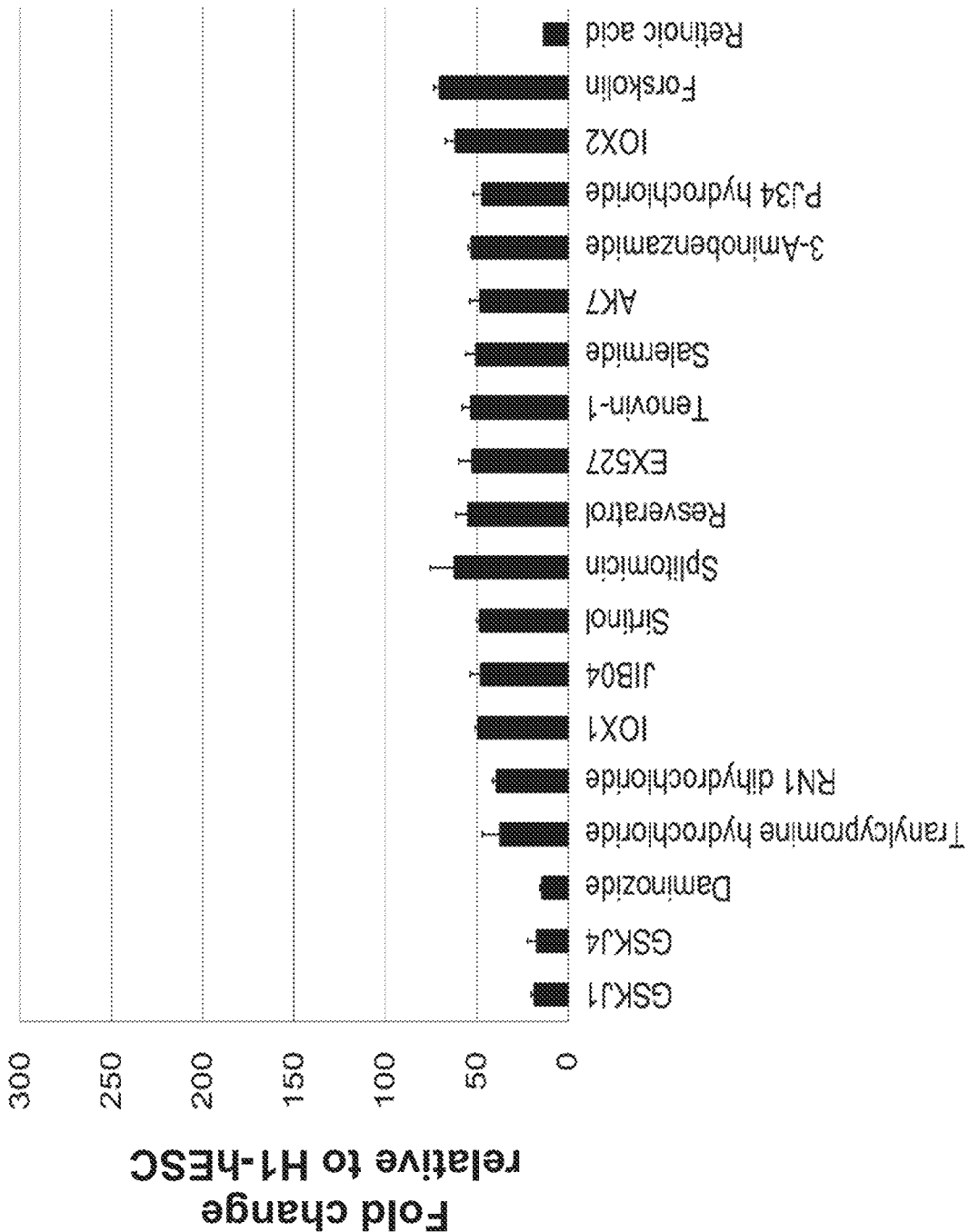
Figure 1F:
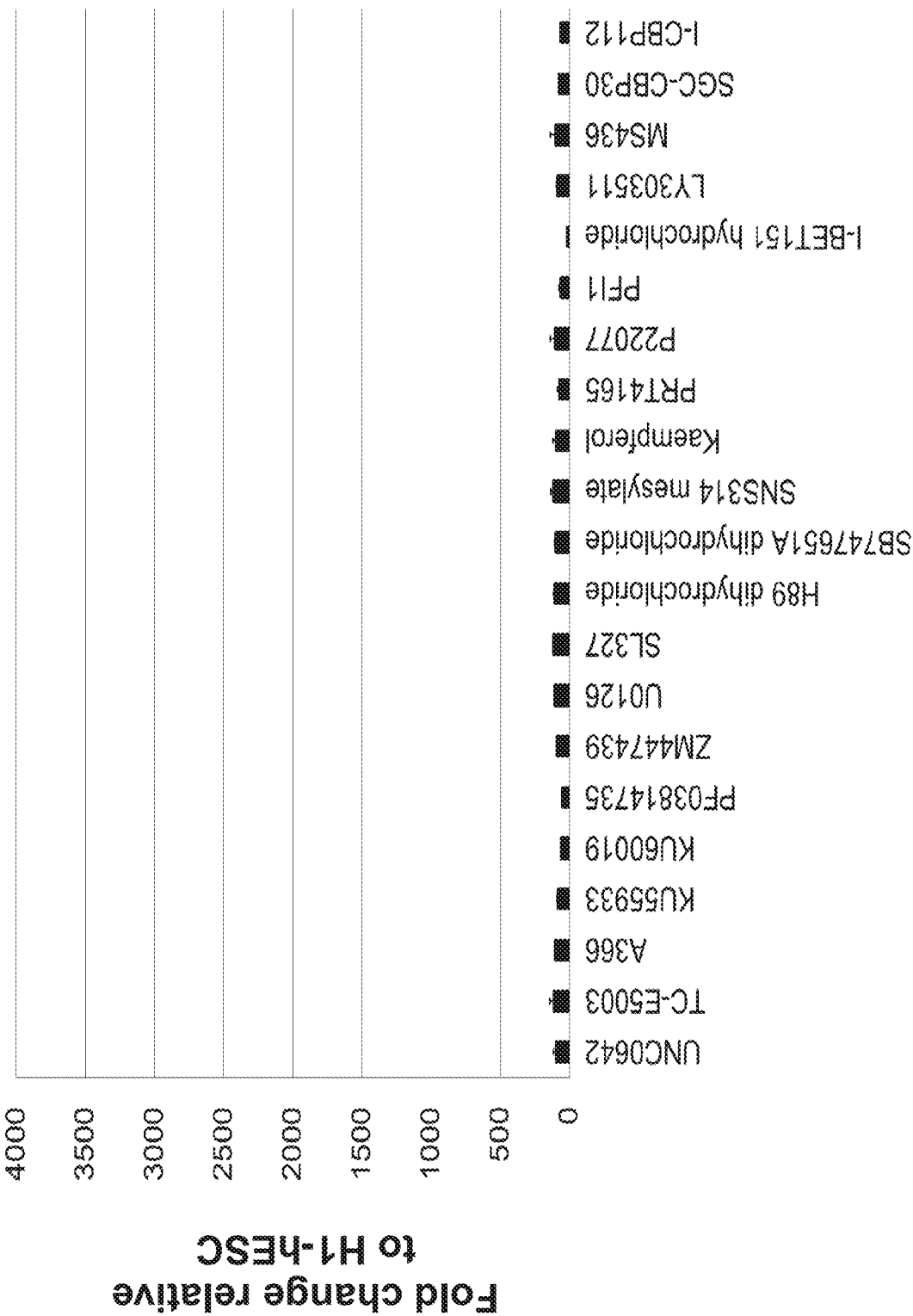
Figure 1G:
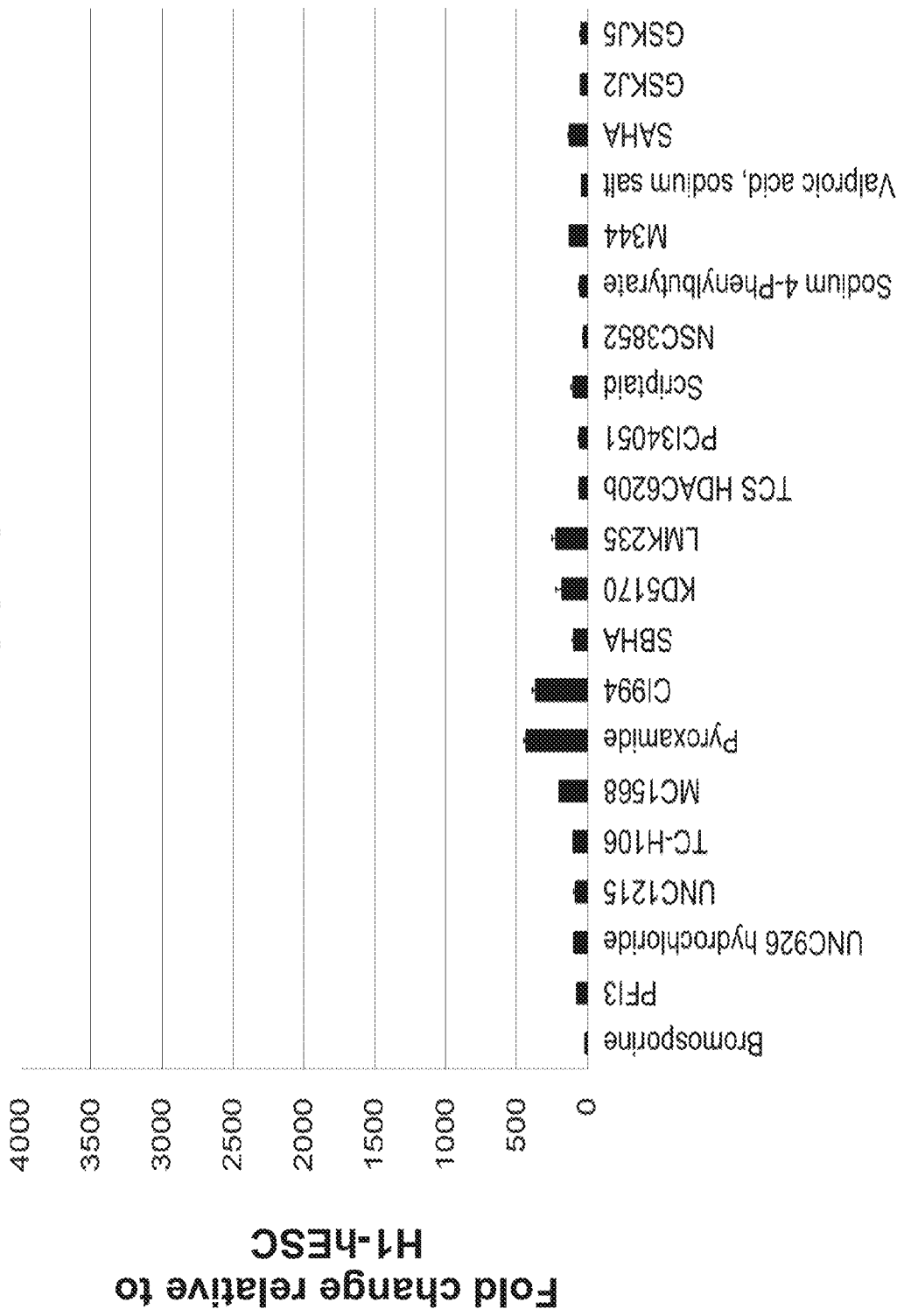
Figure 1H:
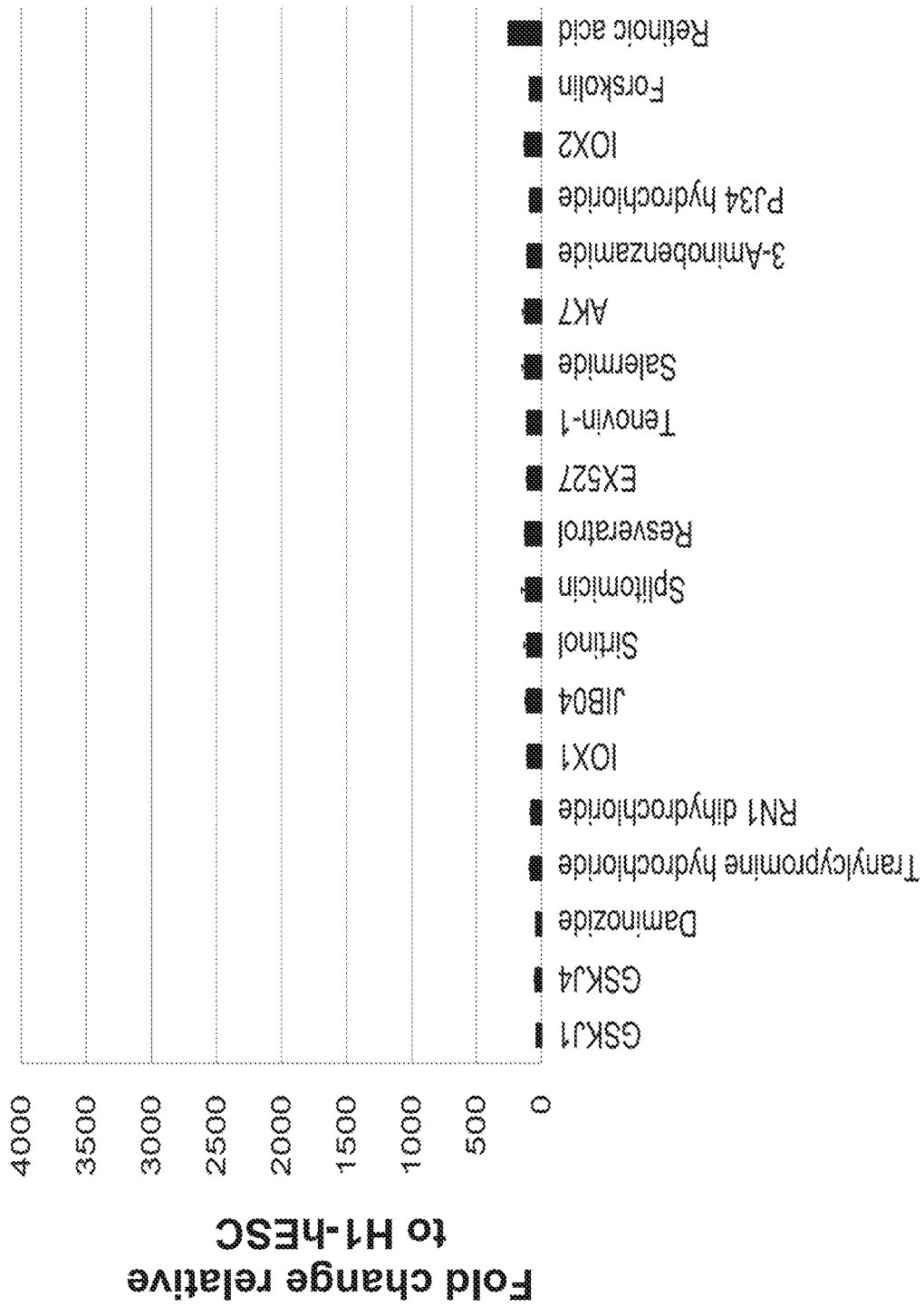

The following detailed description of the invention will be better understood when read in conjunction with the appended figures. Figures are provided for illustrating certain embodiments of the invention. However, the invention is not limited to the precise arrangements, examples, and instrumentalities shown. For clarity of disclosure, and not by way of limitation, the detailed description of the invention is divided into subsections that describe or illustrate certain features, embodiments or applications of the present invention.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm, and ectoderm). Stem cells also give rise to tissues of multiple germ layers following transplantation and contribute substantially to most, if not all, tissues following injection into blastocysts. Stem cells are classified by their developmental potential. Pluripotent stem cells are able to give rise to all embryonic cell types.

Differentiation is the process by which an unspecialized ("uncommitted") or less specialized cell acquires the features of a specialized cell, for example a nerve cell or a muscle cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and to what cells it can give rise. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker as compared to an undifferentiated cell or a cell at another stage of differentiation. The detectable level of the marker nucleic acid or polypeptide is sufficiently higher or lower in the cells of interest compared to other cells, such that the cell of interest can be identified and distinguished from other cells using any of a variety of methods known in the art.

As used herein, "cell density" and "seeding density" are used interchangeably herein and refer to the number of cells seeded per unit area of a solid or semisolid planar or curved substrate.

As used herein, "suspension culture" refers to a culture of cells, single cells or clusters, suspended in medium rather than adhering to a surface.

As used herein, a cell is "positive for" a specific marker, "positive", or "+" when the specific marker is sufficiently detected in the cell. Similarly, the cell is "negative for", "negative" or " " for a specific marker when the specific marker is not sufficiently detected in the cell. In particular, positive by fluorescence activated cell sorting cytometry ("FACS") is usually greater than about 2%, whereas the negative threshold by FACS is usually less than about 1%. Positive by polymerase chain reaction cytometry ("PCR") is usually less than or equal to about 30 cycles (Cts); whereas negative by PCR is usually more than about 31 cycles.

In attempts to replicate the differentiation of pluripotent stem cells into functional pancreatic endocrine cells in static in vitro cell cultures, the differentiation process is often viewed as progressing through a number of consecutive stages. In particular, the differentiation process is commonly viewed as progressing through multiple stages. In this stepwise differentiation, "Stage 1" refers to the first step in the differentiation process, the differentiation of pluripotent stem cells into cells expressing markers characteristic of the definitive endoderm ("Stage 1 cells"). "Stage 2" refers to the second step, the differentiation of cells expressing markers characteristic of the definitive endoderm cells into cells expressing markers characteristic of primitive gut tube cells ("Stage 2 cells"). "Stage 3" refers to the third step, differentiation of cells expressing markers characteristic of primitive gut tube cells into cells expressing markers characteristic of foregut endoderm cells ("Stage 3 cells"). "Stage 4" refers to the fourth step, the differentiation of cells expressing markers characteristic of foregut endoderm cells into cells expressing markers characteristic of pancreatic endoderm cells ("Stage 4 cells"). "Stage 5" refers to the fifth step, the differentiation of cells expressing markers characteristic of pancreatic endoderm cells into cells expressing markers characteristic of one or both of pancreatic endoderm cells and pancreatic endocrine precursor cells (collectively referred to as "Stage 5 cells" or, alternatively, "pancreatic endoderm/endocrine precursor cells"). Stage 6 refers to the sixth step, the differentiation of cells expressing markers characteristic of pancreatic endocrine precursor cells into cells expressing markers characteristic of immature beta-cells ("Stage 6 cells"). In the process of, and for purposes of producing the cells of and populations of cells of the invention, a seventh step, "Stage 7", is used and refers to differentiation of cells expressing markers characteristic of immature beta-cells (pancreatic endocrine cells) into cells expressing markers characteristic of functional beta-cells and that have a more matured phenotype as compared to Stage 6 cells. By "functional beta-cells that have a more matured phenotype" or "Stage 7 cells" is meant a pancreatic endocrine cell that, when compared to a Stage 6 cell, is not only single hormonal insulin+, MAFA+, NKX6.1+, UCN3+, SLC2A1+ and PDX1+, but also expresses MAFA at a higher level than a less mature pancreatic endocrine cell, in particular an immature beta-cell.

It is to be noted that not all cells in a particular population progress through these stages at the same rate. Consequently, it is not uncommon in in vitro cell cultures to detect the presence of cells that have progressed less, or more, down the differentiation pathway than the majority of cells present in the population, particularly at the later differentiation stages. For example, it is not uncommon to see the appearance of markers characteristic of pancreatic endocrine cells during the culture of cells at Stage 5. For purposes of illustrating the present invention, characteristics of the various cell types associated with the above-identified stages are described herein.

"Definitive endoderm" as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3-β ("HNF3-β")), GATA4, SOX17, CXCR4, Brachyury, Cerberus, OTX2, goosecoid, C-Kit, CD99, and MIXL1. Markers characteristic of the definitive endoderm cells are CXCR4, FOXA2, and SOX17. Thus, definitive endoderm cells may be characterized by their expression of CXCR4, FOXA2, and SOX17. In addition, depending on the length of time cells are allowed to remain in Stage 1, an increase in HNF4a may be observed.

"Primitive gut tube cells", as used herein, refers to cells derived from definitive endoderm and that can give rise to all endodermal organs, such as lungs, liver, pancreas, stomach, and intestine. Gut tube cells may be characterized by their substantially increased expression of HNF4a over that expressed by definitive endoderm cells. For example, a ten- to forty-fold increase in mRNA expression of HNF4α may be observed during Stage 2.

"Foregut endoderm cells", as used herein, refers to cells that give rise to the esophagus, lungs, stomach, liver, pancreas, gall bladder, and a portion of the duodenum. Foregut endoderm cells express at least one of the following markers: PDX1, FOXA2, CDX2, SOX2, and HNF4a. Foregut endoderm cells may be characterized by an increase in expression of PDX1 compared to gut tube cells. For example, greater than fifty percent of the cells in Stage 3 cultures typically express PDX1.

"Pancreatic endoderm cells", as used herein, refers to cells that express at least one of the following markers: PDX1, NKX6.1, HNF1β, PTF1α, HNF6, HNF4a, SOX9, NGN3, gastrin; HB9, or PROX1. Pancreatic endoderm cells may be characterized by their lack of substantial expression of CDX2 or SOX2.

"Pancreatic endocrine precursor cells", as used herein, refers to pancreatic endoderm cells capable of becoming a pancreatic hormone expressing cell. Pancreatic endocrine precursor cells express at least one of the following markers: NGN3; NKX2.2; NeuroD1; ISL1; PAX4; PAX6; or ARX. Pancreatic endocrine precursor cells may be characterized by their expression of NKX2.2 and NeuroD1.

"Pancreatic endocrine cells", as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NeuroD1, ISL1, PDX1, NKX6.1, PAX4, ARX, NKX2.2, HB9 and PAX6.

"Beta cells" ("β cells") are pancreatic endocrine cells capable of expressing insulin, but not glucagon, somatostatin, ghrelin, and pancreatic polypeptide. Pancreatic endocrine cells expressing markers characteristic of β cells can be characterized by their expression of insulin and at least one of the following transcription factors: PDX1, NKX2.2, NKX6.1, NeuroD1, ISL1, HNF3β, HB9, MAFA and PAX6.

"Functional beta-cells" are pancreatic endocrine cells that display the well-established processes that ensure rapid and regulated glucose-stimulated insulin secretion ("GSIS"), specifically an increase in mitochondrial respiration/activity followed by the first phase and second phase of insulin secretion ("biphasic GSIS"). In detail, functional beta-cells exhibit at least one of the following characteristics of biphasic GSIS: (i) coupling of mitochondrial respiration/activity with insulin secretion; (ii) rapid insulin secretion response to heightened demand (here defined as high glucose concentration); (iii) ability to rapidly turn off insulin secretion after demand has subsided; (iv) ability for multiple rounds of "on-off" switching of insulin secretion; (v) ability to secrete the correct amount of insulin as dictated by demand; and (vi) ability to respond to multiple insulin secretagogues (for example, Exendin-4, or amino acids L-Glutamine and L-Arginine). Functional beta-cells can be characterized by their expression of insulin and at least one of the following transcription factors: PDX1, NKX2.2, NKX6.1, NeuroD1, ISL1, HNF3β, HB9, PAX6, MAFA, SLC2A1, UCN3, and GLP1R.

"Immature beta cells" are pancreatic endocrine cells that do not display glucose-dependent mitochondrial respiration/activity, and biphasic GSIS. Immature beta cells expressing markers characteristic of β cells can be characterized by their expression of insulin and at least one of the following transcription factors: PDX1, NKX2.2, NKX6.1, NeuroD1, ISL1, HNF3β, HB9, MAFA, and PAX6.

"Air-liquid interface" or "ALI", as used herein, refers to the air-liquid interface that exists in an open culture vessel or a culture vessel partially filled with medium. Although referred to herein as "air" for convenience, the invention is not limited to the mixture of gases and compositions found in the ambient environment. The invention specifically contemplates and includes gaseous mixtures having compositions different from the ambient environment including, for example, mixtures enriched for a particular component or in which a particular component has been depleted or eliminated.

Used interchangeably herein are "d1", "1d", and "day 1"; "d2", "2d", and "day 2", and so on. These number letter combinations refer to a specific day of incubation in the different stages during the stepwise differentiation protocol of the instant application.

First phase ($1^{st}$) insulin secretion represents the rapid exocytosis of a small pool of bound and readily releasable insulin granules upon a sudden increase in glucose concentration.

Second phase ($2^{nd}$) of insulin secretion, lower in amplitude but longer in duration compared to $1^{st}$ phase insulin secretion, represents the translocation of granules from a reserve pool of granules, and their binding/priming for release.

OCR is defined as the oxygen consumption rate, and is an indicator of mitochondrial respiration, specifically via the electron transport chain ("ETC"); a direct measure of mitochondrial activity.

"Effective amount" or "therapeutic amount" or equivalents therein refers to the amount of the compound that should be present to provide some degree of differentiation of the hESCs or further differentiation of partially differentiated hESCs such as those subjected to one or more previous differentiation stages. In additional examples, the compound may be present in the culture medium of the hESCs or may be added to the hESCs' during some stage of growth. In some embodiments, a compound, agent, small molecule or growth factor is used to produce definitive endoderm, foregut, pancreatic foregut and pancreatic endoderm-lineage cells including pancreatic hormone secreting cells. In certain examples, the stem cells may be exposed to the compound, agent, small molecule or growth factor prior to any differentiation or during the first stage of differentiation, whereas in other examples, the stem cell may first be differentiated to an intermediate cell type such as, for example, definitive endoderm, and then exposed to the compound, agent, small molecule or growth factor.

"Compounds", "small molecule compounds" or equivalents thereof the invention refers to compounds encompassed by generic formulae disclosed herein (e.g. Table XI) and includes any specific compounds within that formula whose structure is disclosed herein or analogues thereof. The compounds of the invention may be identified either by their chemical structure or chemical name. When the chemical structure and chemical name conflict, the chemical structure is determinative of the identity of the compound. The compounds of the invention may contain one or more chiral centers or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention also include isotopically labeled compounds where one or more atoms have an atomic mass different from the atomic mass conventionally found in nature. Examples of isotopes that may be incorporated into the compounds of the invention include, but are not limited to, 2H, 3H, 13C, 14C, 15N, 18O, 17O, 31P, 32P, 35S, 18F and 36Cl. Further, it should be understood, when partial structures of the compounds of the invention are illustrated, that brackets indicate the point of attachment of the partial structure to the rest of the molecule.

Characterization of Pluripotent Stem Cells

Pluripotent stem cells may express one or more of the designated TRA-1-60 and TRA-1-81 antibodies (Thomson et al. 1998, Science 282:1145-1147). Differentiation of pluripotent stem cells in vitro results in the loss of TRA-1-60 and TRA-1-81 expression. Undifferentiated pluripotent stem cells typically have alkaline phosphatase activity, which can be detected by fixing the cells with 4% paraformaldehyde, and then developing with an alkaline phosphatase substrate kit sold under the trademark VECTOR® Red, as described by the manufacturer (Vector Laboratories, Inc., Burlingame, California). Undifferentiated pluripotent stem cells also typically express OCT4 and TERT, as detected by reverse transcription polymerase chain reaction ("RT-PCR").

Another desirable phenotype of propagated pluripotent stem cells is a potential to differentiate into cells of all three germinal layers: endoderm, mesoderm, and ectoderm.

Pluripotency of stem cells may be confirmed, for example, by injecting cells into severe combined immunodeficiency ("SCID") mice, fixing the teratomas that form using 4% paraformaldehyde, and then examining histologically for evidence of cell types from these three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

Any pluripotent stem cells may be used in the methods of the invention. Exemplary types of pluripotent stem cells that may be used include established lines of pluripotent cells, including pre-embryonic tissue (such as, a blastocyst), embryonic tissue, or fetal tissue taken any time during gestation, typically but not necessarily, before approximately 10 to 12 weeks gestation. Non-limiting examples are established lines of human embryonic stem cells ("hESCs") or human embryonic germ cells, such as, the human embryonic stem cell lines H1 (NIH Code: WA01), H7 (NIH Code: WA07), H9 (NIH Code: WA09) (WiCell Research Institute, Madison, WI, USA), and SA002 (Cellartis AB Corporation, Goteburg, Sweden).

Cells taken from a pluripotent stem cell population already cultured in the absence of feeder cells are also suitable. Induced pluripotent cells (IPS), or reprogrammed pluripotent cells, derived from adult somatic cells using forced expression of a number of pluripotent related transcription factors, such as OCT4, NANOG, SOX2, KLF4, and ZFP42 (*Annu Rev Genomics Hum Genet* 2011, 12:165-185; see also IPS, *Cell,* 126(4): 663-676) may also be used. The human embryonic stem cells used in the methods of the invention may also be prepared as described by Thomson et al. (U.S. Pat. No. 5,843,780; *Science,* 1998, 282:1145-1147; *Curr Top Dev Biol* 1998, 38:133-165; *Proc Natl Acad Sci U.S.A.* 1995, 92:7844-7848). Mutant human embryonic stem cell lines, such as, BG01v (BresaGen, Athens, Georgia), or cells derived from adult human somatic cells, such as, cells disclosed in Takahashi et al., *Cell* 131: 1-12 (2007) may also be used. In certain embodiments, pluripotent stem cells suitable for use in the present invention may be derived according to the methods described in: Li et al. (*Cell Stem Cell* 4: 16-19, 2009); Maherali et al. (*Cell Stem Cell* 1: 55-70, 2007); Stadtfeld et al. (*Cell Stem Cell* 2: 230-240); Nakagawa et al. (*Nature Biotechnol* 26: 101-106, 2008); Takahashi et al. (*Cell* 131: 861-872, 2007); and U.S. Patent App. Pub. No. 2011/0104805. In certain embodiments, pluripotent stem cells suitable for use in the present invention may be considered "naïve" and derived according to the methods described in: Gafni et al. (*Nature,* 504:282, 2013), and Ware et al. (*PNAS,* 111: 4484-4489, 2014). All of these references, patents, and patent applications are herein incorporated by reference in their entirety, in particular, as they pertain to the isolation, culture, expansion and differentiation of pluripotent cells.

Other sources of pluripotent stem cells include induced pluripotent stem cells (IPS, Cell, 126(4): 663-676). Yet other sources of suitable cells include human umbilical cord tissue-derived cells, human amniotic fluid-derived cells, human placental-derived cells, and human parthenotes. In one embodiment, the umbilical cord tissue-derived cells may be obtained by the method of U.S. Pat. No. 7,510,873. In another embodiment, the placental tissue-derived cells may be obtained using the methods of U.S. Patent App. Pub. No. 2005/0058631. In another embodiment, the amniotic fluid-derived cells may be obtained using the methods of U.S. Patent App. Pub. No. 2007/0122903. The disclosure of each of these patent applications is incorporated in its entirety herein as it pertains to the isolation and characterization of the cells. In certain embodiments, the pluripotent stem cells may be of non-embryonic origins.

Expansion and Culture of Pluripotent Stem Cells

Many different known methods of expanding and culturing pluripotent stem cells may be used in the claimed invention. For example, the pluripotent stem cells may be plated onto a suitable culture substrate. In one embodiment, the suitable culture substrate is an extracellular matrix component, such as those derived from basement membrane or that may form part of adhesion molecule receptor-ligand couplings. A suitable culture substrate is a reconstituted basement membrane sold under the trademark MATRIGEL™ (Corning Incorporated, Corning, New York). MATRIGEL™ is a soluble preparation from Engelbreth-Holm Swarm tumor cells that gels at room temperature to form a reconstituted basement membrane.

Other extracellular matrix components and component mixtures known in the art are suitable as an alternative. Depending on the cell type being proliferated, this may include laminin, fibronectin, proteoglycan, entactin, heparin sulfate, and the like, alone or in various combinations.

The pluripotent stem cells may be plated onto the substrate in a suitable distribution and in the presence of a medium, which promotes cell survival, propagation, and retention of the desirable characteristics. All these characteristics benefit from careful attention to the seeding distribution and can readily be determined by one of skill in the art. Suitable culture media may be made from the following components, Dulbecco's Modified Eagle's medium ("DMEM") sold under the trademark GIBCO® (Catalog No. 11965-092) by Life Technologies Corporation, Grand Island New York; Knockout Dulbecco's Modified Eagle's medium ("KO DMEM") sold under the trademark GIBCO® (Catalog No. 10829-018) by Life Technologies Corporation; Ham's F12/50% DMEM basal medium; 200 mM L-glutamine sold under the trademark GIBCO® (Catalog No. 25030-081) by Life Technologies; non-essential amino acid solution sold under the trademark GIBCO® (Catalog No. 11140-050) by Life Technologies; (3-mercaptoethanol, Sigma-Aldrich Company, LLC Saint Louis, MO, (Catalog No. M7522); human recombinant basic fibroblast growth factor ("bFGF") sold under the trademark GIBCO® (Catalog No. 13256-029) by Life Technologies. Large-scale expansion and controlled differentiation processes of human embryonic stem cells can also be achieved using suspension bioreactors.

Differentiation of Pluripotent Stem Cells

As pluripotent cells differentiate towards functional β cells, they differentiate through various stages each of which may be characterized by the presence or absence of particular markers. Differentiation of the cells into these stages is achieved by the specific culturing conditions including the presence and lack of certain factors added to the culture media. In general, this differentiation may involve differentiation of pluripotent stem cells into definitive endoderm lineage, and definitive endoderm cells. These cells may then be further differentiated into primitive gut tube cells, which in turn may then be differentiated into foregut endoderm cells. Foregut endoderm cells may be differentiated into pancreatic endoderm cells, which may then be further differentiated into pancreatic endocrine precursor cells or pancreatic endoderm/pancreatic endocrine precursor cells. These cells may be differentiated into pancreatic hormone producing or secreting cells. This application provides for the staged differentiation of pluripotent stem cells towards pancreatic endocrine cells, preferably by culturing the cells at the air-liquid interface, or in suspension, that exists within a culture vessel partially filled with medium, specifically by culturing cells at the air-liquid interface, or in suspension, in one or more of Stages 5 through 7.

One or more of the thyroid hormones triiodothyronine ("T3") and thyroxine ("T4"), and analogues thereof, alone or in further combination with an ALK-5 inhibitor may be used in the cell culturing at one or more of Stages 1 through 7 of differentiation, and preferably at each of Stages 5 through 7. Alternatively, the ALK-5 inhibitor may be used alone in one or more stages of differentiation, but preferably at each of Stages 5 through 7 and more preferably at each of Stages 5 to 6. More preferably, one or more of the thyroid hormones or their analogues and an ALK5 inhibitor is used in one or more differentiation stages, preferably at each of Stages 5 through 7 and more preferably at each of Stages 5 to 6. Suitable thyroid hormone analogues may include, without limitation: GC-1 (Sobertirome) (available from R&D Systems, Inc. Minneapolis, Minnesota); 3,5-diiodothryopropionic acid ("DIPTA"); KB-141 discussed in *J. Steroid Biochem. Mol. Biol.*, 2008, 111: 262-267 and *Proc. Natl. Acad. Sci.* U.S. Pat. No. 2,003,100: 10067-10072; MB07344 discussed in Proc. *Natl. Acad. Sci.* U.S. Pat. No. 2,007,104: 15490-15495; T0681 discussed in *J. Lipid Res.*, May 2009, 50:938 and *Endocr. Pract.* 2012, 18(6): 954-964, the disclosures of which are incorporated herein by reference in their entireties. Useful ALK5 inhibitors include: ALK5 inhibitor II (Enzo Life Sciences, Inc., Farmingdale, New York), which is also the preferred ALK5 inhibitor; ALK5i (Axxora, Inc., San Diego, California), SD208 (R&D Systems); TGF-β inhibitor SB431542 (Xcess Biosciences, Inc., San Diego, California); ITD-1 (Xcess Biosciences); LY2109761 (Xcess Biosciences); A83-01 (Xcess Biosciences); LY2157299 (Xcess Biosciences); TGF-β receptor inh V (EMD Millipore Chemical, Gibstown, New Jersey); TGF-β receptor inh I (EMD Millipore); TGF-β receptor inh IV (EMD Millipore); TGF-β receptor inh VII (EMD Millipore); TGF-β receptor inh VIII (EMD Millipore); TGF-β receptor inh II (EMD Millipore); TGF-β receptor inh VI (EMD Millipore); and TGF-β receptor inh VI (EMD Millipore).

In additional preferred embodiments of the invention, the methods include treating cells at one or more stages, but preferably treating cells during Stage 7, with a differentiation medium that includes one or both of an antioxidant, such as vitamin E, acetyl cysteine, vitamin C, antioxidant supplement (Catalog No. A1345, Sigma-Aldrich Company, LLC Saint Louis, Missouri), glutathione, superoxide dismutase, catalase and the like and combinations thereof. In still more preferred embodiments, in carrying out Stage 6, a gamma secretase inhibitor is used, which can be gamma secretase inhibitor XX (EMD Millipore), gamma secretase inhibitor XXI (EMD Millipore), gamma secretase inhibitor XVI (EMD Millipore), N-[(3,5-difluorophenyl)acetyll-L-alanyl-2-phenyl]glycine-1,1-dimethylethyl ester ("DAPT") (Catalog No. 2634, Tocris Bioscience, Bristol, United Kingdom), and the like and combinations thereof. Useful amounts of gamma secretase inhibitor may be about 50 nM to 5000 nM, preferably about 50 nM to 500 nM. The amount of antioxidant may be about 0.1 to 100 µM, alternatively about 0.1 to 20 µM, and preferably about 1 to 10 µM. Alternatively, useful amounts of antioxidant may be about 100 nM to 5 mM, about 1000 nM to 2 mM, and preferably about 0.1 to 1 mM.

In embodiments of the invention, certain small molecules are used in the medium of one or more stages of differentiation, preferably at one or both of Stages 6 and 7. The small molecules of interest are those capable of inhibiting aurora kinase, p90 ribosomal S6 kinase, or methyl transferase receptor DOT1L and preferably are used along with antioxidants that reduce oxidative stress of cultured cells. Of particular interest are aurora kinase inhibitor II and RSK inhibitor II. Aurora kinase inhibitor II is a cell permeable compound known by the name of (4-(4'-benzamidoanilino)-6,7-dimethoxyquinazoline). RSK inhibitor II is a racemic mixture of a the dihydropteridinone 2-(3,5-difluoro-4-hydroxy-anilino)-8-isopentyl-5,7-dimethyl-7H-pteridin-6-one. Other aurora kinase inhibitors of interest include ZM447439 and PF03814735. Also of interest are protein methyltransferase receptor inhibitors of DOT1L, particularly EPZ-5676. EPZ-5676 is an S-adenosyl methionine ("SAM") inhibitor of protein methyltransferase DOT1L. This compound is a DOT1L (disruptor of telomere silencing 1-like) methyltransferase inhibitor shown to inhibit cell proliferation. It is known by the chemical names 9H-Purin-6-amine, 9-[5-deoxy-5-[[cis-3-[2-[6-(1,1-dimethylethyl)-1H-benzimidazol-2-yl]ethyl]cyclobutyl](1-methylethyl)amino]-O-D-ribofuranosyl]- and (2R,3R,4S,5R)-2-(6-aminopurin-9-yl)-5-[[[3-[2-(6-tert-butyl-1H-benzimidazol-2-yl)ethyl] cyclobutyl]-propan-2-ylamino]methyl]oxolane-3,4-diol.

Further inhibitors of interest are a DNA methyltransferase inhibitor such as 5-Azacytidine ("AZT"), histone deacetylase inhibitors, such as Pyroxamide and CI994. Additional small molecules of interest include UNC0638, UNC0646, UNC0642 and A366 (G9a and GLP histone lysine methyltransferase inhibitors), TC-E5003 (PRMT1 arginine methyltransferase inhibitor), SB747651A dihydrochloride (MSK1 inhibitor; also inhibits other AGC group kinases), PFI1 (BET bromodomain inhibitor), LY303511 (BRD2, BRD3 and BRD4 inhibitor), MS436 (BRD4 bromodomain inhibitor), and MC1568 (selectively inhibits HDAC class II), and 3-Deazaneplanocin A ("DEZA").

In a preferred embodiment of the invention, the small molecule is used in the medium of one or more of Stage 6 and 7 and more preferably in Stage 7. The amount of small molecule useful may be determined by selecting the amount showing the best expression of maturation markers and which amounts are not producing toxic effects. Typically, the amounts useful will be about 500 nM to 10 alternatively, about 500 nM to 5 and preferably about 500 nM to 2 µM.

Differentiation of Pluripotent Cells into Cells Expressing Markers Characteristic of Pancreatic Endocrine Cells with a Matured Phenotype (Functional Beta-Cells)

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, TRA-1-60, TRA-1-81. These may be detectable by RT-PCR.

Exemplary pluripotent stem cells include the human embryonic stem cell line H9 (NIH code: WA09), the human embryonic stem cell line H1 (NIH code: WA01), the human embryonic stem cell line H7 (NIH code: WA07), and the human embryonic stem cell line SA002. Also suitable are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, TRA-1-60, and TRA-1-81.

Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Also suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell wherein the expression of PDX1 and NKX6.1 are substantially higher than the expression of CDX2 and SOX2. In certain embodiments, more than 30% of the cells express PDX1 and NKX6.1 and less than 30% of the cells express CDX2 or SOX2 as measured by FACS. Particularly useful are cells in which the expression of PDX1 and NKX6.1 is at least two-fold higher than the expression of CDX2 or SOX2.

Still also suitable for use in the present invention is a cell that expresses at least one of the markers characteristic of the pancreatic endocrine lineage. In one aspect of the invention, a cell expressing markers characteristic of the pancreatic endocrine lineage is a pancreatic endocrine cell. The pancreatic endocrine cell may be a pancreatic hormone-expressing cell capable of expressing at least one of the following hormones: insulin, glucagon, somatostatin, ghrelin, or pancreatic polypeptide. In a preferred embodiment, the pancreatic endocrine cell is an insulin-producing cell.

In certain embodiments of the invention, to arrive at the cells expressing markers characteristic of a functional beta-cell (pancreatic endocrine beta cells of a matured phenotype), a protocol starting with pluripotent stem cells is employed. This protocol includes:

Stage 1: Pluripotent stem cells, such as embryonic stem cells obtained from cell culture lines, are treated with the appropriate factors to induce formation of definitive endoderm cells.

Stage 2: Cells resulting from Stage 1 are treated with the appropriate factors to induce formation of cells into markers expressing characteristic of primitive gut tube cells.

Stage 3: Cells resulting from Stage 2 cells are treated with the appropriate factors to induce further differentiation into cells expressing markers characteristic of foregut endoderm cells.

Stage 4: Cells resulting from Stage 3 are treated with the appropriate factors to induce further differentiation into cells expressing markers characteristic of pancreatic endoderm cells. The cells are optionally further cultured at the air-liquid interface or in suspension culture at late Stage 4; for late Stage 4 cells are transitioned to the air-liquid interface or aggregated as clusters that are cultured in suspension.

Stage 5: Cells resulting from Stage 4 are treated with the appropriate factors, including in certain embodiments: (i) one or more of T3, T4 or an analogue thereof; (ii) an ALK5 inhibitor; or (iii) both of (i) and (ii) and cultured, optionally at the air-liquid interface or in suspension, to induce differentiation to cells expressing markers characteristic of pancreatic endoderm/endocrine precursor cells.

Stage 6: Cells resulting from Stage 5 cells are treated with the appropriate factors including in certain embodiments: (i) one or more of T3, T4 or an analogue thereof; (ii) an ALK5 inhibitor; (iii) one or more of a gamma secretase inhibitor, an RSK inhibitor, a bone morphogenic protein (BMG) receptor inhibitor and a protein methyltransferase inhibitor of DOT1L; (iv) both of (i) and (ii); (v) (i), (ii) and (iii); (vi) (i) and (iii); or (vii) (ii) and (iii) and cultured, optionally at the air-liquid interface or in suspension, to induce differentiation into cells expressing markers characteristic of pancreatic endocrine cells, in particular immature beta-cells.

Stage 7: Cells resulting from Stage 6 cells are treated with appropriate factors including in certain embodiments: (i) one or more of T3, T4 or thereof; (ii) an ALK5 inhibitor; (iii) an anti-oxidant, (iv) one or more of an aurora kinase inhibitor, an RSK inhibitor and a protein methyltransferase inhibitor of DOT1L; (v) (i) and (ii); (vi) (i) and (iii); (vii) (i) and (iv); (viii) (ii) and (iii); (ix) (ii) and (iv); (x) (i), (ii), and (iii); (xi) (i), (iii), and (iv); (xii) (ii), (iii), and (iv); (xiii) (i), (ii) and (iv); (xiv) (iii) and (iv); or (xv) (i), (ii), (iii) and (iv) and cultured, at the air-liquid interface or in suspension, to induce formation of functional beta-cells, pancreatic endocrine cells that express single hormonal insulin and are PDX1, NKX6.1, UCN3, SLC2A1 and MAFA positive and which have a higher level of expression of MAFA than the Stage 6 cells and the resulting cell population has a higher percentage of both MAFA positive and single hormonal insulin expressing cells than the Stage 6 cells.

While the invention in certain embodiments encompasses differentiating pluripotent stem cells (e.g. pre-Stage 1 cells) to Stage 7 cells, the invention also encompasses differentiating cells at other stages towards Stage 7. In particular, the invention encompasses differentiation of Stage 4 to Stage 7 cells. Although the process is described in discrete stages, the treatment, as well as the progress of the cells through the differentiation process, may be sequential or continuous. Differentiation of pluripotent stem cells to Stage 6 or Stage 7 cells can be carried out in suspension cultures.

The efficiency of differentiation may be determined by exposing a treated cell population to an agent, such as an antibody, that specifically recognizes a protein marker expressed by the differentiated cells of interest. Methods for assessing expression of protein and nucleic acid markers in cultured or isolated cells are standard in the art. These methods include RT-PCR, Northern blots, in situ hybridization (see, e.g., *Current Protocols in Molecular Biology* (Ausubel et al., eds. 2001 supplement)), and immunoassays such as immunohistochemical analysis of sectioned material, western blotting and for markers that are accessible in intact cells, flow cytometry analysis (FACS) (see, e.g., *Harlow and Lane, Using Antibodies: A Laboratory Manual*, New York: Cold Spring Harbor Laboratory Press (1998)).

The differentiated cells may also be further purified. For example, after treating pluripotent stem cells with the methods of the present invention, the differentiated cells may be purified by exposing a treated cell population to an agent, such as an antibody, that specifically recognizes a protein marker characteristically expressed by the differentiated cells being purified. In certain embodiments, the differentiated cells are not purified.

Any suitable growth medium containing sufficient quantities of vitamins, minerals, salts, glucose, amino acids and carrier proteins desirable for cells differentiation may be used for the various Stages 1 through 7. Preferably, the following are used: Stage 1—MCDB-131 (available from Life Technologies Corporation, Grand Island, NY) or RPMI (available from Sigma-Aldrich); Stage 2 MCDB-131 or Dulbecco's Modified Eagle's Medium F12 ("DMEM F12"); Stage 3 through 5 MCDB-131, BLAR (Table 1 and Table IV), or DMEM; and Stages 6 and 7 BLAR or CMRL (Life Technologies). Preferably, the glucose concentration of the medium is kept at or, more preferably, lower than about 10 mM for Stages 1 through 4 and greater than about 10 mM for Stages 5 through 7. Preferably for Stage 7, the medium contains sufficient quantity of vitamins, non-essential amino acid, lipids, sodium pyruvate and trace elements, for example Formulation I.

Stage 1: Differentiation of Pluripotent Cells into Cells Expressing Markers Characteristic of Definitive Endoderm Cells.

Pluripotent stem cells may be differentiated into cells expressing markers characteristic of definitive endoderm cells by methods known in the art, or by methods proposed in the invention. Methods reported as useful for differentiating pluripotent stem cells into cells expressing markers characteristic of the definitive endoderm lineage are disclosed in: D'Amour et al., Nature Biotechnology 23, 1534-1541 (2005); Shinozaki et al., Development 131, 1651-1662 (2004); McLean et al., Stem Cells 25, 29-38 (2007); and D'Amour et al., Nature Biotechnology 24, 1392-1401 (2006). Additional suitable differentiation methods are disclosed in: U.S. Patent App. Pub. No. 2007/0254359; U.S. Patent App. Pub. 2009/0170198; U.S. Patent App. Pub. 2011/0091971; U.S. Patent App. Pub. 2010/0015711; U.S. Patent App. Pub. 2012/0190111; U.S. Patent App. Pub. 2012/0190112; and U.S. Patent App. Pub. 2012/0196365. These disclosures are incorporated herein by reference in their entireties as they pertain to the differentiation of pluripotent stem cells into definitive endoderm cells.

In one embodiment, the pluripotent cells are treated with a suitable growth medium, preferably MCDB-131 or RPMI. The medium is preferably supplemented with a growth differentiation factor, such as growth differentiation factor 8 ("GDF8"), and a glycogen synthase kinase-3 β ("GSK3β") inhibitor, such as the cyclic aniline-pyridintriazine compounds disclosed in U.S. Patent App. Pub. No. 2010/0015711 (incorporated herein in its entirety by reference) to induce differentiation into cells expressing markers characteristic of definitive endoderm cells. A preferred GSK3P inhibitor is 14-prop-2-en-1-yl-3,5,7,14,17,23,27-heptaazatetracyclo[19.3.1.1 2,6.~1~8,12~]heptacosa-1(25),2(27),3, 5,8(26),9,11,21,23-nonaen-16-one ("MCX compound"). Treatment may involve contacting pluripotent stem cells with a medium supplemented with about 50 ng/ml to about 150 ng/ml, alternatively about 75 ng/ml to about 125 ng/ml, preferably about 100 ng/ml of GDF8. The treatment may also involve contacting cells with about 0.1 to about 5 alternatively about 0.5 to about 2.5 preferably about 1 µM of MCX compound. The pluripotent cells may be cultured for about two to five days, preferably about two to three days, to facilitate differentiation into cells expressing markers characteristic of the definitive endoderm cells.

In a preferred embodiment, the cells are cultured in the presence of GDF8 and MCX compound for one day, followed by culturing in the presence of GDF8 and a lower concentration of MCX compound for one day, followed by culturing in the presence of GDF8 for one day in the absence of MCX compound. In particular, the cells are cultured in the presence of GDF8 and about MCX compound for one day, followed by culturing in the presence of GDF8 and about 0.1 µM 1 µM MCX compound for one day, followed by culturing in the presence of GDF8 for one day in the absence of MCX compound. Alternatively, the cells may be cultured in the presence of GDF8 and about 1 µM MCX compound for one day, followed by culturing in the presence of GDF8 and about 0.1 µM MCX compound for one day.

Alternatively, the pluripotent stem cells may be cultured in medium containing activin A in the absence of serum, then culturing the cells with activin A and serum, and then culturing the cells with activin A and serum of different concentration as disclosed in D'Amour et al., Nature Biotechnology 23, 1534-1541 (2005). In another alternative, the pluripotent stem cells may be differentiated into cells expressing markers characteristic of definitive endoderm cells by culturing the pluripotent stem cells in medium containing activin A in the absence of serum, then culturing the cells with activin A with serum as disclosed in D'Amour et al., Nature Biotechnology, 2005. Pluripotent stem cells may also be differentiated into cells expressing markers characteristic of the definitive endoderm lineage by culturing the pluripotent stem cells in medium containing activin A and a WNT ligand in the absence of serum, then removing the WNT ligand and culturing the cells with activin A with serum as disclosed in D'Amour et al., Nature Biotechnology 24, 1392-1401 (2006).

In one embodiment of the invention, pluripotent stem cells are treated with activin A and WNT3A to result in the formation of cells expressing markers characteristic of definitive endoderm cells. Treatment may involve contacting pluripotent stem cells with about 50 ng/ml to about 150 ng/ml, alternatively about 75 ng/ml to about 125 ng/ml, alternatively about 100 ng/ml of activin A. The treatment may also involve contacting the cells with about 10 ng/ml to about 50 ng/ml, alternatively about 15 ng/ml to about 30 ng/ml, alternatively about 20 ng/ml of WNT3A. The pluripotent cells may be cultured for approximately three days to arrive at the definitive endoderm cells. In one embodiment, the cells are cultured in the presence of activin A and WNT3A for one day followed by culturing in the presence of activin A (without WNT3A being present) for the remainder.

In order to detect formation of cells expressing markers characteristic of definitive endoderm cells, the cells may be tested for the presence of the markers before and after carrying out a particular protocol. Pluripotent stem cells typically do not express such markers. Thus, differentiation of pluripotent cells can be detected when cells begin to express markers characteristic of definitive endoderm.

Stage 2: Differentiation of Cells Expressing Markers Characteristic of Definitive Endoderm Cells into Cells Expressing Markers Characteristic of Primitive Gut Tube Cells.

The cells expressing markers characteristic of the definitive endoderm cells may be further differentiated into cells expressing markers characteristic of gut tube cells in a growth medium, such as MCDB-131 or DMEM-F12. In one embodiment, the formation of cells expressing markers characteristic of gut tube cells includes culturing the cells expressing markers characteristic of the definitive endoderm cells with a medium containing fibroblast growth factor ("FGF"), preferably FGF7 or FGF10, to differentiate the cells. For example, the cell culture may include from about 10 ng/ml to about 75 ng/ml, alternatively from about 25 ng/ml to about 75 ng/ml, still alternatively from about 30 ng/ml to about 60 ng/ml, alternatively about 50 ng/ml of a fibroblast growth factor, preferably FGF7 or FGF10, more preferably FGF7, and most preferably about 25 ng/ml FGF7. The cells may be cultured under these conditions for about two to three days, preferably about two days.

In another embodiment, the formation of cells expressing markers characteristic of gut tube cells includes culturing the cells expressing markers characteristic of the definitive endoderm lineage with a fibroblast growth factor, preferably, FGF7 or FGF10, and ascorbic acid (Vitamin C). The culture medium may include from about 0.1 mM to about 0.5 mM ascorbic acid, alternatively from about 0.2 mM to about 0.4 mM ascorbic acid, alternatively about 0.25 mM of ascorbic acid. The cell culture may also include from about 10 ng/ml to about 35 ng/ml, alternatively from about 15 ng/ml to about 30 ng/ml, alternatively about 25 ng/ml of the fibroblast growth factor, preferably FGF7 or FGF10, more preferably FGF7. For example, the cell culture may include about 0.25 mM of ascorbic acid and about 25 ng/ml of FGF7. In one embodiment, the Stage 1 cells are treated for 2 days with FGF7 and ascorbic acid.

Stage 3: Differentiation of Cells Expressing Markers Characteristic of Primitive Gut Tube Cells into Cells Expressing Markers Characteristic of Foregut Endoderm Cells.

The primitive gut tube cells resulting from Stage 2 may be further differentiated into Stage 3 cells, or cells expressing markers characteristic of the foregut endoderm, by culturing these cells in a growth medium such as MCDB-131, DMEM, or a custom media such as BLAR (Table I). The medium may be supplemented with: (i) a fibroblast growth factor, preferably, FGF7 or FGF10 and more preferably FGF7; (ii) retinoic acid ("RA"); (iii) a Sonic Hedgehog ("SHH") signaling pathway antagonist (such as Smoothened Antagonist 1 ("SANT-1") which is 1-piperazinamine, N-[(3, 5-dimethyl-1-phenyl-1H-pyrazol-4-yl)methylene]-4-(phenylmethyl)- or ((E)-4-benxyl-N-((3,5-dimethyl-1-phenyl-1H-pyrazol-4-yl),ethylene-piperazin-1-amine), HPI-1 which is 2-methoxyethyl 1,4,5,6,7,8-hexahydro-4-(3hydroxyphenyl)-7-(2-methoxyphenyl)-2-methyl-5-oxo-3-quinolinecarboxylate, and preferably SANT-1; (iv) a protein kinase C ("PKC") activator, such as ((2S,5S)-(E,E)-8-(5-(4-(trifluoromethyl)phenyl)-2,4-pentadieneoylamino)benzolactam) ("TPB"), phorbol-12,13-dibutyrate ("PDBu"), phorbol-12-myristate-13-acetate ("PMA") or indolactam V ("ILV") and preferably TPB; (v) a bone morphogenic protein ("BMP") inhibitor, such as LDN-193189, noggin, or chordin and preferably LDN-193189; and (vi) ascorbic acid. Alternatively, a smoothened ("SMO") receptor inhibitor (such as MRT10 (N[[[3-benzoylamino)phenyl]amino]thioxomethyl]-3,4,5-trimethoxybenzamide)) or cyclopamine may also be used. For example, the cell culture may include from about 100 nM to about 500 nM, alternatively from about 100 nM to about 400 nM, alternatively about 200 nM of a PKC activator. The cells may be cultured in the presence of these growth factors, small molecule agonists and antagonists for about two to four days, preferably about two to three days, more preferably about two days.

Alternatively, Stage 3 cells may be obtained from the Stage 2 cells by culturing these cells in a culture medium supplemented with an SMO receptor inhibitor, SANT-1, retinoic acid and noggin. The cells may be cultured for approximately two to four days, preferably about two days.

In one embodiment, the medium is supplemented with: from about 10 ng/ml to about 35 ng/ml, alternatively from about 15 ng/ml to about 30 ng/ml, alternatively about 25 ng/ml of the fibroblast growth factor, preferably FGF7 or FGF10, more preferably FGF7; from about 0.1 mM to about 0.5 mM ascorbic acid, alternatively from about 0.2 mM to about 0.4 mM, alternatively about 0.25 mM of ascorbic acid; from about 0.1 µM to about 0.4 µM of SANT-1; from about 100 to about 300 nM of TPB; and from about 50 nM to about 200 nM, and about 100 nM of LDN-193189. In another embodiment, the medium is supplemented with about 25 ng/ml of FGF-7, about 1 µM of retinoic acid, about 0.25 µM of SANT-1, about 200 nM of TPB, about 100 nM of LDN-193189, and about 0.25 mM of ascorbic acid.

In one embodiment, the medium is supplemented with from about 0.1 µM to about 0.3 µM of SANT-1, from about 0.5 µM to about 3 µM of retinoic acid and from about 75 ng/ml to about 125 ng/ml of noggin.

Stage 4: Differentiation of Cells Expressing Markers Characteristic of Foregut Endoderm Cells into Cells Expressing Markers Characteristic of Pancreatic Endoderm Cells.

In one embodiment, the methods of the invention include deriving Stage 4 cells by treating Stage 3 cells with a differentiation medium that may be any suitable growth medium and preferably is MCDB-131, DMEM, or a custom media such as BLAR (Table I). The medium may be supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-β inhibitor SB431542, SD-208, ITD-1, LY2109761, A83-01, LY2157299, ALK5i and ALK5 inhibitor II; (b) a thyroid hormone selected from the group consisting of T3, T4, analogues of T3, analogues of T4 and mixtures thereof; (c) an SHH signaling pathway antagonist selected from SANT-1 or HIP-1; (d) a BMP receptor inhibitor selected from LDN-193189, noggin or chordin; (e) a PKC activator selected from TPB, PPBu, PMA and ILV; (f) a fibroblast growth factor selected from FGF-7 or FGF-10; (g) retinoic acid; and (h) ascorbic acid. For example, a growth medium such as MCDB131 or, and preferably, BLAR may be supplemented with an SHH signaling pathway antagonist (such as SANT-1 or HPI-1), a BMP inhibitor (such as LDN-193189, noggin or chordin), ascorbic acid, and a PKC activator (such as TPB, PDBu, PMA or ILV), to provide a useful differentiation media.

Culturing Stage 3 cells in such medium for about two to four days, preferably about two to three days, more preferably about three days usually is sufficient to differentiate the Stage 3 cells into Stage 4 cells. In another embodiment, the medium may be supplemented with an SMO inhibitor and SHH signaling pathway antagonist. In a preferred embodiment, the Stage 3 cells may be treated with a medium supplemented with about 0.25 µM SANT-1; about 100 nM RA; about 2 ng/ml FGF7; about 100 nM LDN-193189; about 0.25 mM ascorbic acid; and about 200 nM of TPB for three days.

In Stage 4, cells may be cultured at the air-liquid interface, either during the entire stage or after about 2 to 3 days of planar culturing. Specifically, the present invention provides an in vitro cell culture for differentiating cells derived from pluripotent stem cells at the air-liquid interface comprising: (a) a culture vessel; (b) a volume of growth medium within said vessel sufficient to fill only a portion of the volume of the vessel; (c) air within the vessel that fills a portion of the vessel adjoining the medium; (d) a porous substrate located at the interface between the medium and the air; and (e) cells derived from pluripotent stem cells disposed upon the surface of the substrate such that the medium contacts only a portion of the surface of the cells. Alternatively, Stage 4 may be carried out entirely in planar culture.

Alternatively in Stage 4, after about 2 to 3 days of planar culture, cells may be aggregated to cell clusters. Specifically, the present invention provides an in vitro cell culture for differentiating cells prepared as aggregated cells such as cell clusters comprising: (a) a culture vessel that facilitates aggregation of cells, or forming cell clusters; (b) a volume of growth medium (culture medium) within said vessel; and (c) cells derived from pluripotent stem cells disposed within the vessel such that the cells are induced to aggregate and form clusters. In embodiments, the vessel is a plate with wells or microwells, such as AGGREWELL™ plates (microwell plates; STEMCELL Technologies Inc., Vancouver, Canada). In particular, cell clusters prepared in plates with microwells to form aggregates of cells of uniform size and shape, for example using AGGREWELL™ plates. In embodiments, about 500 to 2000 cells are seeded per well or microwell to prepare aggregated cells or cell clusters. In particular, about 50 to about 3000 cells are seeded per well or microwell, preferably about 50 to about 2000 cells, about 50 to 1000 cells, about 50 to about 900 cells, about 50 to about 800 cells, about 100 to about 800 cells, about 250 to about 800 cells, or about 500 to about 800 cells are seeded. More preferably, about 700 to about 800 cells are seeded per well or microwell.

In a further embodiment, the cell clusters formed by the method of aggregating cells may be further cultured in suspension (suspension culture), comprising removing the aggregated cells or cell clusters from the wells or microwells and seeding the aggregated cells/cell clusters in a suspension culture vessel. In embodiments, aggregated cells/cell clusters are seeded in a suspension culture at a cell density of about $0.75 \times 10^6$ cells/ml to about $2.0 \times 10^6$ cells/ml, preferably about $1 \times 10^6$ cells/ml to about $2.0 \times 10^6$ cells/ml, more preferably about $1.5 \times 10^6$ cells/ml to about $2.0 \times 10^6$ cells/ml. Any suspension culture system known to those skilled in the art may be useful for suspension culturing the aggregated cells. In particular, the suspension culture system may include seeding aggregated cells or cell clusters in a flask, such as a spinner flask or a spinner wheel flask.

In a further embodiment, the cells at the completion of Stage 4 (after 2 or 3 days of culture) may be treated with a Rho-associated kinase ("ROCK") inhibitor such as Y27632 ((1R,4r)-4-((R)-1-aminoethyl)-N-(pyridin-4-yl)cyclohexanecarboxamide), GSK269962 (N-[3-[[2-(4-Amino-1,2,5-oxadiazol-3-yl)-1-ethyl-1H-imidazo[4,5-c]pyridin-6-yl[oxy]phenyl]-4-[2-(4-morpholinyl)ethoxy]benzamide), H1152 ((S)-(+)-2-Methyl-1-[(4-methyl-5-isoquinolinyl)sulfonyl]homopiperazine, 2HCl,) and, SR3677 (N-[2-[2-(Dimethylamino)ethoxy]-4-(1H-pyrazol-4-yl)phenyl-2,3-dihydro-1,4-benzodioxin-2-carboxamide dihydrochloride). In certain embodiments about 1 to 20 µM, about 1 to 15 µM, about 1 to 10 µM or about 10 µM of the ROCK inhibitor may be used.

In certain embodiments of the invention herein, only late Stage 4 cells, for example, cells that have been cultured for 1 to 2 days or 1 to 3 days in adherent planar cultures, may subsequently be cultured at the air-liquid interface or cultured to aggregated cells, such as cell clusters, for completion of Stage 4. In one embodiment of the invention herein, late Stage 4 cells that were treated with a ROCK inhibitor are cultured at the air-liquid interface. In embodiments, 0.5 to about $0.75 \times 10^5$ cells/micro liter are seeded to be cultured at the air-liquid interface; alternatively, about 2 to $6 \times 10^6$ cells are seeded to be cultured at the air-liquid interface. In another embodiment, late Stage 4 cells that were treated with a ROCK inhibitor are cultured to aggregate the cells to form aggregated cells such as cell clusters. In embodiments, cells are seeded in a vessel that facilitates aggregation of cells, or cell clusters (three dimensional aggregates of cells). In some embodiments, the vessel is a plate with wells or microwells. In particular, cell clusters are prepared in plates with microwells to form aggregates of cells of uniform size and shape, for example using AGGREWELL™ plates (STEMCELL Technologies Inc., Vancouver, Canada). In embodiments, about 50 to 3000 cells are seeded per well or microwell to prepare aggregated cells or cell clusters. In particular, about 50 to about 3000 cells are seeded per well or microwell, preferably about 50 to about 2000 cells, about 50 to 1000 cells, 50 to 900 cells, 50 to 800 cells, 100 to 800 cells, 250 to 800 cells, or about 500 to about 800 cells are seeded. More preferably, about 700 to 800 cells are seeded per well or microwell. In another embodiment, the aggregated cells or cell clusters are further cultured in suspension. In certain embodiments, the adherent cells in planar culture may be treated with a cell detachment solution, such as a solution containing proteolytic and collagenolytic enzymes such as TrypLE™, Accutase™, or Dispase™ prior to culturing at the air-liquid interface or culturing to aggregate cells such as forming cell clusters.

In an alternate embodiment, Stage 4 cells may be obtained from Stage 3 cells by treating the Stage 3 cells with a differentiation medium comprising a growth medium supplemented with an ALK5 inhibitor, noggin, and a PKC activator, such as TPB. In certain embodiments, the medium may be supplemented with about 0.1 µM ALK5 inhibitor, about 100 ng/mL of noggin, and about 500 nM TPB. The cell culture may be in a monolayer format. The treatment may last for a total of about three days. In certain embodiments, the cells may be treated for two days and then on the last day the cells may be treated with proteolytic enzymes, collagenolytic enzymes or both to generate a single cell suspension. The resulting cells may be seeded at the air-liquid interface or seeded to generate aggregated cells or cell clusters. The single cells may be aggregated into cell clusters having a diameter of less than about 100 microns followed by culturing in the presence of an ALK5 inhibitor and LDN-193189. In certain embodiments, the cell clusters having a diameter of less than about 100 microns may be cultured in a medium supplemented with about 200 nM ALK5 inhibitor and about 100 nM LDN-193189. In an alternate embodiment, culturing Stage 4 cells at the air-liquid interface or in suspension may significantly enhance pancreatic endoderm markers along with endocrine-related markers.

Stage 5: Differentiation of Cells Expressing Markers Characteristic of Pancreatic Endoderm Cells into Cells Expressing Markers Characteristic of Pancreatic Endocrine Precursor Cells.

In one embodiment, the methods of the invention include generation of Stage 5 cells by treating Stage 4 cells with a differentiation medium that may be any suitable growth medium and preferably is MCDB-131, DMEM or a custom media such as BLAR (Table I). The medium may be supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-β inhibitor SB431542, SD-208, ITD-1, LY2109761, A83-01, LY2157299, ALK5i and ALK5 inhibitor II; (b) a thyroid hormone selected from the group consisting of T3, T4, analogues of T3, analogues of T4 and mixtures thereof; (c) an SHH signaling pathway antagonist selected from SANT-1 or HIP-1; (d) a BMP Receptor Inhibitor selected from LDN-193189, noggin or chordin; (e) retinoic acid; (f) ascorbic acid; (g) heparin; and (h) zinc sulfate, and culturing the cells, preferably at the air-liquid interface, for about two to four days, preferably about three days, to differentiate the cells into Stage 5 cells. In another embodiment, the growth medium is also supplemented with one or both of an SMO inhibitor (such as MRT10 or cyclopamine) and a fibroblast growth factor selected from FGF-7 or FGF-10. The treatment of the Stage 4 cells is carried out for about two to four days, preferably about three days to differentiate the cells into Stage 5 cells.

In a preferred embodiment, the Stage 4 cells are differentiated into Stage 5 cells by treating the cells with a medium supplemented with from about 0.1 µM to about 0.4 µM of SANT-1and preferably about 0.25 µM SANT-1, about 50 nM RA, from about 0.1 mM to about 0.5 mM ascorbic acid, alternatively from about 0.2 mM to about 0.4 mM and preferably about 0.25 mM ascorbic acid, from about 50 nM to about 200 nM and preferably about 100 nM LDN-193189, about 1 µM of T3, and about 10000 nM ALK5 inhibitor, more preferably ALK 5 inhibitor II. In still another embodiment, the cells are optionally also treated with about 1 to 15 alternatively about 1 to 10 alternatively about 5 to 10 preferably about 10 µM of zinc sulfate ($ZnSO_4$) and about 1 to 100 µg/ml, preferably about 10 µg/ml of heparin. The treatment of the Stage 4 cells is carried out for about two to four days, preferably about 3 days to differentiate the cells into Stage 5 cells.

In yet another embodiment, the methods of the invention include obtaining Stage 5 cells by treating Stage 4 cells with a medium supplemented with heparin, an SMO inhibitor or an SHH signaling pathway antagonist, RA, a BMP receptor inhibitor and an ALK5 inhibitor and culturing the cells at the air-liquid interface for about 3 days to differentiate the cells into Stage 5 cells. In an alternative embodiment, the medium may be supplemented with both an SMO inhibitor and an SHH signaling pathway antagonist, along with RA, a BMP receptor inhibitor and an ALK5 inhibitor. Thus, in one embodiment, the Stage 4 cells may be differentiated into Stage 5 cells by treating the Stage 4 cells with a medium supplemented with heparin, $ZnSO_4$, an SMO inhibitor or an SHH signaling pathway antagonist, RA, LDN-193189 and ALK5 inhibitor II. In an alternative embodiment, the medium may be supplemented with both an SMO inhibitor and an SHH signaling pathway antagonist. In one embodiment, the Stage 4 cells are differentiated into Stage 5 cells by treating the cells with a medium supplemented with about 10 µg/ml of heparin, about 0.25 µM SANT-1, about 50 nM RA, about 50 nM LDN-193189, about 10 nM of T3 and about 1000 nM ALK5 inhibitor. Suitable ALK5 inhibitors include but are not limited to SD-208, ALK5 inhibitor II, TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III and combinations thereof. The treatment of the Stage 4 cells is carried out for about two to four days, preferably about 3 days to differentiate the cells into Stage 5 cells.

In a preferred embodiment, the ALK5 inhibitor is ALK5 inhibitor II. In another preferred embodiment, about 10000 nM of ALK5 inhibitor II is used. In an alternate preferred embodiment, the Stage 4 cells are treated with a medium supplemented with about 10 µg/ml of heparin, about 0.25 µM SANT-1, about 50 nM RA, about 100 nM LDN-193189, and about 10,000 nM (10 mM) of ALK5 inhibitor II. In yet another alternate embodiment, the methods of the invention include treating Stage 4 cells with a medium supplemented with an SMO inhibitor or an SHH signaling pathway antagonist, RA, and an ALK5 inhibitor and culturing the cells, preferably at the air-liquid interface or in suspension for about two days to four days, preferably about 3 days, differentiate the cells into Stage 5 cells. In an alternate embodiment, the medium may be supplemented with both an SMO inhibitor and an SHH signaling pathway antagonist. In one embodiment, the Stage 4 cells are differentiated into Stage 5 cells by treating the cells with a medium supplemented with about 0.25 µM SANT-1, about 50 nM RA, about 50 nM LDN-193189, about 1 µM T3 and about 1000 nM of an ALK5 inhibitor.

The amount of cells seeded for culturing at the air-liquid interface may vary. For example, to culture the cells at the air-liquid interface, droplets of a single-cell suspension containing about 0.5 to $6 \times 10^5$ cells/µl may be seeded on a porous substrate (e.g. filter). The suspension may contain from about $2 \times 10^5$ cells/µl to about $6 \times 10^5$ cells/µl; about $4 \times 10^5$ cells/µl to about $6 \times 10^5$ cells/µl; about $5 \times 10^5$ cells/µl to about $6 \times 10^5$ cells/µl; about $5 \times 10^5$ cells/µl to about $6 \times 10^5$ cells/µl; about $2 \times 10^5$ cells/µl to about $5 \times 10^5$ cells/µl; about $2 \times 10^5$ cells/µl to about $4 \times 10^5$ cells/µl; or about $3 \times 10^5$ cells/µl that may be seeded onto a porous substrate such as a filter located at the air-liquid interface. In some embodiments, droplets of a single-cell suspension containing from about $0.5 \times 10^5$ cells/µl to about $0.75 \times 10^5$ cells/µl; about $0.6 \times 10^5$ cells/µl to about $0.75 \times 10^5$ cells/µl; or about $0.5 \times 10^5$ cells/µl to about $0.6 \times 10^5$ cells/µl are seeded onto a porous support to be cultured at the ALI.

For suspension culture, cell clusters are generated in plates with microwells that are then seeded to suspension culture system. In embodiments, AGGREWELL™ plates are used to induce aggregation in which about 50 to 3000 cells are seeded per well or microwell to prepare aggregated cells or cell clusters. In particular, about 50 to about 3000 cells are seeded per well or microwell, preferably about 50 to about 2000 cells, about 50 to 1000 cells, about 50 to about 900 cells, about 50 to about 800 cells, about 100 to about 800 cells, about 250 to about 800 cells, or about 500 to about 800 cells are seeded. More preferably, about 700 to about 800 cells are seeded per well or microwell. The aggregated cells/cell clusters are seeded in a suspension culture at a cell density of about $0.75 \times 10^6$ cells/ml to about $2.0 \times 10^6$ cells/ml, preferably about $1 \times 10^6$ cells/ml to about $2.0 \times 10^6$ cells/ml, about $1.25 \times 10^6$ cells/ml to about $2.0 \times 10^6$ cells/ml, and more preferably about $1.5 \times 10^6$ cells/ml to about $2.0 \times 10^6$ cells/ml.

In another embodiment, the methods of the invention include treating Stage 4 cells with a medium supplemented with a BMP receptor inhibitor (e.g. LDN-193189, noggin or chordin) and an ALK5 inhibitor for about 1 day to differentiate Stage 4 cells into Stage 5 cells. For example, the medium may be supplemented with about 100 nM of LDN-193189 and with about 100 nM of ALK5 inhibitor and about 1 µM T3. The cells may be in adherent planar culture or in the form of clusters. In certain embodiments, the cells may be treated with a cell detachment solution, such as a solution containing proteolytic and collagenolytic enzymes prior to culturing at the air-liquid interface or culturing to form aggregated cells or cell clusters.

In accordance with the foregoing method, the invention further provides a cell culture for differentiating cells expressing markers characteristic of the pancreatic endoderm into cells expressing markers characteristic of pancreatic endocrine precursor cells (pancreatic endoderm/pancreatic endocrine precursor cells) comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (e) cells expressing markers characteristic of pancreatic endoderm cells derived from pluripotent stem cells disposed upon the surface of said substrate such that said medium contacts only a portion of the surface of said cells.

In accordance with the foregoing method, alternatively the invention further provides a cell culture for differentiating cells expressing markers characteristic of the pancreatic endoderm into cells expressing markers characteristic of pancreatic endocrine precursor cells (pancreatic endoderm/pancreatic endocrine precursor cells) comprising: (a) a culture vessel that facilitates aggregation of cells, or forming cell clusters; (b) a volume of growth medium (culture medium) within said vessel; (c) cells derived from pluripotent stem cells disposed within the vessel such that the cells are induced to aggregate and form clusters; and (d) generated cell clusters disposed in suspension (suspension culture). In embodiments, the vessel for cell aggregation is a plate with wells or microwells, such as AGGREWELL™ plates (microwell plates; STEMCELL Technologies Inc., Vancouver, Canada). In embodiments, the suspension culture system may include seeding aggregated cells or cell clusters in a suspension culture vessel, such as flask, for example a spinner flask or a spinner wheel flask.

Stage 6: Differentiation of Cells Expressing Markers Characteristic of Pancreatic Endocrine Precursor Cells into Cells Expressing Markers Characteristic of Immature Beta-Cells.

In one embodiment, the methods of the invention include obtaining Stage 6 cells by treating Stage 5 cells with a differentiation medium that may be any suitable growth medium, preferably such as MCDB-131 or CMRL, and more preferably, a custom media such as BLAR (Table I). The medium may be supplemented with one or more of the following:

an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-β inhibitor SB431542, SD-208, ITD-1, LY2109761, A83-01, LY2157299, ALK5i and ALK5 inhibitor II; (b) a thyroid hormone selected from the group consisting of T3, T4, analogues of thereof and mixtures thereof; (c) a BMP receptor inhibitor preferably selected from LDN-193189, noggin or chordin; (d) a gamma secretase inhibitor such gamma secretase inhibitor XX, gamma secretase inhibitor XXI, gamma secretase inhibitor XVI, or DAPT; (e) ascorbic acid; (f) heparin; and (g) zinc sulfate. The cells may be cultured, preferably at the air-liquid interface or in suspension culture, for about two to four, preferably for about three days, to differentiate the Stage 5 cells into Stage 6 cells. Optionally, the medium can further be supplemented with one or more of an SHH signaling pathway antagonist, a smoothened receptor inhibitor, a fibroblast growth factor and retinoic acid.

In a preferred embodiment, the Stage 5 cells may be differentiated into Stage 6 cells by treatment with a medium supplemented with about 50 nM RA, about 0.25 mM ascorbic acid, about 100 nM LDN-193189, about 10,000 nM of ALK5 inhibitor and preferably ALK 5 inhibitor II, 1 µM T3, about 100 nM of a gamma secretase inhibitor for about seven days. Alternatively, Stage 5 cells may be differentiated into Stage 6 cells by treatment with a medium supplemented with about 0.25 µM SANT-1, about 50 nM RA, about 0.25 mM ascorbic acid, about 1000 nM ALK5 inhibitor and 1 µM T3 for about three days. The cells may be cultured in such media for an additional two days, or more, if desired.

Alternatively, Stage 5 cells may be differentiated into Stage 6 cells by treatment with a medium supplemented with heparin, an SMO inhibitor or an SHH signaling pathway antagonist, a BMP inhibitor, T3, T4, analogues thereof and mixtures thereof and an ALK5 inhibitor and culturing, preferably at the air-liquid interface or in suspension culture, for about one to seven days, alternatively about six days, alternatively about seven days. In an alternate embodiment, the medium may be supplemented with both an SMO inhibitor and an SHH signaling pathway antagonist. For example, the cells may be cultured in the medium supplemented with about 10 µg/ml of heparin, about 0.25 µM SANT-1, about 100 nM LDN-193189, about 1000 nM of T3 and about 500 to about 10,000 nM, alternatively about 500 nM, alternatively about 1000 mM, and alternatively about 10,000 nM of an ALK5 inhibitor. Suitable ALK5 inhibitors include but are not limited to SD-208, ALK5 inhibitor II, TGF-0 receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III and combinations thereof.

In a preferred embodiment, the ALK5 inhibitor is ALK5 inhibitor II. In a more preferred embodiment, about 10,000 nM (10 mM) of ALK5 inhibitor II is used. Accordingly, in one embodiment, Stage 5 cells may be differentiated into Stage 6 cells by treatment with a medium supplemented with heparin, an SMO inhibitor or an SHH signaling pathway antagonist, a BMP inhibitor, T3, T4, analogues thereof and mixtures thereof, and ALK5 inhibitor and culturing, preferably at the air-liquid interface or in suspension, preferably for about seven days. In an alternate embodiment, the medium may be supplemented with both an SMO inhibitor and an SHH signaling pathway antagonist. In certain embodiments, the cells may be treated with a cell detachment solution, such as a solution containing proteolytic and collagenolytic enzymes prior to culturing at the air-liquid interface or in suspension.

In another embodiment, Stage 5 cells may be differentiated into Stage 6 cells by treatment with a medium supplemented with heparin, an SMO inhibitor or an SHH signaling pathway antagonist, a BMP inhibitor T3, and ALK5 inhibitor II and culturing at the air-liquid interface for about 5 days to about 7 days, alternatively about 5 days, alternatively about 6 days, alternatively about 7 days In these embodiments, the medium may be supplemented with about 10 µg/ml of heparin, about 0.25 µM SANT-1, about 100 nM LDN-193189, about 1000 nM of T3 and about 10,000 nM of ALK5 inhibitor II. In certain embodiments, the medium may be further supplemented with zinc sulfate ($ZnSO_4$). For example, the medium may be further supplemented with about 10 mM $ZnSO_4$. In an alternate embodiment, the medium may be supplemented with both an SMO inhibitor and an SHH signaling pathway antagonist.

In a particularly preferred embodiment of the invention, one or more of an aurora kinase inhibitor, preferably aurora kinase inhibitor II, an RSK inhibitor, preferably RSK inhibitor II and the protein methyl transferase inhibitor of DOT1L, preferably EPZ-5676, is added to the medium. The amount added may be from about 100 to 5000 nM, alternatively about 1000 to 5000 nM, alternatively about 2000 to 5000 nM, alternatively about 3000 to 5000 nM, and preferably about 1000 to 2000 nM for the aurora kinase and RSK inhibitors and about 100 to 1000 nM for the DOT1L inhibitor, and more preferably about 1 µM to about 10 nM.

In accordance with the foregoing method, the invention further provides a cell culture for differentiating cells expressing markers characteristic of pancreatic endoderm/endocrine precursor cells into cells expressing markers characteristic of immature beta cells, comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (e) cells expressing markers characteristic of pancreatic endoderm/endocrine precursor cells derived from pluripotent stem cells disposed upon the surface of said substrate such that said medium contacts only a portion of the surface of said cells.

In accordance with the foregoing method, alternatively the invention further provides a cell culture for differentiating cells expressing markers characteristic of the pancreatic endocrine precursor cells (or pancreatic endoderm/endocrine precursor cells) into cells expressing markers characteristic of immature beta cells comprising: (a) a culture vessel that facilitates aggregation of cells, or forming cell clusters; (b) a volume of growth medium (culture medium) within said vessel; (c) cells derived from pluripotent stem cells disposed within the vessel such that the cells are induced to aggregate and form clusters; and (d) generated cell clusters disposed in suspension (suspension culture). In embodiments, the vessel for cell aggregation is a plate with wells or microwells, such as AGGREWELL™ plates. In embodiments, the suspension culture system may include seeding aggregated cells or cell clusters in a suspension culture vessel, such as flask, for example a spinner flask or a spinner wheel flask.

In one embodiment, Stage 5 cells cultured according to embodiments of the invention are utilized and differentiated into Stage 6 cells, while in other embodiments Stage 5 cells cultured according to other protocols may be utilized in the current method to obtain Stage 6 and Stage 7 cells.

In an embodiment, the methods of the invention result in the formation of Stage 6 cells that are single-hormone positive. Thus, in one embodiment, the methods of the invention result in Stage 6 cells, which co-express NKX6.1, insulin, chromogranin and PDX1. In another embodiment, the methods of the invention result in Stage 6 cells, which co-express NKX6.1 and insulin. In certain embodiments of the invention, the method employs a custom medium, BLAR (see Table I), at Stages 4 to 6 or late Stage 4 to 6 or Stages 5 and 6. The medium may be exchanged every day or alternatively every other day.

In another embodiment, the invention relates to a method of forming Stage 6 cells co-expressing NKX6.1 and chromogranin comprising culturing Stage 4, preferably late Stage 4 cells to Stage 6 cells at the air-liquid interface or in suspension. In yet another embodiment, the invention relates to a method of forming single hormone insulin positive cells expressing NKX6.1 Stage 6 cells by culturing Stage 4, preferably late Stage 4 cells, to Stage 6 cells at the air-liquid interface or in suspension.

Stage 7: Differentiation of Cells Expressing Markers Characteristic of Immature Beta-Cells to Cells Expressing Markers Characteristic of Functional Beta-Cells Capable of a Two Phase GSIS and Mitochondrial Respiration Response.

In one embodiment, the methods of the invention include treating Stage 6 cells with a differentiation medium that may be any suitable growth medium, preferably such as MCDB-131 or CMRL or, and more preferably, a custom media such as BLAR001 (Table 1) or BLAR004 (Table IV) for seven days.

The medium is supplemented with one or more of the following: 2.7 g/1000 ml sodium bicarbonate, and supplemented with a 1:200 dilution of ITS-X; 1× GlutaMAX™; 2% FAF-BSA; 10 µg/ml of heparin ("H"); 10 nM of T3 ("low T3"); 1 mM N-Acetyl cysteine ("NAC"); 0.5 µM of ZM447439 ("ZM"); and the following components which constitute Formulation I ("FI") (Table XII) 1:200 dilution of RPMI Vitamin Supplement; 1:200 dilution of MEM non-essential amino acid supplement; 1:2000 dilution of chemically defined lipid concentrate; 1:200 dilution of sodium pyruvate; 1:2000 dilution of trace elements A (Corning, Catalog No. 25-021); 1:2000 dilution of trace elements B (Corning, Catalog No. 25-022). Additional compounds that may be added to obtain Stage 7 include about 10 nM of T3 ("low T3"); 5 µM 5-Azacytidine ("AZT") (Sigma Aldrich, Catalog No. A2385); or about 1 µM 3-Deazaneplanocin A ("DEZA") (Biovision, Inc., Catalog No. 2060). In embodiments to obtain Stage 7 cells, the medium does not contain an ALK5 inhibitor.

In one embodiment, the Stage 6 cells may be differentiated into Stage 7 cells by treatment with a medium supplemented with, about 10 nM of T3, about 0.5 µM of one or more of aurora kinase inhibitor II, and about 1 mM N-acetyl cysteine. Alternatively, Stage 6 cells may be differentiated into Stage 7 cells by treatment with a medium supplemented with heparin, T3, T4, analogues thereof or mixtures thereof, an antioxidant, and aurora kinase inhibitor, or mixtures thereof and culturing, at the air-liquid interface or suspension cultures, for about seven to twenty-one days, alternatively about seven to ten days, preferably about seven days.

In accordance with the foregoing method, the invention further provides a cell culture for differentiating cells expressing markers characteristic of pancreatic endocrine precursor cells into cells expressing markers characteristic of functional beta-cells, comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (e) cells expressing markers characteristic of pancreatic endoderm/endocrine precursor cells derived from pluripotent stem cells disposed upon the surface of said substrate such that said medium contacts only a portion of the surface of said cells.

In one embodiment, Stage 6 cells cultured according to embodiments of the invention are utilized and differentiated into Stage 7 cells, while in other embodiments Stage 6 cells cultured according to other protocols may be utilized in the current method to obtain Stage 7 cells. In another embodiment, the methods of the invention result in the formation of Stage 7 cells that are single-hormone positive. Thus, in one embodiment, the methods of the invention result in Stage 7 cells, which co-express NKX6.1, chromogranin, PDX1, UCN3, SLC2A1 and MAFA. In another embodiment, the methods of the invention result in Stage 7 cells, which co-express NKX6.1, PDX1, insulin, UCN3, SLC2A1 and MAFA. In still another embodiment, a population of cells in which each of the cells, at least about 10%, alternatively at least about 20%, alternatively at least about 30%, alternatively at least about 40%, alternatively at least about 50%, alternatively at least about 60%, alternatively at least about 70%, alternatively at least about 80%, or alternatively at least about 90% of the cell population express insulin, PDX1, NKX6.1, UCN3, SLC2A1 and MAFA result.

In some embodiments, at least 10% of the cells of the resulting cell population express insulin, PDX1, NKX6.1, UCN3, SLC2A1 and MAFA. In other embodiments, at least 20% of the cells of the population express insulin, PDX1, NKX6.1, UCN3, SLC2A1 and MAFA. In other embodiments, at least 30% of the cells of the population express insulin, PDX1, NKX6.1, UCN3, SLC2A1 and MAFA. In still other embodiments, at least 40% of the cells of the population express insulin, PDX1, NKX6.1, UCN3, SLC2A1 and MAFA. In yet other embodiments, at least 50% of the cells of the population express insulin, PDX1, NKX6.1, UCN3, SLC2A1 and MAFA. In still other embodiments, at least 60%, 70%, 80% or 90% of the cells express insulin, PDX1, NKX6.1, UCN3, SLC2A1 and MAFA. In alternative embodiments, at least 91, 92, 93, 94, 95, 96, 97, 98, or 99% of the cells of the population express insulin, PDX1, NKX6.1, UCN3, SLC2A1 and MAFA.

In certain and preferred embodiments of the invention, the method employs a custom medium, BLAR (Table I), at Stages 4 through 7 or late Stage 4 through 7, or Stages 5, 6 and 7. The medium may preferably be exchanged every day or alternatively every other day.

In another embodiment, the invention relates to a method of forming Stage 7 cells co-expressing NKX6.1, PDX1, MAFA, UCN3, SLC2A1 and chromogranin comprising culturing Stage 4, preferably late Stage 4 cells to Stage 7 cells at the air-liquid interface, or in suspension. In yet another embodiment, the invention relates to a method of forming single hormone insulin positive cells (functional beta-cells) expressing NKX6.1, PDX1, UCN3, SLC2A1 and MAFA Stage 7 cells by culturing Stage 4, preferably late Stage 4 cells, to Stage 7 cells at the air-liquid interface or in suspension.

Although the present invention contemplates culturing at the air-liquid interface for all stages in the path from pluripotent cell to pancreatic endocrine cell, the invention provides for the formation of Stage 1 to Stage 4 cells in planar or submerged culture and Stage 5, 6 and 7 cells by culturing the cells at the air-liquid interface or in suspension culture. In other embodiments, the present invention relates to a stepwise method of differentiation of pluripotent cells comprising culturing Stage 4, 5 and 6 cells at the air-liquid interface. In certain embodiments, cells cultured during Stages 4 through 7 may be cultured at the air-liquid interface. In other embodiments, only late Stage 4 to Stage 6 cells, or Stage 5 and Stage 6 cells, are cultured at the air-liquid interface or in suspension. In yet another alternative embodiment, Stage 1 through 4 are carried out by culturing the cells in planar cultures, and Stage 5 through Stage 7, or Stage 6 through Stage 7, or only Stage 7 are carried out by culturing in suspension culture.

Additionally, culturing during one, or all of Stages 5, 6 and 7 is carried out in the presence of one or more of T3, T4, their analogues and an ALK5 inhibitor, or one or more of T3, T4 and their analogues; or an ALK5 inhibitor. In preferred embodiments, culturing during one or more, and preferably all of Stages 5, 6 and 7 is carried out in the presence of T3 and an ALK5 inhibitor and more preferably in the presence of T3 and ALK5 inhibitor II. In more preferred embodiments, culturing during Stage 7 is carried out in the presence of T3 at low concentration. In preferred embodiments, culturing during Stage 7 is carried out with no ALK5 inhibitor included.

When cells are cultured at the air-liquid interface ("ALI"), the cells may be cultured on a porous substrate such that the cells are in contact with air on the top side and with cell culture media at the bottom side. For example, a sufficient volume of media may be added to the bottom of a culture vessel containing the porous substrate (e.g. a filter insert) such that the media contacts the bottom surface of cells residing on the substrate but does not encapsulate or submerge them. Suitable porous substrates can be formed of any material that will not adversely affect the growth and differentiation of the cells. Exemplary porous substrates are made of polymers such as polyethylene terephthalate ("PET"), polyester or polycarbonate. Suitable porous substrates may be coated or uncoated. In one embodiment, the coating may be MATRIGEL™. In another embodiment of the invention, the porous substrate is a porous filter insert, which may be coated with MATRIGEL™. In another embodiment of the invention, the porous substrate is an uncoated filter insert. The porosity of the substrate should be sufficient to maintain cell viability and promote differentiation of the cells.

Culturing of the cells at the air-liquid interface includes seeding the cells on a porous substrate such as a porous filter insert. In certain embodiments, the substrate pore size may range from about 0.3 to about 3 microns. Seeding may be accomplished by releasing cells as single cells from monolayer cultures or clusters of cells from monolayer cultures into a suspension and subsequently aliquoting the single cell suspension or suspended cell culture onto a porous substrate at the ALI. The cells may be seeded onto the porous substrate from a suspension having about 1000 cells/µl to about 100,000 cells/µl. The cells may be seeded as droplets of the cell suspension containing individual cells or aggregates or clusters of cells. In certain embodiment, the cells may be cultured at the air-liquid interface using the methods disclosed in U.S. Patent App. Pub. No. 2014/0186305, the disclosure of which is herein incorporated as it pertains to the culturing and differentiating pluripotent stem cells at the air liquid interface.

The media may be exchanged or refreshed every other day or, preferably, daily. The cells grown on top of the porous substrate are generally not single cells, but rather they are in the form of a sheet or exist as an aggregate cell cluster. Cells cultured at the ALI may experience higher oxygen tension as compared to cells submerged in media.

In certain embodiments, the methods of the invention may be carried out by culturing and differentiating the cells as clusters in a suspension culture. Exemplary suitable methods for the suspension culture and differentiation of pluripotent stem cells are disclosed in U.S. Patent App. Pub. Nos. 2014/0242693 and 2014/0295552, the disclosures of which are herein incorporated as it pertains to the culturing and differentiating pluripotent stem cells using suspension clusters. In particular embodiments, the present invention provides an in vitro cell culture including differentiating cells prepared as aggregated cells such as cell clusters comprising seeding cells in a culture vessel that facilitates aggregation of cells, or forming cell clusters, with a growth medium (culture medium) such that the cells are induced to aggregate and form clusters. In embodiments, the vessel useful for inducing aggregation of cells is a plate with wells or microwells, such as AGGREWELL™ plates. The resulting aggregated cells or cell clusters are further cultured in suspension (suspension culture), comprising removing the aggregated cells/cell clusters from the microwells and seeding them in a suspension culture vessel such that the aggregated cells are differentiated in suspension.

Embodiments of the present invention encompass formation of late Stage 4 to 7, preferably Stage 5 to 7 cells, at the air-liquid interface or in suspension. The cells may be formed by differentiating pluripotent stem cells or by further differentiating Stage 3, 4, 5 or 6 cells. Stage 4 cells may be cultured entirely at the air-liquid interface or the cells may be cultured in submerged planar culture during the early portion of Stage 4, (about one to two days) and then cultured at the air-liquid interface or in suspension for the latter portion of Stage 4 (about day two to day three). Preferably, Stage 4 is not carried out at the ALI, or in suspension, but rather in submerged culture.

In one embodiment, the present invention provides a method for producing cells expressing markers characteristic of functional beta-cells from pluripotent stem cells, comprising: culturing pluripotent stem cells; differentiating the pluripotent stem cells into cells expressing markers characteristic of the pancreatic endoderm; and differentiating the cells expressing markers characteristic of the pancreatic endoderm into cells expressing markers characteristic of the pancreatic endocrine cells by culturing, at the air-liquid interface or in suspension. The method may include treatment with a medium supplemented with: (i) T3, T4 or their analogues; (ii) an ALK5 inhibitor; or both (i) and (ii). The method may include differentiating the cells expressing markers characteristic of foregut endoderm cells (Stage 3 cells) into cells expressing markers characteristic of pancreatic endoderm cells (Stage 4 cells) by treatment with a medium supplemented with: (i) one or both of T3, T4 or their analogues; (ii) ALK5 inhibitor; or both (i) and (ii); and culturing in a planar culture. The method may also include differentiating cells expressing markers characteristic of pancreatic endoderm cells (Stage 4 cells) into cells expressing markers characteristic of the immature beta-cells (Stage 6 cells) by treatment with a medium supplemented with: (i) one or both of T3, T4 or their analogues; (ii) ALK5 inhibitor; or both (i) and (ii); and culturing in a planar culture or culturing at the air-liquid interface or in suspension. The method further includes differentiating Stage 6 cells into cells expressing markers characteristic of functional beta-cells and that have a more matured phenotype as compared to Stage 6 (Stage 7 cells) by treatment with a medium supplemented with: (i) one or both of T3, T4 or their analogues; (ii) ALK5 inhibitor; or both (i) and (ii); along with an one or more of an aurora kinase inhibitor, an RSK inhibitor, and an inhibitor of protein methyltransferase DOT1L and, optionally an anti-oxidant such as vitamin E or acetyl cysteine. The preferred amount of acetyl cysteine that is useful is about 0.1 to about 2 mM. The preferred amount of vitamin E is about 0.1 to about 10 In yet another embodiment, the method further includes carrying out Stage 6 by treatment of Stage 5 cells with a medium supplemented with: (i) one or both of T3, T4 or their analogues; (ii) ALK5 inhibitor or; both (i) and (ii); along with one or more of a gamma secretase inhibitor, an RSK inhibitor and an inhibitor of protein methyltransferase DOT1L. In still another embodiment, Stage 6 is carried out by treatment of Stage 5 cells with a medium supplemented with: (i) one or both of T3, T4 or their analogues; (ii) ALK5 inhibitor; or both (i) and (ii); along with one or more of a gamma secretase inhibitor, an RSK inhibitor and an inhibitor of protein methyltransferase DOT1L followed by carrying out Stage 7 by treatment with a medium supplemented with: (i) one or both of T3, T4 or their analogues; (ii) ALK5 inhibitor; or both (i) and (ii); along with an one or more of an aurora kinase inhibitor, an RSK inhibitor, an inhibitor of protein methyltransferase DOT1L and, optionally anti-oxidant such as vitamin E or acetyl cysteine.

One embodiment of the invention is a method of forming functional beta-cells (pancreatic endocrine cells expressing markers characteristic of a matured phenotype) (Stage 7 cells) comprising differentiating cells expressing markers characteristic of the pancreatic endoderm cells (Stage 4 cells) into cells expressing markers characteristic of Stage 7 cells by culturing at the air-liquid interface or in suspension. A cell expressing markers characteristic of functional beta-cells of a more matured phenotype expresses PDX1 and at least one of the following transcription factors: NKX2.2, NKX6.1, NeuroD1, ISL1, HNF3β, MAFA, UCN3, SLC2A1, PAX4, HB9 and PAX6. In one embodiment, the methods of the invention result in the formation of Stage 6 cells, which are positive for NKX6.1, PDX1, HB9 and MAFA. Preferably, at least during Stages 5 through 7, the method includes treatment with a medium supplemented with T3, T4 or an analogue thereof, an ALK5 inhibitor, or both. The Stage 6 cells may be cells that are positive for NKX6.1, PDX1, HB9 and MAFA. In other embodiments, the Stage 6 or 7 cells are single hormone positive cells. For example, the Stage 6 and 7 cells may be cells that: (a) co-express NKX6.1 and chromogranin; (b) co-express NKX6.1 and insulin; or (c) co-express NKX6.1, PDX1, MAFA and single hormonal insulin. The Stage 7 cells express single hormonal insulin and MAFA at increased levels and increased numbers of cells within a cell population as compared to Stage 6 cells.

In another embodiment, the invention provides a method of enhancing the number of single hormone positive cells (e.g. cells that co-express NKX6.1 and insulin or cells that co-express NKX6.1 and chromogranin) by culturing and differentiating a population of PDX1 and NKX6.1 co-expressing cells, preferably at an air-liquid interface or in suspension. In another embodiment, pancreatic endoderm cells cultured at the air-liquid interface or in suspension are further differentiated to functional beta-cells by treatment with a compound selected from the following: ALK5 inhibitor, BMP inhibitor, gamma-secretase inhibitor, Ephrin ligands, EphB inhibitor, PKC inhibitor, EGFr inhibitor, retinoic acid, vitamin C, T3/T4, glucose, cell cycle regulators, WNT regulators, SHH inhibitor, aurora inhibitor, antioxidants, vitamin E, acetyl-cysteine, or combinations thereof.

In further embodiments, the present invention relates to a stepwise method of differentiating pluripotent cells that includes culturing Stage 4 through Stage 6 cells in a media containing sufficient amounts of: (i) one or more of T3, T4 and their analogues; (ii) an ALK5 inhibitor; or both (i) and (ii); and further culturing the Stage 6 cells in a media that optionally contains one or more of an aurora kinase inhibitor, an RSK inhibitor, and an inhibitor of protein methyltransferase DOT1L, and an antioxidant to generate functional beta-cells (pancreatic endocrine cells of a matured phenotype) and populations of functional beta-cells that express insulin, PDX1, NKX6.1, UCN3, SLC2A1 and MAFA.

Stage 6 and 7 cells generated according to the methods described herein are also well-suited for use in screening compounds for their effect on the secretion of pancreatic hormones and endocrine markers. In particular, Stage 4 through Stage 7 cells cultured at ALI, or in suspension culture, can be tested in different culture formats from 384 to 6-well formats. Such formats allow for evaluation of a variety of small molecules or biologics at various doses and time intervals on subsequent expression of pancreatic endoderm, pancreatic endocrine precursor, pancreatic endocrine, and pancreatic beta cell markers. Such an evaluation may be accomplished by measuring gene expression by PCR, protein expression by FACS or immune staining, or by ELISA for secretion of factors by cells affected by addition of small molecules/biologics.

Cells Obtainable by the Methods of the Invention.

The invention provides for Stage 7 cells or a population of Stage 7 cells obtainable by a method of the invention. In certain embodiments, the cells or cell populations are not purified after differentiation. In certain embodiments, these Stage 7 cells express single hormonal insulin and are PDX1, NKX6.1, UCN3, SLC2A1 and MAFA positive; in addition these cells have a higher level of expression of MAFA than the Stage 6 cells. The cells express UCN3 at a higher level than Stage 6 cells (immature beta-cells). The resulting cell population has a higher percentage of both MAFA positive and single hormonal insulin-expressing cells than the Stage 6 cells. The invention also provides an insulin positive cell or population of insulin positive cells, expressing markers characteristic of functional beta-cells (pancreatic endocrine cells of a matured phenotype), characterized by NKX6.1 expression (preferably greater than about 30%), PDX1 expression (preferably greater than about 30%), UCN3 expression (preferably greater than about 10%), SLC2A1 expression (preferably greater than about 10%), and MAFA expression (preferably greater than about 10%).

In embodiments of the invention, the Stage 7 cells or cell populations are insulin producing cells or a population of insulin producing cells. The insulin producing cells are functionally mature beta cells that exhibit mitochondrial respiration/activity and GSIS response to glucose similar to human islet cells. In embodiments of the invention, functionally mature beta cells are generated in suspension culture.

In embodiments, the functional beta-cell exhibits glucose-stimulated insulin secretion and glucose-dependent mitochondrial respiration. In embodiments, the glucose-stimulated insulin secretion and glucose-dependent mitochondrial respiration is similar to that of human islet cells. In embodiments of the invention, the functional beta-cell secretes insulin in multiple phases.

In the embodiments, the glucose-dependent mitochondrial respiration has a maximum oxygen consumption rate response following glucose stimulation in the range of about 20% to about 80% over basal oxygen consumption rate, preferably about 20% to about 70%, 20% to about to about 60%, more preferably about 20%, about 25%, about 30%, about 35%, about 40%, about 45%, about 50%, about 55%, about 60%, about 65%, about 70%, about 75% or about 80%. In embodiments, the oxygen consumption rate response occurs at least 10 minutes to about 15 minutes following glucose stimulation, preferably about 10 minutes, about 11 minutes, about 12 minutes, about 13 minutes, about 14 minutes, about 15 minutes. In embodiments, the higher oxygen consumption rate over basal OCR is maintained for at least 60 minutes to at least 80 minutes, preferably at least 70 minutes to at least 80 minutes, more preferably at least 70, 71, 72, 73, 74, 75, 76, 77, 78, 79 or 80 minutes.

In the embodiments above, the glucose-stimulated insulin secretion comprises a rapid, bi-phasic insulin secretion in response to glucose stimulation. In embodiments, a first phase of the bi-phasic insulin secretion has at least a four-fold increase to at least an eight-fold increase over baseline secretion, preferably at least a four-fold increase, a five-fold increase, a six-fold increase, a seven-fold increase, or an eight-fold increase over baseline secretion. In embodiments, a second phase of the bi-phasic insulin secretion has at least a two-fold to at least a four-fold increase over baseline secretion, preferably at least a two-fold increase, a three-fold increase or a four-fold increase over baseline secretion. In embodiments, the insulin secretion occurs at least five minutes to at least ten minutes following glucose stimulation, preferably at least 5 minutes, at least 6 minutes, at least 7 minutes, at least 8 minutes, at least 9 minutes or at least 10 minutes following glucose stimulation.

Tables A and B illustrate exemplary culture conditions suitable for use in embodiments of methods of the invention. As used in Tables A and B below, "MCX" is MCX compound, "AA" is activin, "ALK5 inh." is ALK5 inhibitor, "RA" is retinoic acid, "Vit. C" is ascorbic acid, "inh." is inhibitor, and "act." is activator. In certain embodiments, any one of the treatments at one stage (e.g. any one of Stage 1, 2, 3, 4, 5, 6 or 7) may be combined with any one of the treatments at another stage (e.g. any one of Stage 1, 2, 3, 4, 5, 6 or 7). In other embodiments, Stage 4 cells obtained by methods different from those in Table A may be differentiated into Stage 5 to Stage 7 cells using the culture conditions shown in Table B. In other embodiments, Stage 5 cells obtained by methods different from those in Tables A and B may be differentiated into Stage 6 or Stage 7 cells using the culture conditions shown in Table B. In yet other embodiments, Stage 6 cells obtained by methods different from those in Tables A and B may be differentiated into Stage 7 cells using the culture conditions shown in Table B.

TABLE A

Exemplary culture conditions to obtain Stage 1 to Stage 4 cells according to embodiments of the invention

|  | Stage 1 | Stage 2 | Stage 3 | Stage 4 |
|---|---|---|---|---|
| Treatment of | Pluripotent stem cells | Stage 1 cells | Stage 2 cells | Stage 3 cells |
| With at least | AA & Wnt3A GDF8 & MCX | | | |
|  |  | FGF7 | | |
|  |  | FGF7 & Vit. C | | |
|  |  |  | SANT-1, RA & noggin | |
|  |  |  | FGF7, retinoic acid, SANT-1, a PKC act. (e.g. TPB), a BMP inh. (e.g. LDN-193189), & Vit. C | |
|  |  |  | FGF7, retinoic | |

TABLE A-continued

Exemplary culture conditions to obtain Stage 1 to Stage 4 cells according to embodiments of the invention

|  | Stage 1 | Stage 2 | Stage 3 | Stage 4 |
|---|---|---|---|---|
|  |  |  | acid, SANT-1, a PKC act. (e.g. TPB) & Vit. C | FGF7, retinoic acid, SANT-1, a PKC act.(e.g. TPB), a BMP inh. (e.g. LDN-193189), & Vit. C |
| Other optional components | 0.5% FAF-BSA | 0.5% FAF-BSA |  | BLAR medium 2% FAF-BSA |
| Duration of Treatment | Approximately 2-5 days; preferably about 3-4 days | Approximately 2-3 days; preferably about 2 days; preferably about 3 days when AA & Wnt3A at Stage 1 | Approximately 2-4 days, preferably about 2 days | Approximately 2-4 days, preferably about 3 days |
| Culture condition | Planar Culture or cell clusters (suspension culture) (roller bottles) | Planar Culture or cell clusters (roller bottles) | Planar Culture or cell clusters (roller bottles) | Planar Culture optionally cells at end of Stage 4 are seeded at the ALI using Y-compound alternatively cells are transitioned to clusters; cell clusters or roller bottles |

TABLE B

Exemplary culture conditions to obtain Stage 5 to Stage 7 cells according to embodiments of the invention

|  | Stage 5 | Stage 6 | Stage 7 |
|---|---|---|---|
| Treatment of With at least | Stage 4 cells SANT-1, a PKC act. (e.g. TPB), a BMP inh. (e.g. LDN-193189), Vit C, an ALK5 inh. (e.g. ALK5 inh. II), T3 SANT-1, a PKC act. (e.g. TPB), a BMP inh. (e.g. LDN-193189), an ALK5 inh. (e.g. ALK5 inh. II), T3 | Stage 5 cells BMP inh. (e.g. LDN-193189), an ALK5 inh. (e.g. ALK5 inh. II), T3, gamma secretase inh., heparin BMP inh. (e.g. LDN-193189), Vit C, an ALK5 inh. (e.g. ALK5 inh. II), T3, gamma secretase inh., heparin | Stage 6 cells T3, N-Acetyl Cysteine, ZM447439, heparin, ± ALK5 T3, N-Acetyl Cysteine, ZM447439, heparin, ALK5 + one of: UNC0638, UNC0642, TC-E5003, A366, PF03814735 SB747651, PFI1, LY303511, MS436 or MC1568 T3, N-Acetyl Cysteine, ZM447439, heparin, no |

TABLE B-continued

Exemplary culture conditions to obtain Stage 5 to Stage 7 cells according to embodiments of the invention

| | Stage 5 | Stage 6 | Stage 7 |
|---|---|---|---|
| Other optional components | Replace T3 with T4 or thyroid hormone analogue ZnSO$_4$ | ZnSO$_4$ | ALK5 + one of: UNC0638, UNC0642, TC-E5003, A366, PF03814735 SB747651, PFI1, LY303511, MS436 or MC1568 no ALK5, low T3, ZM, H, NAC no ALK5, low T3, ZM, H, NAC, AZT & DEZA ZnSO$_4$ an ALK5 inh. Replace T3 with T4 or thyroid hormone analogue AZT DEZA |
| Duration of Treatment | Approximately 2-4 days, preferably about 3 days | Approximately 6-8 days, preferably about 7 days | Approximately 6-7 days; alternatively approximately 7-14 days; alternatively about 7-23 days |
| Culture condition | ALI or cell clusters (suspension culture) (roller bottles) | ALI or cell clusters (roller bottles) | ALI or cell clusters (roller bottles) |

Publications cited throughout this document are hereby incorporated by reference in their entirety. The present invention is further illustrated, but not limited, by the following non-limiting examples.

EXAMPLES

The suppliers of the materials and compounds used in the following examples are identified in Table X.

Example 1

Screening and Identification of Small Molecules that Upregulate MAFA or UCN3 Expression The following example is directed to identification of small molecules that can enhance the maturation status of a pancreatic beta cell, via increasing the gene expression of mature beta cell markers including MAFA (v-maf avian musculoaponeurotic fibrosarcoma oncogene homolog A) or UCN3 (urocortin 3). Cells of the human embryonic stem cell line H1 ("H1-hESC") with EZ8 media at passage 28 were seeded as single cells at 0.094×10$^6$ cells/cm$^2$ on MATRIGEL™ at a 1:30 dilution on coated dishes in a media of Dulbecco's Modified Eagle's Medium Nutrient mixture F-12 ("DMEM-F12"), GlutaMAX™ in a 1:100 dilution ("1x concentration"), 0.25 mM ascorbic acid, 100 ng/ml fibroblast growth factor 2 ("FGF2"), 1 ng/ml of transforming growth factor beta ("TG93"), insulin-transferrin-selenium-ethanolamine ("ITS-X") at a 1:100 dilution, 2% fatty-acid free bovine serum albumin ("FAF-BSA"), and 20 ng/ml of insulin-like growth factor-1 ("IGF-1"), supplemented with 10 μM of Rock Inhibitor Y-27632 ("Y-compound"). Y-compound was added to only during the first 24 hours post-seeding. Forty-eight hours post-seeding, the cultures were washed in incomplete PBS (phosphate buffered saline without magnesium or calcium).

For FIGS. 1A to 1H the cultures were differentiated using the following protocol. During Stages 1 through 4 of the protocol, cultures were maintained on planar adherent cultures.

Stage 1 (3 Days):

Cells were cultured for one day in the following Stage 1 media: MCDB-131 medium containing 2.7 g/1000 ml sodium bicarbonate (Sigma-Aldrich Co. LLC, St. Louis, Missouri, Catalog No. 5761), and supplemented with 0.5% FAF-BSA, GlutaMAX™ in a 1:100 dilution ("1x concentration"), 4.5 mM D-glucose to obtain a concentration of 10 mM of D-glucose, 100 ng/ml growth differentiation factor 8 ("GDF8"), and 1.5 μM of a 14-Prop-2-en-1-yl-3,5,7,14,17, 23,27-heptaazatetracyclo [19.3.1.1~2,6~.1-8,12~]hepta-cosa-1(25),2(27),3,5,8(26),9,11,21,23-nonaen-16-one ("MCX compound"). Cells were then cultured for an additional day in MCDB-131 medium containing 2.7 g/1000 ml sodium bicarbonate, and supplemented with 0.5% FAF-BSA, 1x concentration of GlutaMAX™, 4.5 mM D-glucose to obtain a concentration of 10 mM D-glucose, 100 ng/ml GDF8, and 0.1 μM MCX compound. Cells were then cultured for an additional day in MCDB-131 containing 2.7 g/1000 ml sodium bicarbonate, and supplemented with 0.5% FAF-BSA, 1x concentration of GlutaMAX™, 4.5 mM D-glucose to obtain a concentration of 10 mM D-glucose, and 100 ng/ml GDF8.

Stage 2 (2 Days):

Cells were treated for two days with MCDB-131 medium containing 2.7 g/1000 ml sodium bicarbonate, and supplemented with 0.5% FAF-BSA, 1x GlutaMAX™, 4.5 mM D-glucose to obtain a concentration of 10 mM D-glucose, 0.25 mM Ascorbic acid, and 50 ng/ml fibroblast growth factor 7 ("FGF7").

Stage 3 (2 Days):

Cells were treated for two days with BLAR001 custom medium (see Table I) containing 3.6 g/1000 ml sodium bicarbonate, and supplemented with a 1:200 dilution of ITS-X; 4.5 mM D-glucose to obtain a concentration of 10 mM D-glucose; 1× GlutaMAX™; 2% FAF-BSA; 25 ng/ml FGF7; 0.25 µM SANT-1 (N-[(3,5-dimethyl-1-phenyl-1H-pyrazol-4-yl)methylene]-4-(phenylmethyl)-1-piperazineamine); 1 µM retinoic acid ("RA"); 0.25 mM ascorbic acid; 300 nM of the PKC activator ((2S, 5S-(E,E)-8-(5-(4-trifluoromethyl)phenyl-2,4,-pentadienoylamino)benzolactam ("TPB"); and the bone morphogenic protein ("BMP") receptor inhibitor LDN-193189-HCl ("LDN-HCl") for two days. The concentration of LDN-HCl used for the first day of stage 3 was 100 nM, and for the second day of stage 3 was 10 nM.

Stage 4 (3 Days):

Cells were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1× concentration of GlutaMAX™; 2% FAF-BSA; 0.25 µM SANT-1; 50 nM RA; 2 ng/ml FGF7; 50 nM LDN-HCl; 0.25 mM ascorbic acid; and 200 nM TPB for three days. At the end of Stage 4 (3 days), cells cultured on planar dishes were seeded on an air-liquid-interface ("ALI"). Specifically, cells were treated for 4 hours with 10 µM of Y-27632, rinsed with PBS and treated for approximately 2 minutes with the enzyme TrypLE™ Express Enzyme at a concentration of 1× followed by removal of the enzyme, and removal of the cells from the on MATRIGEL™ surface by gentle tapping of the flask. The resulting suspension of cells were seeded at a density of 0.5-1.0×10⁶ cells (in 5 µl aliquots) on either 0.4 micron or 3.0 micron porous cell culture filter inserts on 10 cm plates. 8.0 ml of media was added to the bottom of each insert and no further media was added to the apical, or top, side of the filter. The media was replaced daily for the duration of Stages 5, 6, and 7.

Stage 5 (3 Days):

Cells were treated on the ALI with BLAR001 medium containing 2.7 g/1000 ml sodium bicarbonate, and supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 0.25 µM SANT-1; 50 nM RA; 100 nM LDN-HCl; 1 µM of T3 in the form of 3,3', 5-triiodo-L-thryonine sodium salt; 10 µM of 2-(3-(6-Methylpyridin-2-yl)-1H-pyrazol-4-yl)-1,5-naphthyridine ("ALK5 inhibitor II" or "ALK5") for three days.

Stage 6 (7 Days):

Cells were treated on the ALI with BLAR001 medium containing 2.7 g/1000 ml sodium bicarbonate, and supplemented with a 1:200 dilution of ITS-X; 14.5 mM D-glucose to achieve a final concentration of 20 mM D-glucose; 1× GlutaMAX™; 2% FAF-BSA; 10 µg/ml of heparin; 10 µM ZnSO$_4$; 100 nM LDN-HCl; 1 µM of T3; 10 µM ALK5 inhibitor II; and 100 nM (S,S)-2-[2-(3,5-Difluorophenyl)acetylamino]-N-(5-methyl-6-oxo-6,7-dihydro-5H-dibenzo[b,d]azepin-7-yl)propionamide ("gamma secretase inhibitor XX") for seven days.

Stage 7 (7 Days):

Cells were treated on the ALI with BLAR001 medium containing 2.7 g/1000 ml sodium bicarbonate, and supplemented with a 1:200 dilution of ITS-X; 1× GlutaMAX™; 2% FAF-BSA; 10 µg/ml of heparin ("H"); 10 µM ZnSO$_4$; 1 µM of T3; 10 µM of ALK5 inhibitor II; 1 mM N-Acetyl cysteine ("NAC").

In addition, during Stage 7 (S7), for FIGS. 1A-1H, the cells were conditioned at 20 mM D-glucose plus BME Vitamin supplement (1:100 dilution of 100×) and exposed to all 79 small molecules as listed and described in Table XI. Of the 79 small molecules, the following compounds induced expression of the MAFA or UCN3: (i) Zebularine; (ii) Lomeguatrib; (iii) 5-Azacytidine; (iv) Mitoxantrone dihydrochloride; (v) EGCG; (vi) Fisetin; (vii) SGI 1027; (viii) Temozolomide; (ix) L002; (x) C646; and (xi) SGC0946.

Figure 2A:
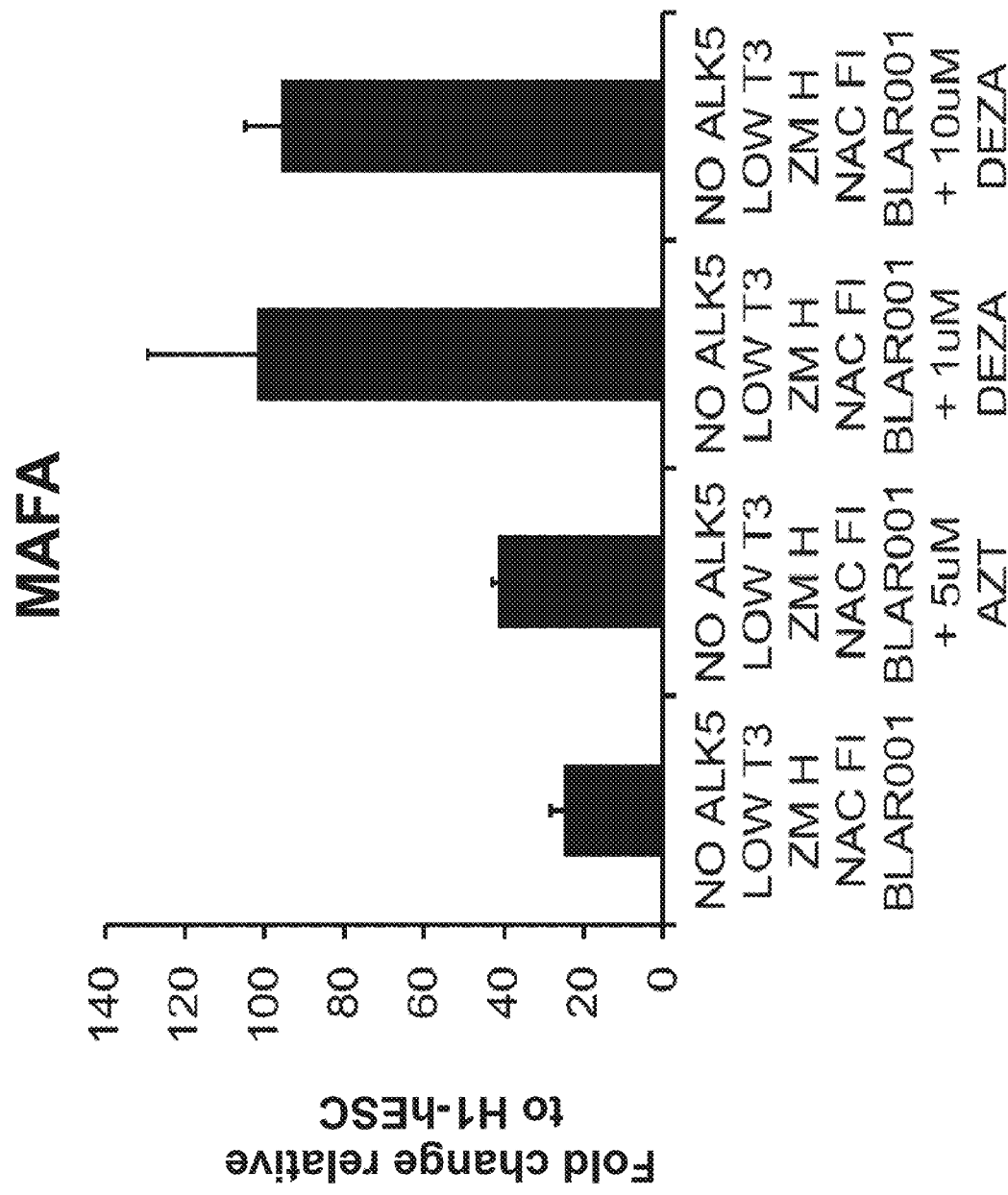
FIGS. 2A and 2B demonstrate the robustness of selected small molecules as either MAFA or UCN3 up-regulators, as their effect was maintained across different Stage 7 conditioning protocols. 3-Deazaneplanocin A ("DEZA") was found to be an effective up-regulator of MAFA, but not UCN3 (FIG. 2A). AZT was confirmed as an UCN3, but not MAFA, up-regulator during Stage 7 (FIG. 2B). All conditions S7D7; ALI clusters.
Figure 2B:
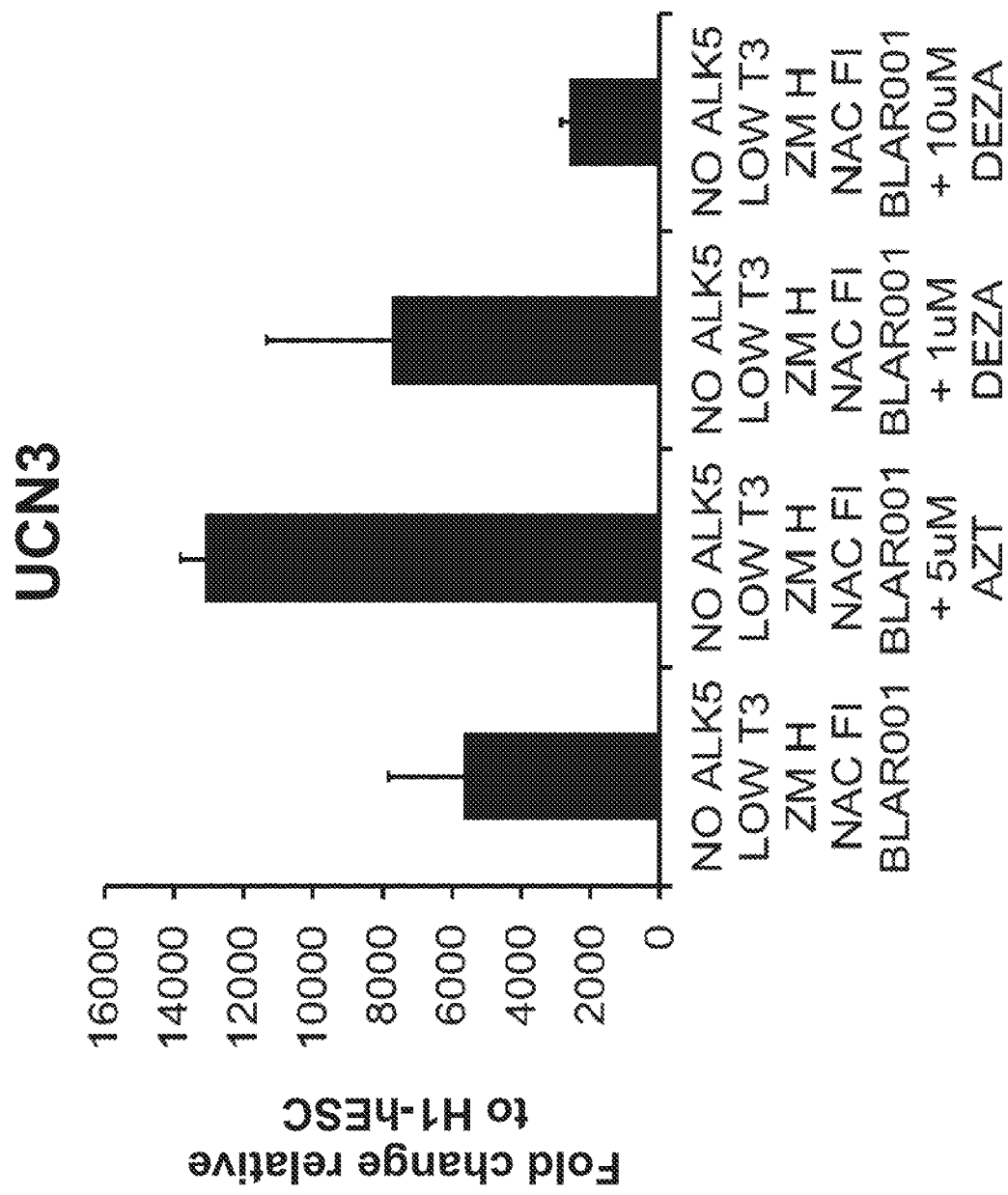

For FIGS. 2A to 2B the cultures were differentiated using the following protocol: during Stages 1 through 4 of the protocol, cultures were maintained on planar adherent cultures.

Stage 1 (3 Days):

Cells were cultured for one day in the following Stage 1 media: MCDB-131 medium containing 2.7 g/1000 ml sodium bicarbonate, and supplemented with 0.5% FAF-BSA, GlutaMAX™ in a 1:100 dilution ("1× concentration"), 4.5 mM D-to obtain a concentration of 10 mM of D-glucose, 100 ng/ml growth differentiation factor 8 ("GDF8"), and 1.5 µM of a 14-Prop-2-en-1-yl-3,5,7,14,17, 23,27-heptaazatetracyclo [19.3.1.1~2,6~.1~8,12~]heptacosa-1(25),2(27),3,5,8(26),9,11,21,23-nonaen-16-one ("MCX compound"). Cells were then cultured for an additional day in MCDB-131 medium containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, 100 ng/ml GDF8, and 0.1 µM MCX compound. Cells were then cultured for an additional day in MCDB-131 containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, and 100 ng/ml GDF8.

Stage 2 (2 Days):

Cells were treated for two days with MCDB-131 medium containing 2.7 g/1000 ml sodium bicarbonate, and supplemented with 0.5% FAF-BSA, 1× GlutaMAX™, 4.5 mM D-glucose to obtain a concentration of 10 mM D-glucose, 0.25 mM Ascorbic acid, and 50 ng/ml Fibroblast growth factor 7 ("FGF7").

Stage 3 (2 Days):

Cells were treated for two days with BLAR001 custom medium containing 3.6 g/1000 ml sodium bicarbonate, and supplemented with a 1:200 dilution of ITS-X; 4.5 mM D-glucose to obtain a concentration of 10 mM D-glucose; 1× GlutaMAX™; 1% FAF-BSA; 25 ng/ml FGF7; 0.25 µM SANT-1 (N-[(3,5-dimethyl-1-phenyl-1H-pyrazol-4-yl) methylene]-4-(phenylmethyl)-1-piperazineamine); 1 µM retinoic acid ("RA"); 0.25 mM ascorbic acid; 300 nM of the PKC activator ((2S, 5S-(E,E)-8-(5-(4-trifluoromethyl)phenyl-2,4,-pentadienoylamino)benzolactam ("TPB"); and the bone morphogenic protein ("BMP") receptor inhibitor LDN-193189-HCl ("LDN-HCl") for two days. The concentration of LDN-HCl used for the first day of stage 3 was 100 nM, and for the second day of stage 3 was 50 nM.

Stage 4 (3 Days):

Cells were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1× concentration of GlutaMAX™; 1% FAF-BSA; 0.25 µM SANT-1; 50 nM RA; 2 ng/ml FGF7; 70 nM LDN-HCl; 0.25 mM ascorbic acid; and 200 nM TPB for three days. At the end of Stage 4 (3 days), cells cultured on planar dishes were seeded on an air-liquid-interface ("ALI"). Specifically, the cells were treated for 4 hours with 10 µM of Y27632, rinsed with PBS and treated for approximately 2 minutes with the enzyme TrypLE™ Express Enzyme at a concentration of 1× followed by removal of the enzyme, and removal of the cells from the on MATRIGEL™ surface by gentle tapping of the flask. The resulting suspension of cells were seeded at a density of 0.5-1.0×10⁶ cells (in 5 μl aliquots) on either 0.4 micron or 3.0 micron porous cell culture filter inserts in 10 cm plates. 8.0 ml of media was added to the bottom of each insert and no further media was added to the apical, or top, side of the filter. The media was replaced daily for the duration of Stages 5, 6, and 7.

Stage 5 (3 Days):

Cells were treated on the ALI with BLAR001 medium containing 2.7 g/1000 ml sodium bicarbonate, and supplemented with a 1:200 dilution of ITS-X; 14.5 mM D-glucose to achieve a final concentration of 20 mM D-glucose; 1× GlutaMAX™; 2% FAF-BSA; 10 μg/ml of heparin ("H"); 10 μM $ZnSO_4$; 0.25 μM SANT-1; 50 nM RA; 100 nM LDN-HCl; 1 μM of T3 in the form of 3,3', 5-triiodo-L-thryonine sodium salt; 10 μM of 2-(3-(6-Methylpyridin-2-yl)-1H-pyrazol-4-yl)-1,5-naphthyridine ("ALK5 inhibitor II" or "ALK5") for three days.

Stage 6 (7 Days):

Cells were treated on the ALI with BLAR001 medium containing 2.7 g/1000 ml sodium bicarbonate, and supplemented with a 1:200 dilution of ITS-X; 14.5 mM D-glucose to achieve a final concentration of 20 mM D-glucose; 1× GlutaMAX™; 2% FAF-BSA; 10 μg/ml of heparin ("H"); 10 μM $ZnSO_4$; 100 nM LDN-HCl; 1 μM of T3; 10 μM ALK5 inhibitor II; and 100 nM (S,S)-2-[2-(3,5-Difluorophenyl)acetylamino]-N-(5-methyl-6-oxo-6,7-dihydro-5H-dibenzo[b,d]azepin-7-yl)propionamide ("gamma secretase inhibitor XX") for seven days.

Stage 7 (7 Days):

Cells were treated on the ALI with BLAR001 medium containing 2.7 g/1000 ml sodium bicarbonate, and supplemented with a 1:200 dilution of ITS-X; 1× GlutaMAX™; 2% FAF-BSA; 10 μg/ml of heparin ("H"); 10 nM of T3 ("low T3"); 1 mM N-Acetyl cysteine ("NAC").

Further for FIGS. 2A and 2B, 0.5 μM of ZM447439 ("ZM"); and the following components which constitute Formulation I ("FI") (Table XII) 1:200 dilution of RPMI vitamin supplement; 1:200 dilution of MEM non-essential amino acid supplement; 1:2000 dilution of chemically defined lipid concentrate; 1:200 dilution of sodium pyruvate; 1:2000 dilution of trace elements A; and 1:2000 dilution of trace elements B were added for seven days. Additional compounds added during Stage 7 included either 5 μM 5-Azacytidine ("AZT"); or 1 μM or 10 μM 3-Deazaneplanocin A ("DEZA").

The embodiments described herein use Applicant's proprietary BLAR media, specifically BLAR001 or BLAR004 media. BLAR media was first described in PCT/US13/75939 and U.S. Ser. No. 13/998,884, both filed on Dec. 18, 2013, which claim the benefit of 61/747,662 filed on Dec. 31, 2012; and then again in Rezania et al. (2014) *Nature Biotech*, 32 (11) 1124-1134, Supplemental Table 3 (published online, Sep. 11, 2014), which references are incorporated herein in their entireties. BLAR001 and BLAR004 are different in the concentrations or levels of the listed agent or excipient.

TABLE I

List of components of BLAR001 medium

| | Concentration (mM) |
|---|---|
| Amino Acids | |
| Glycine | 3.0E−02 |
| Alanine | 3.0E−02 |
| Arginine | 3.0E−01 |
| Aspargine | 1.0E−01 |
| Aspartic Acid | 1.0E−01 |
| Cysteine | 2.0E−01 |
| Glutamic acid | 3.0E−02 |
| Histidine | 1.1E−01 |
| Isoleucine | 1.0E−02 |
| Leucine | 9.0E−02 |
| Lysine hydrochloride | 1.5E−01 |
| Methiane | 3.0E−02 |
| Phenylalanine | 3.0E−02 |
| Proline | 1.0E−01 |
| Serine | 1.0E−01 |
| Theronine | 3.0E−02 |
| Tryptophan | 2.0E−03 |
| Tyrosine disodium | 1.0E−02 |
| Valine | 3.0E−02 |
| Vitamins | |
| Biotin | 3.0E−05 |
| Choline chloride | 5.0E−03 |
| D-Calcium pantothenate | 1.5E−03 |
| Folinic Acid Calcium salt | 2.3E−03 |
| Niacinamide | 4.9E−03 |
| Pyridoxine hydrochloride | 9.7E−04 |
| Riboflavin | 1.0E−05 |
| Thiamine hydrochloride | 3.0E−03 |
| Vitamin B12 | 3.7E−06 |
| i-Inositol | 2.8E−03 |
| Salts/Minerals | |
| Calcium Chloride ($CaCl_2$—$2H_2O$) | 3.0E−01 |
| Cupric sulfate ($CuSO_4$—$5H_2O$) | 4.8E−06 |
| Ferric sulfate ($FeSO_4$—$7H_2O$) | 1.0E−03 |
| Magnesium Sulfate ($MgSO_4$—$7H_2O$) | 4.1E−01 |
| Potassium Chloride (KCl) | 3.8E+00 |
| Sodium Bicarbonate ($NaHCO_3$) | 1.4E+01 |
| Sodium Chloride (NaCl) | 1.1E+02 |
| Sodium Phosphate dibasic ($Na2HPO_4$—$7H_2O$) | 5.0E−01 |
| Zinc Sulfate ($ZnSO_4$—$H_2O$) | 1.0E−04 |
| Other | |
| Adenine | 1.0E−03 |
| D-glucose (Dextrose) | 5.0E+00 |
| Lipoic Acid | 1.2E−05 |
| Phenol Red | 1.0E−02 |
| Sodium Pyruvate | 1.0E+00 |
| Thymidine | 9.8E−05 |

In general, the embodiments herein differentiate human pluripotent cells substantially as described above in Stages 1-7. For Stage 7, various small molecules were added and their effect was evaluated by quantitative real-time PCR. Table II lists the small molecules and their targets. These small molecules were evaluated and 2 μM of each was added at Stage 7. The chemical names and structures of the compounds tested in this Example are shown in Table XI.

TABLE II

Small molecules evaluated

| Molecule Name | Target | Tocris Biosciences Catalog No. |
| --- | --- | --- |
| Zebularine | DNA methyltransferase and cytidine deaminase inhibitor | 2293 |
| Decitabine | DNA methyltransferase inhibitor | 2624 |
| RG 108 | Non-nucleoside DNA methyltransferase inhibitor | 3295 |
| Lomeguatrib | O6-methylguanine-DNA methyltransferase (MGMT) inhibitor | 4359 |
| 5-Azacytidine | DNA methyltransferase inhibitor | 3842 |
| mitoxantrone dihydrochloride | Topoisomerase II inhibitor; immunosuppressive and antineoplastic agent | 4250 |
| EGCG | DNMT1 inhibitor | 4524 |
| Fisetin | DNMT1 inhibitor | 5016 |
| SGI 1027 | DNA methyltransferase inhibitor | 5155 |
| Temozolomide | DNA-methylating antitumor agent | 2706 |
| L002 | p300 inhibitor | 5045 |
| C 646 | Selective p300/CBP HAT inhibitor | 4200 |
| SGC 0946 | Highly potent and selective DOT1L inhibitor; cell permeable | 4541 |
| UNC 0224 | Potent G9a histone lysine methyltransferase inhibitor | 3861 |
| UNC 0638 | Selective G9a and GLP histone lysine methyltransferase inhibitor | 4343 |
| BIX 01294 | G9a-like protein and G9a histone lysine methyltransferase inhibitor | 3364 |
| UNC 0646 | Potent and selective G9a/GLP inhibitor | 4342 |
| UNC 0642 | Potent and selective G9a and GLP histone lysine methyltransferase inhibitor | 5132 |
| TC-E 5003 | Selective PRMT1 arginine methyltransferase inhibitor | 5099 |
| A 366 | Potent and selective G9a/GLP histone lysine methyltransferase inhibitor | 5163 |
| KU 55933 | Potent and selective ATM kinase inhibitor | 3544 |
| KU 60019 | Potent ATM kinase inhibitor | 4176 |
| PF 03814735 | Aurora kinase A and B inhibitor | 4821 |
| ZM 447439 | Inhibits Aurora kinase B | 2458 |
| U0126 | Potent, selective inhibitor of MEK1 and 2 | 1144 |
| SL 327 | Selective inhibitor of MEK1 and MEK2; brain penetrant | 1969 |
| H 89 dihydrochloride | Protein kinase A inhibitor | 2910 |
| SB 747651A dihydrochloride | Potent MSK1 inhibitor; also inhibits other AGC group kinases | 4630 |
| SNS 314 mesylate | Potent pan-Aurora kinase inhibitor | 4584 |
| Kaempferol | RSK2 inhibitor; blocks histone H3Ser10 phosphorylation | 3603 |
| PRT 4165 | Inhibitor of Bmi1/Ring1A; blocks histone H2A ubiquitination | 5047 |
| P 22077 | USP7 inhibitor; blocks deubiquitination of Tip60 (KAT5) histone lysine acetyltransferase | 4485 |
| PFI 1 | BET bromodomain inhibitor | 4445 |
| I-BET 151 hydrochloride | BET bromodomain inhibitor | 4650 |
| LY 303511 | BRD2, BRD3 and BRD4 inhibitor | 2418 |
| MS 436 | Potent and selective BRD4 bromodomain inhibitor | 5173 |
| SGC-CBP 30 | Potent CREBBP/EP300 bromodomain inhibitor | 4889 |
| I-CBP 112 | Selective CREBBP/EP300 bromodomain inhibitor | 4891 |
| Bromosporine | Broad spectrum bromodomain inhibitor | 4758 |
| PFI 3 | Potent and selective SMARCA4 and polybromo 1 inhibitor; also inhibits SMARCA2 | 5072 |
| UNC 926 hydrochloride | L3MBTL1 domain inhibitor | 4516 |
| UNC 1215 | Potent inhibitor of L3MBTL3 Kme reader domain; cell permeable | 4666 |

TABLE II-continued

Small molecules evaluated

| Molecule Name | Target | Tocris Biosciences Catalog No. |
|---|---|---|
| TC-H 106 | Class I histone deacetylase inhibitor | 4270 |
| MC 1568 | Selectively inhibits HDAC class II (IIa) | 4077 |
| Pyroxamide | Histone deacetylase inhibitor | 4403 |
| CI 994 | Histone deacetylase inhibitor | 2952 |
| SBHA | Histone deacetylase inhibitor | 3810 |
| KD 5170 | Histone deacetylase inhibitor | 4001 |
| LMK 235 | Selective HDAC4/HDAC5 inhibitor | 4830 |
| TCS HDAC6 20b | Selective HDAC6 inhibitor | 4805 |
| PCI 34051 | Potent and selective histone deacetylase 8 (HDAC8) inhibitor; induces apoptosis in T cell-derived cell lines | 4643 |
| Scriptaid | Histone deacetylase inhibitor | 2421 |
| NSC 3852 | Histone deacetylase inhibitor | 2521 |
| Sodium 4-Phenylbutyrate | Histone deacetylase inhibitor | 2682 |
| M 344 | Histone deacetylase inhibitor | 2771 |
| Valproic acid, sodium salt | Histone deacetylase inhibitor | 2815 |
| SAHA | Class I and II HDAC inhibitor | 4652 |
| GSK J2 | Inactive isomer of GSK-J1 (Cat. No. 4593) | 4688 |
| GSK J5 | Inactive isomer of GSK J4 (Cat. No. 4594); cell permeable | 4689 |
| GSK J1 | Potent histone demethylase JMJD3/UTX inhibitor | 4593 |
| GSK J4 | Histone demethylase JMJD3/UTX inhibitor; cell permeable | 4594 |
| Daminozide | Selective histone demethylase KDM2/7 subfamily inhibitor | 4684 |
| Tranylcypromine hydrochloride | Irreversible inhibitor of lysine-specific demethylase 1 (LSD1); also inhibits MAO | 3852 |
| RN 1 dihydrochloride | LSD1 inhibitor | 4977 |
| IOX 1 | Histone demethylase inhibitor; cell permeable | 4464 |
| JIB 04 | Pan Jumonji histone demethylase inhibitor; active in vivo | 4972 |
| Sirtinol | Selective sirtuin family deacetylase inhibitor | 3521 |
| Splitomicin | Sir2p inhibitor | 1542 |
| Resveratrol | SIRT1 activator | 1418 |
| EX 527 | Selective SIRT1 inhibitor | 2780 |
| Tenovin-1 | SIRT1 and SIRT2 inhibitor; activates p53 | 3365 |
| Salermide | SIRT1 and SIRT2 inhibitor | 4127 |
| AK 7 | Selective SIRT2 inhibitor; brain penetrant | 4754 |
| 3-Aminobenzamide | PARP inhibitor; demethylates DNA | 0788 |
| PJ 34 hydrochloride | Potent PARP inhibitor; alters epigenetic marks in thyroid cancer cells | 3255 |
| IOX 2 | Potent, selective HIF-1α prolyl hydroxylase-2 (PHD2) inhibitor | 4451 |
| Forskolin | PKA activator; blocks nuclear export of HDAC5 | 1099 |
| Retinoic acid | Endogenous retinoid; alters HDAC-mediated gene repression | 0695 |

Quantification and Characterization of Differentiated Cells:

For quantification of gene expression at various stages, human islets, H1-hESC, Stage 6 day 7 (S6D7), and Stage 7 day 7 to Stage 7 day 14 (S7D7-S7D14) cells were harvested as ALI clusters, substantially as described in Rezania et al. (2014), supra. Gene expression was assessed in cells using custom Taqman Arrays (Applied Biosystems, Foster City, California). Data were analyzed using Sequence Detection Software (Applied Biosystems, Foster City, California), and normalized using GAPDH as a housekeeping gene to undifferentiated H1-hESC using the ΔΔCt method. Primer details are outlined in Table III.

TABLE III

List of RT-qPCR primers.

| Gene | Assay ID |
|---|---|
| MAFA | Hs04419861_sH |
| UCN3 | Hs00846499_s1 |
| GAPDH | Hs99999905_m1 |

FIGS. 1A to 1D are graphs depicting data from quantitative real-time PCR analysis of the expression of MAFA after treatment with small molecules, in which various small molecules increase expression of MAFA compared to S6D7, or untreated or DMSO treated cultures at Stage 7 (S7D7). Addition of UNC0638 (FIG. 1A; selective G9a and GLP histone lysine methyltransferase inhibitor), UNC0646 (FIG.

1A; potent and selective G9a/GLP inhibitor), UNC0642 (FIG. 1A; potent and selective G9a and GLP histone lysine methyltransferase inhibitor), TC-E5003 (FIG. 1B; selective PRMT1 arginine methyltransferase inhibitor), A366 (FIG. 1B; potent and selective G9a/GLP histone lysine methyltransferase inhibitor), PF03814735 (FIG. 1B; Aurora kinase A and B inhibitor), ZM447439 (FIG. 1B; inhibits Aurora kinase B), SB747651A dihydrochloride (FIG. 1B; potent MSK1 inhibitor; also inhibits other AGC group kinases), PFI1 (FIG. 1B; BET bromodomain inhibitor), LY303511 (FIG. 1B; BRD2, BRD3 and BRD4 inhibitor), MS436 (FIG. 1B; Potent and selective BRD4 bromodomain inhibitor), and MC1568 (FIG. 1C; selectively inhibits HDAC class II (IIa)) significantly upregulated the expression of MAFA as compared to S6D7, or untreated or DMSO treated cultures at Stage 7. FIGS. 1E to 1H are graphs depicting data from quantitative real-time PCR analysis of the expression of UCN3 after treatment with small molecules, addition of 5-Azacytidine ("AZT") (FIG. 1E; DNA methyltransferase inhibitor), Pyroxamide (FIG. 1G; histone deacetylase inhibitor), and CI994 (FIG. 1G; histone deacetylase inhibitor) significantly upregulated the expression of UCN3 as compared to S6D7, or untreated or DMSO treated cultures at Stage 7.

FIGS. 2A and 2B demonstrate the robustness of selected small molecules as either MAFA or UCN3 up-regulators, as their effect is maintained across different Stage 7 conditioning protocols.

The culturing conditions shown in FIGS. 2A and 2B differ from FIG. 1 by the following changes in Stage 7 (S7): (i) removal of ALK5 inhibitor II ("ALK5"); (ii) lowering of T3 concentration ("low T3"); (iii) addition of ZM447439 ("ZM"); and (iv) the addition of a cocktail of vitamins, trace elements, lipids, and amino acids (Formulation I Table XII). Specifically, the basal condition tested was: (1) no ALK5 inhibitor II ("ALK5"); (2) low T3; (3) low ZM; (4) low H; (5) low NAC; (6) FI; and BLAR 001. AZT was confirmed as an UCN3 (FIG. 2B), but not MAFA (FIG. 2A), up-regulator during Stage 7. In addition to the small molecules tested, 3-Deazaneplanocin A ("DEZA"; FIG. 2A) was found to be an effective up-regulator of MAFA, but not UCN3 (FIG. 2B), expression, even in the presence of ZM447439.

In summary, this example demonstrates the identification of small molecules that either up-regulate maturation markers MAFA, or UCN3 expression during Stage 7.

Example 2

Generation of Endocrine Cells with Improved Maturation Marker Expression, and with Human-Islet-Similar Glucose-Dependent Mitochondrial Respiration Kinetics on an Air-to-Liquid Interface The following example demonstrates the generation of C-PEPTIDE (short 31 amino acid polypeptide connecting insulin A- and B-chain in pro-insulin molecule) cells that co-express the following maturation markers, PDX1 (Pancreatic and duodenal homeobox 1); NKX6.1 (NK6 homeobox 1); MAFA; UCN3; SLC2A1 (Solute carrier family 2 member 1; also called GLUT1/Glucose transporter 1); and show glucose-dependent mitochondrial respiration kinetics similar to human islet cells. Cells of the human embryonic stem cell line H1 ("H1-hESC") (with EZ8 media at passage 28 were seeded as single cells at $0.094\times10^6$ cells/cm$^2$ on MATRIGEL™ at a 1:30 dilution coated dishes in a media of Dulbecco's Modified Eagle's Medium Nutrient mixture F-12 ("DMEM-F12"), GlutaMAX™ in a 1:100 dilution ("1x concentration"), 0.25 mM ascorbic acid, 100 ng/ml fibroblast growth factor 2 ("FGF2"), 1 ng/ml of transforming growth factor beta ("TGFβ"), insulin-transferrin-selenium-ethanolamine ("ITS-X") at a 1:100 dilution, 2% fatty-acid free bovine serum albumin ("FAF-BSA"), and 20 ng/ml of insulin-like growth factor-1 ("IGF-1"), supplemented with 10 µM of Rock Inhibitor Y-27632 ("Y-compound"). Forty-eight hours post-seeding, the cultures were washed in incomplete PBS (phosphate buffered saline without magnesium or calcium).

For FIGS. 3A-3M, 4A-4E and 5A-5F the cultures were differentiated using the following protocol. During Stages 1 through 4 of the protocol, cultures were maintained on planar adherent cultures.

Stage 1 (3 Days):

Cells were cultured for one day in the following Stage 1 media: MCDB-131 medium containing 2.7 g/1000 ml sodium bicarbonate, and supplemented with 0.5% FAF-BSA, GlutaMAX™ in a 1:100 dilution ("1x concentration"), 4.5 mM D-glucose to obtain a concentration of 10 mM of D-glucose, 100 ng/ml growth differentiation factor 8 ("GDF8"), and 1.5 µM of a 14-Prop-2-en-1-yl-3,5,7,14,17,23,27-heptaazatetracyclo [19.3.1.1~2,6~.1~8,12~]hepta-cosa-1(25),2(27),3,5,8(26),9,11,21,23-nonaen-16-one ("MCX compound"). Cells were then cultured for an additional day in MCDB-131 medium containing 2.7 g/1000 ml sodium bicarbonate, and supplemented with 0.5% FAF-BSA, 1x concentration of GlutaMAX™, 4.5 mM D-glucose to obtain a concentration of 10 mM D-glucose, 100 ng/ml GDF8, and 0.1 µM MCX compound. Cells were then cultured for an additional day in MCDB-131 containing 2.7 g/1000 ml sodium bicarbonate, and supplemented with 0.5% FAF-BSA, 1x concentration of GlutaMAX™, 4.5 mM D-glucose to obtain a concentration of 10 mM D-glucose, and 100 ng/ml GDF8.

Stage 2 (2 Days):

Cells were treated for two days with MCDB-131 medium containing 2.7 g/1000 ml sodium bicarbonate, and supplemented with 0.5% FAF-BSA, 1x GlutaMAX™, 4.5 mM D-glucose to obtain a concentration of 10 mM D-glucose, 0.25 mM ascorbic acid, and 50 ng/ml fibroblast growth factor 7 ("FGF7").

Stage 3 (2 Days):

Cells were treated for two days with BLAR001 custom medium containing 3.6 g/1000 ml sodium bicarbonate, and supplemented with a 1:200 dilution of ITS-X; 4.5 mM D-glucose to obtain a concentration of 10 mM D-glucose; 1x GlutaMAX™; 1% FAF-BSA; 25 ng/ml FGF7; 0.25 µM SANT-1 (N-[(3,5-dimethyl-1-phenyl-1H-pyrazol-4-yl)methylene]-4-(phenylmethyl)-1-piperazineamine); 1 µM retinoic acid ("RA"); 0.25 mM ascorbic acid; 300 nM of the PKC activator ((2S, 5S-(E,E)-8-(5-(4-trifluoromethyl)phenyl-2,4,-pentadienoylamino)benzolactam ("TPB"); and the bone morphogenic protein ("BMP") receptor inhibitor LDN-193189-HCl ("LDN-HCl") for two days. The concentration of LDN-HCl used for the first day of stage 3 was 100 nM, and for the second day of stage 3 was 50 nM.

Stage 4 (3 Days) and ALI-Transition at S4D3:

Cells were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1x concentration of GlutaMAX™; 1% FAF-BSA; 0.25 µM SANT-1; 50 nM RA; 2 ng/ml FGF7; 70 nM LDN-HCl; 0.25 mM ascorbic acid; and 200 nM TPB for three days. At the end of Stage 4 (3 days), cells cultured on planar dishes were seeded on an air-liquid-interface ("ALI"). For the ALI transition, cells were treated for 4 hours with 10 µM of Y-compound, rinsed with PBS and treated for approximately 2 minutes with the enzyme TrypLE™ Express Enzyme at a concentration of 1× followed by removal of the enzyme, and removal of the cells from the on MATRIGEL™ surface by gentle tapping of the flask. The resulting suspension of cells were seeded at a density of 0.5-1.0×10⁶ cells (in 5 µl aliquots) on either 0.4 micron or 3.0 micron porous cell culture filter inserts in 10 cm plates. 8.0 ml of media was added to the bottom of each insert and no further media was added to the apical, or top, side of the filter. The media was replaced daily for the duration of Stages 5, 6, and 7.

Stage 5 (3 Days):

Cells were treated on the ALI with BLAR001 medium containing 2.7 g/1000 ml sodium bicarbonate, and supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 0.25 µM SANT-1; 50 nM RA; 100 nM LDN-HCl; 1 µM of T3 in the form of 3,3', 5-triiodo-L-thryonine sodium salt (Sigma Aldrich, Catalog No. T6397); 10 µM of 2-(3-(6-Methylpyridin-2-yl)-1H-pyrazol-4-yl)-1,5-naphthyridine ("ALK5 inhibitor II" or "ALK5") for three days.

Stage 6 (7 Days):

Cells were treated on the ALI with BLAR001 medium containing 2.7 g/1000 ml sodium bicarbonate, and supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 100 nM LDN-HCl; 1 µM of T3; 10 µM ALK5 inhibitor II; and 100 nM (S,S)-2-[2-(3,5-Difluorophenyl)acetylamino]-N-(5-methyl-6-oxo-6,7-dihydro-5H-dibenzo[b,d]azepin-7-yl)propionamide ("gamma secretase inhibitor XX") (for seven days.

Stage 7 (7 Days):

Cells on the ALI were treated with two kinds of custom BLAR media: BLAR001 and BLAR004. The first medium is BLAR001 medium (list of components is outlined on Table I) containing 2.7 g/1000 ml sodium bicarbonate, and supplemented with a 1:200 dilution of ITS-X; 1× GlutaMAX™; 2% FAF-BSA; 10 µg/ml of heparin ("H"); 10 nM of T3 ("low T3"); 1 mM N-Acetyl cysteine ("NAC"); 0.5 µM of ZM447439 ("ZM"); and the following components which constitute Formulation I ("FI") 1:200 dilution of RPMI vitamin supplement; 1:200 dilution of MEM non-essential amino acid supplement; 1:2000 dilution of chemically defined lipid concentrate; 1:200 dilution of sodium pyruvate; 1:2000 dilution of trace elements A; 1:2000 dilution of trace elements B for seven days. Additional compounds added during Stage 7 included either 1 µM of T3 or 10 nM of T3 ("low T3"); 10 µM ALK5 inhibitor II; 5 µM 5-Azacytidine ("AZT"); or 1 µM or 10 µM 3-Deazaneplanocin A ("DEZA").

The second medium was BLAR004 (list of components is outlined in Table IV) medium containing 2.7 g/1000 ml sodium bicarbonate, and supplemented with a 1:200 dilution of ITS-X; 1× GlutaMAX™; 2% FAF-BSA; 10 µg/ml of heparin ("H"); 1 mM N-Acetyl cysteine ("NAC"); 0.5 µM of ZM447439 ("ZM"); and the following components which constitute Formulation I ("FI") 1:200 dilution of RPMI vitamin supplement; 1:200 dilution of MEM non-essential amino acid supplement; 1:2000 dilution of chemically defined lipid concentrate; 1:200 dilution of sodium pyruvate; 1:2000 dilution of trace elements A; 1:2000 dilution of trace elements B for seven days. Additional compounds added during Stage 7 included either 1 µM of T3 or 10 nM of T3 ("low T3"); 10 µM ALK5 inhibitor II; 5 µM 5-Azacytidine ("AZT"); or 1 µM or 10 µM 3-Deazaneplanocin A ("DEZA").

TABLE IV

List of components of BLAR004 medium

| | Concentration (mM) |
|---|---|
| Amino Acids | |
| Glycine | 2.0E−01 |
| Alanine | 2.0E−01 |
| Arginine | 5.0E−02 |
| Aspargine | 2.0E−02 |
| Aspartic Acid | 2.0E−02 |
| Cysteine | 3.0E−02 |
| Glutamic acid | 5.0E−02 |
| Histidine | 8.0E−02 |
| Isoleucine | 7.0E−02 |
| Leucine | 1.5E−01 |
| Lysine hydrochloride | 2.0E−01 |
| Methionine | 2.0E−02 |
| Phenylalanine | 6.0E−02 |
| Proline | 1.0E−01 |
| Serine | 1.0E−01 |
| Theronine | 1.4E−01 |
| Tryptophan | 5.0E−02 |
| Tyrosinedisodium | 6.0E−02 |
| Valine | 2.0E−01 |
| Vitamins | |
| Biotin | 3.0E−05 |
| Choline chloride | 5.0E−03 |
| D-Calcium pantothenate | 1.5E−03 |
| Folinic Acid Calcium salt | 2.3E−03 |
| Niacinamide | 4.9E−03 |
| Pyridoxine hydrochloride | 9.7E−04 |
| Riboflavin | 1.0E−05 |
| Thiamine hydrochloride | 3.0E−03 |
| Vitamin B12 | 3.7E−06 |
| i-Inositol | 2.8E−03 |
| DL-alpha-Tocopherol Acetate | 1.0E−03 |
| Asocrbic acid | 5.0E−02 |
| Retinol, all trans (vit. A) | 1.0E−04 |
| 25-hydroxyvitamin D | 3.0E−05 |
| Vitamin K1 - (phylloquinone) | 1.0E−09 |
| Para-Aminobenzoic Acid | 3.0E−04 |
| Cholesterol | 1.0E−04 |
| Salts | |
| Calcium Chloride (CaCl$_2$—2H$_2$O) | 3.0E−01 |
| Cupric sulfate (CuSO$_4$—5H$_2$O) | 4.8E−06 |
| Ferric sulfate (FeSO$_4$—7H$_2$O) | 1.0E−03 |
| Magnesium Sulfate (MgSO$_4$—7H$_2$O) | 4.1E−01 |
| Potassium Chloride (KCl) | 3.8E+00 |
| Sodium Bicarbonate (NaHCO$_3$) | 1.4E+01 |
| Sodium Chloride (NaCl) | 1.1E+02 |
| Sodium Phosphate dibasic (Na2HPO$_4$—7H2O) | 5.0E−01 |
| Zinc Sulfate (ZnSO$_4$—H$_2$O) | 1.0E−04 |
| Other | |
| Adenine | 1.0E−03 |
| D-glucose (Dextrose) | 5.0E+00 |
| Lipoic Acid | 1.2E−05 |
| Phenol Red | 1.0E−02 |
| Sodium Pyruvate | 1.0E−01 |
| Thymidine | 9.8E−05 |
| Putrescine | 1.0E−02 |
| Glutathione | 1.0E−03 |

Characterization and Quantification of Differentiated Cells:

For quantification of gene expression at various stages, human islets, H1-hESC, Stage 6 day 7 (S6D7), and Stage 7 day 7 to Stage 7 day 14 (S7D7-S7D14) cells were harvested as ALI clusters, as described in Rezania et al., *Nature Biotechnology*, 2014; 32(11): 1121-1133. Gene expression was assessed in cells using custom Taqman Arrays (Applied Biosystems, Foster City, California). Data were analyzed using Sequence Detection Software (Applied Biosystems, Foster City, California), and normalized using GAPDH as a housekeeping gene to undifferentiated H1-hESC using the ΔΔCt method. Primer details are outlined in Table V.

TABLE V

List of qRT-PCR primers.

| | Gene | Assay ID |
|---|---|---|
| 1 | GJD2 | Hs00950432_m1 |
| 2 | GLP1R | Hs00157705_m1 |
| 3 | INHA | Hs00171410_m1 |
| 4 | INHBB | Hs00173582_m1 |
| 5 | PDK1 | Hs00176853_m1 |
| 6 | SIX2 | Hs00195590_m1 |
| 7 | UCP2 | Hs01075227_m1 |
| 8 | SLC2A1 | Hs00892681_m1 |
| 9 | G6PC2 | Hs01549773_m1 |
| 10 | INS | Hs00355773_m1 |
| 11 | NKX6.1 | Hs00232355_m1 |
| 12 | PDX1 | Hs00236830_m1 |
| 13 | NEUROD1 | Hs00159598_m1 |
| 14 | CHGA | Hs00154441_m1 |
| 15 | MAFA | Hs04419861_sH |
| 16 | UCN3 | Hs00846499_s1 |
| 17 | GAPDH | Hs99999905_m1 |

For quantification of protein co-localization at various stages, human islets, and S7D7 cells were harvested as a ALI cell clusters and analyzed by immunofluorescence ("IF"). H1-hESC-derived cells were prepared and stained as substantially described in Rezania et al. (2014) above, and using the antibodies listed in Table VI herein. For cryosectioning, cells were rinsed with PBS followed by overnight fixation in 4% PFA at 4° C. Following fixation, 4% PFA was removed, the cells were rinsed twice with PBS, and incubated overnight at 4° C. in 30% sucrose solution. The samples were cryopreserved in OCT solution, and 5 μm sections were placed on Superfrost plus slides (VWR International, LLC, Radnor, PA, Catalog No. 48311-703).

For IF-staining, primary antibodies were added at appropriate dilutions overnight at 4° C., while secondary antibodies were added for 30 min at room temperature followed by rinsing with PBS and adding Vectastain mounting reagent with DAPI (Vector Laboratories Inc., Burlingame, California, Catalog No. H-1200). The sections were visualized using a Nikon Ti fluorescence microscope (Nikon Instruments, Inc., Melville, NY).

TABLE VI

List of antibodies used for IF analysis.

| Antigen | Species | Source | Dilution |
|---|---|---|---|
| C-PEPTIDE | Mouse | Abcam (Catalog No. ab8297) | 1:100 |
| GLUCAGON | Rabbit | Abcam (Catalog No. ab92517) | 1:100 |
| PDX1 | Goat | R&D Systems (Catalog No. AF2419) | 1:33 |
| MAFA | Rabbit | Life Span Biosciences (Catalog No. LP9872) | 1:100 (Antigen retrieval) |
| GLUT1 | Rabbit | Abcam (Catalog No. ab115730) | 1:300 |
| NKX6.1 | Rabbit | Novus Biologicals (Catalog No. NBP1-49672) | 1:100 |
| UCN3 | Rabbit | Novus Biologicals (Catalog No. NB P1-80732) | 1:100 (Antigen retrieval) |

TABLE VI-continued

List of antibodies used for IF analysis.

| Antigen | Species | Source | Dilution |
|---|---|---|---|
| NEUROD1 | Rabbit | Abcam (Catalog No. 16508) | 1:100 |
| KI67 | Rabbit | Abcam (Catalog No. ab16667) | 1:100 (Antigen retrieval) |
| SOX2 | Goat | Sigma (Catalog No. sc-17320) | 1:50 |
| CDX2 | Mouse | BioGenex (Catalog No. MU392A-UC) | 1:50 |
| Donkey anti-mouse IgG (H + L) Secondary antibody, Alexa Fluor 488 | Mouse | Life Technologies (Catalog No. A21202) | 1:50 |
| Donkey anti-rabbit IgG (H + L) Secondary Antibody, Alexa Fluor 546 | Rabbit | Life Technologies (Catalog No. A10040) | 1:100-1:200 |
| Donkey anti-goat IgG (H + L) Secondary Antibody, Alexa Fluor 546 | Goat | Life Technologies (Catalog No. A11056) | 1:50 |

For quantification of glucose-dependent mitochondrial activity at various stages, matured human islets, S6D7 ALI clusters, and S7D7 ALI clusters were harvested, and their oxygen consumption rate ("OCR") measured on the $XF^e24$ Extracellular Flux Analyzer (Seahorse Bioscience, Catalog No. 102238-100) before and after injection of 20 mM D-glucose. ALI clusters were removed from their Stage 7 conditioning and incubated for 2 hours in both a 37° C. non-$CO_2$ environment and medium designed to achieve a baseline OCR. The pre-incubation medium contains 1 mM D-glucose, 1 mM L-glutamine, and 1 mM sodium pyruvate in XF Base medium. After pre-incubation, ALI clusters were loaded onto the Seahorse machine in which the following measurements were made: (i) 3× baseline OCR (pre-D-glucose injection); and (ii) 5× post-D-glucose (post-injection incubation time: 72 minutes). All OCR measurements were normalized to DNA content of individual samples of ALI or AGGREWELL clusters in spinners. DNA was isolated by the QIAamp DNA MicroKit (Qiagen, Catalog No. 56304), and DNA content measured by the NanoDrop 8000 UV-Vis Spectrophotometer (Thermo Scientific, Catalog No. ND8000).

Figure 3B:
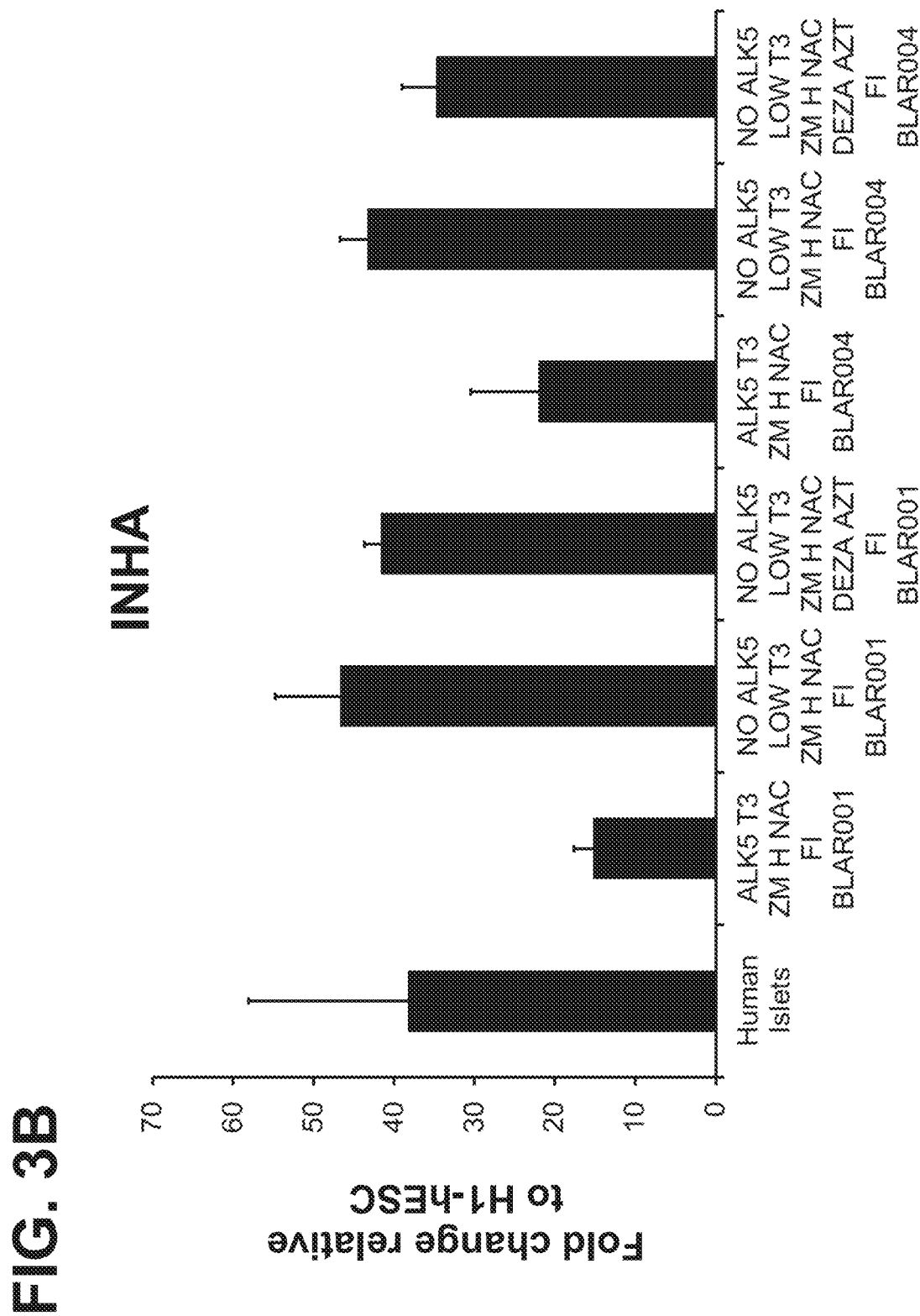
Figure 3E:
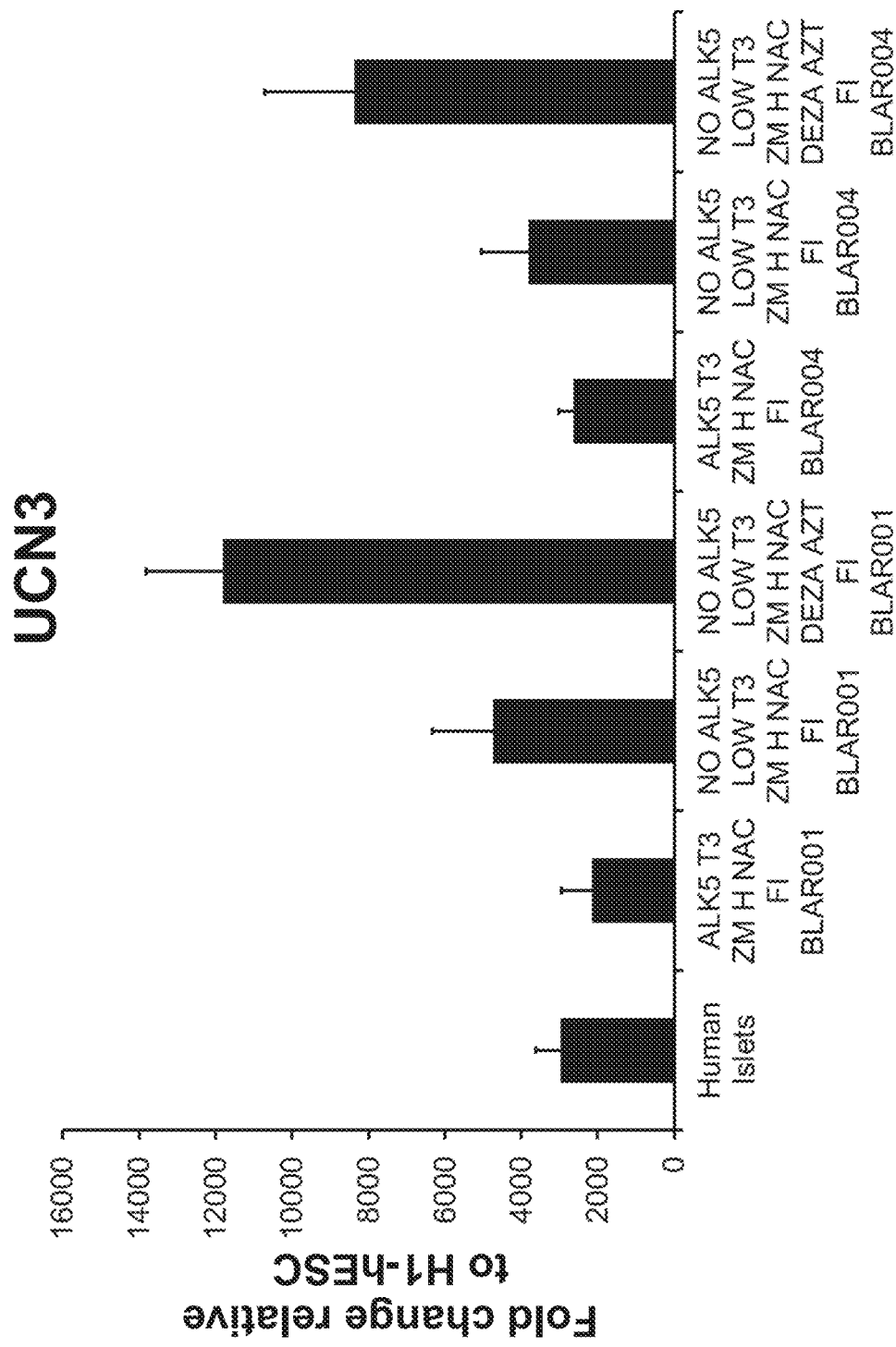

FIGS. 3A-3M demonstrate an increase in the gene expression, after seven days of Stage 7 conditioning, of a set of maturation markers in ALI cell clusters to levels observed in human islets. A maturation marker is defined here as a gene involved in positively stimulating a rapid glucose-stimulated insulin secretion (GSIS). The following list details the changes in the Stage 7 differentiation protocol that were observed to improve the gene expression of maturation markers by S7D7 in ALI clusters: (i) removal of ALK5 inhibitor II; (ii) lowering of T3 concentration; (iii) addition of DEZA; (iv) addition of AZT; (v) addition of ZM; (vi) lowering glucose concentration to 5.56 mM; and (vii) the addition of a defined cocktail of vitamins, non-essential amino acids, lipids, sodium pyruvate, and trace elements (Formulation I "FI"). Similar observations and results were seen regarding the gene expression signature of maturation genes for both BLAR001- and BLAR004-based conditioning during Stage 7. FIG. 3A shows that INHBB was enriched above the expression seen in human islets in conditions utilizing ALK5 inhibitor II. The observation suggests that in S7-cells, the inhibition of TGFB1 (Transforming growth factor beta 1) by ALK5 inhibitor II elicits a negative TGF-beta signaling profile that inhibits GSIS processes. Removal of ALK5 inhibitor in the absence or presence of AZT/DEZA was observed to decrease INHBB to levels seen in human islets, thus eliminating the negative TGF-beta signaling influences on GSIS during Stage 7. In addition, FIG. 3B shows that INHA expression was observed to increase to human islet levels in ALI clusters by the removal of ALK5 inhibitor II.

Figure 3F:
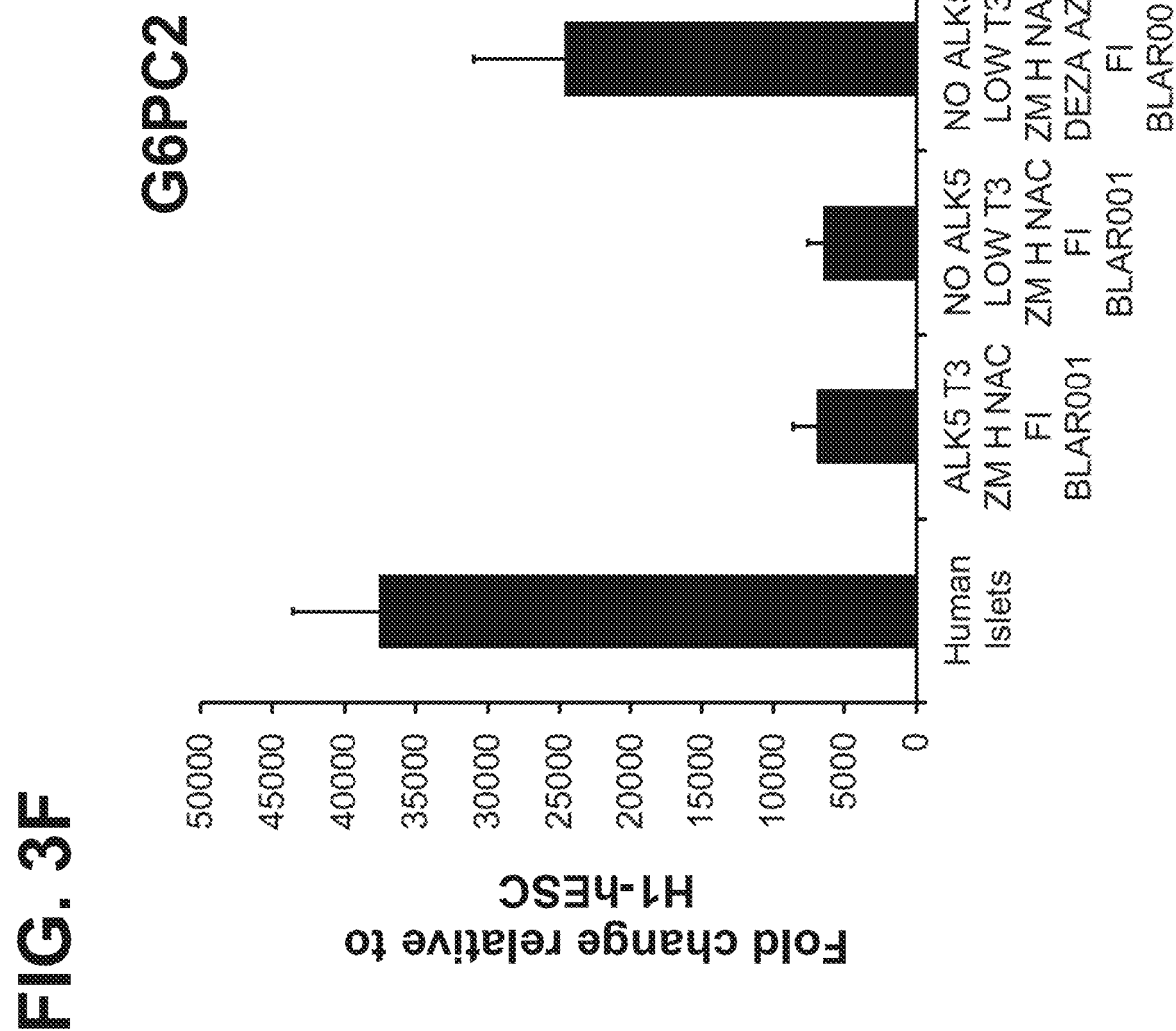
Figure 3H:
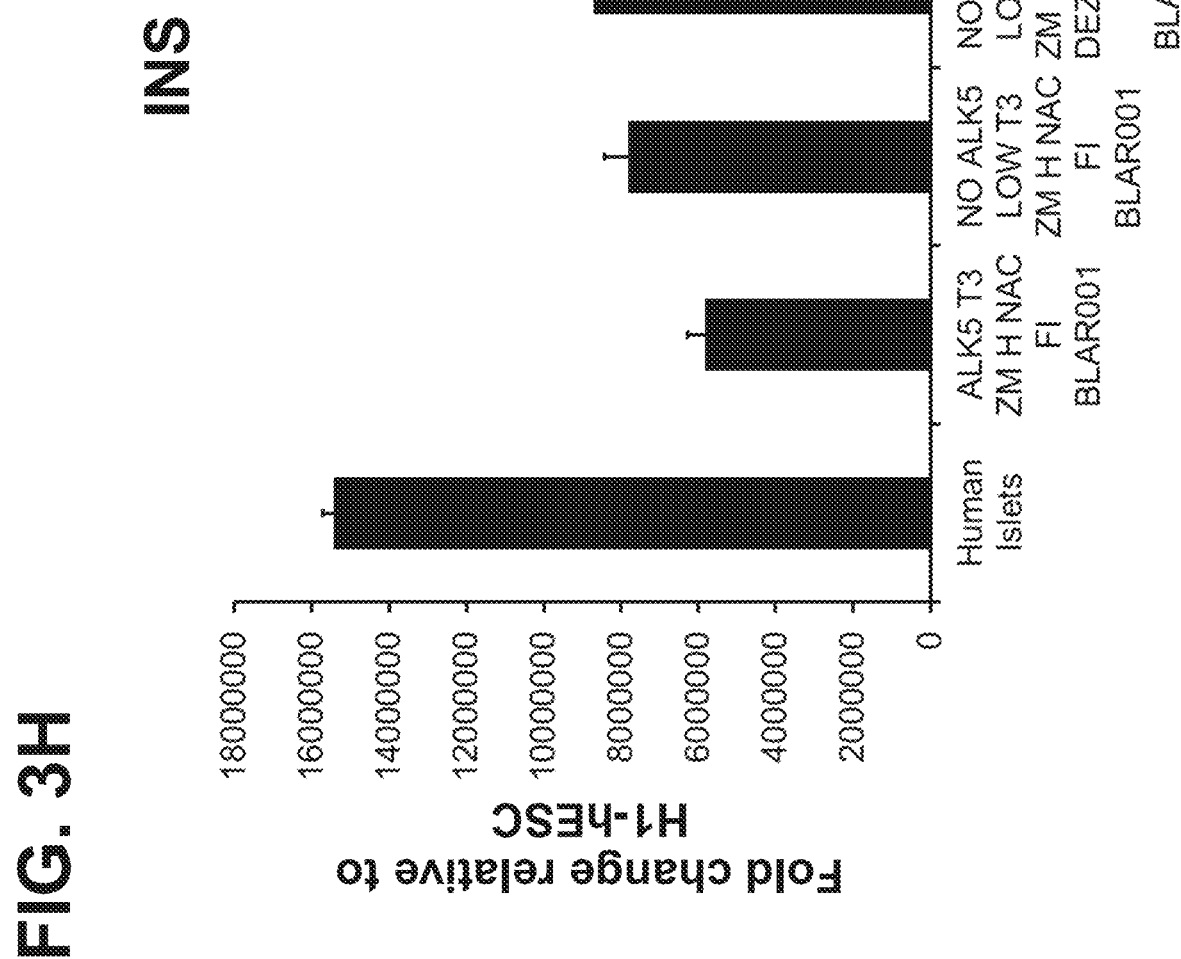
Figure 3I:
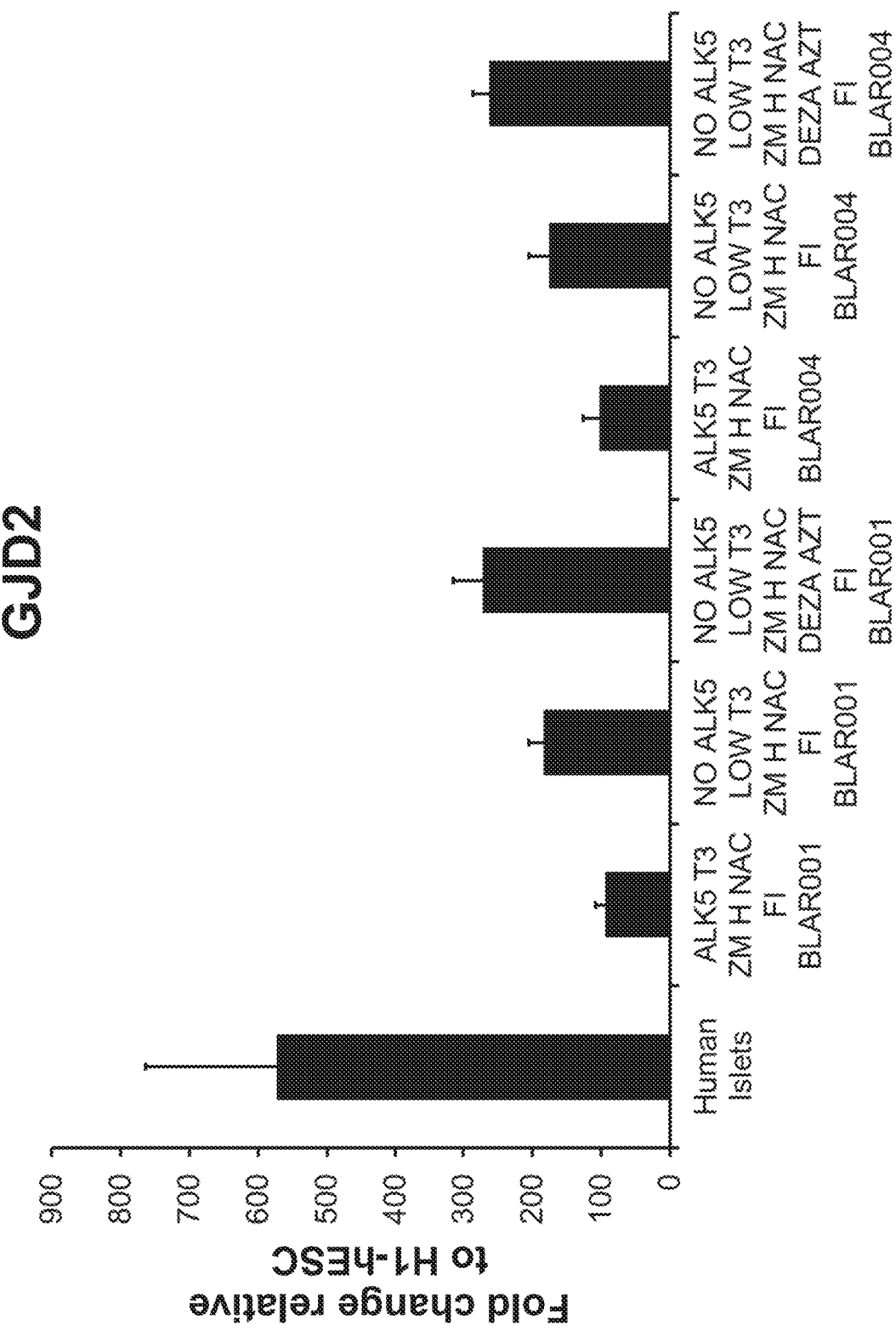
Figure 3K:
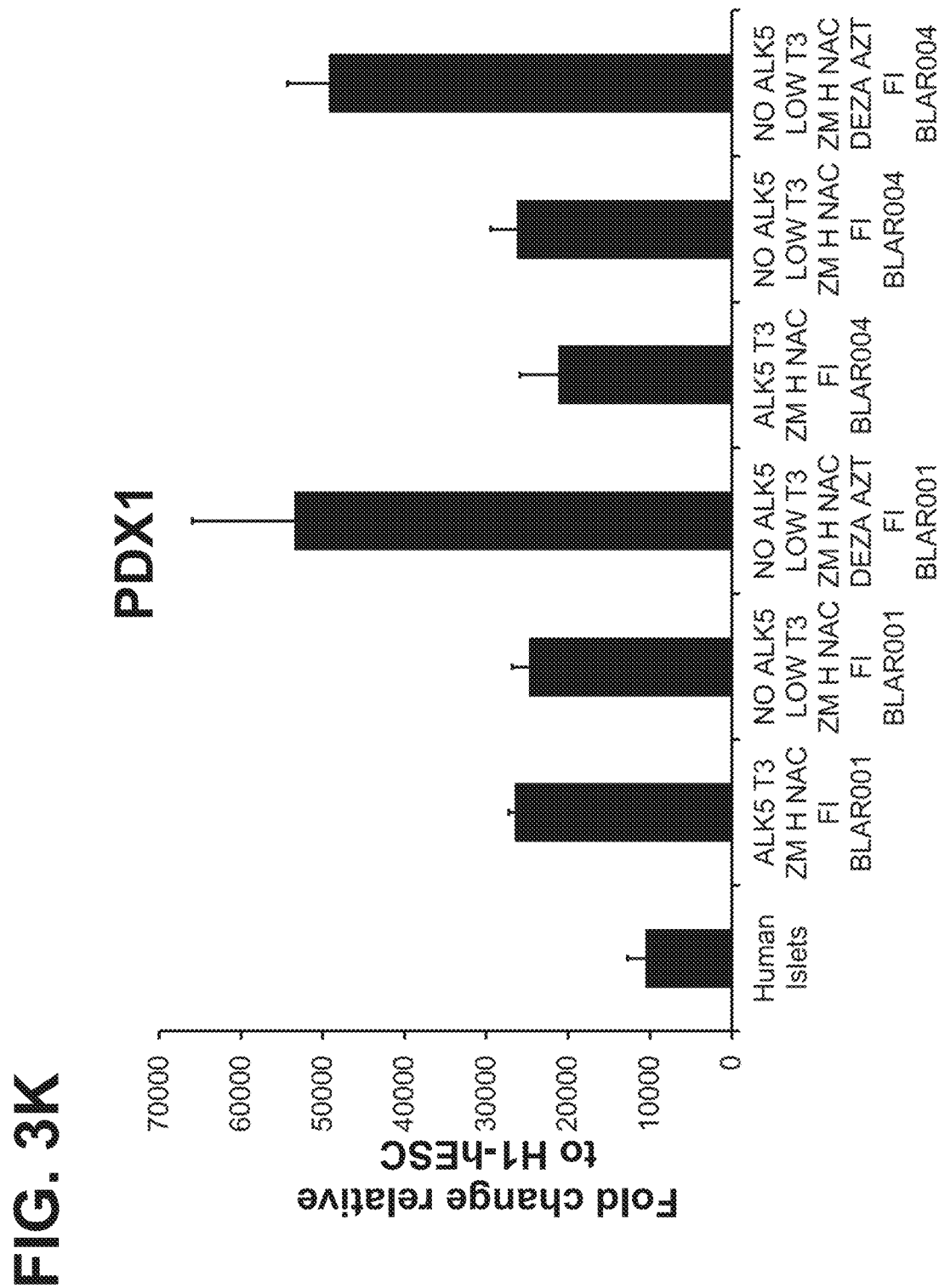
Figure 4A:
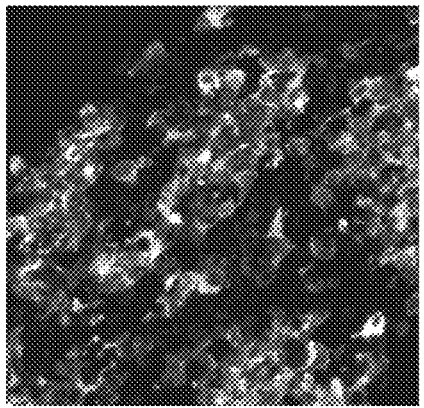
FIGS. 4A-4E demonstrate the generation of C-PEPTIDE cells in ALI cell clusters that co-express, in terms of protein presence, maturation markers: PDX1 (FIG. 4A), NKX6.1 (FIG. 4B), MAFA (FIG. 4C), SLC2A1 (FIG. 4D), and UCN3 (FIG. 4E) at S7D7. Representative human islet staining is shown in the left column. No ALK5, low T3, ZM, H, NAC, AZT/DEZA, FI, BLAR001 condition is shown in the middle column. No ALK5, low T3, ZM, H, NAC, AZT/DEZA, FI, BLAR004 condition is shown in the right column. All conditions S7D7; ALI clusters.
Figure 4A:
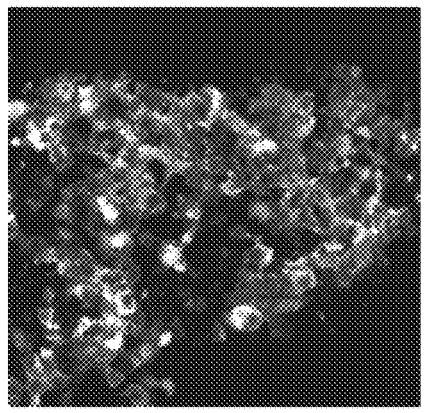
Figure 4A:
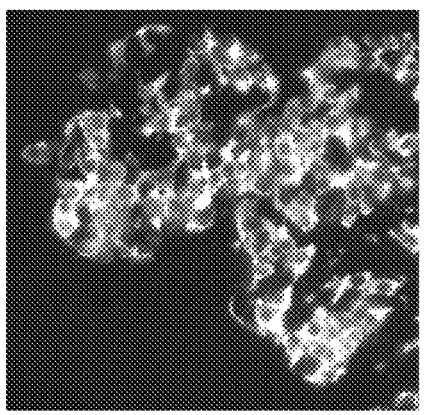
Figure 4A:
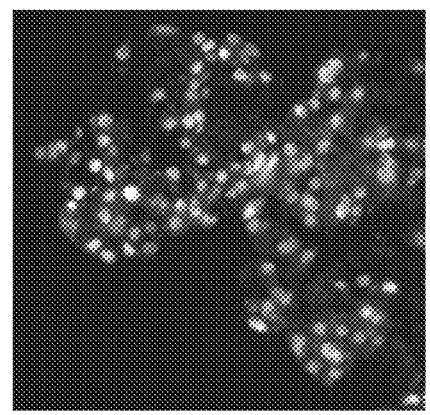
Figure 4B:
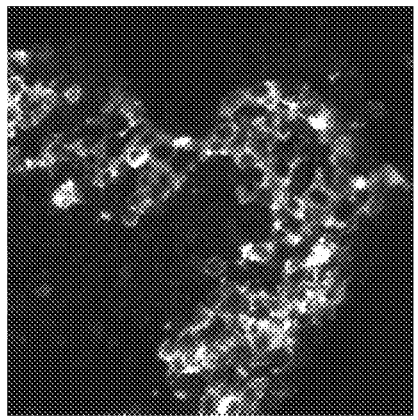
Figure 4B:
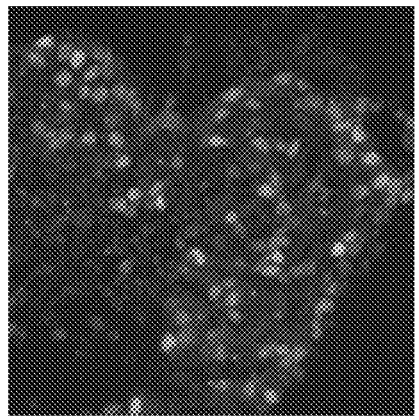
Figure 4B:
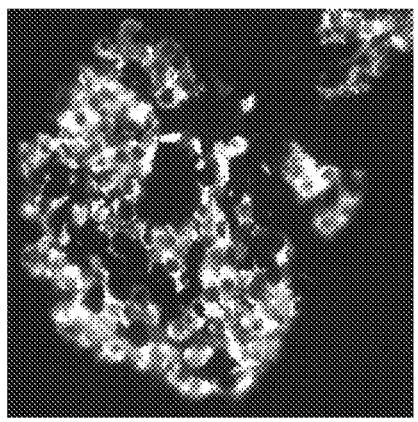
Figure 4B:
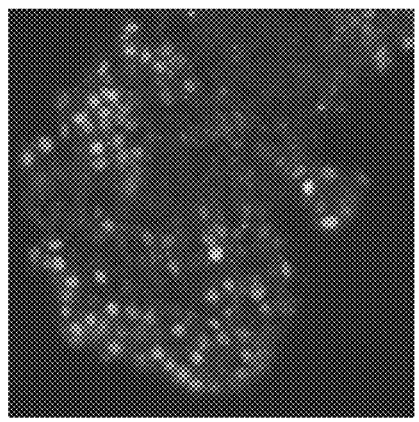
Figure 4C:
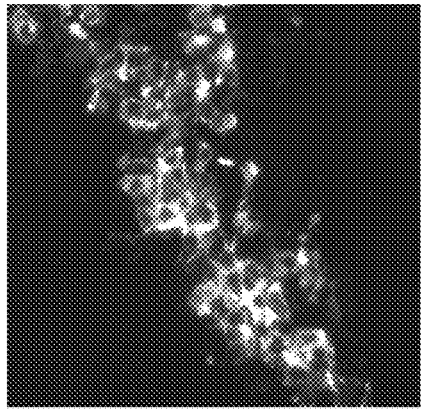
Figure 4C:
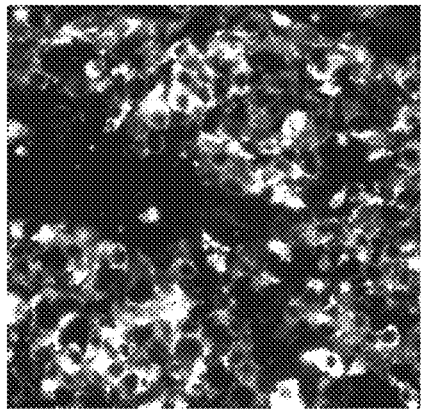
Figure 4C:
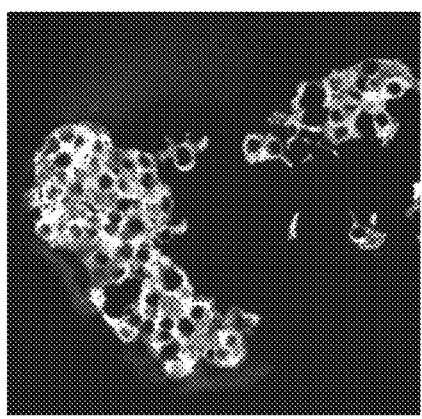
Figure 4D:
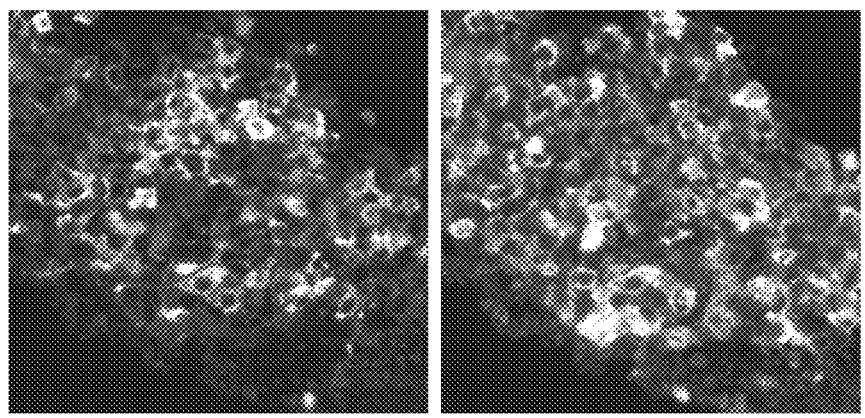
Figure 4D:
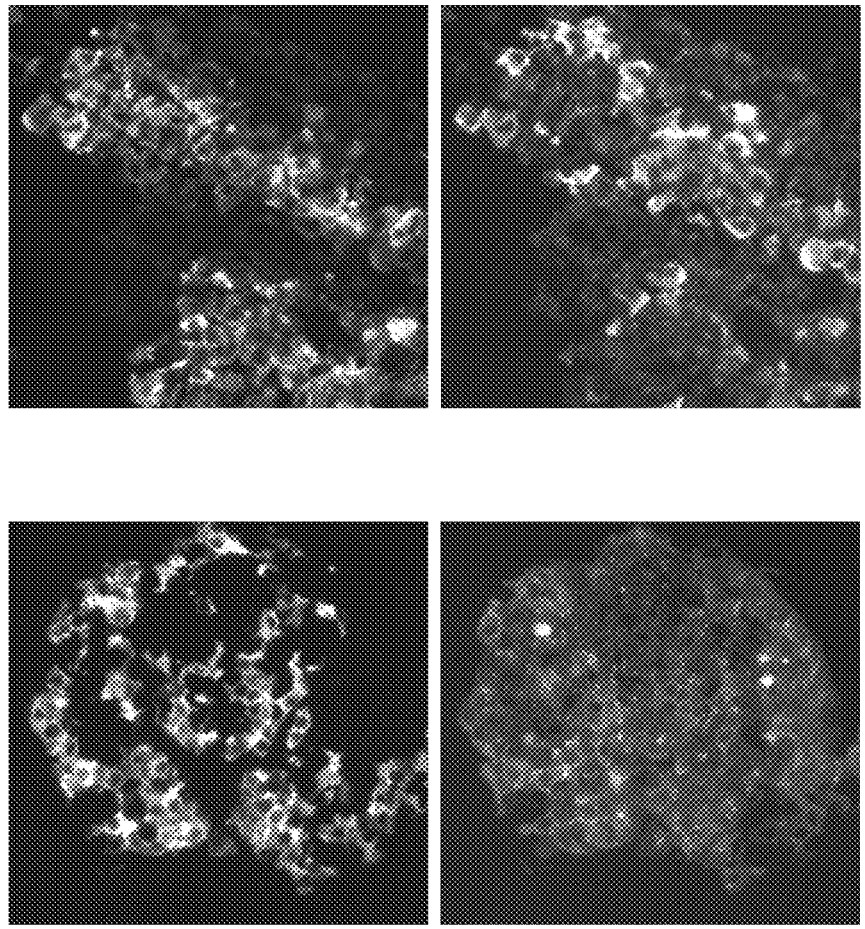
Figure 4E:
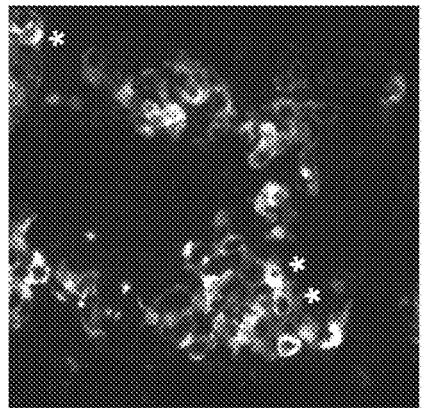
Figure 4E:
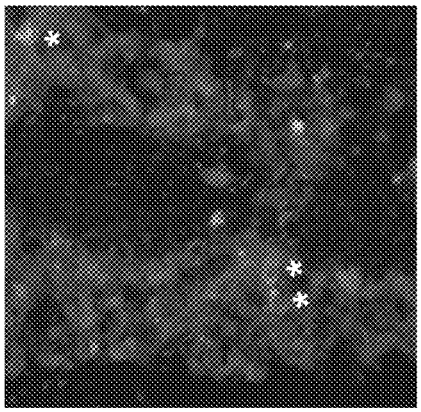
Figure 4E:
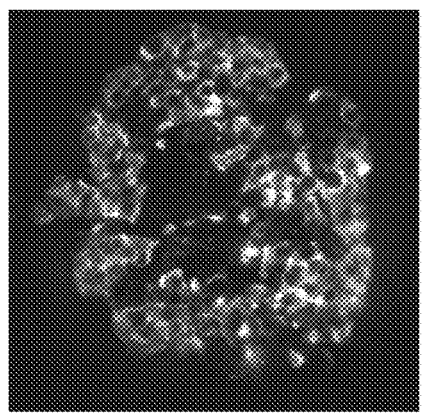
Figure 4E:
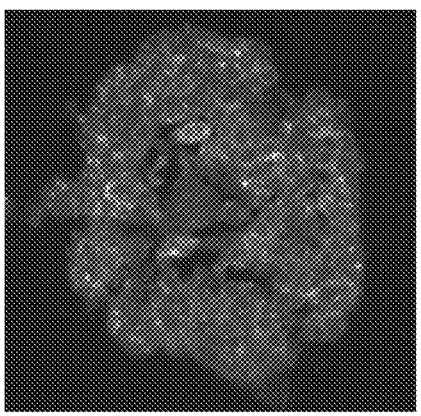

While MAFA and SLC2A1 expression, shown in FIGS. 3C and 3D respectively, was observed to have decreased by the removal of ALK5 inhibitor II, the addition of AZT/DEZA rescues MAFA and SLC2A1 expression to human islet levels. UCN3 (FIG. 3E), G6PC2 (Glucose-6-phosphatase catalytic subunit 2; FIG. 3F), and PDK1 (Pyruvate dehydrogenase kinase 1; FIG. 3G) expression was increased to levels at or above human islets by the addition of AZT/DEZA and removal of ALK5 inhibitor II in ALI clusters. The expression of INS (Insulin; FIG. 3H), GJD2 (Gap junction protein, delta 2; also CX36/connexin 36; FIG. 3I), SIX2 (SIX homeobox 2; FIG. 3J), and PDX1 (FIG. 3K) was observed to increase in a gradual step-wise manner, first by removal of ALK5 inhibitor II and second by the addition of AZT/DEZA. No change was observed in expression of NKX6.1 (FIG. 3L), and GLP1R (Glucagon like peptide 1 receptor; FIG. 3M) across conditions, but their expression in ALI clusters were consistently at or above levels observed in human islets.

FIG. 4A-4E demonstrate the generation of C-PEPTIDE cells in ALI cell clusters that co-express, in terms of protein presence, the following maturation markers: PDX1 (FIG. 4A), NKX6.1 (FIG. 4B), MAFA (FIG. 4C), SLC2A1 (FIG. 4D), and UCN3 (FIG. 4E) at S7D7. For each of FIG. 4A-4E, IF-staining is shown as single channels with C-PEPTIDE on the top row and maturation protein of interest in the bottom row. Representative human islet staining is shown in the left column, No ALK5, low T3, ZM, H, NAC, AZT/DEZA, FI, BLAR001 condition in the middle column, and No ALK5, low T3, ZM, H, NAC, AZT/DEZA, FI, BLAR004 condition in the right column. Most, if not all, C-PEPTIDE positive cells were co-positive for PDX1 (FIG. 4A) and NKX6.1 (FIG. 4B), as seen in human islets. A significant portion of C-PEPTIDE positive cells were also co-positive for MAFA (FIG. 4C), SLC2A1 (FIG. 4D), and UCN3 (FIG. 4E) across both BLAR001 and BLAR004 conditions. However, the expression of MAFA, SLC2A1 and UCN3 was not restricted to C-PEPTIDE co-positive cells.

Figure 5A:
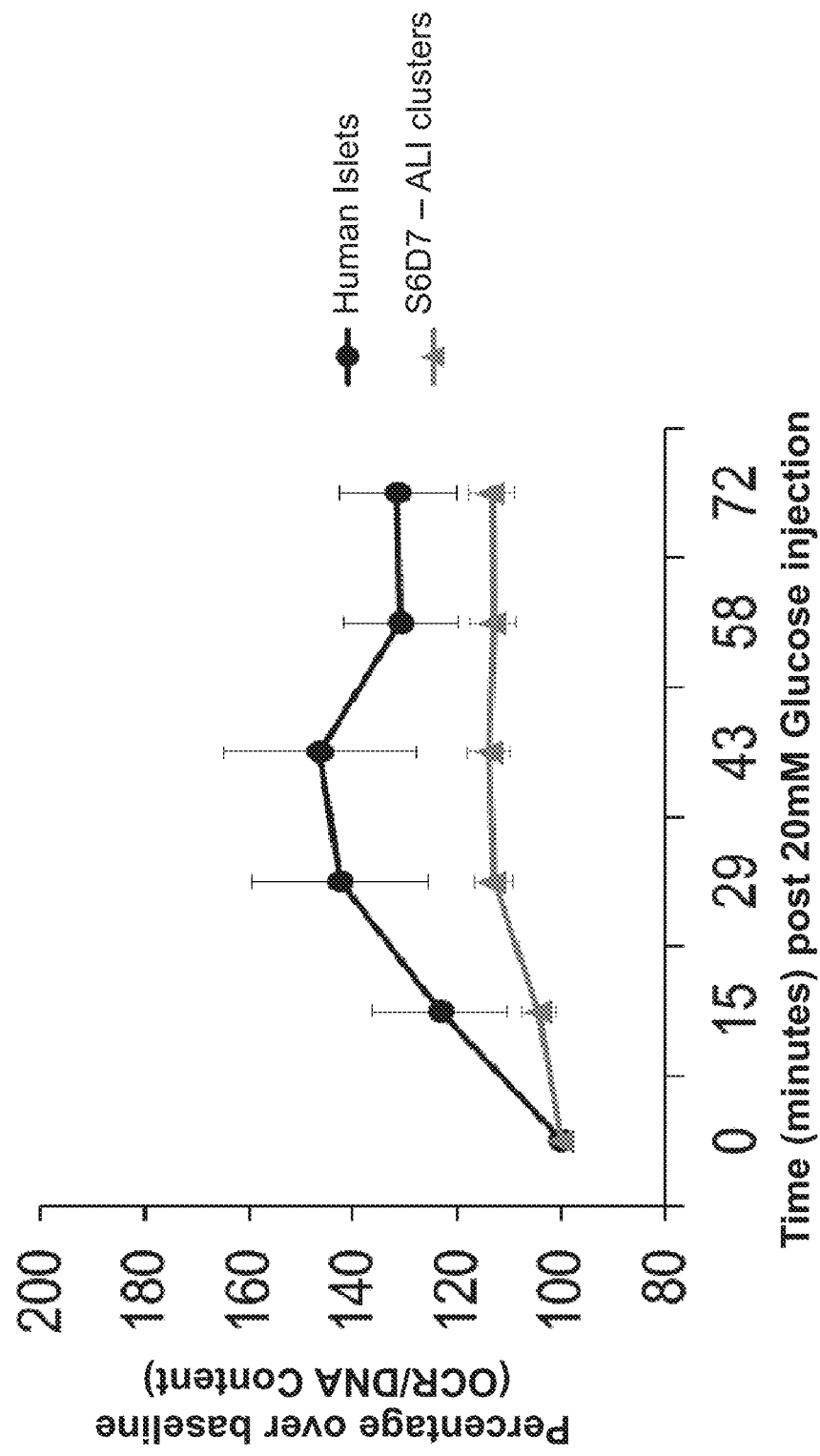
Figure 5B:
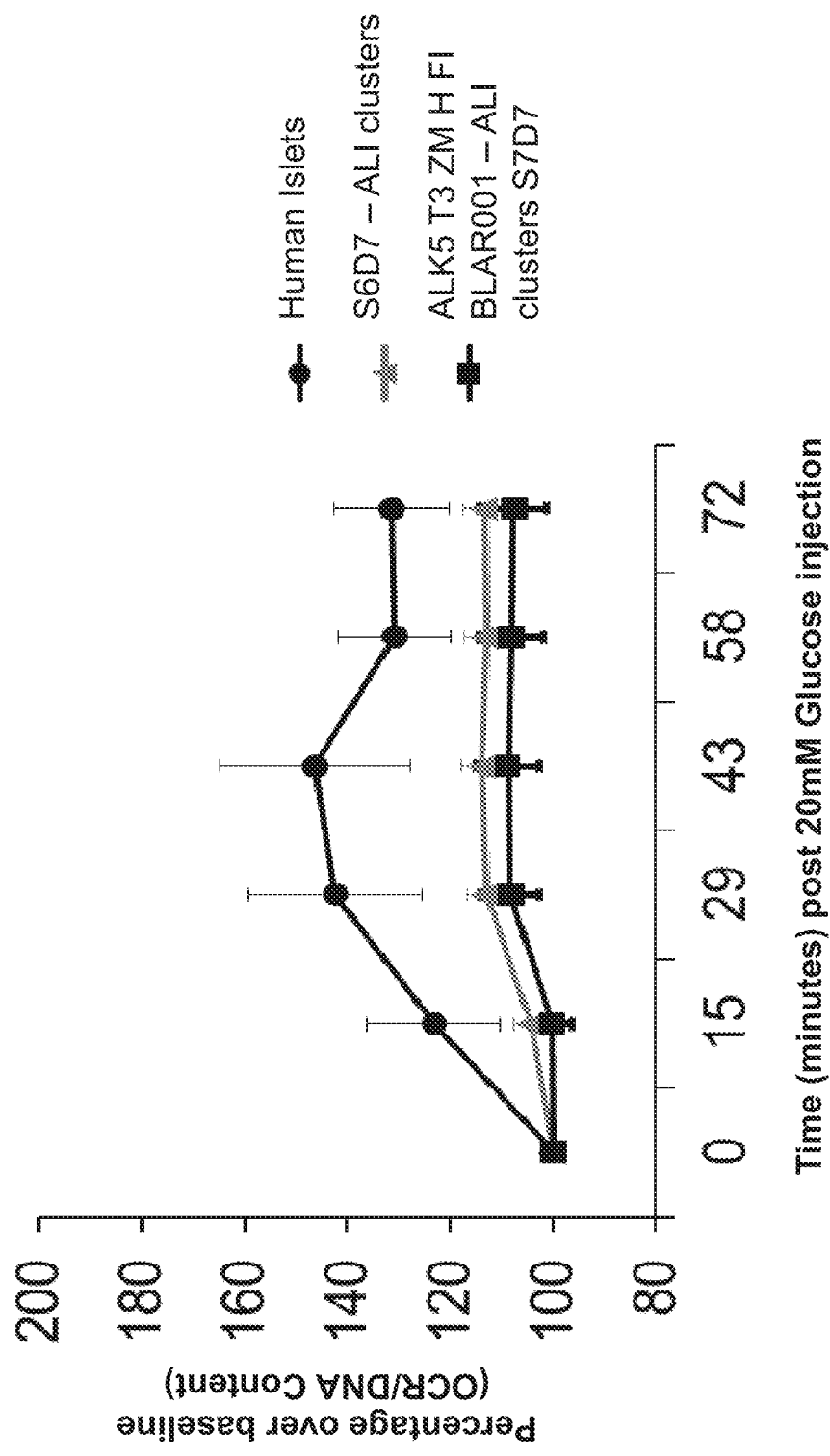
Figure 5C:
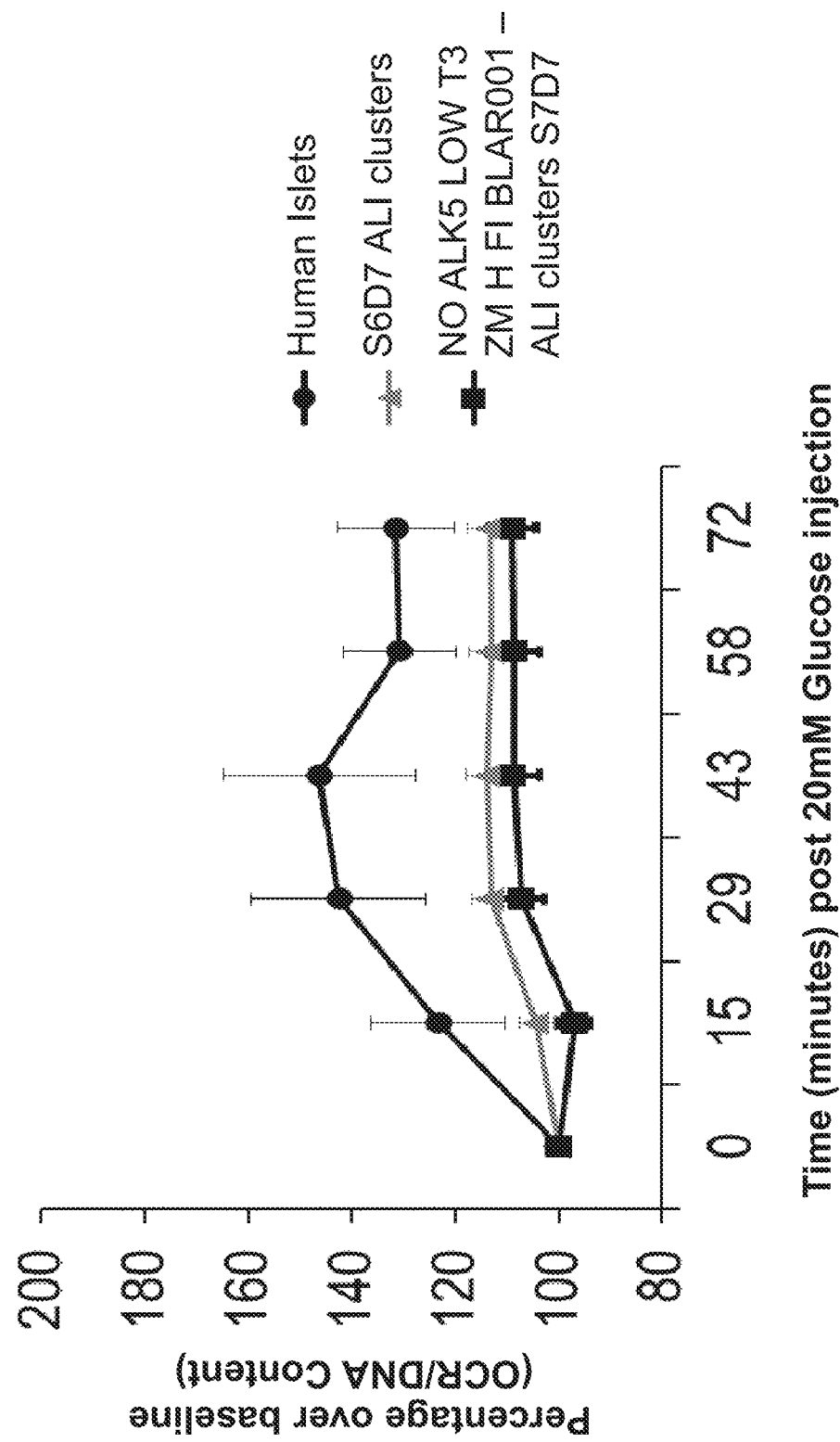
Figure 5E:
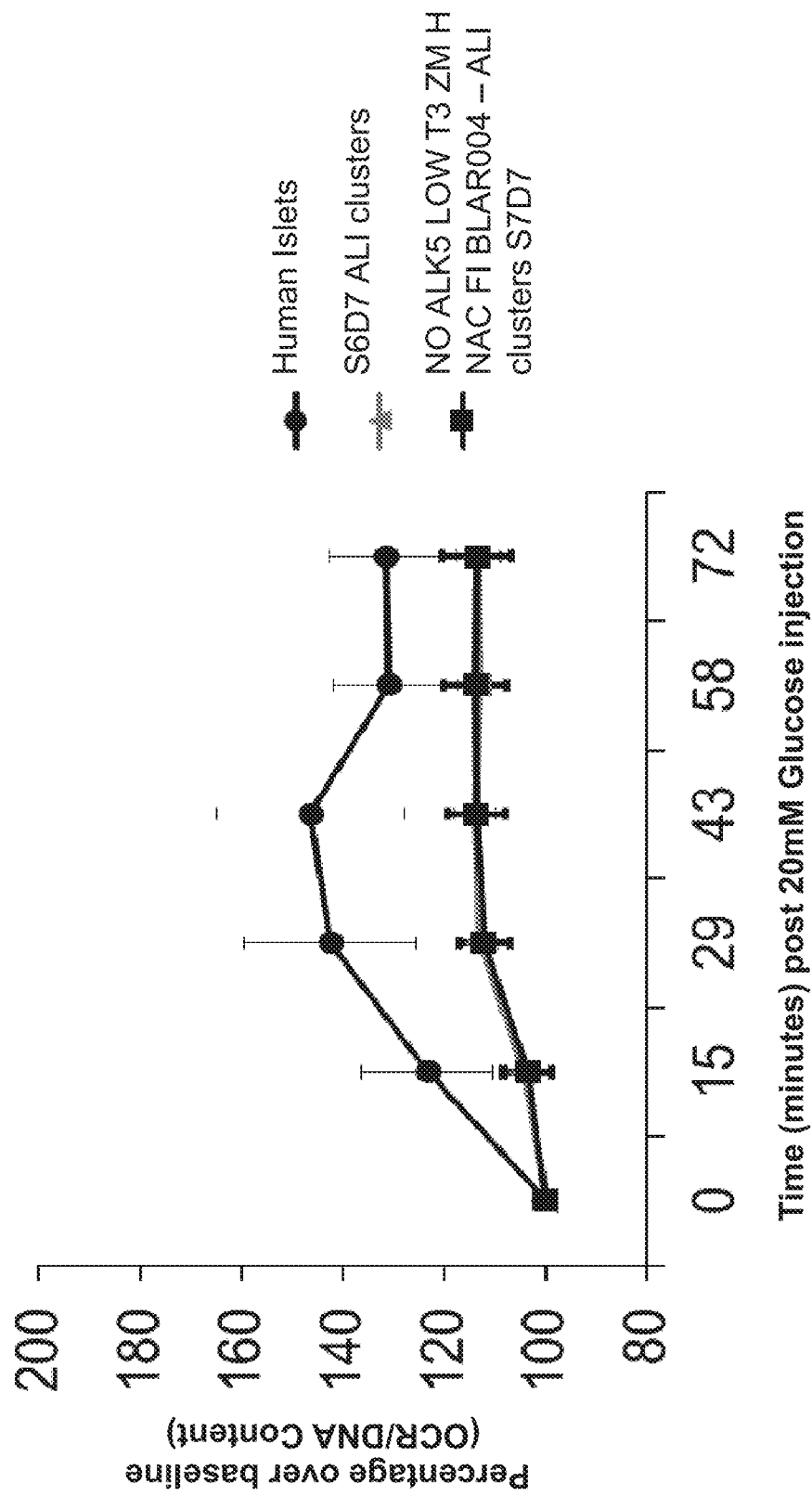
Figure 5F:
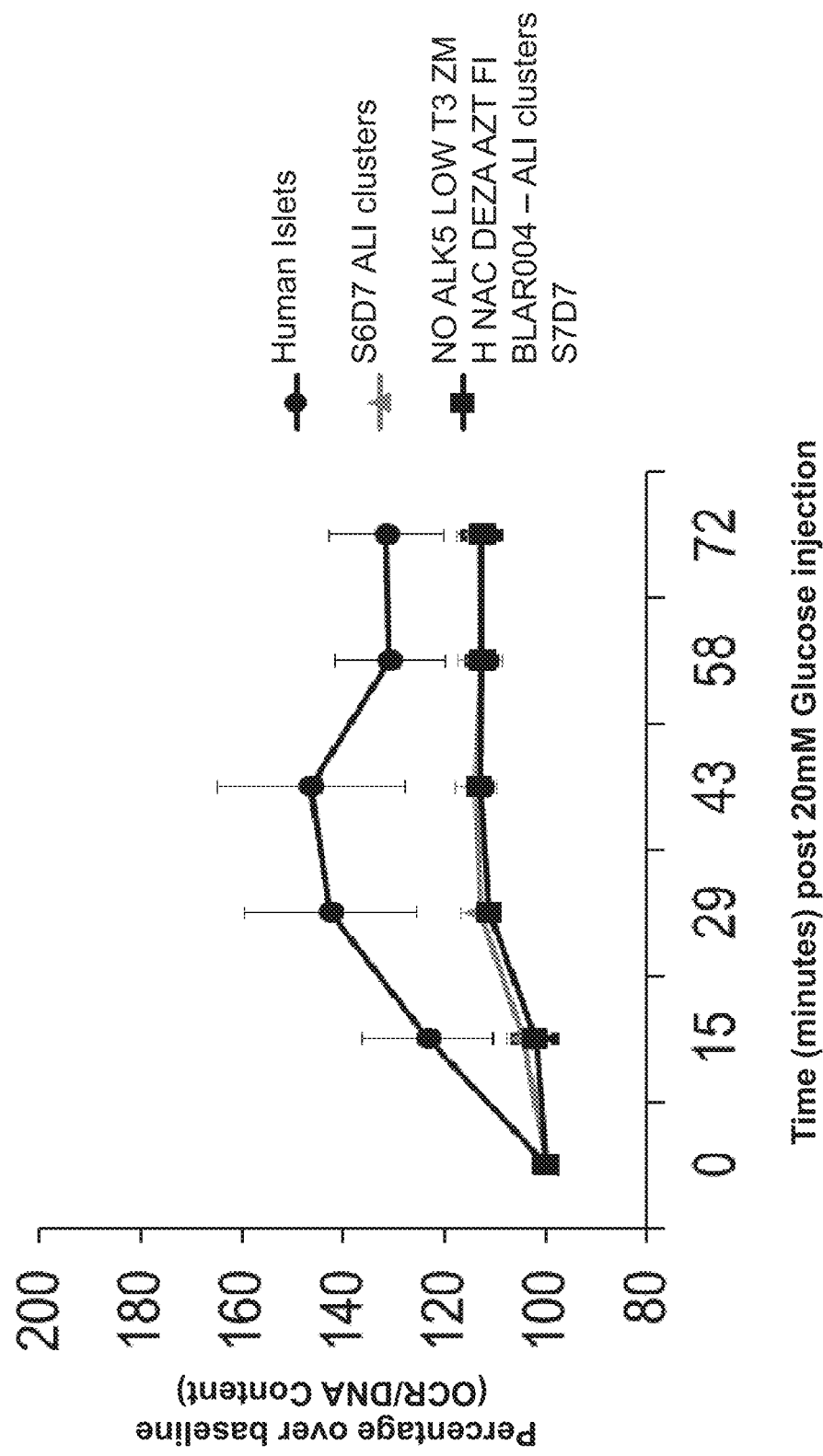

FIGS. 5A-5E show the generation of C-PEPTIDE cells at S7D7 that exhibit human-islet-similar glucose-dependent mitochondrial respiration kinetics on air-to-liquid interface ("ALI"), specifically by Stage 7 specific 'No ALK5, low T3, ZM, H, NAC, AZT, DEZA, FI, BLAR001' conditioning. Mitochondrial respiration or activity, represented by the oxidative consumption rate ("OCR"), was measured at baseline and post-20 mM D-glucose injection. Five OCR measurements over a period of 72 minutes were made post-20 mM D-glucose injection, and measurements are depicted as the percentage over baseline of OCR normalized by DNA content of each individual sample. FIG. 5A shows that human islets (black circle line) rapidly responded to high D-glucose, demonstrated by an OCR 123.3%±12.92 over baseline after 15 minutes ("min") post-injection ("ip"), and maintained a high OCR over time (131.5%±11.32; 72 min ip). Conversely, S6D7 ALI clusters (grey triangle line), which were enriched for immature C-PEPTIDE positive cells were observed to lack a rapid OCR response to high D-glucose (104.4%±3.37; 15 min ip) and exhibit a relatively weak OCR response over time (113.3%±4.51; 72 min ip). FIG. 5D depicts that within the S7D7 ALI cluster group only the No ALK5, low T3, ZM, H, NAC, AZT/DEZA, FI, BLAR001 condition (grey square line) were observed to exhibit human-islet-similar glucose-dependent mitochondrial respiration kinetics (112.4%±3.25—15 min ip; 129.5%±3.78—72 min ip). The following S7D7 ALI cluster conditions (black square line) were seen to exhibit glucose-dependent mitochondrial kinetics indistinguishable from immature S6D7 ALI clusters: ALK5, T3, ZM, H, NAC, FI, BLAR001 (100.3%±4.04—15 min ip; 107.8%±6.51—72 min ip) (FIG. 5B); No ALK5, low T3, ZM, H, NAC, FI, BLAR001 (96.9%±3.06—15 min ip; 109.0%±4.58—72 min ip) (FIG. 5C); No ALK5, low T3, ZM, H, NAC, FI, BLAR004 (103.4%±4.76—15 min ip; 113.6%±6.72—72 min ip) (FIG. 5E); and No ALK5, low T3, ZM, H, NAC, AZT/DEZA, FI, BLAR004 (102.1%±4.04—15 min ip; 112.7%±3.38—72 min ip) (FIG. 5F).

In summary, this example demonstrates that incorporating improvements in Stage 7 conditioning enhances the maturation status of hESC-derived maturing beta-cells on the ALI. Specifically, this example shows the generation on the ALI of C-PEPTIDE cells that co-express a multitude of beta-cell maturation markers, and exhibit beta-cell-specific functionality similar to human islets, such as glucose-dependent mitochondrial respiration.

Example 3

Generation of Robust Pancreatic Endoderm and Immature Beta-Cells in Cell Cluster Format Amenable to Scalable Suspension Culture The following example demonstrates the generation of either robust pancreatic endoderm or immature beta cells in AGGREWELL™ cell cluster format amenable to scalable suspension culture. The suspension culture used in this Example was AGGREWELL™ clusters cultured in spinner flasks ("AGGREWELL™ clusters in spinners"). Cells of the human embryonic stem cell line H1 ("H1-hESC") with EZ8 media at passage 28 were seeded as single cells at $0.094 \times 10^6$ cells/cm$^2$ on MATRIGEL™ at a 1:30 dilution coated dishes in a media of Dulbecco's Modified Eagle's Medium Nutrient mixture F-12 ("DMEM-F12"), GlutaMAX™ in a 1:100 dilution ("1× concentration"), 0.25 mM ascorbic acid, 100 ng/ml fibroblast growth factor 2 ("FGF2"), 1 ng/ml of transforming growth factor beta ("TG93"), insulin-transferrin-selenium-ethanolamine ("ITS-X") at a 1:100 dilution, 2% fatty-acid free bovine serum albumin ("FAF-BSA"), and 20 ng/ml of insulin-like growth factor-1 ("IGF-1"), supplemented with 10 μM of Rock Inhibitor Y-27632 ("Y-compound"). Y-compound was added only during the first 24 hours post-seeding. Forty-eight hours post-seeding, the cultures were washed in incomplete PBS (designated as "−/−" meaning phosphate buffered saline without magnesium or calcium).

For FIGS. 6A to 6L, the cultures were differentiated using the following protocol. S6D6 ALI cell clusters shown in FIGS. 6I to 6L were cultured as described above, with the exception that at Stage 4 day 3, AGGREWELL™ cell clusters were prepared either from fresh S4D3 monolayer or cryopreserved S4D3 cells (as described in more detail below) by being cultured for an additional 48 hours (Stage 4 day 5 or S4D5). Media was exchanged daily throughout the differentiation protocol.

Stage 1 (3 Days):

Cells were cultured for one day in the following Stage 1 media: MCDB-131 medium containing 2.7 g/1000 ml sodium bicarbonate, and supplemented with 0.5% FAF-BSA, GlutaMAX™ in a 1:100 dilution ("1× concentration"), 4.5 mM D-glucose to obtain a concentration of 10 mM of D-glucose, 100 ng/ml growth differentiation factor 8 ("GDF8"), and 1.5 µM of a 14-Prop-2-en-1-yl-3,5,7,14,17, 23,27-heptaazatetracyclo [19.3.1.1~2,6~.1~8,12~]heptacosa-1(25),2(27),3,5,8(26),9,11,21,23-nonaen-16-one ("MCX compound") (a GSK-30 inhibitor). Cells were then cultured for an additional day in MCDB-131 medium containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, 100 ng/ml GDF8, and 0.1 µM MCX compound. Cells were then cultured for an additional day in MCDB-131 containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, and 100 ng/ml GDF8.

Stage 2 (2 Days):

Cells were treated for two days with MCDB-131 medium containing 2.7 g/1000 ml sodium bicarbonate, and supplemented with 0.5% FAF-BSA, 1× GlutaMAX™, 4.5 mM D-glucose to obtain a concentration of 10 mM D-glucose, 0.25 mM Ascorbic acid, and 50 ng/ml Fibroblast growth factor 7 ("FGF7").

Stage 3 (2 Days):

Cells were treated for two days with BLAR001 custom medium (see Table I) containing 3.6 g/1000 ml sodium bicarbonate, and supplemented with a 1:200 dilution of ITS-X; 4.5 mM D-glucose to obtain a concentration of 10 mM D-glucose; 1× GlutaMAX™; 1% FAF-BSA; 25 ng/ml FGF7; 0.25 µM SANT-1 (N-[(3,5-dimethyl-1-phenyl-1H-pyrazol-4-yl)methylene]-4-(phenylmethyl)-1-piperazineamine); 1 µM retinoic acid ("RA") (Sigma Aldrich, Catalog No. R2625); 0.25 mM ascorbic acid; 300 nM of the PKC activator (2S,5S-(E,E)-8-(5-(4-trifluoromethyl)phenyl-2,4,-pentadienoylamino)benzolactam ("TPB"); and the bone morphogenic protein ("BMP") receptor inhibitor LDN-193189-HCl ("LDN-HCl") for two days. The concentrations of LDN-HCl used for the first day of stage 3 were 100 nM, and for the second day of stage 3 was 10 nM.

Stage 4 (3 Days):

Cells were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1× concentration of GlutaMAX™; 1% FAF-BSA; 0.25 µM SANT-1; 50 nM RA; 2 ng/ml FGF7; 70 nM LDN-HCl; 0.25 mM ascorbic acid; and 200 nM TPB for three days.

Cryopreservation of Stage 4 Day 3 Monolayer:

Cryopreserved cell banks from S4D3 monolayer were established by the following procedure. Briefly, a S4D3 monolayer was treated for 4 hours with 10 µM Y-compound. Cells were then released with TrypLE™ Express Enzyme as a single cell suspension, followed by a neutralization of the enzyme with a 'release' medium (Stage 4 complete medium, as detailed in "section k" supplemented with 4 kU/ml DNase I and 10 µM Y-compound). Single cells were spun down, resuspended in a cold 'release' medium, and counted by the Nucleocounter® NC-100. Cold 'cryopreservation' media (60% KSR; 15% BLAR001; 5% HEPES (1M concentration); 20% DMSO) was added in a 1-to-1 ratio add to the single cell suspension in cold 'release' medium. $5.0 \times 10^6$ cells in 4.5 ml of 1-to-1 'cryoperservation/release' medium were added to a single 5 ml cryopreservation vial. Vial(s) were transferred to the CRF (Controlled rate Freezer) (Planar PLC, Catalog No. Kryo 360) in which the cells were frozen by the following freezing profile, and stored long-term in liquid nitrogen. The CRF freezing procedure is shown in Table VII.

Thawing of Cryopreserved S4D3 Monolayer Cells:

Frozen 5 ml vials containing $5.0 \times 10^6$ S4D3 monolayer cells were thawed in a 37° C. water bath for 2 minutes. Cells were collected in post-S4D3 medium (detailed below in section "g"), and added at a density of approximately 787 cells per AGGREWELL™ well of an AGGREWELL™ 400 EX plate.

Stage 4 (2 Days) for AGGREWELL™ Cluster Transition:

For AGGREWELL™ cluster generation, Stage 4 day 3 monolayer cells, or thawed cryopreserved Stage 4 day 3 cells, were treated with Y-compound for 4 hours, rinsed with PBS, and treated for 3 minutes with Accutase Cell Detachment Solution, followed by removal of the enzyme, and removal of the cells from the on MATRIGEL™ surface by gentle tapping of the flask. The resulting suspension of cells were added at a density of approximately 787 cells per AGGREWELL™ well of an AGGREWELL™ 400 EX plate, and the plate gently spun down at 100×g to generate AGGREWELL™ clusters. The amount of cells per cluster can range from 50 to 3000 cells. The medium used to transit Stage 4 day 3 monolayer cells to AGGREWELL™ clusters, and 48 hour post-aggregation culturing is as follows ("post-S4D3 medium"): Cells were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1× concentration of GlutaMAX™; 1% FAF-BSA; 0.25 µM SANT-1; 50 nM RA; 2 ng/ml FGF7; 70 nM LDN-HCl; 0.25 mM ascorbic acid; and 200 nM TPB for two days. Ten (10)µ.M Y-compound and 2 µg/ml human recombinant laminin was added to the medium only during the first 24 hours. After two days, here referred to as S4D5, the AGGREWELL™ clusters were removed from the wells of the AGGREWELL™ plates, and transferred to a PBS0.1MAG spinners ("AGGREWELL clusters in suspension").

Stage 5 (3 Days):

S4D5 AGGREWELL™ clusters were retrieved from AGGREWELL™ 400 EX plates and transferred to PBS0.1MAG spinners at a cell density of 1.5-2.0 million cells/ml with the rotation speed of 27 rpm (rounds per minute) in Stage 5 medium for three days. Cells were treated with BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 0.25 µM SANT-1; 50 nM RA; 100 nM LDN-HCl; 1 µM of T3 in the form of 3,3', 5-triiodo-L-thryonine sodium salt; and 10 µM of 2-(3-(6-Methylpyridin-2-yl)-1H-pyrazol-4-yl)-1,5-naphthyridine ("ALK5 inhibitor II" or "ALK5"). 4 kU/ml DNaseI and 5 µM Y-compound were supplemented only on Stage 5 day 1.

Stage 6 (6 Days to 8 Days):

AGGREWELL™ clusters were treated in BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 100 nM LDN-HCl; 1 µM of T3; 10 µM of ALK5 inhibitor II"), and 100 nM of (S,S)-2-[2-(3,5-

Difluorophenyl)acetylamino]-N-(5-methyl-6-oxo-6,7-di-hydro-5H-ibenzo[b,d]azepin-7-yl)propionamide ("gamma secretase inhibitor "XX").

TABLE VII

CRF Freezing procedure.
S4D3 monolayer Freezing Profile

| Step | Cooling Rate (° C./min) | Target Temp (° C.) | Cool To |
|---|---|---|---|
| 1 | WAIT | 4 | N/A |
| 2 | WAIT for TEMPERATURE | 4 | Chamber |
|  |  | 6 | Sample |
| 3 | 1 | −7 | Sample |
| 4 | 25 | −45 | Chamber |
| 5 | 10 | −25 | Chamber |
| 6 | 0.2 | −45 | Sample |
| 7 | 25 | −160 | Chamber |
| 8 | HOLD (20 min) | −160 | N/A |

Quantification and Characterization of Differentiated Cells:

For quantification of protein co-localization at various stages, S4D5 AGGREWELL™ clusters, and S6D6 AGGREWELL™ clusters were harvested and analyzed by immunofluorescence ("IF"). The characterization procedure and reagents used were as shown Table VI of Example 2.

For quantification of gene expression at various stages, Stage 4 Day 5 AGGREWELL™ clusters, and Stage 6 Day 6 AGGREWELL™ clusters were harvested and analyzed by reverse transcriptase quantitative polymerase chain reaction ("qRT-PCR"), as described in *Nature Biotechnology*, (32) 11, 1121-1133. The characterization procedure and reagents used were as shown in Table V of Example 2.

For quantification of protein presence co-localization, Stage 4 Day 5 AGGREWELL™ clusters, and Stage 6 D6 AGGREWELL™ clusters were harvested and analyzed by fluorescence-activated flow cytometry ("FACS"). FACS staining was conducted as described in *Nature Biotechnology*, 2014 (32) 11, 1121-1133, and used the antibodies listed in Table VII. Differentiated cells were incubated in TrypLE™ Express for 5-10 minutes at 37° C., released into a single-cell suspension, after which they were washed twice with a staining buffer of PBS containing 0.2% BSA. Intracellular antibody staining was accomplished by utilizing the LIVE/DEAD Violet Fluorescent reactive dye at 4° C. for 30 minutes followed by a single wash in cold PBS. Fixing of cells was in 3000 of Cytofix/Cytoperm Buffer followed by two washes in Perm/Wash Buffer. Cells were then incubated with the appropriate antibodies at 4° C. for 30 minutes (for unconjugated antibodies) or 1 µl hour (for conjugated antibodies), and then washed twice prior to analysis on the BD FACS Canto II using BD FACS Diva Software with at least 30,000 events being acquired. Non-viable cells were excluded during FACS analysis, and gating was determined by using isotype antibodies ("IgG").

TABLE VIII

List of antibodies used for FACS analysis.

| Antigen | Species | Source/Catalog Number | Dilution |
|---|---|---|---|
| Alexa Fluor 647 anti-KI67 | Mouse | BD, Catalog No. 561126 | Neat |
| PE anti-PDX1 | Mouse | BD, Catalog No. 562161 | Neat |
| Alexa Fluor 647 anti-INSULIN | Rabbit | Cell Signaling, Catalog No. 9008S | 1:80 |
| INSULIN | Rabbit | Cell Signaling, Catalog No. 3014S | 1:10 |
| PE anti-NKX6.1 | Mouse | BD, Catalog No. 563023 | 1:40 |
| CHGA | Rabbit | DAKO, Catalog No. IS502 | 1:10 |
| PE anti-NEUROD1 | Mouse | BD, Catalog No. 563001 | 1:40 |
| GLUCAGON | Mouse | Sigma-Aldrich, Catalog No. G2654 | 1:250 |
| Anti-Mouse IgG(H + L) Secondary Antibody, Alexa Fluor 647 conjugate | Goat | Life technology, Catalog No. A21235 | 1:4000 |
| F(ab')2 anti-rabbit IgG(H + L) Secondary Antibody, RPE conjugate | Goat | Life technology, Catalog No. A10542 | Neat |

Figure 6A:
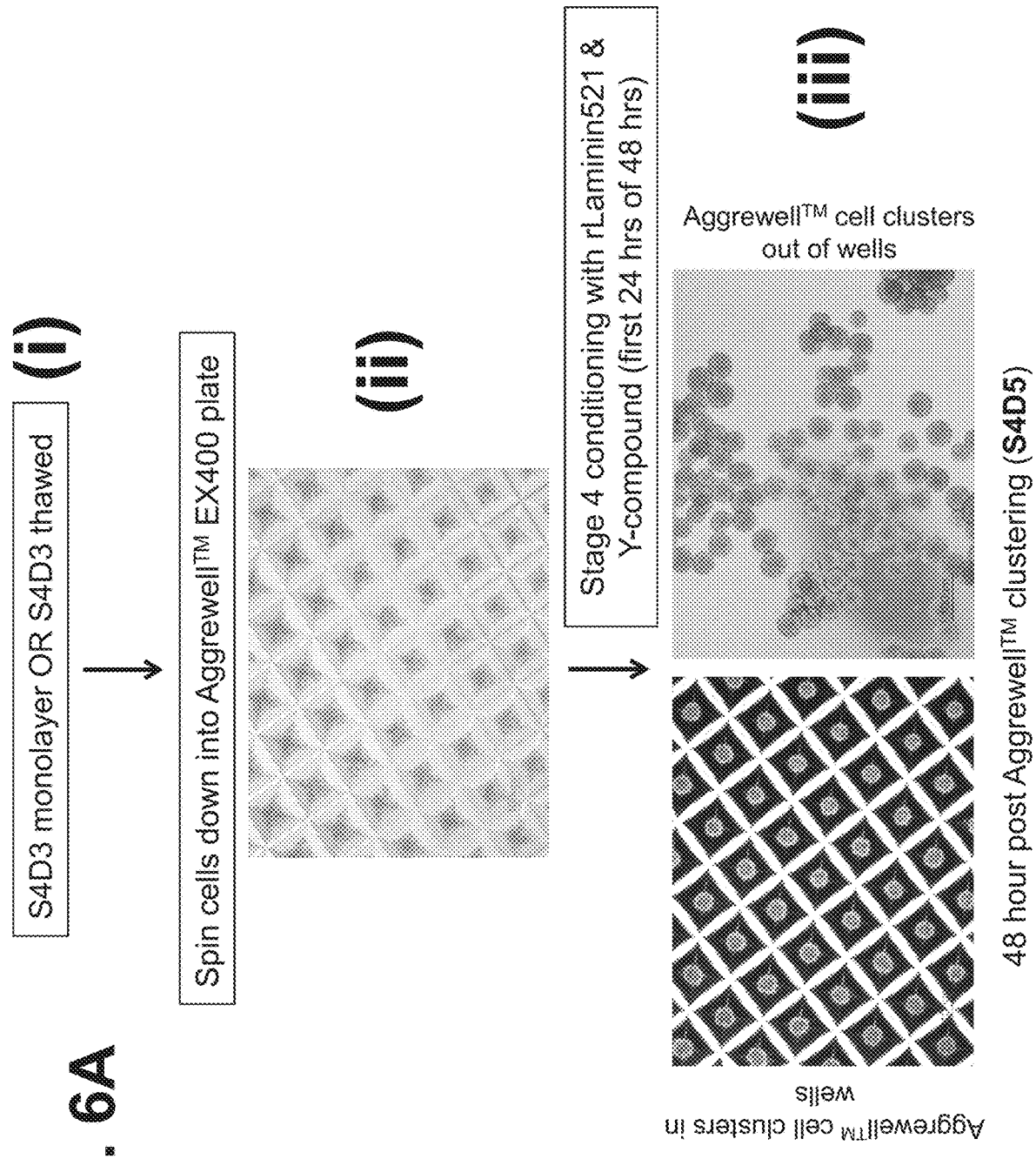
Figure 6B:
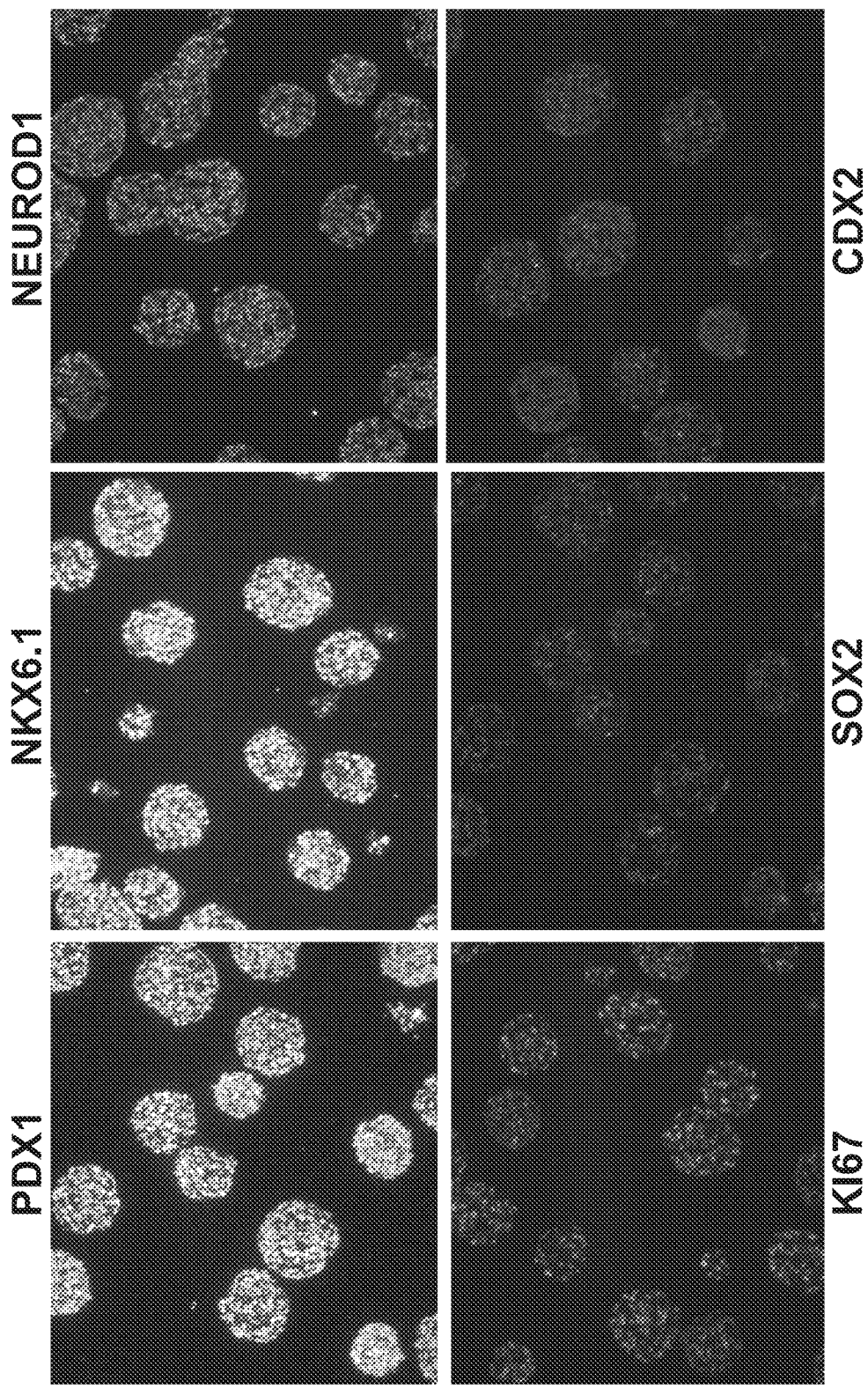
Figure 6C:
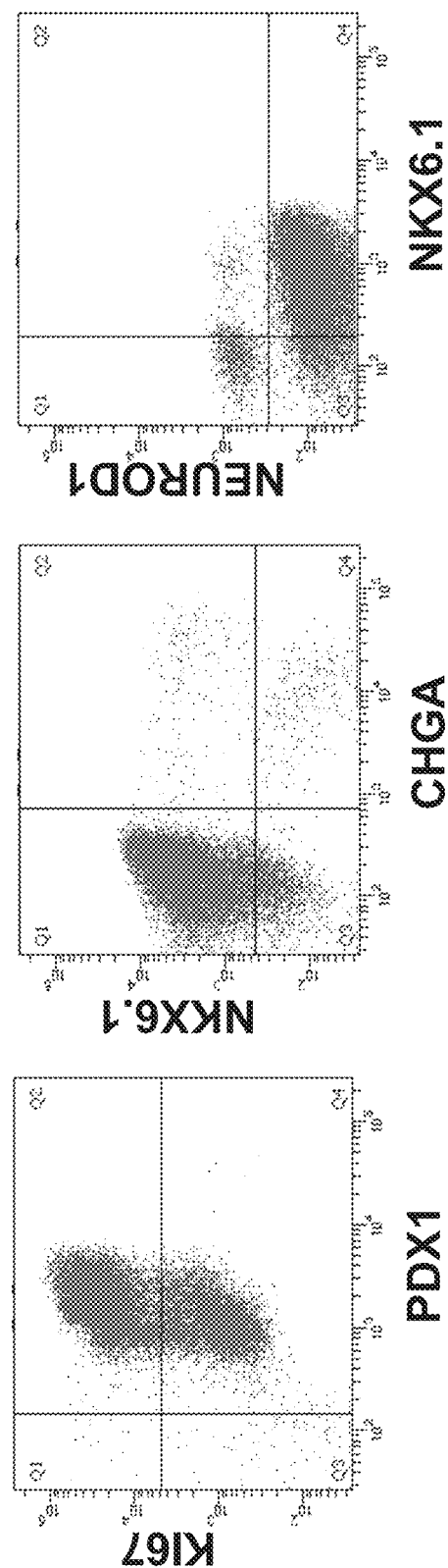
Figure 6D:
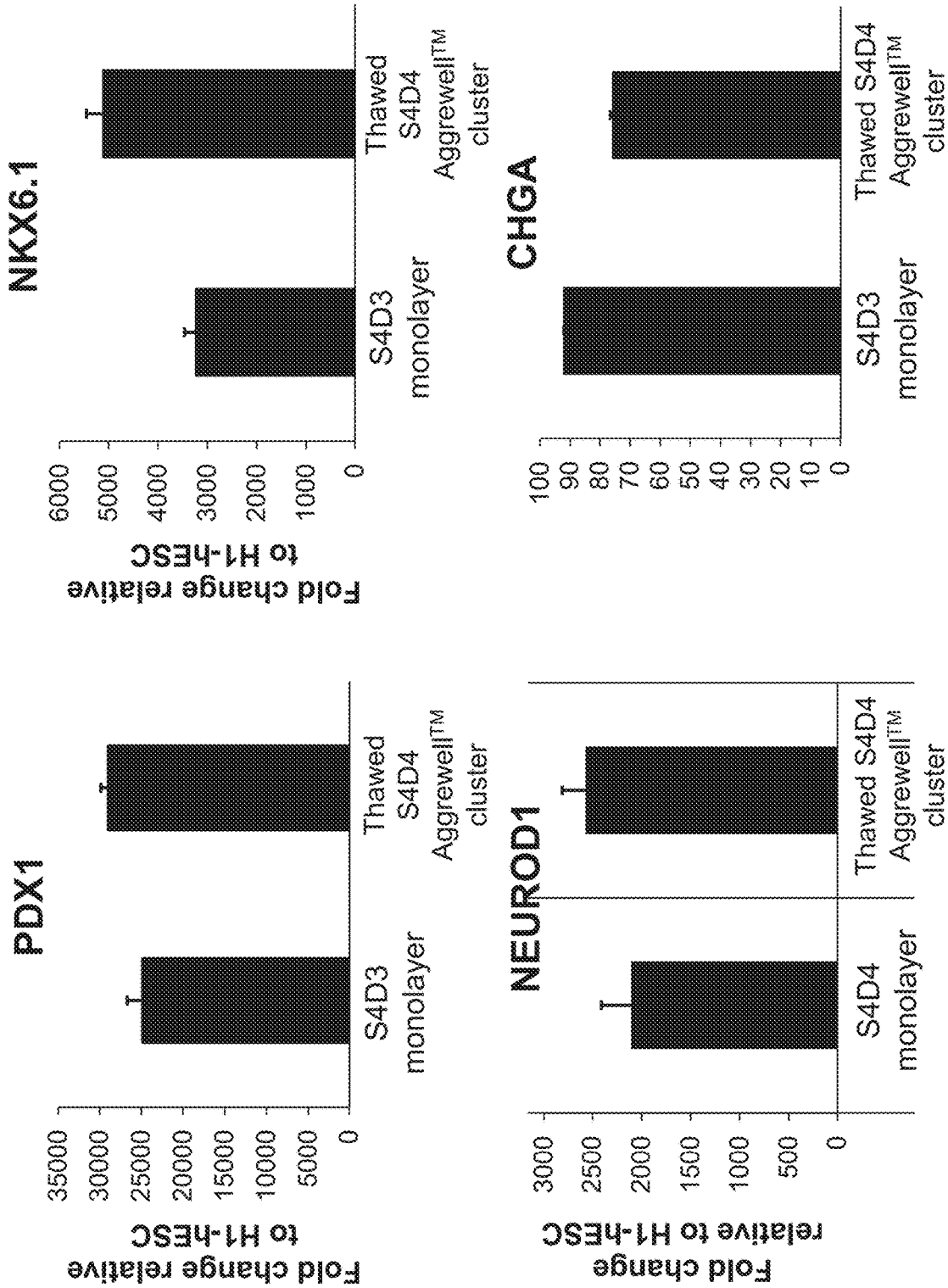

FIG. 6A depicts the procedure through which a (i) fresh S4D3 monolayer or S4D3 cryopreserved cells was assembled (ii) via the AGGREWELL™ method into (iii) cell clusters. FIG. 6B shows that high protein presence of pancreatic endoderm TF PDX1 (top, left), and NKX6.1 (top, middle), but low protein presence of endocrine TF NEUROD1 (top, right), alternate non-pancreatic endoderm lineage allocating TF SOX2 (bottom, middle), and CDX2 (bottom, right) was detected in S4D5 AGGREWELL™ clusters. FACS analysis (FIG. 6C) shows that 99.3±0.1% of the cells were PDX1+(left), 84.4±0.1% NKX6.1±(middle), but 2.2±0.4% NKX6.1±NEUROD1+(right) or 1.35±0.55% NKX6.1$^+$ CHGA$^+$ (middle). FIG. 6D shows that the robust pancreatic endoderm characteristics were maintained in S4D4 AGGREWELL™ clusters derived from S4D3 cryopreserved cells, as the high gene expression of PDX1 (top, left), NKX6.1 (top, right), and low expression of NEUROD1 (bottom, left), and CHGA (bottom, right) was maintained as compared to a S4D3 monolayer. Overall, S4D5 AGGREWELL™ clusters exhibited a greater degree of non-endocrine pancreatic endoderm characteristics than previous Stage 4 cells reported in *Nature Biotechnology*, 2014 (32) 11, 1121-1133. The results are significant as AGGREWELL™ clusters provide a scalable starting point with which to develop suspension culture based of differentiation towards the beta cell.

Figure 6E:
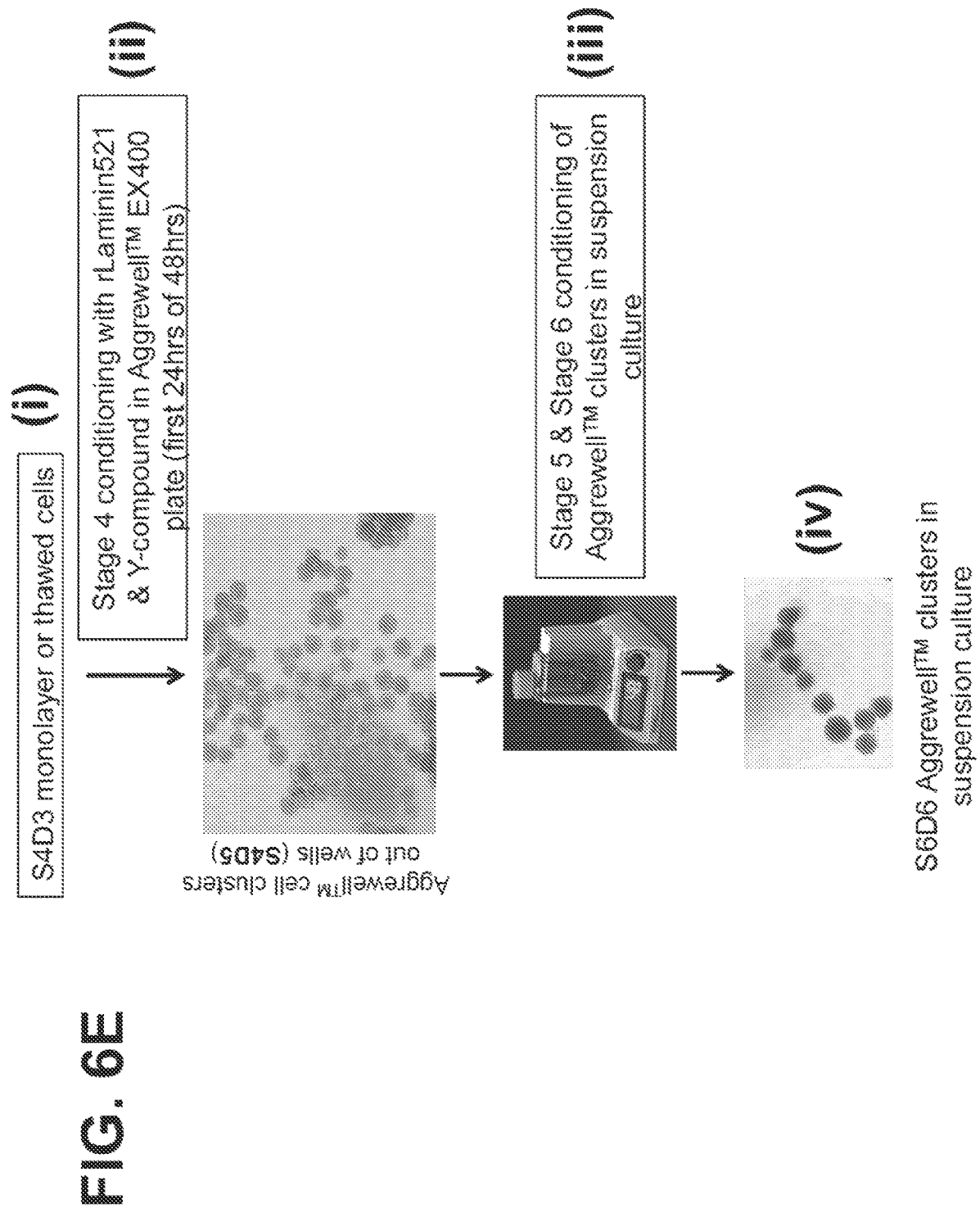
Figure 6F:
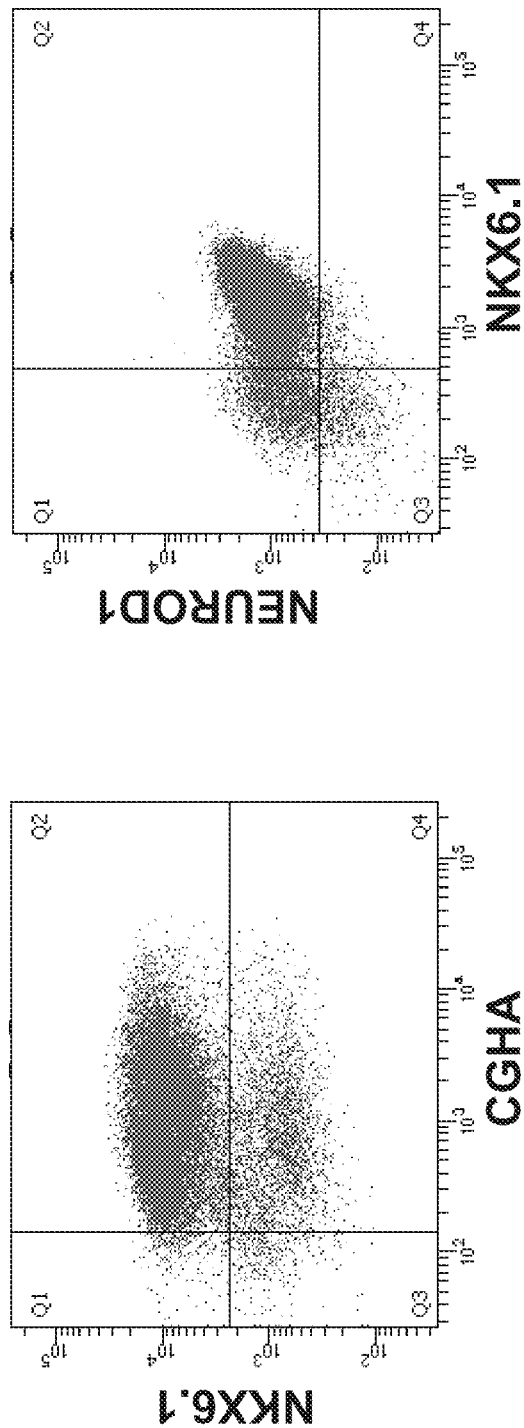
Figure 6G:
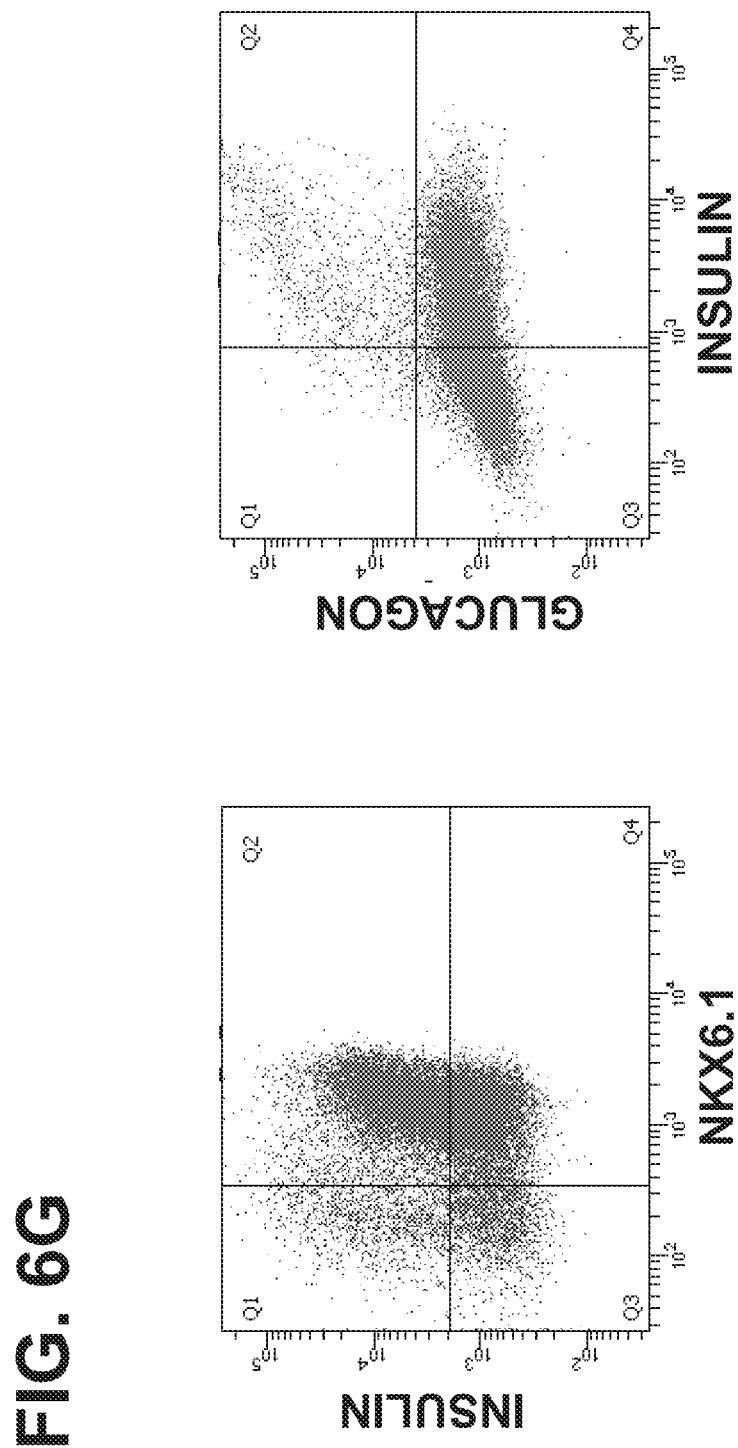
Figure 6H:
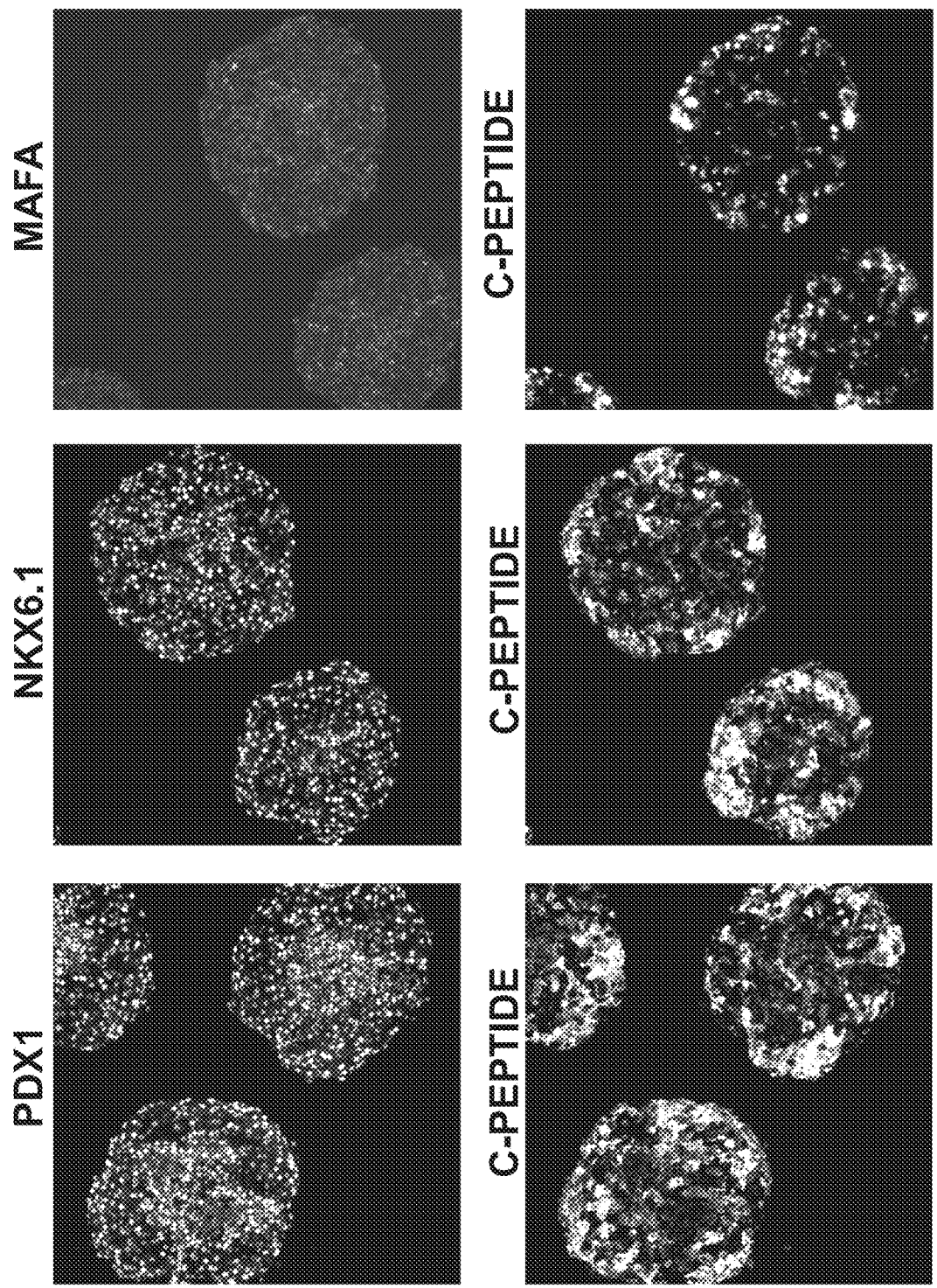
Figure 6I:
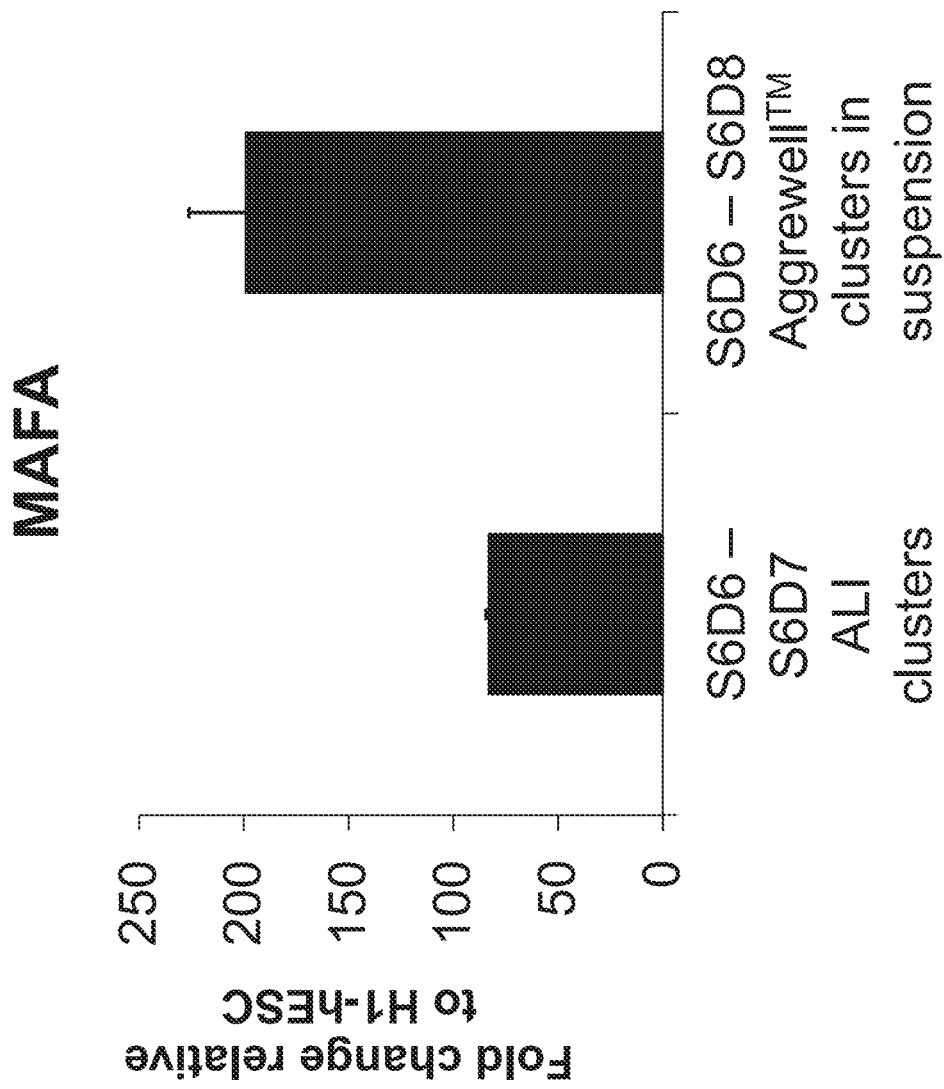

FIG. 6E depicts the procedure through which a (i) fresh S4D3 monolayer or S4D3 cryopreserved cells was assembled (ii) via the AGGREWELL™ method into cell clusters, and (iii) differentiated in suspension culture to (iv) immature beta-cells by S6D6. FACS analysis of S6D6 AGGREWELL™ clusters shows an immature beta-cell protein profile, as 78.5±1.87% of cells were NKX6.1$^+$ CHGA$^+$ (left, FIG. 6F), 73.6±4.34% NKX6.1±NEUROD1+(right, FIG. 6F), and 38.4±5.96% NKX6.1$^+$ INSULIN$^+$ (left, FIG. 6G). The majority of the INSULIN-positive population (50.2±6.92% of total cells were INSULIN$^+$) was NKX6.1± (left, FIG. 6G) and not GLUCAGON-positive (7.43±1.49% INSULIN$^+$ GLUCAGON$^+$; (right, FIG. 6G). FIG. 6H shows by IF that at S6D6 the majority of C-PEPTIDE-positive cells in AGGREWELL™ clusters were both PDX1$^+$ (left) and NKX6.1$^+$ (middle). Surprisingly, the protein presence of the maturation gatekeeper TF MAFA (right) was already easily detected at S6D6, and was expressed at a higher level than previous ALI clusters at S6D6-S6D7 (*Nature Biotechnology*, 2014 (32) 11, 1121-1133) (FIG. 6I; see also FIG. 3C for ALI S7D7 comparison). Similarly, the expression of INSULIN (FIG. 6J), PDX1 (FIG. 6K), and NKX6.1 (FIG. 6L) was higher than previous ALI clusters at S6D6-S6D7. The results prove that S4D5 AGGREWELL™ clusters can be cultured in suspension culture towards an immature beta-cell state, providing a scalable and primed starting point towards suspension culture based differentiation to a functional, mature beta-cell.

In summary, this example demonstrates that Stage 4 cells can be made to aggregate into cell clusters, while maintaining their phenotype of pancreatic endoderm. Moreover, these Stage 4 cell clusters can be further differentiated towards a robust immature beta-cell phenotype (Stage 6) by scalable suspension culture.

Example 4

Suspension Culture Generation of Endocrine Cells with Enhanced Beta-Cell Maturation Marker Expression and Protein Presence Similar to Matured Human Islets The following example demonstrates the generation by suspension culture of C-PEPTIDE cells that exhibit co-expression and protein presence of the following maturation markers, PDX1, NKX6.1, MAFA, UCN3, and SLC2A1. Cells of the H1-hESC cell line cultured with EZ8 media at passage 28 were seeded as single cells at 0.094×106 cells/cm2 on MATRIGEL™ at a 1:30 dilution coated dishes in a media of DMEM-F12, GlutaMAX™ in a 1:100 dilution ("lx concentration"), 0.25 mM ascorbic acid, 100 ng/ml FGF2, 1 ng/ml of TGFβ, ITS-X at a 1:100 dilution, 2% FAF-BSA, and 20 ng/ml of IGF-1", supplemented with 10 µM of Y-compound. Y-compound was added only during the first 24 hours post-seeding. Forty-eight hours post-seeding, the cultures were washed in PBS (−/−).

For FIGS. 7A to 7M, the cultures were differentiated using the following protocol. During Stages 1 through 4 of the protocol, cultures were maintained on planar adherent cultures. Beginning from the S4D3 monolayer, or cryopreserved S4D3 cells, AGGREWELL™ cell clusters were prepared, and cultured for an additional 48 hours (Stage 4 day 5 or S4D5). Media was exchanged daily throughout the differentiation protocol. During stages 5, 6, and 7 AGGREWELL™ clusters were cultured in suspension culture as described in Example 3, except that Stage 6 occurs over 7 days as compared to 6 days.

Stage 1 (3 days): Cells were cultured for one day in the following Stage 1 media: MCDB-131 medium containing 2.7 g/1000 ml sodium bicarbonate, and supplemented with 0.5% FAF-BSA, GlutaMAX™ in a 1:100 dilution ("lx concentration"), 4.5 mM D-glucose to obtain a concentration of 10 mM of D-glucose, 100 ng/ml GDF8, and 1.5 µM of MCX compound. Cells were then cultured for an additional day in MCDB-131 medium containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, 100 ng/ml GDF8, and 0.1 µM GSK-30 inhibitor. Cells were then cultured for an additional day in MCDB-131 containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, and 100 ng/ml GDF8.

Stage 2 (2 Days):
Cells were treated for two days with MCDB-131 medium containing 2.7 g/1000 ml sodium bicarbonate, and supplemented with 0.5% FAF-BSA, 1× GlutaMAX™, 4.5 mM D-glucose to obtain a concentration of 10 mM D-glucose, 0.25 mM Ascorbic acid, and 50 ng/ml FGF7.

Stage 3 (2 Days):
Cells were treated for two days with BLAR001 custom medium containing 3.6 g/1000 ml sodium bicarbonate, and supplemented with a 1:200 dilution of ITS-X; 4.5 mM D-glucose to obtain a concentration of 10 mM D-glucose; 1× GlutaMAX™; 1% FAF-BSA; 25 ng/ml FGF7; 0.25 µM SANT-1; 1 µM RA; 0.25 mM ascorbic acid; 300 nM of TPB"); and LDN-HCl for two days. The concentration of LDN-HCl used for the first day of stage 3 were 100 nM, and for the second day of stage 3 was 10 nM.

Stage 4 (3 Days):
Cells were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1× concentration of GlutaMAX™; 1% FAF-BSA; 0.25 µM SANT-1; 50 nM RA; 2 ng/ml FGF7; 70 nM LDN-HCl; 0.25 mM ascorbic acid; and 200 nM TPB for three days.

Cryopreservation of Stage 4 Day 3 Monolayer:
Cryopreserved cell banks from S4D3 monolayer were established by the procedure outlined in Example 3 and Table VII.

Thawing of Cryopreserved S4D3 Monolayer Cells:
Frozen 5 ml vials containing 5.0×10$^6$ S4D3 monolayer cells were thawed as described in Example 3.

Stage 4 (2 Days) for AGGREWELL™ Cluster Transition:
AGGREWELL™ clusters were generated from Stage 4 day 3 monolayer cells, or thawed cryopreserved Stage 4 day 3 cells, as described in Example 3.

Stage 5 (3 Days):
S4D5 AGGREWELL™ clusters were retrieved from AGGREWELL™ 400 EX plates and transferred to PBS0.1MAG spinners (at a cell density of 1.5-2.0 million cells/ml with the rotation speed of 27 rpm (rounds per minute) in Stage 5 medium for three days. Cells were treated with BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 0.25 µM SANT-1; 50 nM RA; 100 nM LDN-HCl; 1 µM of T3; and 10 µM of ALK5 inhibitor II. 4 kU/ml DNaseI and 5 µM Y-compound were supplemented only on Stage 5 day 1.

Stage 6 (7 Days):
AGGREWELL™ clusters were treated in BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 100 nM LDN-HCl; 1 µM of T3; 10 µM of ALK5 inhibitor II, and 100 nM of gamma secretase inhibitor XX.

Stage 7 (6 Days to 7 Days):
AGGREWELL™ clusters were treated in either BLAR001 or BLAR004 medium containing 2.7 g/1000 ml sodium bicarbonate, and supplemented with a 1:200 dilution of ITS-X; 1× GlutaMAX™; 2% FAF-BSA; 10 µg/ml of heparin ("H"), 10 nM of T3 ("low T3"); 1 mM NAC; 0.5 µM ZM"); and the following components which constitute Formulation I ("FI") 1:200 dilution of RPMI vitamin supplement; 1:200 dilution of MEM non-essential amino acid supplement; 1:2000 dilution of chemically defined lipid concentrate; 1:200 dilution of sodium pyruvate; 1:2000 dilution of trace elements A; 1:2000 dilution of trace elements B for seven days. Additional compounds added during Stage 7 included either 4 µM AZT; or 1 µM DEZA. For clarity, AGGREWELL™ clusters in suspension were cultured during Stage 7 in two conditions utilizing the concentrations described above (in either BLAR001 or BLAR004 base medium): (i) no ALK5, low T3, ZM, H, NAC; (ii) no ALK5, low T3, ZM, H, NAC, AZT, DEZA.

For Stages 5, 6 and 7, the cell cultures were conditioned by starting with either S4D5 AGGREWELL™ clusters or S4D3-transitioned ALI clusters. S4D5 AGGREWELL™ clusters were retrieved from AGGREWELL™ 400 EX plates and transferred to PBS0.1MAG spinners at a cell density of 1.5-2.0 million cells/ml with the rotation speed of 27 rpm (rounds per minute).

Quantification and Characterization of Differentiated Cells:

Stage 7 AGGREWELL™ clusters and human islets were characterized by IF, FACS, and qRT-PCR as described in Examples 2 and 3.

Figure 7A:
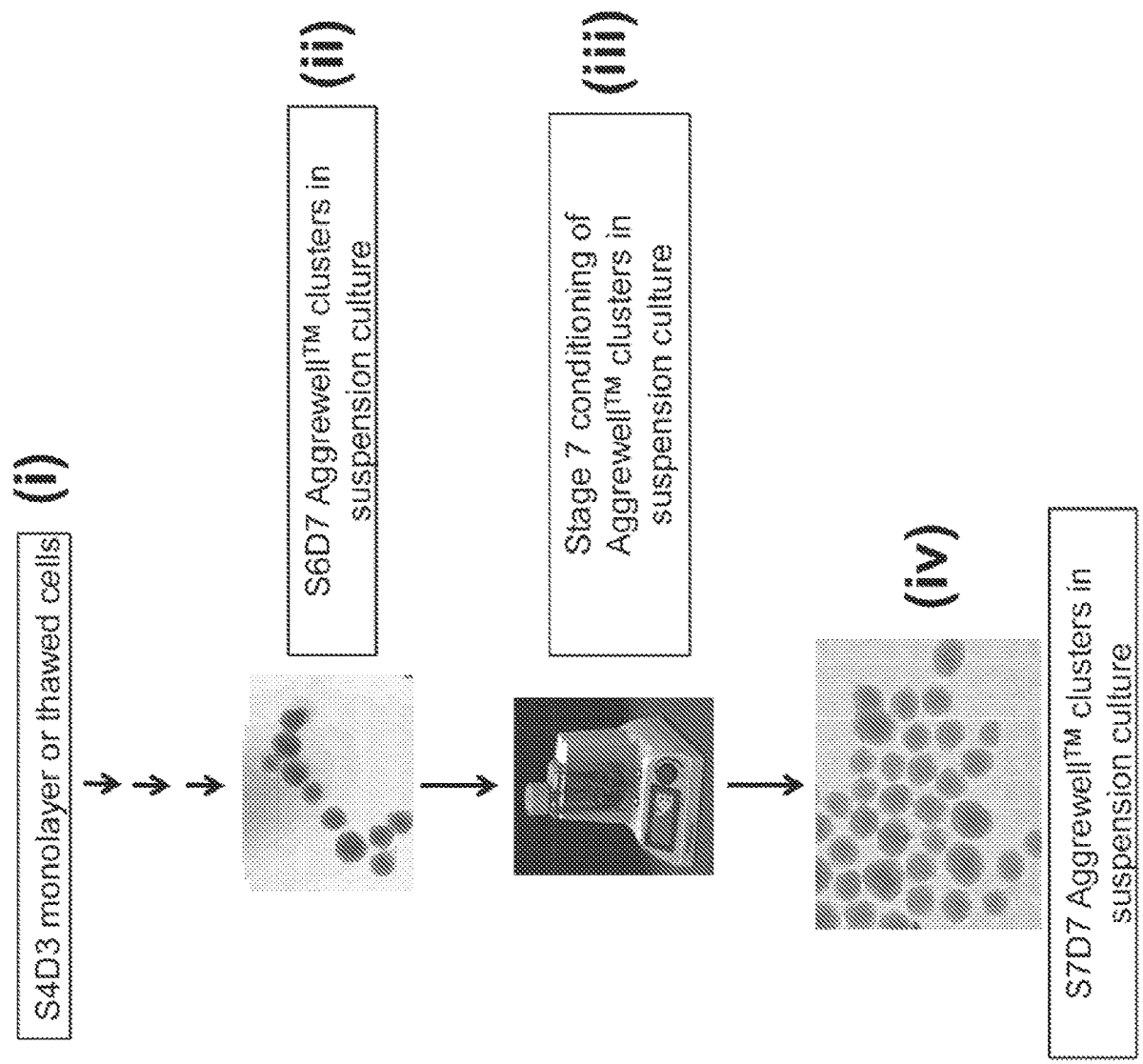
Figure 7B:
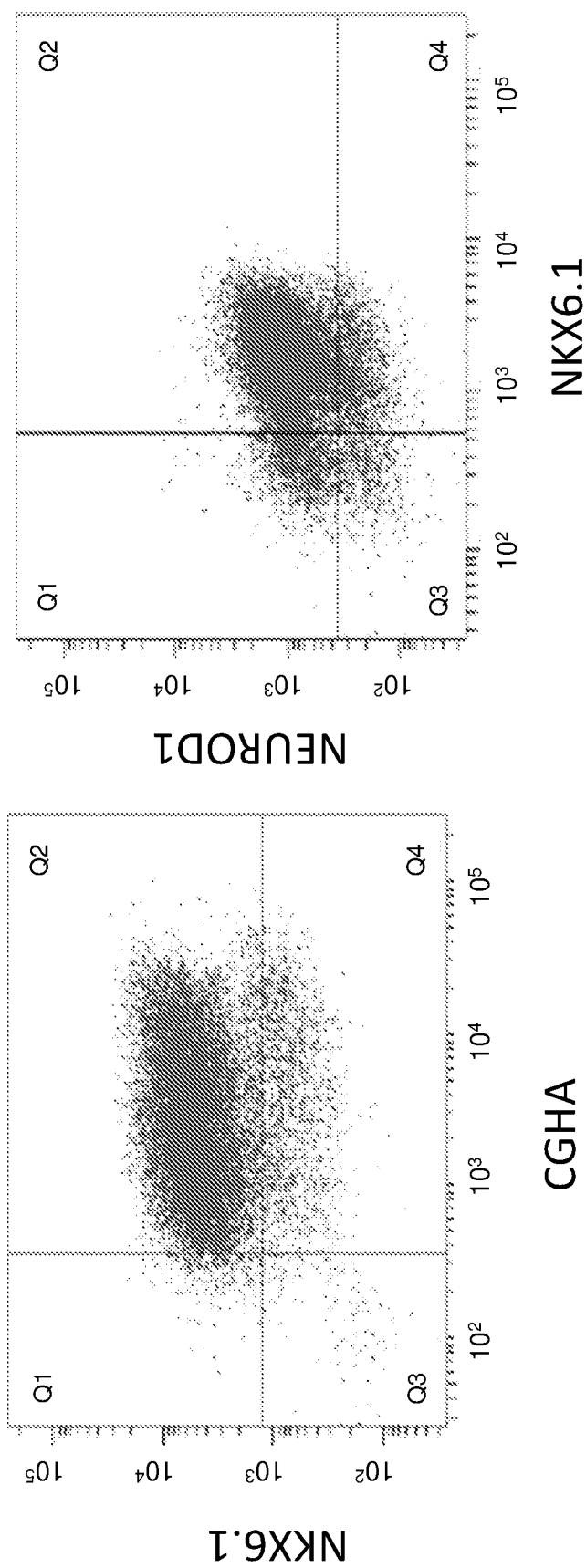
Figure 7D:
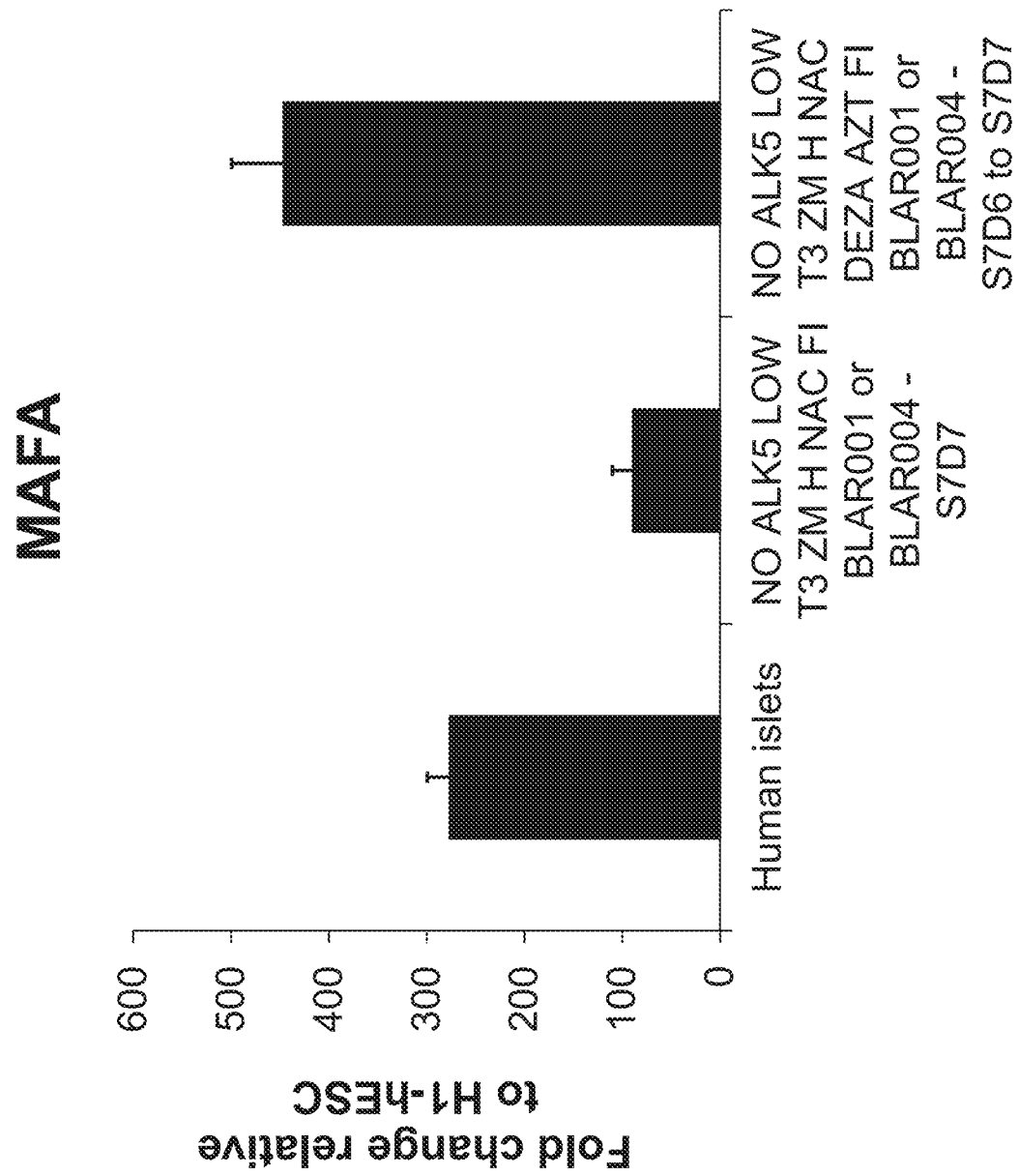
Figure 7F:
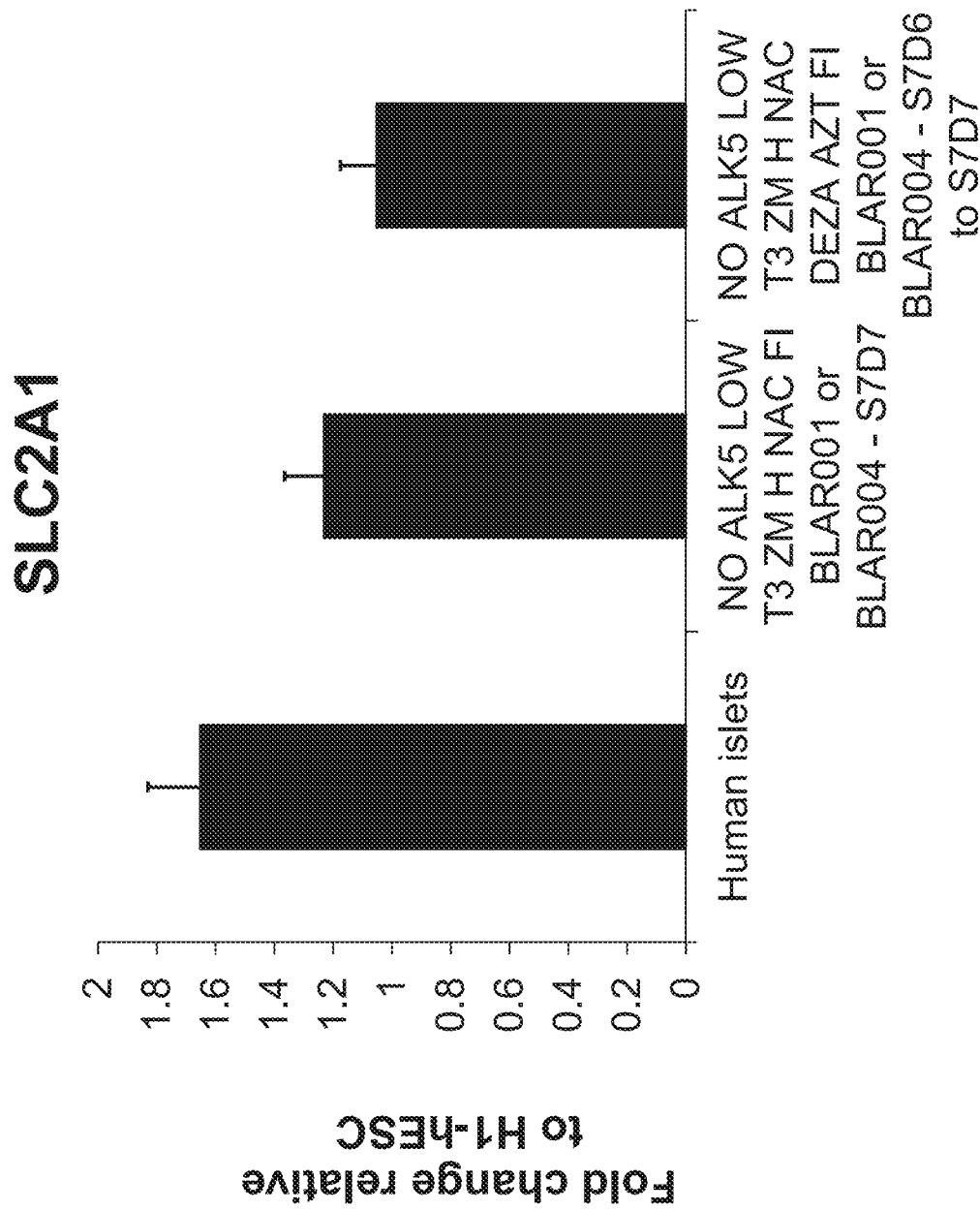
Figure 7G:
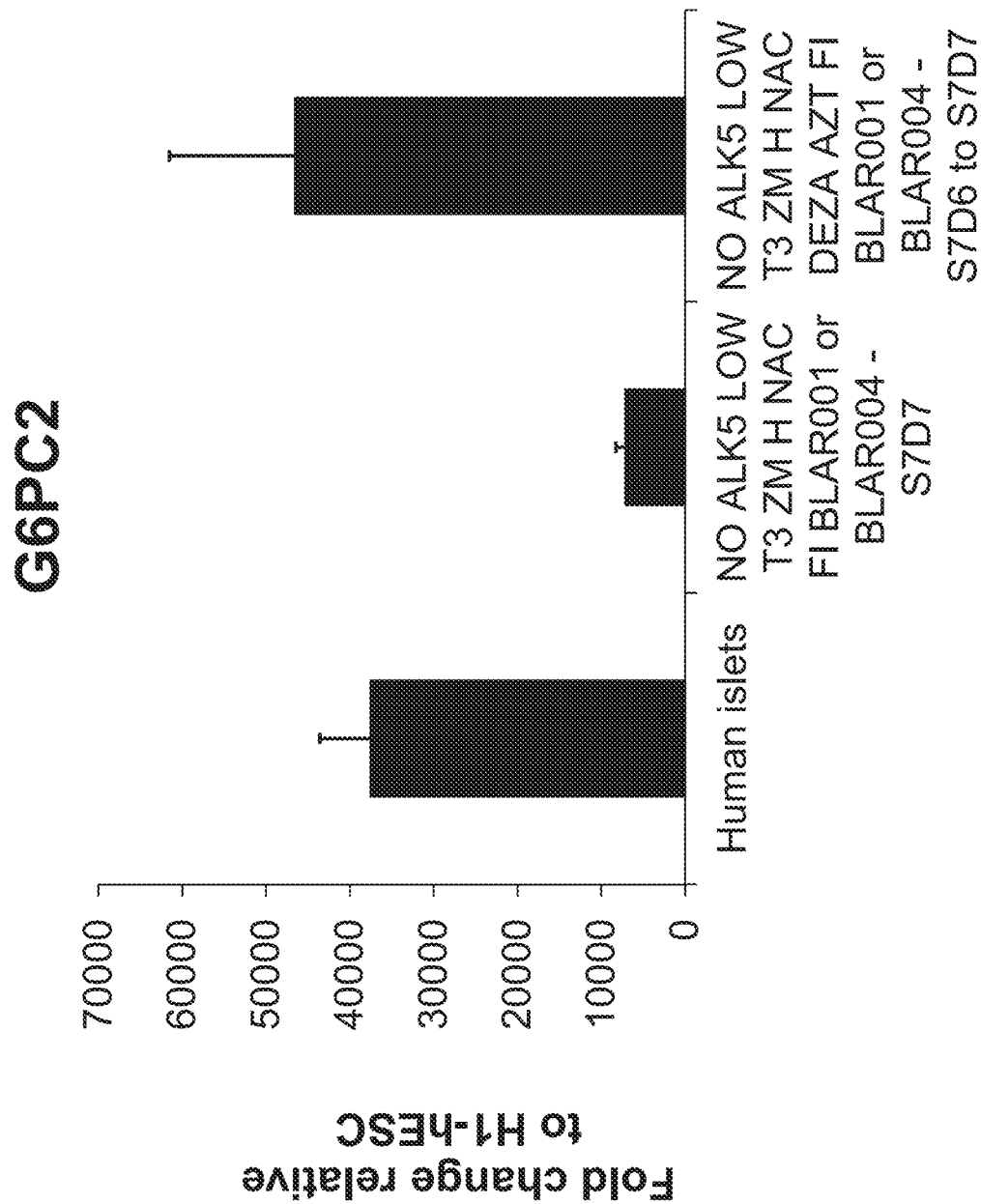
Figure 7I:
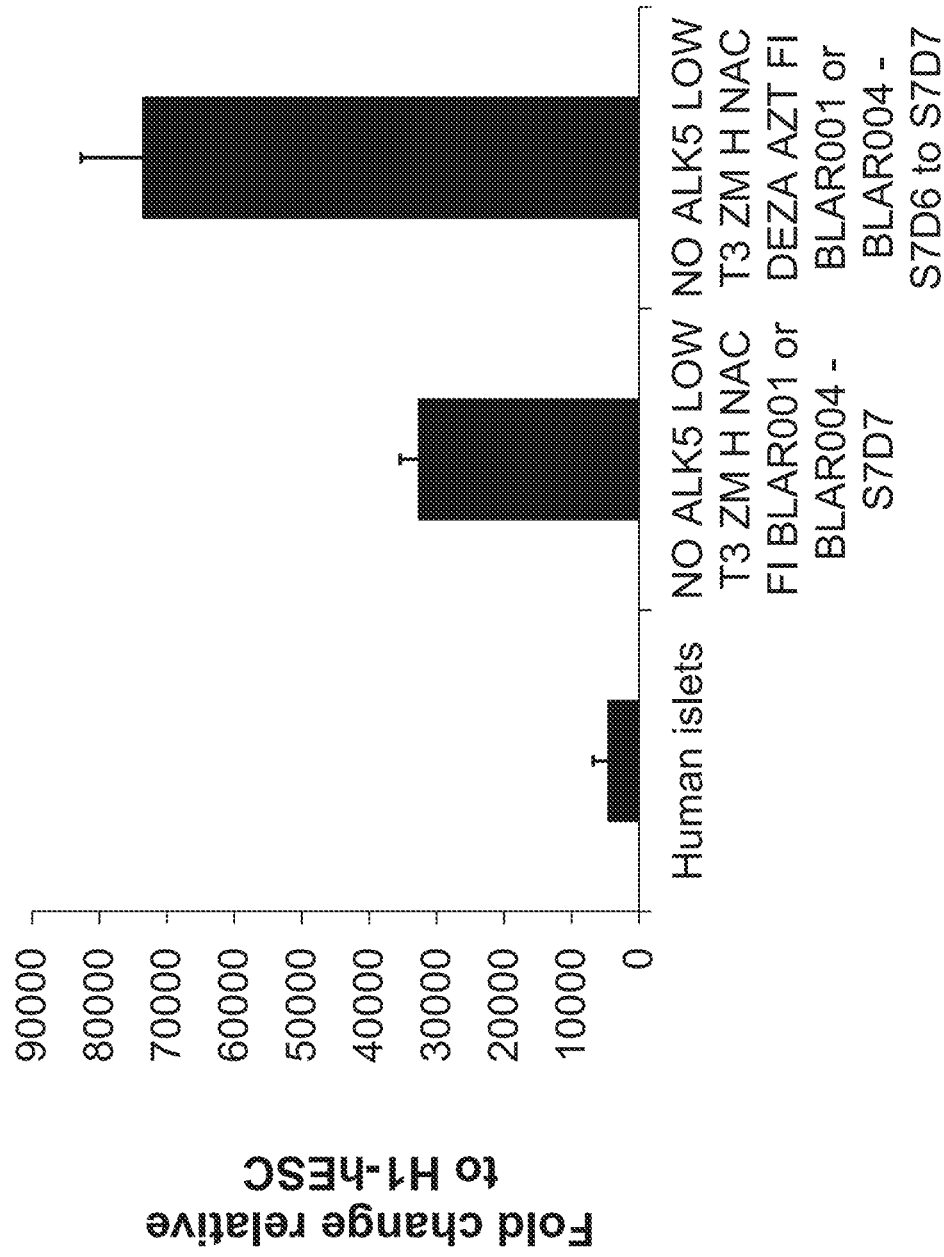
Figure 7J:
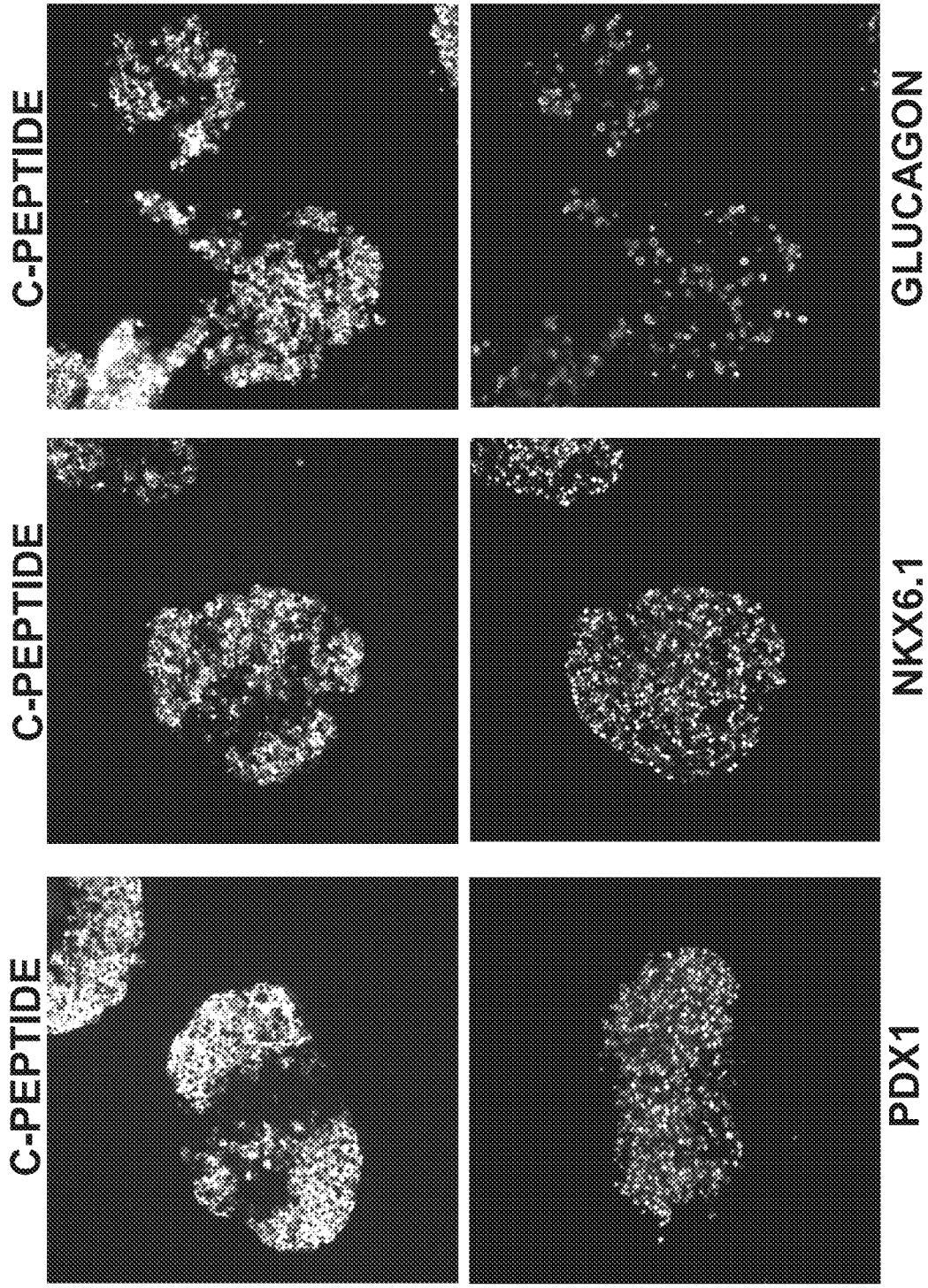

FIG. 7A depicts the procedure through which a (i) fresh S4D3 monolayer or S4D3 cryopreserved cells were assembled into AGGREWELL™ clusters, conditioned by suspension culture through (ii & iii) Stages 5, 6 and 7 to generate (iv) S7D7 AGGREWELL™ clusters. As observed in S6D6 AGGREWELL™ clusters (FIGS. 6F-6G), S7D7 AGGREWELL™ clusters cultured by 'NO ALK5 LOW T3 ZM H NAC DEZA AZT FI BLAR001' during Stage 7 maintained a baseline beta-cell protein profile (FIGS. 7B-7C). 89% of cells were NKX6.1$^+$ CHGA$^+$ (left, FIG. 7B), 77.7% NKX6.1$^+$ NEUROD1$^+$ (right, FIG. 7B), and 40.8% NKX6.1$^+$ INSULIN$^+$ (left, FIG. 7C). The majority of the INSULIN-positive population (46.4% of total cells were INSULIN$^+$) was NKX6.1$^+$ (left, FIG. 7C) and not GLUCAGON-positive (3.9% INSULIN$^+$ GLUCAGON$^+$; (right, FIG. 7C).

In addition to the baseline beta-cell profile, the gene expression of maturation markers MAFA (FIG. 7D), UCN3 (FIG. 7E), SLC2A1 (FIG. 7F), G6PC2 (FIG. 7G), INSULIN (FIG. 7H), and NKX6.1 (FIG. 7I), were at or above human islet levels in Stage 7 'NO ALK5 LOW T3 ZM H NAC DEZA AZT FI BLAR001 or BLAR004' conditioned S7D7 AGGREWELL™ clusters. The expression levels at S7D7 of maturation markers such as: MAFA (FIG. 3C); G2PC2 (FIG. 3F); INSULIN (FIG. 3H); and NKX6.1 (FIG. 3L) were much greater in AGGREWELL™ (NO ALK5 LOW T3 ZM H NAC DEZA AZT FI BLAR001 or BLAR004') then in ALI clusters.

Figure 7K:
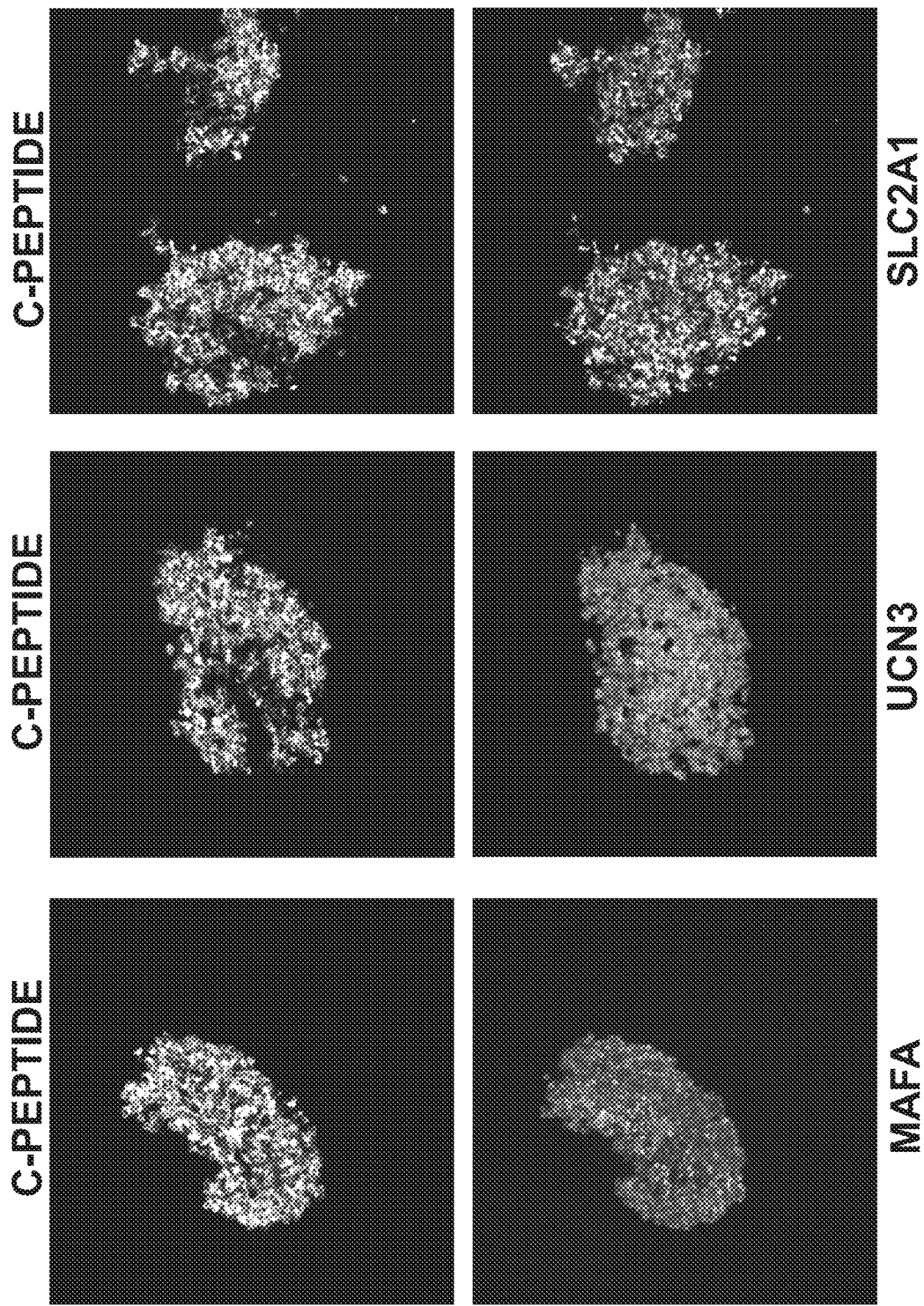
Figure 7L:
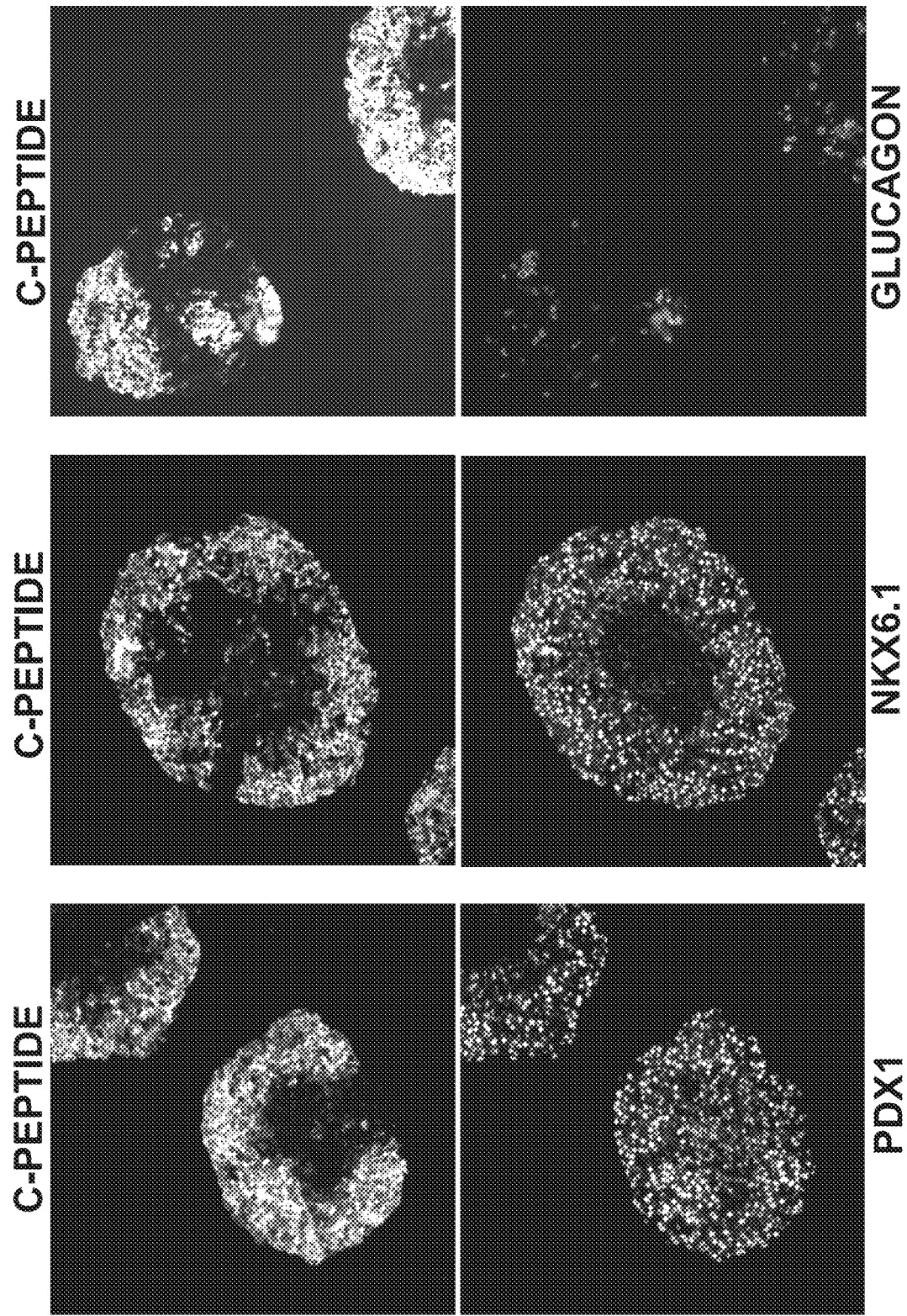
Figure 7M:
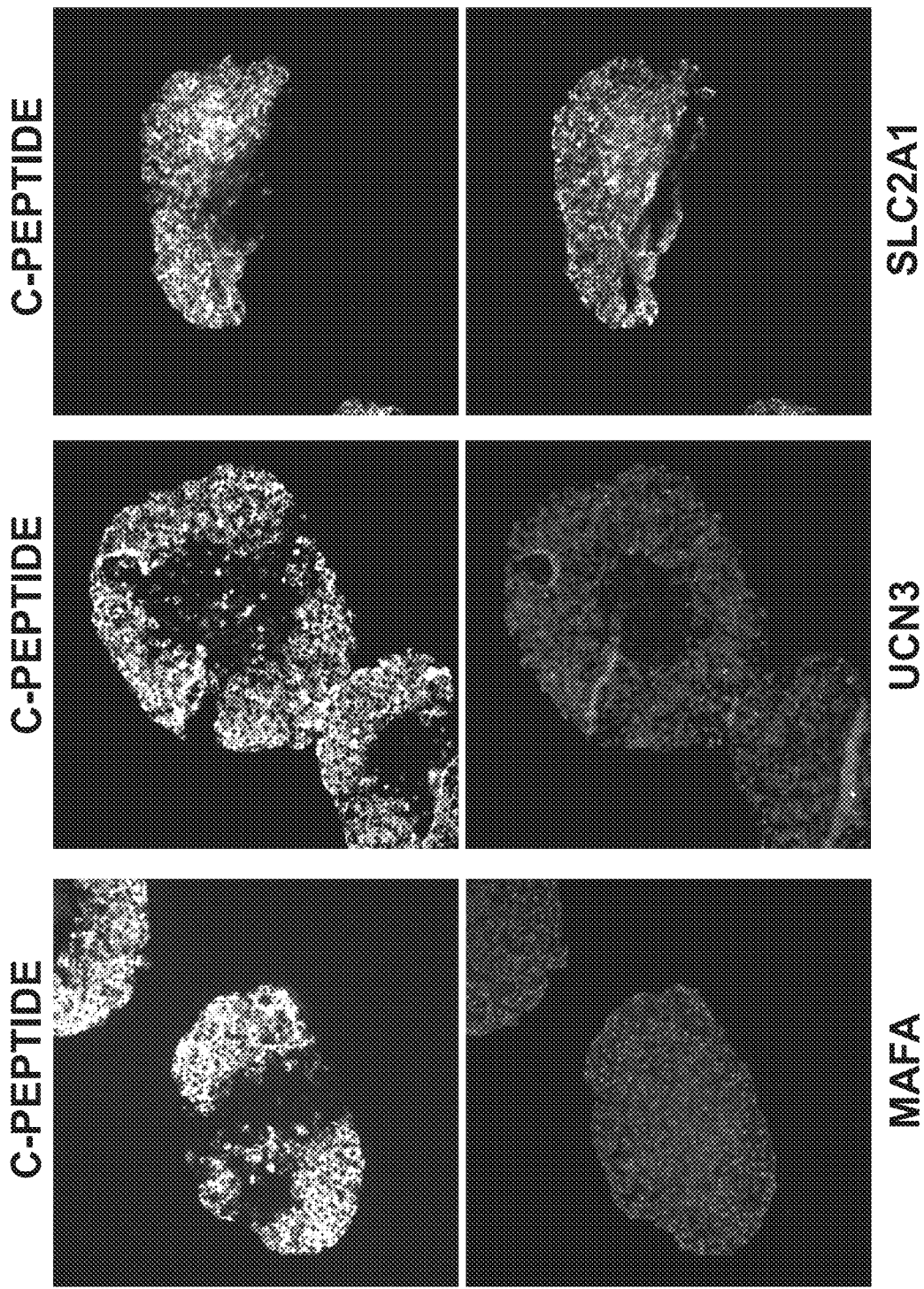

Indeed, FIGS. 7J-7M demonstrate that the addition of DEZA and AZT to 'NO ALK5 LOW T3 ZM H NAC FI BLAR004' Stage 7 conditioning generated a significant number of non-GLUCAGON (FIG. 7J; bottom, right)C-PEPTIDE cells that co-expressed at S7D7, in terms of protein presence, PDX1 (FIG. 7J; bottom, left), NKX6.1 (FIG. 7J; bottom, middle), MAFA (FIG. 7K; bottom, left), UCN3 (FIG. 7K; bottom, middle), and SLC2A1 (FIG. 7K; bottom, right). For each figure, IF-staining is shown as single channels with C-PEPTIDE on the top row. While the protein presence of MAFA, SLC2A1 and UCN3 is not restricted to C-PEPTIDE positive cells, it is expected that at least about 10% of the cell population would show the co-expression of C-PEPTIDE, PDX1, NKX6.1, MAFA, SLC2A1, and UCN3. In contrast, FIGS. 7L-7M, demonstrates the generation, by 'NO ALK5 LOW T3 ZM H NAC FI BLAR004'-specific Stage 7 conditioning, of C-PEPTIDE cells that co-expressed, in terms of protein presence, by S7D7 a partial set of maturation markers: PDX1 (FIG. 7L; bottom, left), NKX6.1 (FIG. 7L; bottom, middle), MAFA (FIG. 7M; bottom, left), SLC2A1 (FIG. 7M; bottom, right), but not GLUCAGON (FIG. 7L; bottom, right) and UCN3 (FIG. 7M; bottom, middle). Stage 7 'NO ALK5 LOW T3 ZM H NAC DEZA AZT FI BLAR004' conditioning of AGGREWELL™ clusters, generated a significant number of mature beta-cells, similar to matured adult human islets, as assessed by gene expression and protein presence.

In summary, this example demonstrates that Stage 4 cell clusters can be further differentiated in suspension culture towards functional beta-cells, by changes in Stage 7 conditioning. Specifically, example 4 shows the generation of C-PEPTIDE cells, within cell clusters in suspension culture, that co-express beta-cell maturation markers essential for proper functionality of the beta-cell Example 5

Suspension Culture Generation of Endocrine Cells with Mature Human-Islet-Similar Glucose-Dependent Mitochondrial Respiration and Glucose Stimulated Insulin Secretion Kinetics The following example demonstrates the generation of functionally mature beta-cells by suspension culture with human-islet-similar glucose-dependent mitochondrial respiration and glucose stimulated insulin secretion ("GSIS") kinetics. Culturing conditions are the same as in Example 4. Cells of the H1-hESC cell line cultured with EZ8 media at passage 28 were seeded as single cells at $0.094 \times 10^6$ cells/cm$^2$ on MATRIGEL™ at a 1:30 dilution coated dishes in a media of DMEM-F12, GlutaMAX™ in a 1:100 dilution ("1x concentration"), 0.25 mM ascorbic acid, 100 ng/ml FGF2, 1 ng/ml of TGFβ, ITS-X at a 1:100 dilution, 2% FAF-BSA, 20 ng/ml of IGF-1 supplemented with 10 µM of Y-compound. Y-compound was added only during the first 24 hours post-seeding. Forty-eight hours post-seeding, the cultures were washed in PBS (−/−).

For FIGS. 8A to 8I, the cultures were differentiated using the following protocol. During Stages 1 through 4 of the protocol, cultures were maintained on planar adherent cultures. Beginning from the S4D3 monolayer, or cryopreserved S4D3 cells, AGGREWELL™ cell clusters were prepared, and cultured for an additional 48 hours (Stage 4 day 5 or S4D5). Media was exchanged daily throughout the differentiation protocol. During stages 5, 6, and 7 AGGREWELL™ clusters were cultured in suspension culture, as described in Example 3. ALI clusters, shown in FIG. 8E to 8F, were cultured as described in Example 2. Briefly:

Stage 1 (3 Days):

Cells were cultured for one day in the following Stage 1 media: MCDB-131 medium containing 2.7 g/1000 ml sodium bicarbonate, and supplemented with 0.5% FAF-BSA, GlutaMAX™ in a 1:100 dilution ("1x concentration"), 4.5 mM D-glucose to obtain a concentration of 10 mM of D-glucose, 100 ng/ml GDF8, and 1.5 µM of MCX compound. Cells were then cultured for an additional day in MCDB-131 medium containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, 100 ng/ml GDF8, and 0.1 µM GSK-30 inhibitor. Cells were then cultured for an additional day in MCDB-131 containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, and 100 ng/ml GDF8.

Stage 2 (2 Days):

Cells were treated for two days with MCDB-131 medium containing 2.7 g/1000 ml sodium bicarbonate, and supplemented with 0.5% FAF-BSA, 1× GlutaMAX™, 4.5 mM D-glucose to obtain a concentration of 10 mM D-glucose, 0.25 mM Ascorbic acid, and 50 ng/ml FGF7.

Stage 3 (2 Days):

Cells were treated for two days with BLAR001 custom medium containing 3.6 g/1000 ml sodium bicarbonate, and supplemented with a 1:200 dilution of ITS-X; 4.5 mM D-glucose to obtain a concentration of 10 mM D-glucose; 1× GlutaMAX™; 1% FAF-BSA; 25 ng/ml FGF7; 0.25 µM SANT-1; 1 µM RA; 0.25 mM ascorbic acid; 300 nM of TPB"); and LDN-HCl for two days. The concentration of LDN-HCl used for the first day of stage 3 were 100 nM, and for the second day of stage 3 was 10 nM.

Stage 4 (3 Days):

Cells were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1× concentration of GlutaMAX™; 1% FAF-BSA; 0.25 µM SANT-1; 50 nM RA; 2 ng/ml FGF7; 70 nM LDN-HCl; 0.25 mM ascorbic acid; and 200 nM TPB for three days.

Cryopreservation of Stage 4 Day 3 Monolayer:

Cryopreserved cell banks from S4D3 monolayer were established using the procedure outlined in Example 3 and Table VII.

Thawing of Cryopreserved S4D3 Monolayer Cells:

Frozen 5 ml vials containing 5.0×10$^6$ S4D3 monolayer cells were thawed as described in Example 3. The same procedure can be applied to transition to either ALI or AGGREWELL™ clusters.

Stage 4 (2 Days) for AGGREWELL™ Cluster Transition or S4D3 ALI Cluster Transition:

AGGREWELL™ clusters were generated from Stage 4 day 3 monolayer cells, or thawed cryopreserved Stage 4 day 3 cells, as described in Example 3. ALI clusters were generated at Stage 4 day 3 cells, as described in Example 2.

Similar to Example 4, for Stages 5, 6 and 7, the cell cultures were conditioned by starting with either S4D5 AGGREWELL™ clusters or 54D3-transitioned ALI clusters. S4D5 AGGREWELL™ clusters were retrieved from AGGREWELL™ 400 EX plates and transferred to PBS0.1MAG spinners at a cell density of 1.5-2.0 million cells/ml with the rotation speed of 27 rpm (rounds per minute).

Stage 5 (3 Days):

AGGREWELL™ or ALI clusters were treated with BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 0.25 µM SANT-1; 50 nM RA; 100 nM LDN-HCl; 1 µM of T3; and 10 µM of ALK5 inhibitor II for three days. 4 kU/ml DNaseI and 5 µM Y-compound were supplemented only on Stage 5 day 1 for AGGREWELL™ clusters.

Stage 6 (7 Days):

AGGREWELL™ or ALI clusters were treated in BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM ZnSO$_4$; 100 nM LDN-HCl; 1 µM of T3; 10 µM of ALK5 inhibitor II, and 100 nM of gamma secretase XX.

Stage 7 (7 Days to 14 Days):

AGGREWELL™ or ALI clusters were treated in either BLAR001 or BLAR004 medium containing 2.7 g/1000 ml sodium bicarbonate, and supplemented with a 1:200 dilution of ITS-X; 1× GlutaMAX™; 2% FAF-BSA; 10 µg/ml of heparin ("H"), 10 nM of T3 ("low T3"); 1 mM NAC; 0.5 µM ZM"); and the following components which constitute Formulation I ("FI") 1:200 dilution of RPMI vitamin supplement; 1:200 dilution of MEM non-essential amino acid supplement; 1:2000 dilution of chemically defined lipid concentrate; 1:200 dilution of sodium pyruvate; 1:2000 dilution of trace elements A; 1:2000 dilution of trace elements B for seven days. Additional compounds added during Stage 7 included either 4 µM AZT; or 1 µM DEZA. For clarity, AGGREWELL™ or ALI clusters in suspension were cultured during Stage 7 in two conditions utilizing the concentrations described above (in either BLAR001 or BLAR004 base medium): (i) No ALK5, Low T3, ZM, H, NAC; (ii) No ALK5, Low T3, ZM, H, NAC, AZT, DEZA. FIG. 8A, 8B, 8H, 8L During Stage 7, AGGREWELL™ clusters in suspension were cultured to S7D13 or S7D14 in two conditions: (i) No ALK5, Low T3, 0.50/1 ZM, 10 µg/ml H, 1 mM NAC; (ii) S7D1 to S7D5 No ALK5, Low T3, 0.50/1 ZM, 10 µg/ml H, 1 mM NAC; 5 µM AZT; DEZA; S7D6 to S7D13 or S7D14 No ALK5, Low T3, ZM, 10 µg/m; H, 1 mM NAC.

Quantification and Characterization of Differentiated Cells:

For quantification of glucose-dependent mitochondrial activity of S6D7 ALI clusters, Stage 7 AGGREWELL™ clusters, and matured human islets were characterized by the Seahorse XF$^e$24 device as described in Example 2. ALI/AGGREWELL™ clusters, or human islets were harvested, and their oxygen consumption rate ("OCR") measured on the XF$^e$24 Extracellular Flux Analyzer before and after injection of 20 mM D-glucose. ALI/AGGREWELL™ clusters, or human islets were removed from their Stage 7 conditioning and incubated for 2 hours in both a 37° C. non-CO$_2$ environment, and medium designed to achieve a baseline OCR. The pre-incubation medium contains 1 mM D-glucose, 1 mM L-Glutamine, and 1 mM sodium pyruvate in XF Base medium. After pre-incubation, ALUAG-GREWELL™ clusters, or human islets were loaded onto the Seahorse machine in which the following measurements were made: (i) 3× baseline OCR (pre-D-glucose injection); (ii) 5× post-D-glucose (post-injection incubation time: 72 minutes). All OCR measurements were normalized to DNA content of individual samples. DNA was isolated by the QIAamp DNA MicroKit, and DNA content measured by the NanoDrop 8000 UV-Vis Spectrophotometer.

For quantification of glucose-dependent insulin secretion, Stage 7 ALI clusters, AGGREWELL™ clusters and matured human islets were characterized by a cell perifusion system (BioRep Technologies, Miami, Florida, Catalog No. PERI4-02). Briefly, to normalize insulin secretion to a baseline, ALUAGGREWELL™ clusters or human islets were transferred into warm (37° C.) Kreb's Buffer (Table IX). Cells were loaded into perifusion chambers (BioRep Technologies, Catalog No. PERI-CHAMBER), and were continuously perfused (flow rate of 100 µl/min) with four sequential Kreb's buffers supplemented with either: (i) 3 mM D-glucose; (ii) 16.7 mM D-glucose±100 ng/ml Exendin-4 ("Ex4"); and (iii) 25 mM KCl with 3 mM D-glucose. Specific perifusion protocols are indicated in each figure. Perfusate samples were collected every minute, and C-PEP-TIDE protein levels (units in ng/ml) detected by a C-PEP-TIDE ELISA (Mercodia, Uppsala, Sweden, Catalog No. 10-1136-01).

TABLE IX

| Components of Kreb's Buffer (pH 7.4) | | |
| --- | --- | --- |
| | Catalog No. | Concentration |
| NaCl | Sigma-Aldrich S7653 | 7.5 g/1000 ml |
| KCl | Sigma-Aldrich B9333 | 0.357 g/1000 ml |
| CaCl$_2$ | Sigma-Aldrich C1016 | 0.277 g/1000 ml |
| MgSO$_4$ | Sigma-Aldrich M7506 | 0.144 g/1000 ml |
| Na$_2$HPO$_4$ | Sigma-Aldrich 71643 | 0.144 g/1000 ml |
| KH$_2$PO$_4$ | Sigma-Aldrich P5655 | 0.16 g/1000 ml |
| NaHCO$_3$ | Sigma-Aldrich S5761 | 0.42 g/1000 ml |
| HEPES | Thermo Fisher Scientific15630080 | 10 mM |

Figure 8A:
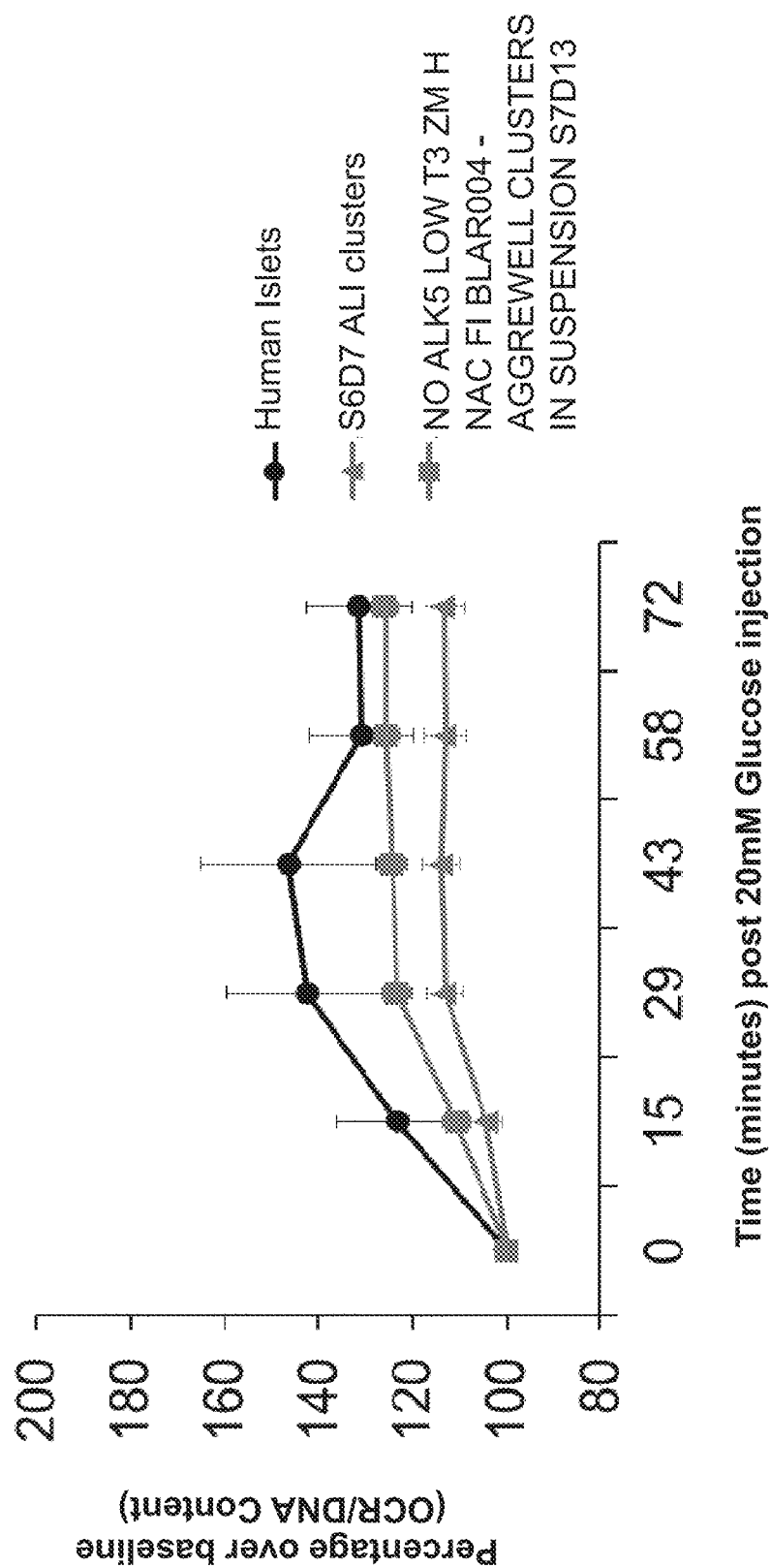
Figure 8B:
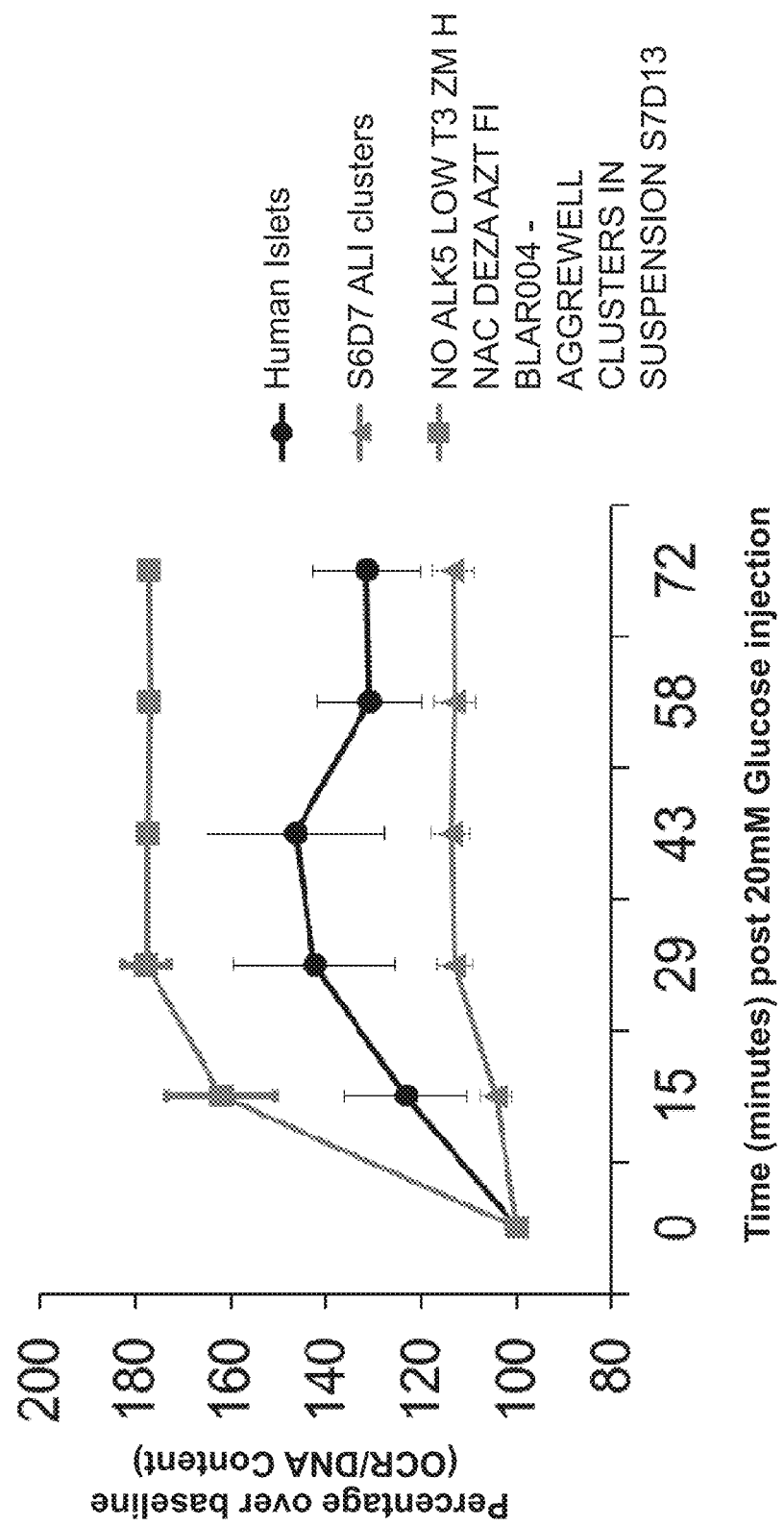
Figure 8F:
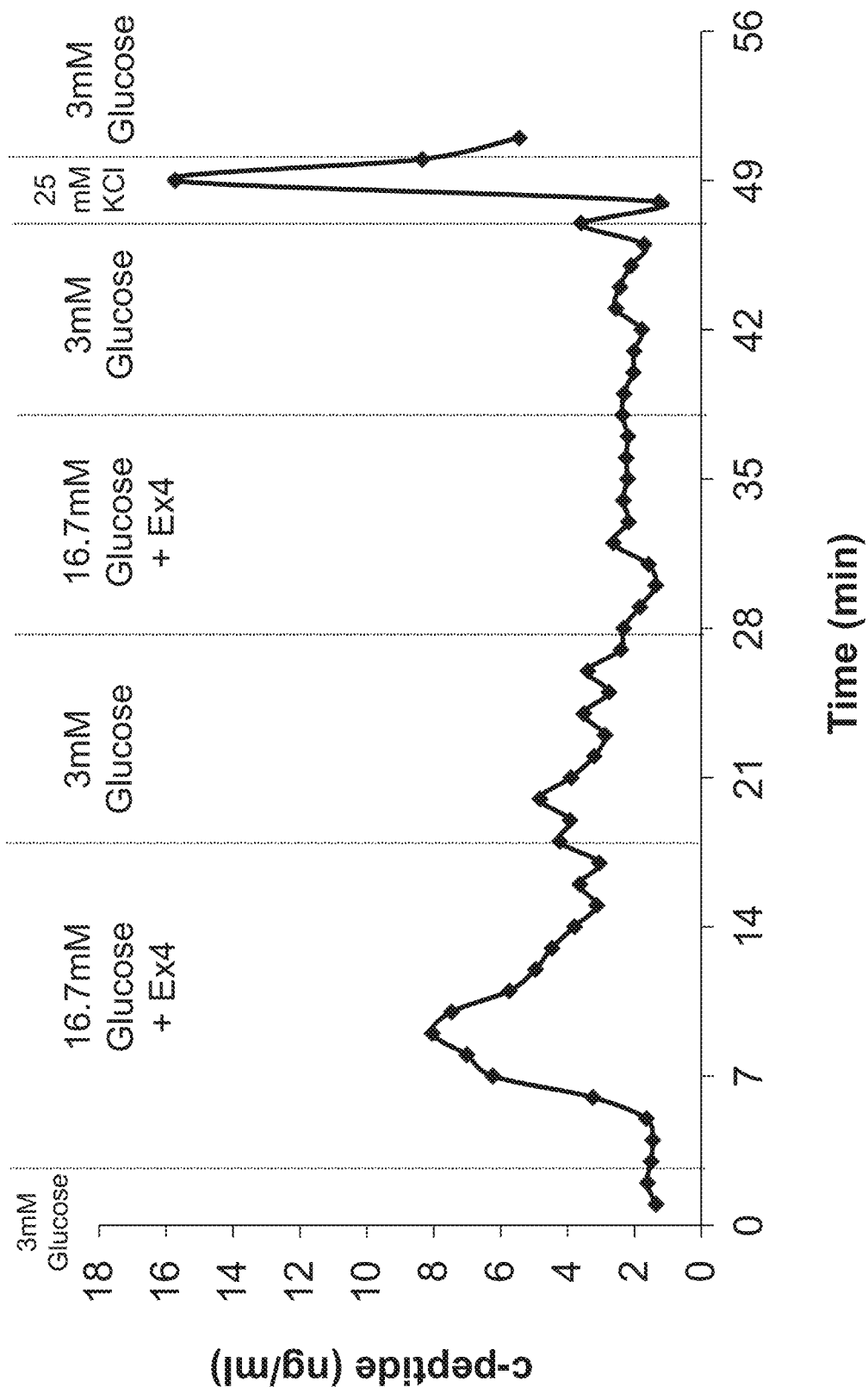

FIGS. 8A and 8B show the mitochondrial response of S7D13 AGGREWELL™ clusters in suspension to 20 mM D-glucose. FIGS. 8A and 8B both show that human islets (black circle line) rapidly responded to high D-glucose, demonstrated by an OCR 123.3%±12.92 over baseline after 15 minutes ("min") post-injection ("ip"), and maintained a high OCR over time (131.5%±11.32; 72 min ip). Conversely, S6D7 ALI clusters (grey triangle line), which were enriched for immature C-PEPTIDE positive cells, lacked a rapid OCR response to high D-glucose (104.4%±3.37; 15 min ip) and exhibit a relatively weak OCR response over time (113.3%±4.51; 72 min ip). Human islet similar glucose-dependent mitochondrial respiration kinetics were observed in the 'No ALK5, low T3, ZM, H, NAC, FI, BLAR004' condition at S7D13 in the context of AGGREWELL™ clusters in suspension (110.7%±2.46—15 min ip; 125.9%±2.27—72 min ip) (grey square line) (FIG. 8A). In contrast, 'No ALK5, low T3, ZM, H, NAC, FI BLAR001 or BLAR004' S7D7 ALI clusters did not display human-islet level glucose-dependent mitochondrial respiration kinetics (FIGS. 5C and 5E). In addition, 'No ALK5, low T3, ZM, H, NAC, AZT, DEZA, FI, BLAR004' AGGREWELL™ clusters in suspension consumed oxygen in response to high glucose stimulation significantly above human islet levels (162.0%±11.51—15 min ip; 177.1%±0.99—72 min ip) (grey square line) (FIG. 8B). DEZA and AZT were only administered during the first four days of Stage 7 conditioning, implying that the functional mitochondrial responsiveness gained by AZT and DEZA were stable for at least 10 days in Stage 7 AGGREWELL™ clusters.

Figure 8H:
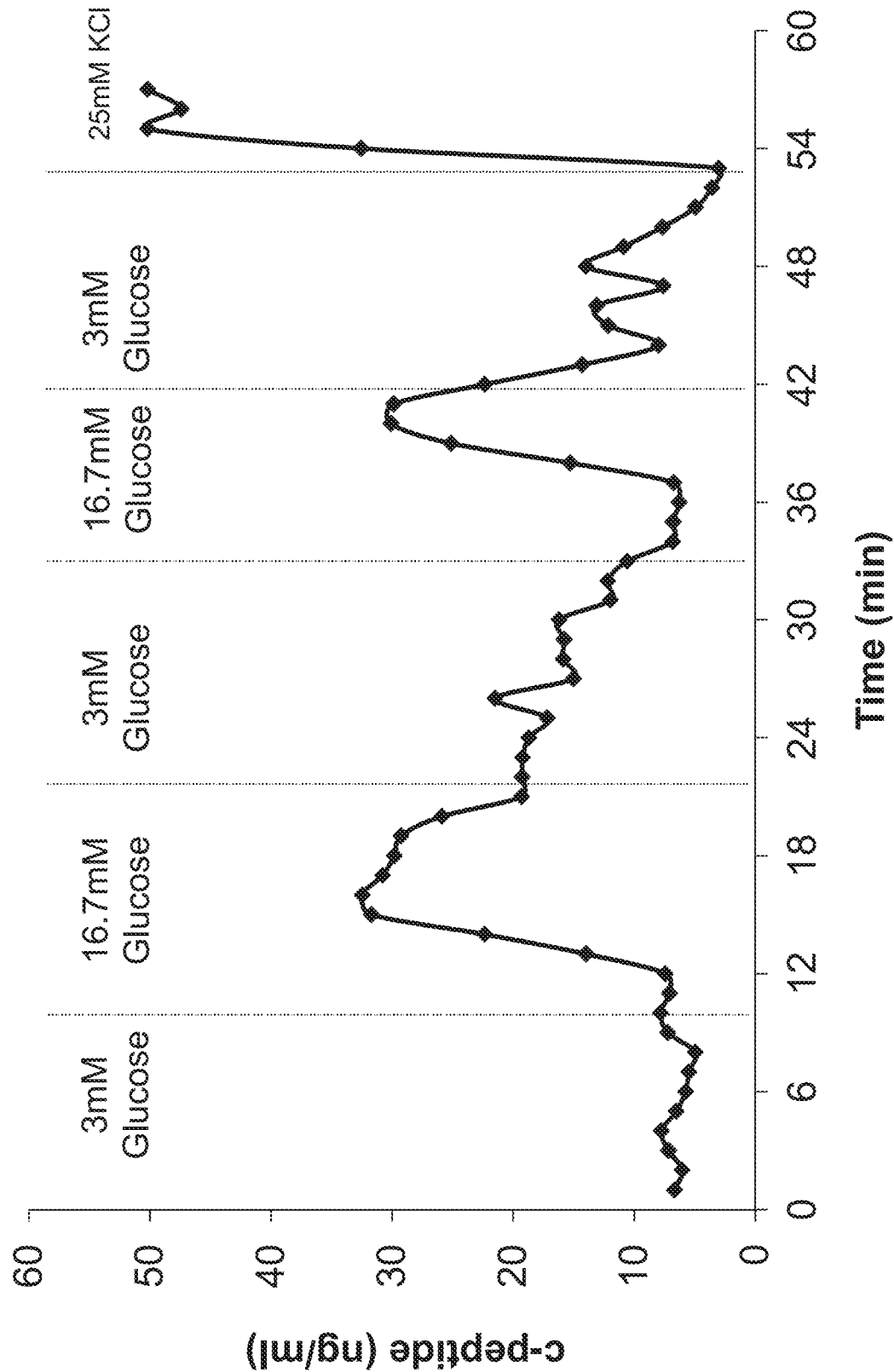
Figure 8I:
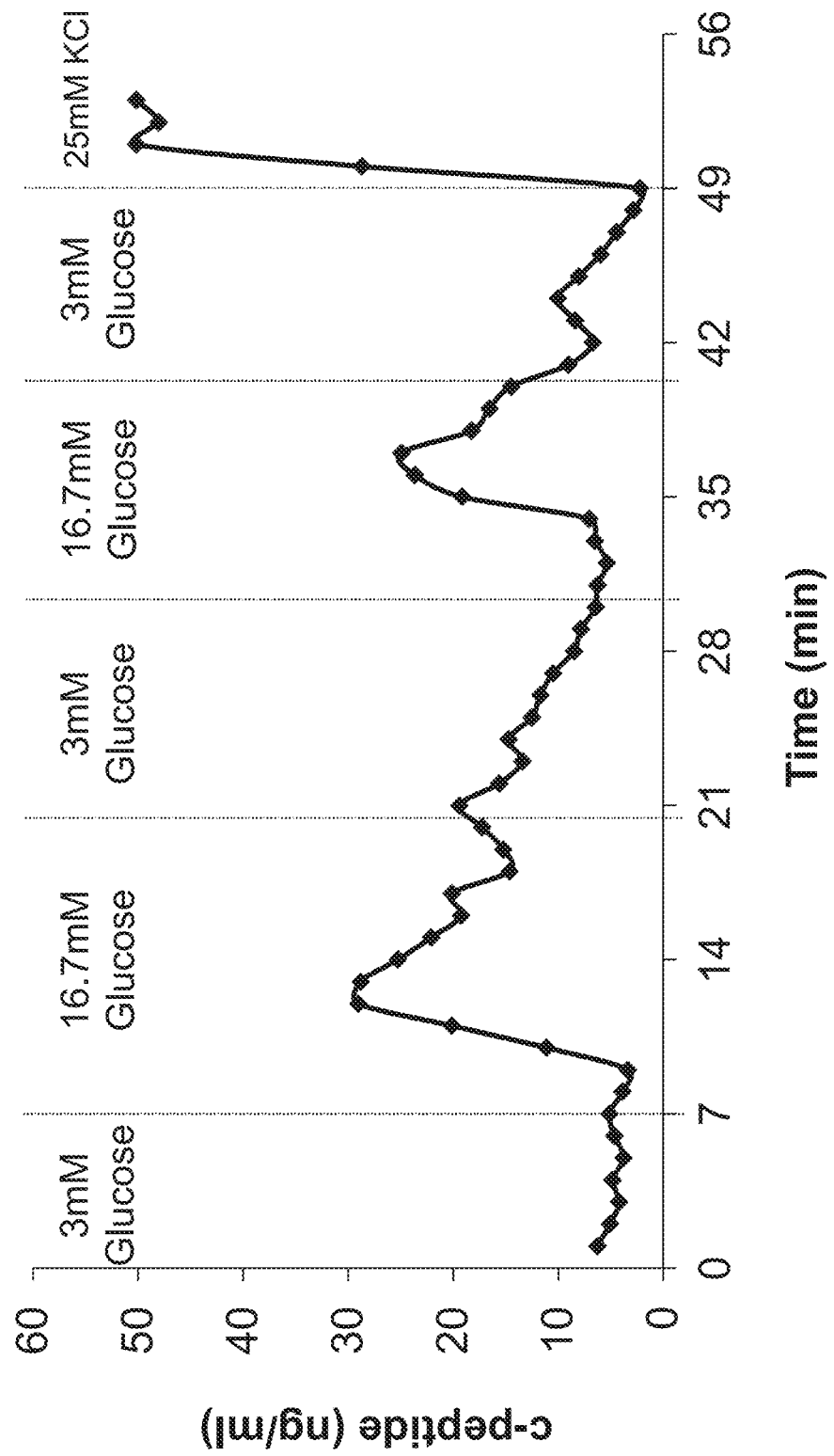

FIG. 8C demonstrates that matured beta-cells within human islets exhibited the ability for multiple rounds of rapid bi-phasic insulin secretion in response to glucose stimuli. The second bi-phasic GSIS response was blunted compared to the first (~7-8 fold first phase of first GSIS response). Also, human islets demonstrated the ability for multiple rounds of "on-off" switching of insulin secretion, and the ability for massive insulin granule release upon KCl-mediated membrane depolarization. All conditions tested exhibited a strong insulin secretion response to KCl (FIG. 8C-8I). The addition of Exendin-4 ("Ex4") did not increase the amplitude of the GSIS response in human islets shown, but was included for comparison to ALI or AGGREWELL™ GSIS profiles (FIG. 8D). S7D8-S7D10 ALI clusters conditioned during Stage 7 in 'No ALK5, low T3, ZM, H, NAC FI,' whether in BLAR001 (FIG. 8E) or BLAR004 (FIG. 8F), did show a single (~4-10 fold first phase of first GSIS response), but not a second, and a relatively slow bi-phasic GSIS response. Also, ALI clusters did not have the ability to shut off the second phase of insulin secretion upon re-perifusion of 3 mM D-glucose after stimulus. In contrast, S7D14 AGGREWELL™ clusters conditioned during Stage 7 in 'No ALK5, low T3, ZM, H, NAC, FI BLAR004,' exhibited a strong first bi-phasic GSIS (~5 fold first phase of first GSIS response) followed by an ability to completely shut-down of GSIS, and a weak second mono-phasic response (FIG. 8G). With the addition of DEZA and AZT to 'No ALK5, low T3, ZM, H, NAC, FI BLAR004' conditioning, S7D14 AGGREWELL™ clusters exhibited multiple rounds of human-islet-similar bi-phasic GSIS (~5-7 fold first phase of first GSIS response), and the ability to completely shut-down GSIS in between high glucose pulses (FIGS. 8H-8I). FIGS. 8H and 8I represent two biological replicates of the 'No ALK5, low T3, ZM, H, NAC, DEZA, AZT BLAR004' S7D14 AGGREWELL™ cluster condition. In FIGS. 8H-8I DEZA and AZT was only administered during the first four days of Stage 7 conditioning, implying that the robust bi-phasic GSIS responses gained by AZT and DEZA were stable for at least 10 days in Stage 7 AGGREWELL™ clusters.

In summary, Example 5 demonstrates the generation of hESC-derived functional beta-cells (Stage 7) by cellular aggregation and suspension culture with human-islet-similar glucose-dependent mitochondrial respiration and GSIS kinetics.

TABLE X

| Suppliers of the materials and compounds used in Examples 1 to 5 | |
| --- | --- |
| Material/Compound | Supplier |
| (S,S)-2-[2-(3,5-Difluorophenyl)acetylamino]-N-(5-methyl-6-oxo-6,7-dihydro-5H-dibenzo[b,d]azepin-7-yl)propionamide ("gamma secretase inhibitor XX") | EMD Millipore, Catalog No. 565789 |
| 0.2% BSA | BD Biosciences, San Jose, California, Catalog No. 554657 |
| 2-(3-(6-Methylpyridin-2-yl)-1H-pyrazol-4-yl)-1,5-naphthyridine ("ALK5 inhibitor II" or "ALK5") | Enzo Life Sciences, Inc., Farmingdale, New York, Catalog No. ALX-270-445 |
| 3,3', 5-triiodo-L-thryonine sodium | Sigma Aldrich, Catalog No. T6397 |
| 30% sucrose solution | Amresco, Solon, Ohio, Catalog No. 0335 |
| 4% PFA | Sigma Aldrich, St. Louis, Missouri, Catalog No. 158127 |
| 5 ml cryopreservation vial | Thermo Fisher Scientific, Catalog No. 5000-0050 |
| 5-Azacytidine ("AZT") | Sigma Aldrich, Catalog No. A2385 |
| Accutase Cell Detachment Solution | Stem Cell Technologies, Catalog No. 07920 |
| AGGREWELL ™ 400EX plate | STEMCELL Technologies Inc.; Vancouver, Canada; Catalog No. 27840 |

TABLE X-continued

Suppliers of the materials and compounds used in Examples 1 to 5

| Material/Compound | Supplier |
|---|---|
| ascorbic acid | Sigma Aldrich Co. LLC, St. Louis, Missouri, Catalog No. A4544 |
| BME Vitamin supplement | Sigma Aldrich, Catalog No. B6891 |
| chemically defined Lipid concentrate | Gibco by Life Technologies, Catalog No. 11905 |
| Cytofix/Cytoperm Buffer | BD Biosciences, San Jose, California, Catalog No. 554723 |
| Deazaneplanocin A ("DEZA") | Biovision, Inc., Catalog No. 2060 |
| D-glucose | Sigma-Aldrich Co. LLC, St. Louis, Missouri, Catalog No. G8769 |
| DMEM-F12 | Life Technologies Corporation, Carlsbad, California, Catalog No. 11330-032 |
| DMSO | Sigma-Aldrich, Catalog No. D2650 |
| DNaseI | Sigma-Aldrich, Catalog No. 9003-98-9 |
| Exendin-4 ("Ex4") | Sigma-Aldrich, Catalog No. E7144 |
| EZ8 media | Gibco by Thermo Fisher Scientific, Catalog No. A151690 |
| fatty-acid free bovine serum albumin | Proliant, Inc., Boone, Idaho, Catalog No. 68700 |
| fibroblast growth factor 2 | R & D Systems Inc., Minneapolis, Minnesota, Catalog No. 233-FB-025 |
| fibroblast growth factor 7 ("FGF7") | R&D Systems, Inc., Minneapolis, Minnesota, Catalog No. 251-KG |
| GlutaMAX ™ | Life Technologies Corporation, Carlsbad, California, Catalog No. 35050-079 |
| growth differentiation factor 8 ("GDF8") | Peprotech, Rocky Hill, New Jersey, Catalog No. 120-00 |
| H1-hESC | WA01 cells, WiCell Research Institute, Madison, Wisconsin |
| heparin ("H") | Sigma Aldrich, Catalog No. H3149 |
| HEPES | Thermo Fisher Scientific, Catalog No. 15630080 |
| human recombinant laminin 521 | BioLamina, Catalog No. LN-521-03 - Human Recombinant Laminin 521 |
| incomplete PBS (phosphate buffered saline without magnesium or calcium) | Life Technologies, Carlsbad, California, Catalog No. 14190 |
| insulin-like growth factor-1 ("IGF-1") | R & D Systems Inc., Minneapolis, Minnesota, Catalog No. 291-G1-200 |
| insulin-transferrin-selenium-ethanolamine | Life Technologies, Carlsbad, California, Catalog No. 51500056 |
| KSR | Thermo Fisher Scientific, Catalog No. 10828028 |
| LDN-193189-HCl ("LDN-HCl") (6-(4-(2-(piperidin-l-yl)ethoxy)phenyl)-3-(pyridin-4-yl)pyrazolo[1,5-a]pyrimidine, hydrochloride, a BMP receptor) | Shanghai ChemPartners Co Ltd., Shanghai, China, Catalog No. CG468-141007, Lot/Batch 20141212 |
| L-Glutamine | Gibco by Life Technologies, Catalog No. 25030-081 |
| LIVE/DEAD Violet Fluorescent reactive dye | Life Technologies, Carlsbad, California, Catalog No. L34955 |
| MATRIGEL ™ | Corning Incorporated, Corning, New York, Catalog No. 356231 |
| MCDB-131 medium | Life Technologies, Carlsbad, California, Catalog No. ME120219L2 |
| MEM Non-essential Amino Acid supplement | Gibco by Life Technologies, Catalog No. 111400 |
| N-Acetyl cysteine ("NAC") | Sigma Aldrich, Catalog No. A9165 |
| Nucleocounter ® NC-100 | Chemometec, Alleroed, Denmark, Catalog No. 900-004 |
| OCT solution | Sakura Finetek USA Inc., Torrance, California, Catalog No. 4583 |
| PBS0.1MAG spinners | PBS Biotech Inc., Camarillo, CA, Catalog No. 1A-0.1-D-001 |
| Perm/Wash Buffer | BD Biosciences, San Jose, California, Catalog No. 554722 |
| porous cell culture filter insert, 0.4 micron | Corning, Catalog No. 3419 |
| porous cell culture filter insert, 3.0 micron | Corning, Catalog No. 3420 |
| retinoic acid ("RA") | Sigma Aldrich, Catalog No. R2625 |
| RPMI vitamin supplement | Sigma Aldrich, Catalog No. R7256 |
| SANT-1 (N-[(3,5-dimethyl-1-phenyl-1H-pyrazol-4-yl)methylene]-4-(phenylmethyl)-1-piperazineamine) | Sigma Aldrich, Catalog No. S4572 |
| sodium bicarbonate | Sigma-Aldrich Co. LLC, St. Louis, Missouri, Catalog No. 5761 |
| sodium pyruvate | Gibco by Life Technologies, Catalog No. 11360 |

TABLE X-continued

Suppliers of the materials and compounds used in Examples 1 to 5

| Material/Compound | Supplier |
|---|---|
| TPB | Shanghai ChemPartners Co Ltd., Shanghai, China, Catalog No. Custom, Lot/Batch CP-0007242-101 |
| trace elements A | Corning, Catalog No. 25-021 |
| trace elements B | Corning, Catalog No. 25-022 |
| transforming growth factor beta ("TGF-β") | R & D Systems Inc., Minneapolis, Minnesota, Catalog No. 240-B-002 |
| TrypLE ™ Express Enzyme | Life Technologies Corporation, Catalog No. 12604-013 |
| XF Base medium | Seahorse Bioscience, Catalog No. 102340-100 |
| Y-27632 ("Y-compound") | Sigma Aldrich Co. LLC, St. Louis, Missouri, Catalog No. Y-0503 |
| ZM447439 ("ZM") | Selleckchem.com, Catalog No. S1103 |
| $ZnSO_4$ | Sigma Aldrich, Catalog No. Z0251 |

TABLE XI

Chemical names and structures of compounds tested in Example 1

Zebularine
Cat. No. 2293

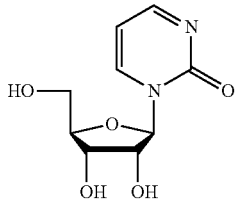

Alternative Name: NSC 309132
Chemical Name: 1-β-D-Ribofuranosyl-2(1H)-pyrimidinone Decitabine
Cat. No. 2624

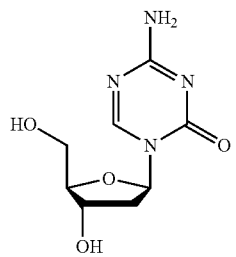

Alternative Names: 2'-Deoxy-5-azacytidine, 5-Aza-2'-deoxycytidine, NSC 127716
Chemical Name: 4-Amino-1-(2-deoxy-β-D-erythro-pento furanosyl)-1,3,5-triazin-2(1H)-one TABLE XI-continued
Chemical names and structures of compounds tested in Example 1
RG 108
Cat. No. 3295
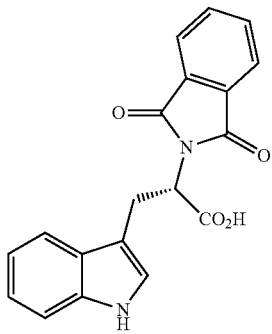
Chemical Name: N-Phthalyl-ι-tryptophan
Lomeguatrib
Cat. No. 4359
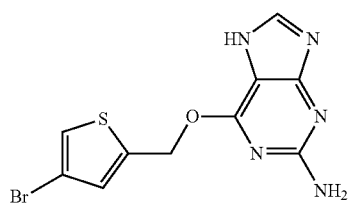
Alternative Name: PaTrin-2
Chemical Name: 6-[(4-Bromo-2-thionyl)methoxy]-9H-purin-2-amine
5-Azacytidine
Cat. No. 3842
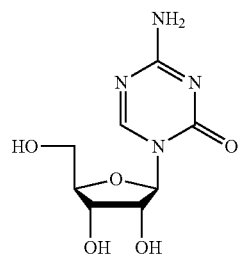
Chemical Name: 4-Amino-1-β-D-ribofuranosyl-1,3,5-triazin-2(1H)-one TABLE XI-continued Chemical names and structures of compounds tested in Example 1

Mitoxantrone dihydrochloride
Cat. No. 4250

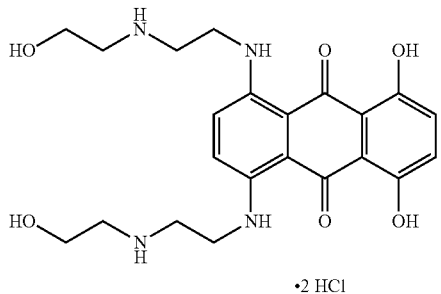

•2 HCl

Chemical Name: 1,4-Dihydroxy-5,8-bis[[2-[(2-hydroxyethyl)amino]ethyl]amino]-9,10-anthracenedione dihydrochloride EGCG
Cat. No. 4524

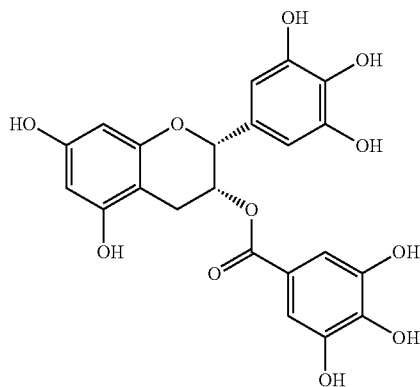

Alternative Name: Epigallocatechin gallate
Chemical Name: 3,4,5-Trihydroxybenzoic acid (2R,3R)-3,4-dihydro-5,7-dihydroxy-2-(3,4,5-trihydroxyphenyl)-2H-1-benzopyran-3-yl ester Fisetin
Cat. No. 5016

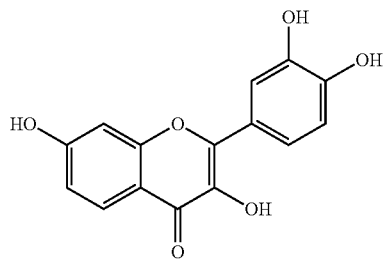

Chemical Name: 2-(3,4-Dihydroxyphenyl)-3,7-dihydroxy-4H-1-benzopyran-4-one

TABLE XI-continued

Chemical names and structures of compounds tested in Example 1

SGI 1027
Cat. No. 5155

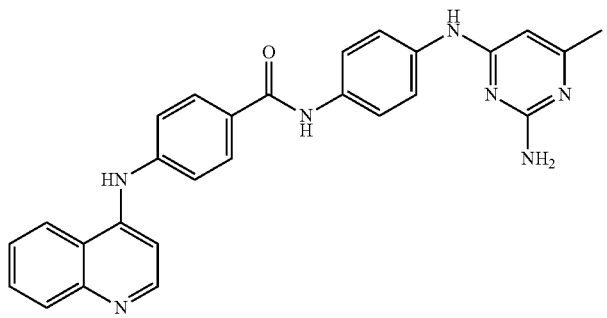

Chemical Name: N-[4-[(2-Amino-6-methyl-4-pyrimidin yl)amino]phenyl]-4-(4-quinolinylamino)benzamide Temozolomide
Cat. No. 2706

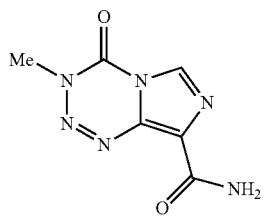

Alternative Names: NSC 362856, CCRG 81045
Chemical Name: 3,4-Dihydro-3-methyl-4-oxoimidazo[5,1-d]-1,2,3,5-tetrazine-8-carboxamide L002
Cat. No. 5045

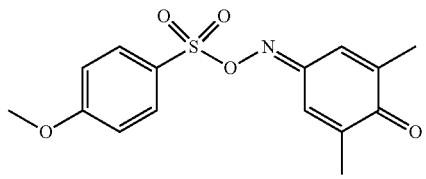

Chemical Name: 4-[O-[(4-Methoxyphenyl)sulfonyl]oxi me]-2,6-dimethyl-2,5-cyclohexadiene-1,4-dione C 646
Cat. No. 4200

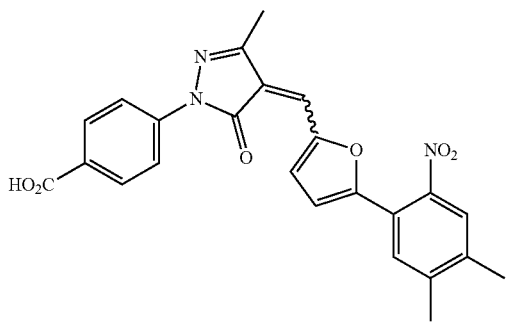

Chemical Name: 4-[4-[[5-(4,5-Dimethyl-2-nitrophenyl)-2-furanyl]methylene]-4,5-dihydro-3-methyl-5-oxo-1H-pyrazol-1-yl]benzoic acid TABLE XI-continued Chemical names and structures of compounds tested in Example 1

SGC 0946
Cat. No. 4541

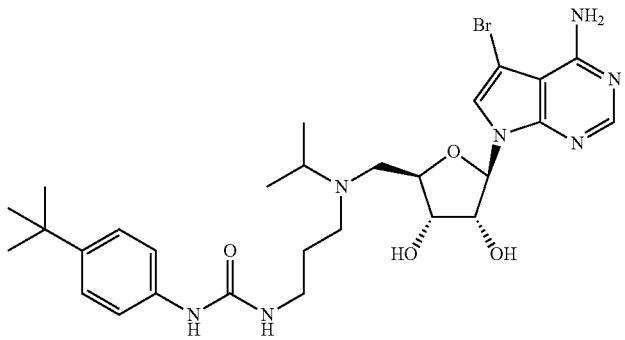

Chemical Name: 1-[3-[[[(2R,3S,4R,5R)-5-(4-Amino-5-bromo-7H-pyrrolo[2,3-d]pyrimidin-7-yl)-3,4-dihydroxytetrahydrofuran-2-yl]methyl](isopropyl)amino]propyl]-3-[4-(2,2-dimethylethyl)phenyl]urea UNC 0224
Cat. No. 3861

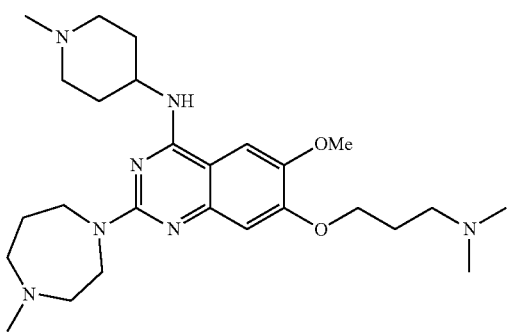

Chemical Name: 7-[3-(Dimethylamino)propoxy]-2-(hexahydro-4-methyl-1H-1,4-diazepin-1-yl)-6-methoxy-N-(1-methyl-4-piperidinyl)-4-quinazolinamine UNC 0638
Cat. No. 4343

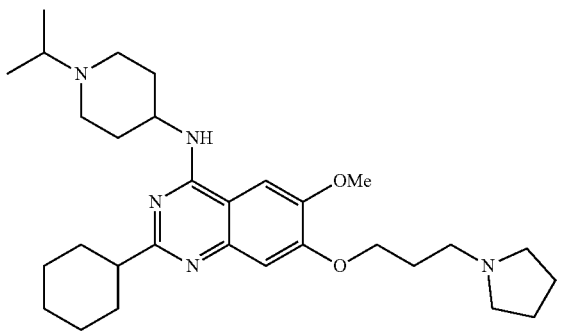

Chemical Name: 2-Cyclohexyl-6-methoxy-N-[1-(1-methylethyl)-4-piperidinyl]-7-[3-(1-pyrrolidinyl)propoxy]-4-quinazolinamine TABLE XI-continued Chemical names and structures of compounds tested in Example 1

BIX 01294
Cat. No. 3364

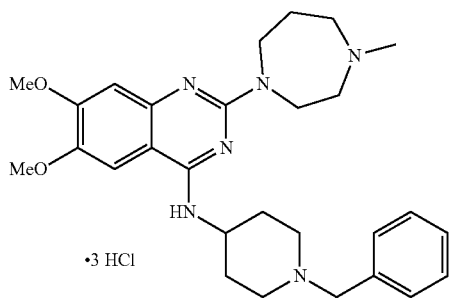

Chemical Name: 2-(Hexahydro-4-methyl-1H-1,4-diazepin-1-yl)-6,7-dimethoxy-N-[1-(phenylmethyl)-4-piperidinyl]-4-quinazolinamine trihydrochloride UNC 0646
Cat. No. 4342

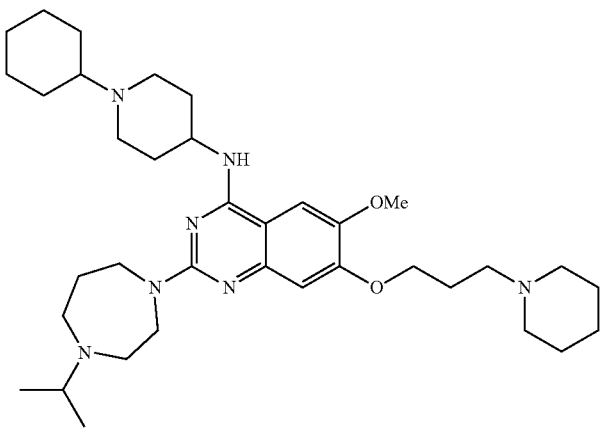

Chemical Name: N-(1-Cyclohexyl-4-piperidinyl)-2-[hexahydro-4-(1-methylethyl)-1H-1,4-diazepin-1-yl]-6-methoxy-7-[3-(1-piperidinyl)propoxy]-4-quinazolinamine UNC 0642
Cat. No. 5132

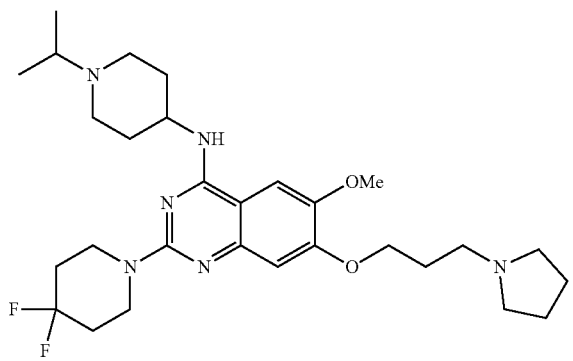

Chemical Name: 2-(4,4-Difluoro-1-piperidinyl)-6-methoxy-N-[1-(1-methylethyl)-4-piperidinyl]-7-[3-(1-pyrrolidinyl)propoxy]-4-quinazolinamine

TABLE XI-continued

Chemical names and structures of compounds tested in Example 1

TC-E 5003
Cat. No. 5099

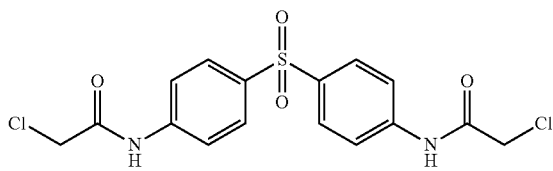

Chemical Name: N,N'-(Sulfonyldi-4,1-phenylene)bis(2-chloroacetamide)

A 366
Cat. No. 5163

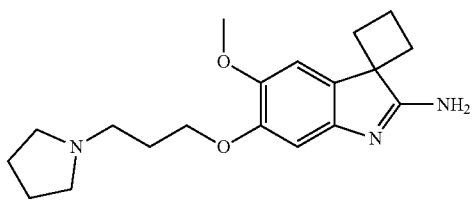

Chemical Name: 5'-Methoxy-6'-[3-(1-pyrrolidinyl)propoxy]spiro[cyclobutane-1,3'-[3H]indol]-2'-amine KU 55933
Cat. No. 3544

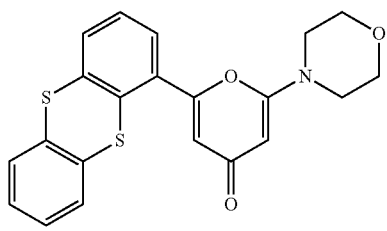

Chemical Name: 2-(4-Morpholinyl)-6-(1-thianthrenyl)-4H-pyran-4-one

KU 60019
Cat. No. 4176

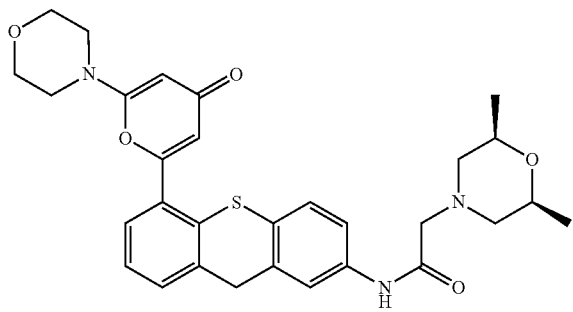

Chemical Name: (2R,6S-rel)-2,6-Dimethyl-N-[5-[6-(4-morpholinyl)-4-oxo-4H-pyran-2-yl]-9H-thioxanthen-2-yl-4-morpholineacetamide TABLE XI-continued Chemical names and structures of compounds tested in Example 1

PF 03814735
Cat. No. 4821

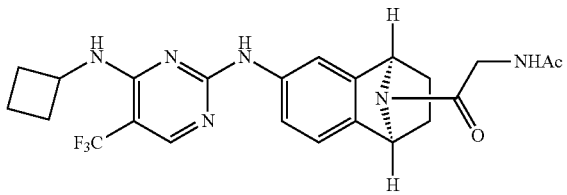

Chemical Name: N-[2-[(1S,4R)-6-[[4-(Cyclobutylamino)-5-
(trifluoromethyl)-2-pyrimidinyl]amino]-1,2,3,4-
tetrahydronaphthalen-1,4-imin-9-yl]-2-oxoethyl]-acetamide ZM 447439
Cat. No. 2458

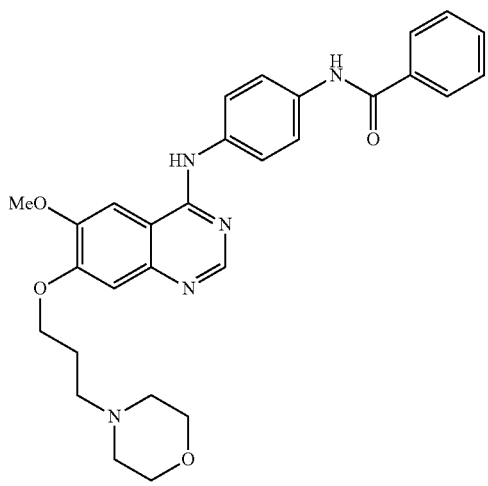

Chemical Name: N-[4-[(6-Methoxy-7-[3-(4-morpholiny
l)propoxy]-4-quinazolinyl]amino]phenyl]benzamide U0126
Cat. No. 1144

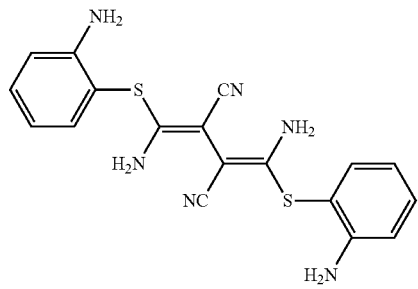

Chemical Name: 1,4-Diamino-2,3-dicyano-1,4-bis[2-a
minophenylthio]butadiene

TABLE XI-continued

Chemical names and structures of compounds tested in Example 1

SL327
Cat. No. 1969

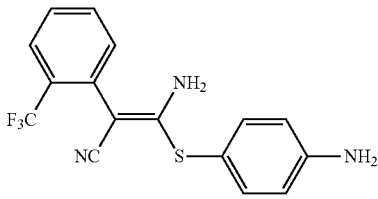

Chemical Name: u-[Amino[(4-aminophenyl)thio]methyle
ne]-2-(trifluoromthyl)benzeneacetonitrile H 89 dihydrochloride
Cat. No. 2910

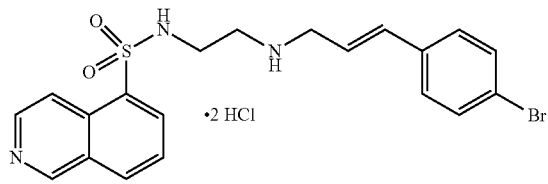

Chemical Name: N-[2-[[3-(4-Bromophenyl-2-propenyl
]amino]ethyl]-5-isoquinolinesulfonamide dihydrochloride SB 747651A dihydrochloride
Cat. No. 4630

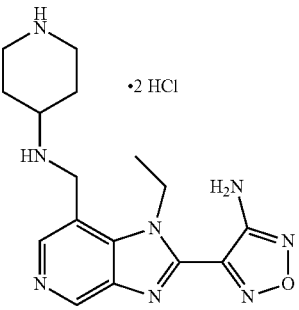

Chemical Name: 2-(4-Amino-1,2,5-oxodiazol-3-yl)-1-ethyl-
N-4-piperidinyl-1H-imidazo[4,5-c]pyridine-7-methanamine
dihydrochloride SNS 314 mesylate
Cat. No. 4584

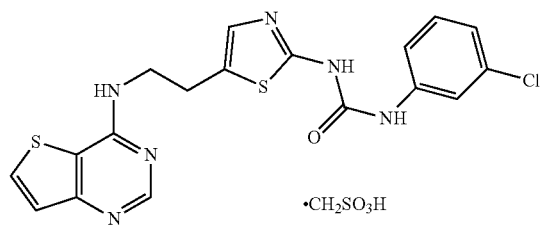

Chemical Name: N-(3-Chlorophenyl)-N'-[5-[2-(thieno[3,2-
d]pyrimidin-4-ylamino)ethyl]-2-thiazolyl]urea
methanesulfonate TABLE XI-continued Chemical names and structures of compounds tested in Example 1

Kaempferol
Cat. No. 3603

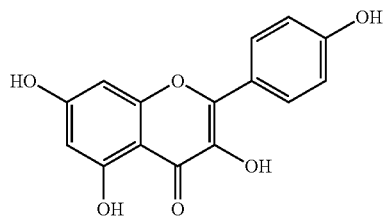

Alternative Name: Kempferol
Chemical Name: 3,5,7-Trihydroxy-2-(4-hydroxyphenyl)-4H-
1-benzopyran-4-one PRT 4165
Cat. No. 5047

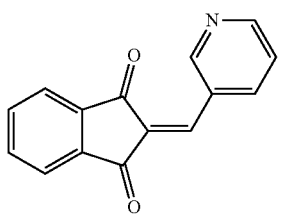

Chemical Name: 2-(3-Pyridinylmethylene-1H-Indene-
1,3(2H)-dione

P 22077
Cat. No. 4485

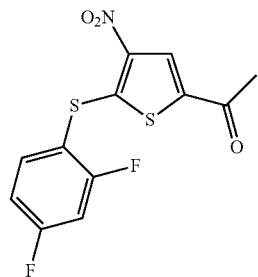

Chemical Name: 1-[5-[(2,4-Difluorophenyl)thio]-4-nitro-2-
thienyl]-ethanone

PFI 1
Cat. No. 4445

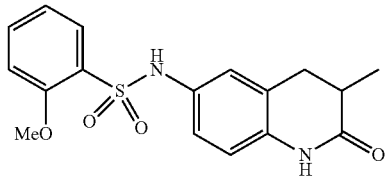

Chemical Name: 2-Methoxy-N-(3-methyl-2-oxo-1,2,3,4-
tetrahydroquinazolin-6-yl)benzenesulfonamide TABLE XI-continued Chemical names and structures of compounds tested in Example 1

I-BET 151 dihydrochloride
Cat. No. 4650

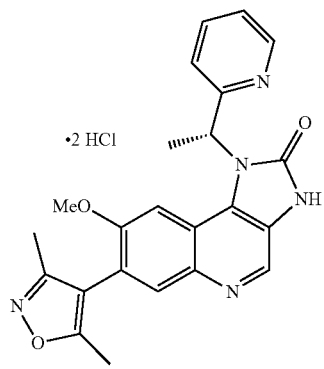

Chemical Name: 7-(3,5-Dimethyl-4-isoxazolyl)-1,3-d
ihydroxy-8-methoxy-1-[(1R)-1-(2-pyridinyl)ethyl]-2H-
imidazo[4,5-c]quinolin-2-one dihydrochloride LY 303511
Cat. No. 2418

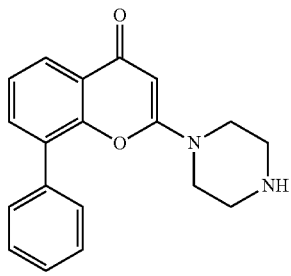

Chemical Name: 2-(1-Piperazinyl)-8-phenyl-4H-1-ben
zopyran-4-one

MS 436
Cat. No. 5173

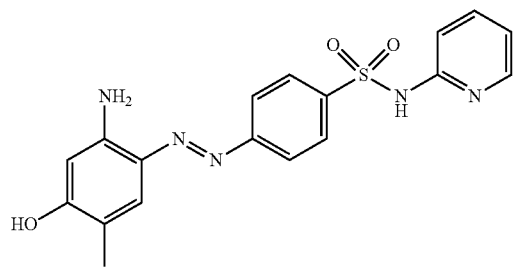

Chemical Name: (E)-4-[2-(2-Amino-4-hydroxy-5-methy
lphenyl)diazenyl]-N-2-pyridinylbenzenesulfonamide

TABLE XI-continued

Chemical names and structures of compounds tested in Example 1

SGC-CBP30
Cat. No. 4889

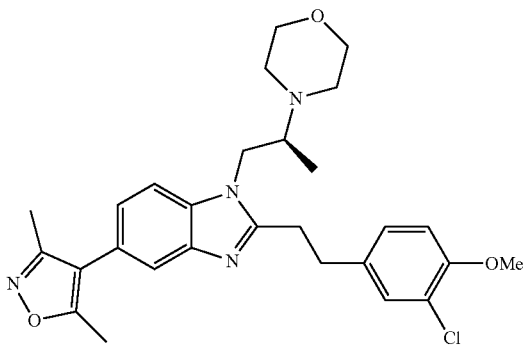

Chemical Name: 2-[2-(3-Chloro-4-methoxyphenyl)ethyl]-5-
(dimethyl-1,2-oxazol-4-yl)-1-[(2S)-2-(morpholin-4-
yl)propyl]-1H-1,3-benzodiazole I-CPB 112
Cat. No. 4891

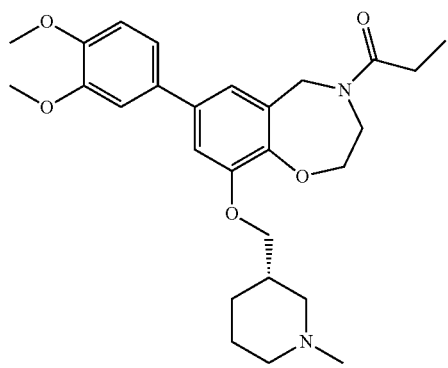

Chemical Name: 1-[7-(3,4-Dimethoxyphenyl)-9-[[(3S)-1-
methylpiperidin-3-yl]methoxy]-2,3,4,5-tetrahydro-1,4-
benzoxazepin-4-yl]propan-1-one Bromosporine
Cat. No. 4758

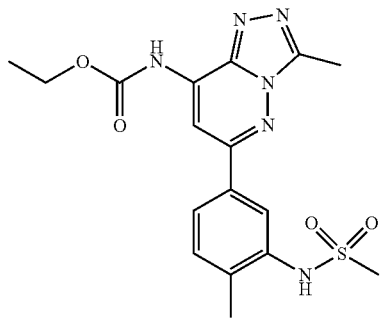

Chemical Name: N-[(6-3-Methanesulfonamido-4-methyl
phenyl)-3-methyl-[1,2,4]triazolo[4,3-b]pyridazin-8-
yl]carbamate TABLE XI-continued Chemical names and structures of compounds tested in Example 1

PFI 3
Cat. No. 5072

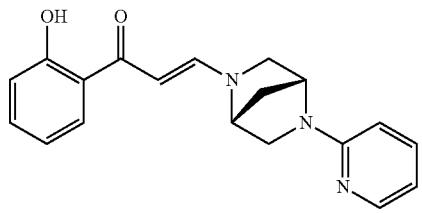

Chemical Name: (2E)-1-(2-Hydroxyphenyl)-3-[(1R,4R)-5-(pyridin-2-yl)-2,5-diazabicyclo[2.2.1]heptan-2-yl]prop-2-en-1-one UNC 926 hydrochloride
Cat. No. 4516

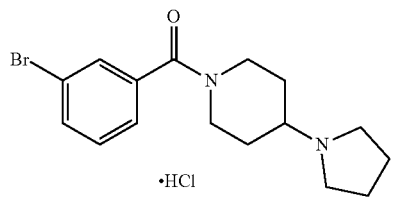

Chemical Name: (3-Bromophenyl)[4-(1-prrolidinyl)-1-piperidinyl]methanone hydrochloride UNC 1215
Cat. No. 4666

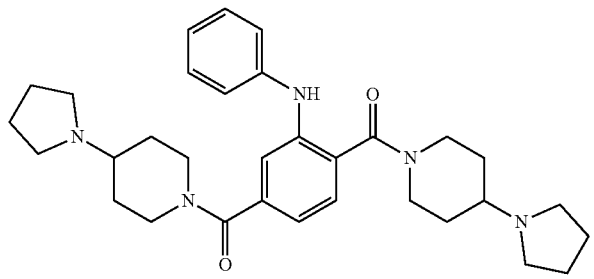

Chemical Name: 2-Phenylamino-1,4-[4-(pyrrolidinyl)piperidinyl)benzamide

TC-H 106
Cat. No. 4270

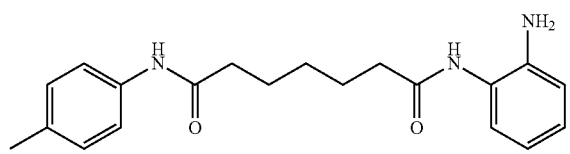

Chemical Name: N1-(2-Aminophenyl)-N7-(4-methylphenyl)heptanediamide

TABLE XI-continued

Chemical names and structures of compounds tested in Example 1

MC 1568
Cat. No. 4077

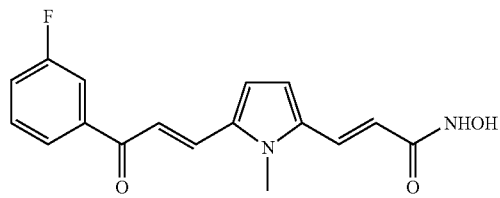

Chemical Name: 3-[5-(3-(3-Fluorophenyl)-3-oxopropen-1-yl)-1-methyl-1H-pyrrol-2-yl]-N-hydroxy-2-propenamide Pyroxamide
Cat. No. 4403

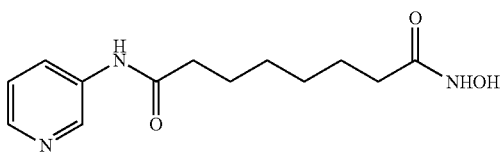

Chemical Name: N-Hydroxy-N'-3-pyridinyloctanediamide

CI 994
Cat. No. 2952

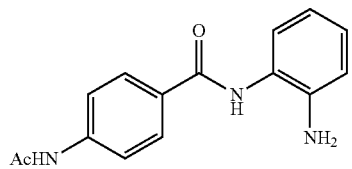

Alternative Name: N-acetyldinaline
Chemical Name: 4-(Acetylamino)-N-(2-aminophenyl)benzamide SBHA
Cat. No. 3810

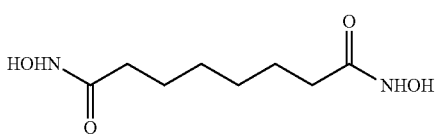

Chemical Name: N,N'-Dihydroxyoctanediamide

KD 5170
Cat. No. 4001

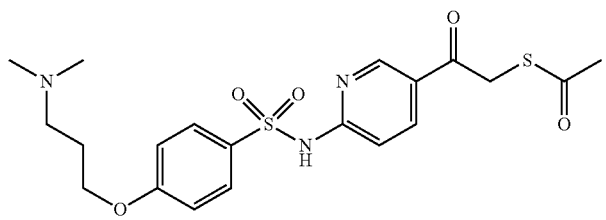

Chemical Name: S-[2-[6-[[[4-[3-(Dimethylamino)propoxy]phenyl]sulfonyl]amino]-3-pyridinyl-2-oxoethyl]ethanethioc acid ester

TABLE XI-continued

Chemical names and structures of compounds tested in Example 1

LMK 235
Cat. No. 4830

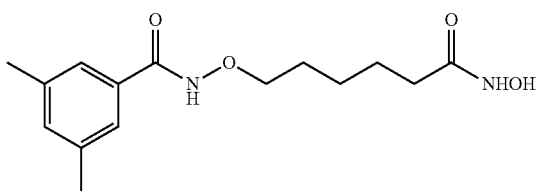

Chemical Name: N-[[6-(Hydroxyamino)-6-oxohexyl]oxy
]-3,5-dimethylbenzamide

TCS HDAC6 20b
Cat. No. 4805

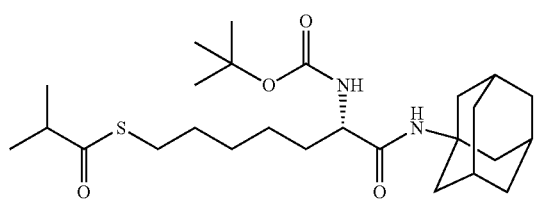

Chemical Name: 2-Methylpropanethioic acid-S-[(6S)-6-
[[(1,1-dimethylethoxy)carbonyl]amino]-7-oxo-7-
(tricyclo[3.3.1.1$^{3,7}$]dec-1-ylamino)heptyl] ester PCI 34051
Cat. No. 4643

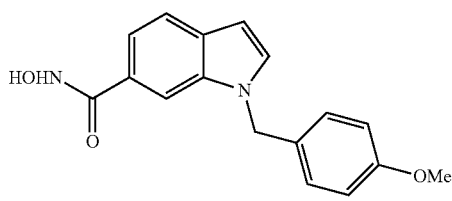

Chemical Name: N-Hydroxy-1-[(4-methoxyphenyl)methy
l]-1H-indole-6-carboxamide

Scriptaid
Cat. No. 2421

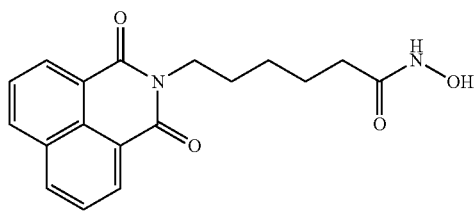

Chemical Name: N-Hydroxy-1,3-dioxo-1H-benz[de]isoq
uinoline-2(3H)-hexanamide

TABLE XI-continued

Chemical names and structures of compounds tested in Example 1

NCS 3852
Cat. No. 2521

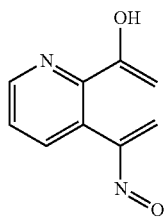

Chemical Name: 5-Nitroso-8-quinolinol

Sodium 4-Phenylbutyrate
Cat. No. 2682

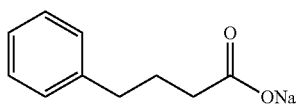

Alternative Names: 4-PB, Sodium phenylbutyrate
Chemical Name: 4-Phenylbutyric acid, sodium salt M 344
Cat. No. 2771

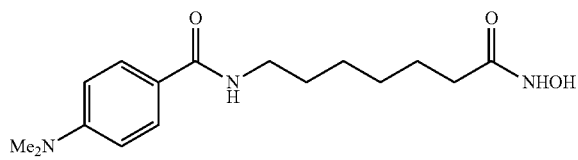

Chemical Name: 4-(Diethylamino)-N-[7-(hydroxyamino)-7-oxoheptyl]benzamide

Valproic acid, sodium salt
Cat. No. 2815

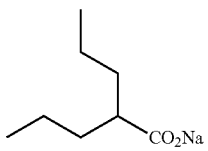

Alternative Names: VPA, Sodium Valproate
Chemical Name: Sodium 2-propylpentanoate SAHA
Cat. No. 4652

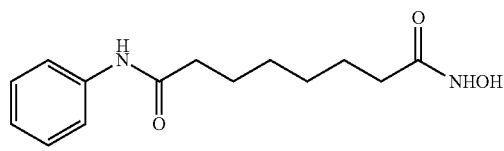

Alternative Name: Vorinostat
Chemical Name: N-Hydroxy-N'-phenyloctanediamide

TABLE XI-continued

Chemical names and structures of compounds tested in Example 1

GSK J2
Cat. No. 4688

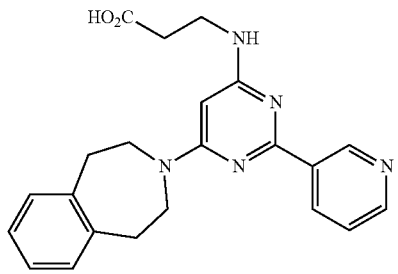

Chemical Name: N-[2-(3-Pyridinyl)-6-(1,2,4,5-tetrahydro-3H-3-benzazepin-3-yl)-4-pyrimidinyl]-β-alanine ethyl ester GSK J5
Cat. No. 4689

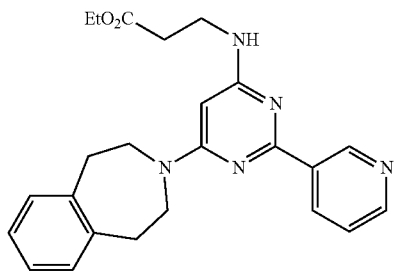

Chemical Name: N-[2-(3-Pyridinyl)-6-(1,2,4,5-tetrahydro-3H-3-benzazepin-3-yl)-4-pyrimidinyl]-β-alanine ethyl ester GSK J1
Cat. No. 4593

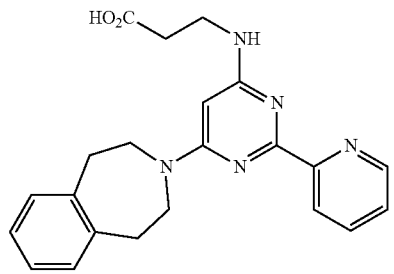

Chemical Name: N-[2-(2-Pyridinyl)-6-(1,2,4,5-tetrahydro-3H-3-benzazepin-3-yl)-4-pyrimidinyl]-β-alanine GSK J4
Cat. No. 4594

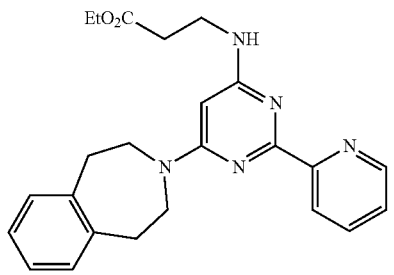

Chemical Name: N-[2-(2-Pyridinyl)-6-(1,2,4,5-tetrahydro-3H-3-benzazepin-3-yl)-4-pyrimidinyl]-β-alanine ethyl ester TABLE XI-continued Chemical names and structures of compounds tested in Example 1

Daminozide
Cat. No. 4684

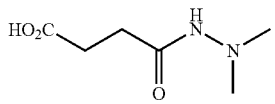

Chemical Name: 1-(2,2-Dimethylhydrazide)butanedioic acid

Tranylcypromine hydrochloride
Cat. No. 3852

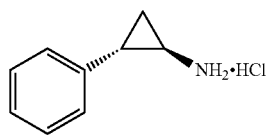

Alternative Name: 2-PCPA
Chemical Name: (±)-trans-2-Phenylcyclopropylamine hydrochloride RN 1 dihydrochloride
Cat. No. 4977

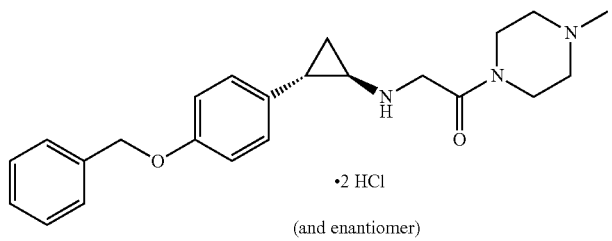

•2 HCl (and enantiomer)

Chemical Name: 1-(4-methyl-1-piperazinyl)-2-[[(1R*,2S*)-2-[4-phenylmethoxy)phenyl]cyclopropyl]amino]ethanone dihydrochloride IOX 1
Cat. No. 4464

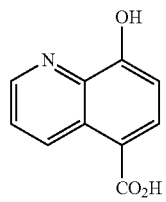

Alternative Name: 5-carboxy-8HQ
Chemical Name: 8-Hydroxy-5-quinolinecarboxylic acid TABLE XI-continued Chemical names and structures of compounds tested in Example 1

JIB 04
Cat. No. 4972

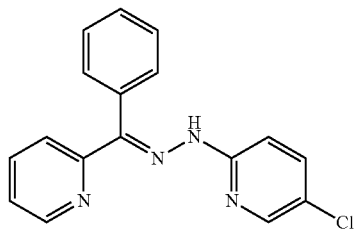

Chemical Name: 5-Chloro-2-[(E)-2-[phenyl(pyridin-2-yl)methylidene]hydrazin-1-yl]pyridine Sirtinol
Cat. No. 3521

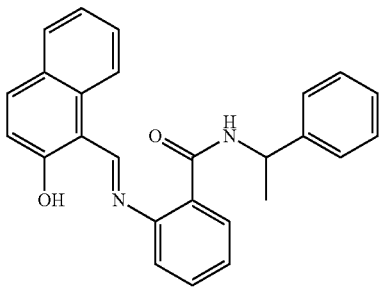

Chemical Name: 2-[[(2-Hydroxy-1-naphthalenyl)methylene]amino]-N-(1-phenylethyl)benzamide Splitomicin
Cat. No. 1542

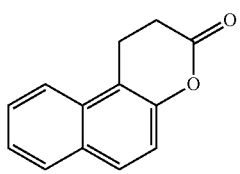

Chemical Name: 1,2-Dihydro-3H-naphtho[2,1-b]pyran-3-one

Resveratrol
Cat. No. 1418

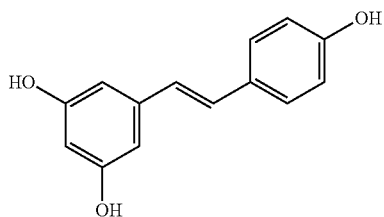

Chemical Name: 5-[(1E)-2-(4-Hydroxyphenyl)ethenyl]-1,3,benzenediol

TABLE XI-continued

Chemical names and structures of compounds tested in Example 1

EX 527
Cat. No. 2780

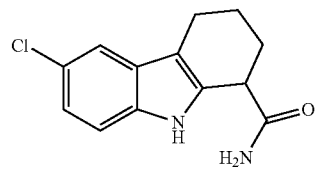

Chemical Name: 6-Chloro-2,3,4,9-tetrahydro-1H-carbazole-1-carboxamide

Tenovin-1
Cat. No. 3365

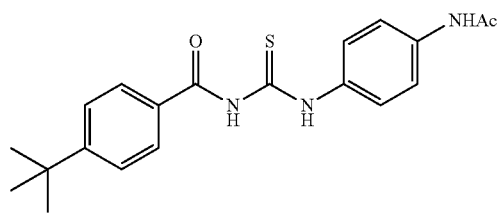

Chemical Name: N-[[[4-(Acetylamino)phenyl]amino]thioxomethyl]-4-(1,1-dimethylethyl)benzamide Salermide
Cat. No. 4127

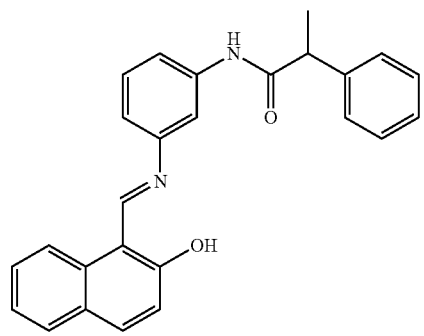

Chemical Name: N-[3-[[(2-Hydroxy-1-naphthalenyl)methylene]amino]phenyl]-α-methylbenzenacetamide AK 7
Cat. No. 4754

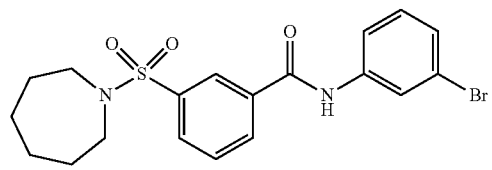

Chemical Name: N-(3-Bromophenyl)-3-[(hexahydro-1H-azepin-1-yl)sulfonyl]benzamide 115
116

TABLE XI-continued

Chemical names and structures of compounds tested in Example 1

3-Aminobenzamide
Cat. No. 0788

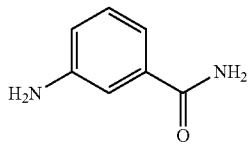

Alternative Name: 3-ABA

PJ 34 hydrochloride
Cat. No. 3255

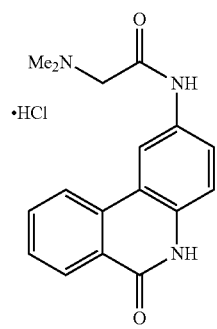

Chemical Name: N-(5,6-Dihydro-6-oxo-2-phenanthridi
nyl)-2-acetamide hydrochloride IOX
Cat. No. 4451

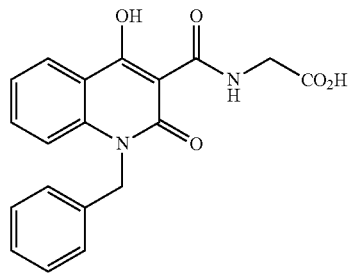

Chemical Name: N-[[1,2-Dihydro-4-hydroxy-2-oxo-1-(
phenylmethyl)-3-quinolinyl]carbonyl]glycine Forskolin
Cat. No. 1099

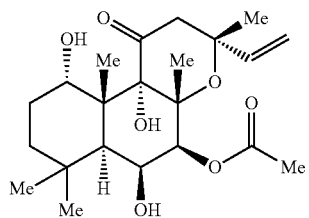

Chemical Name: [3R-(3α,4aβ,5β,6β,6aα,10α,10aβ,10bα)]-5-
(Acetyloxy)-3-ethenyldodecahydro-6,10,10b-trihydroxy-
3,4a,7,7,10a-pentamethyl-1H-naphtho[2,1-b]pyran-1-one TABLE XI-continued Chemical names and structures of compounds tested in Example 1

Retinoic acid
Cat. No. 0695

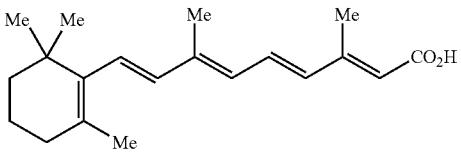

Alternative Names: Tretinoin, ATRA
Chemical Name: 3,7-Dimethyl-9-(2,6,6-trimethyl-1-c
yclohexen-1-yl)-2E,4E,6E,8E,-nonatetraenoic acid

TABLE XII

Component of Formulation I

| Component | Concentration | Supplier |
| --- | --- | --- |
| RPMI Vitamin Supplement | 1:200 dilution | Sigma Aldrich, Catalog No. R7256 |
| MEM non-essential amino acid supplement | 1:200 dilution | Life Technologies, Catalog No. 111400 |
| Chemically defined lipid concentrate | 1:2000 dilution | Gibco by Life Technologies, Catalog No. 11905 |
| sodium pyruvate | 1:200 dilution | Life Technologies, Catalog No. 111360 |
| Trace elements A | 1:2000 dilution | Corning, Catalog No. 25-021 |
| Trace elements B | 1:2000 dilution | Corning, Catalog No. 25-022 |

The above examples describe various small molecules, which typically function as cell cycle inhibitors, but unexpectedly until described in the invention herein, they induce expression of key mature beta-cell markers including PDX1, NKX6.1, MAFA, UCN3 and SLC2A1.

Example 6

Generation of Pancreatic Endoderm Derived from CyT49 hESC in Multiple Types of Suspension Culture The following example demonstrates the improved generation of pancreatic endoderm cells derived from human pluripotent stem cells, in particular CyT49 human embryonic stem cell line ("hESC"), utilizing a differentiation protocol in multiple suspension culture formats (roller bottle and the PBS Biotech MagLift™ vertical wheel bioreactor). Table XIII lists the particular enhancements made to CyT49 hESC-derived pancreatic endoderm. Specially, the pancreatic endoderm generated from CyT49 hESC exhibits a lower prevalence of both alternative endoderm lineages and endocrine differentiation, both important requirements for further efficient generation of insulin-producing cells, and more akin to H1 hESC-derived pancreatic endoderm (Example 3). Moreover, the time required to generate CyT49 hESC-derived pancreatic endoderm is reduced by 5 days. The new CyT49 hESC-derived pancreatic endoderm protocol can be applied to roller bottle and bioreactor formats allowing for both scale-out and scale up manufacturing.

TABLE XIII

Improvements to generation of pancreatic endoderm.

| | CyT49 hESC-derived PEC-01 | H1 hESC-derived (Example 3) | New CyT49 hESC-derived (Example 6) |
| --- | --- | --- | --- |
| Protocol duration | 15 days | 10 days | 10 days |
| Prevalence of other endoderm lineages | Intermediate | Low | Low |
| Prevalence of endocrine differentiation | Intermediate | Low | Low |
| Format | Roller bottle, bioreactors (8,895,300; 8,445,273) | Scale-up; bioreactor (Current disclosure) | Roller bottle, bioreactor (Current disclosure) |

Table XIV outlines major adjustments made to the differentiation protocol for generation of improved CyT49 hESC-derived pancreatic endoderm. Major differences include the lack of BMP-inhibition during Stages 3-4, and the use of MCDB131 (Stages 1-2) and BLAR001 (Stages 3-4) as base mediums.

TABLE XIV hESC-derived differentiation protocol to pancreatic endoderm.

| Stage | Stage 1 | Stage 2 | Stage 3 | Stage 4 |
|---|---|---|---|---|
| CyT49 hESC-derived PEC-01 | Wnt3A, AA, ITS; RPMI1640 | FGF7, TGF-beta inh IV, ITS; RPMI1640 | TTNPB, KAAD-Cyclopamine, Noggin, B27, ITS; DMEM/HI Glucose | EGF, FGF7, Noggin, B27; DMEM/HI Glucose |
| H1-derived (Example 3) | MCX, GDF8; MCDB131 | FGF7; MCDB131 | FGF7, SANT, TPPB, LDN, RA, ITSX; BLAR001 | FGF7, SANT, TPPB, LDN, RA, ITSX; BLAR001 |
| New CyT49 hESC-derived (Example 6) | Wnt3A, AA, ITSX; MCDB131 | FGF7; MCDB131 | FGF7, SANT, TPPB, RA, ITSX; BLAR001 | FGF7, SANT, TPPB, RA, ITSX; BLAR001 |

Cells of the human embryonic stem cell line CyT49 ("CyT49-hESC"; NIH registration 0041) at passage 27 of working cell bank 4A ("WCB4A") were seeded as single cells at $0.033 \times 10^6$ cells/cm$^2$ on tissue culture treated dishes in a growth media of Dulbecco's Modified Eagle's Medium Nutrient (DMEM) mixture F-12 with 1:100× GlutaMAX ("DMEM-F12"; Life Technologies, Carlsbad, California, Catalog No. 10565), XenoFree ("XF") Knockout Serum Replacement ("KSR"; Life Technologies, Catalog No. 12618) in a 1:10 dilution ("10% concentration"), MEM Non-essential amino acids in a 1:100 dilution ("1x concentration") Penicillin-Streptomycin in a 1:100 dilution ("1x concentration"), 10 ng/ml of human Activin A (R&D Systems, Minneapolis, Minnesota, Catalog No. 338-AC), and 10 ng/ml human Heregulin-beta 1 (PeproTech, Rocky Hill, New Jersey, Catalog No. 100-03). Human serum AB in a 1:10 dilution ("10% concentration"; Valley Biomedical, Winchester, Virginia, Catalog No. HP-1022) was used only during the first 24 hours post-seeding. Ninety-six hours post-seeding, the confluent CyT49 hESC cultures were passaged in the growth media mentioned above. Alternatively, confluent CyT49 hESC were released as a single cell suspension by Accumax (Innovative Cell Technologies, San Diego, California, Catalog No. AM105) treatment (3 minutes at 37° C.), and aggregated at a speed of 31 rpm, and at a concentration of one million cells per ml in roller bottles (Corning, Corning, New York, Catalog No. CLS431644) in a media of DMEM-F12 with 1:100× GlutaMAX (Life Technologies, Catalog No. 10565), 1× concentration of Penicillin-Streptomycin, StemPro® Supplement in a 1:50 dilution (Life Technologies, Catalog No. ME130070L1), 10 ng/ml human Activin A, 10 ng/ml human Heregulin-beta 1, and 200 ng/ml LR3-IGF1 (Cell Sciences, Newburyport, Massachusetts, Catalog No. LRM001).

Figure 9D:
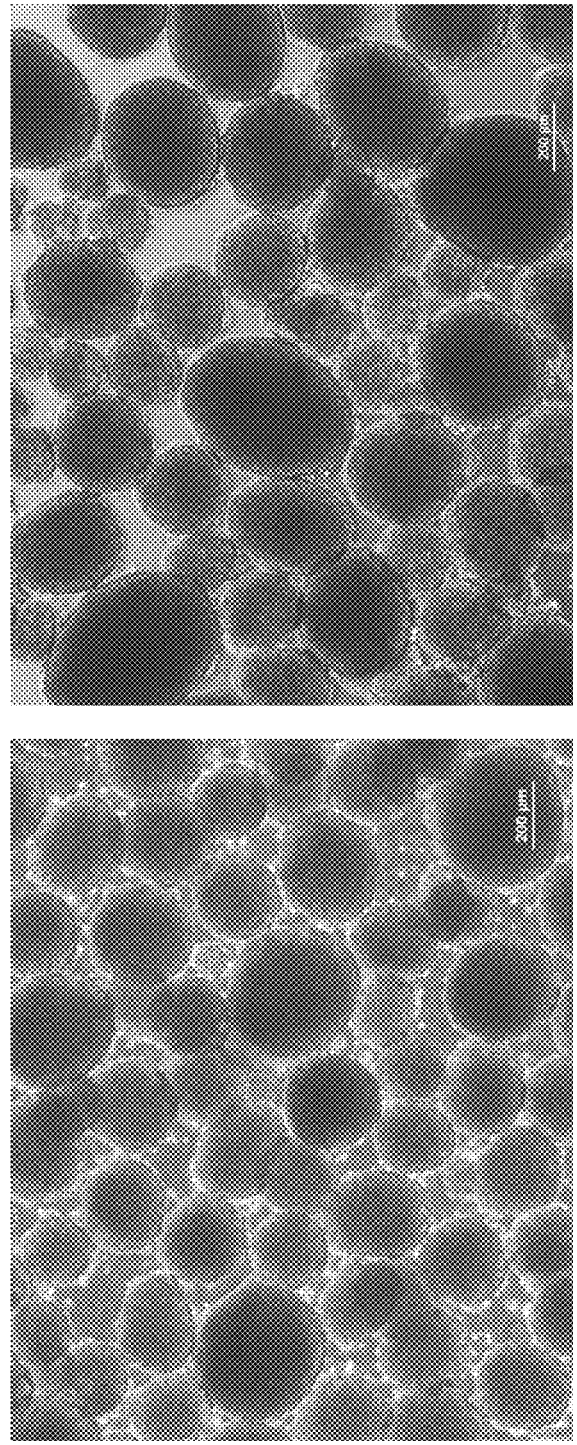
FIGS. 9D and 9E depict phase-contrast images and diameter (in microns) of S4D3 aggregates from 2-liter roller bottle (FIG. 9D right), 0.1 PBS (FIG. 9E middle), and 0.5 PBS (FIG. 9E right) suspension formats; 2-liter roller bottle generated PEC-01 d12 (FIG. 9D left), and PEC-01 d15 (FIG. 9E left) are shown as examples of prior art. S4D3 aggregates generated by 0.1 PBS and 0.5 PBS suspension culture are uniformly smaller than roller bottle generated aggregates.
Figure 9E:
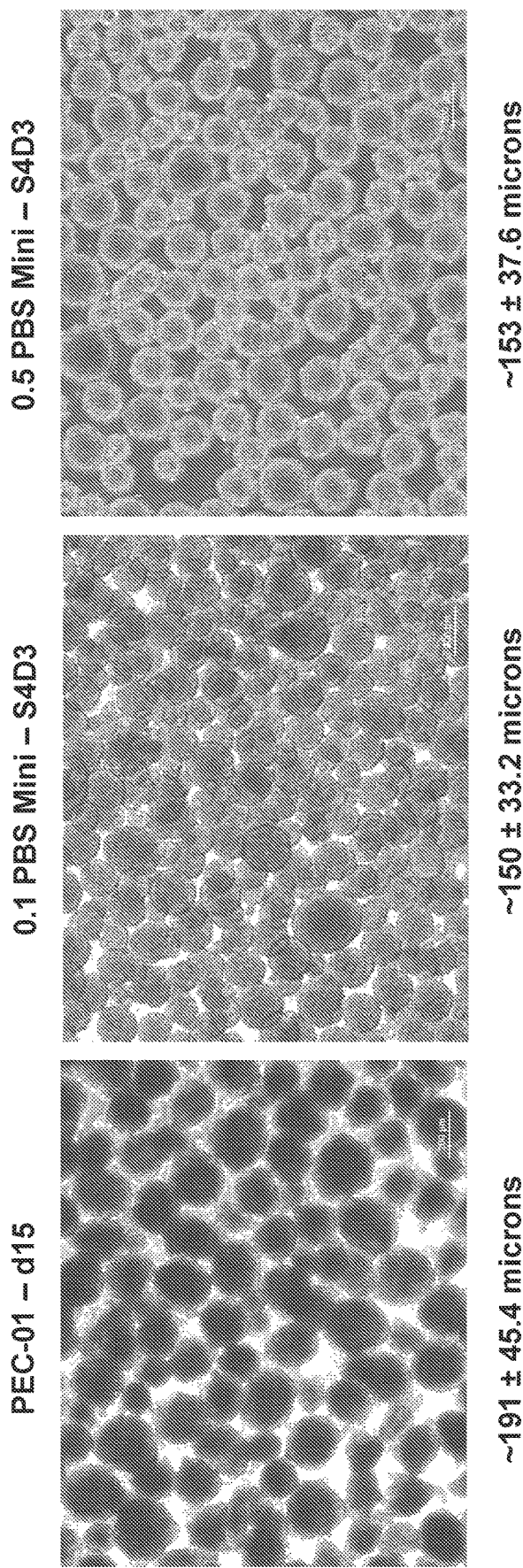
Figure 9G:
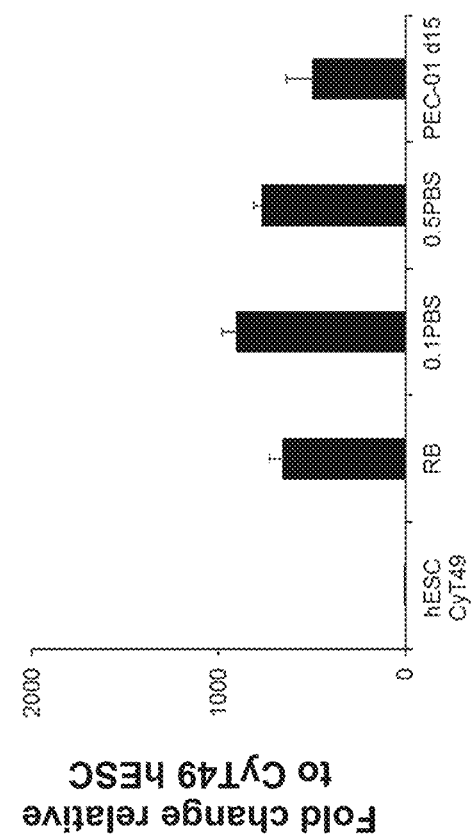
FIG. 9F-9L show the gene expression for S4D3 aggregates. The gene expression of NKX6.1 (FIG. 9F), PTF1A (FIG. 9G), PDX1 (FIG. 9H), SOX2 (FIG. 9I), CDX2 (FIG. 9J), NEUROD1 (FIG. 9K), and CHGA (FIG. 9L), relative to CyT49 hESC is shown for S4D3 aggregates generated in 2-liter roller bottle, 0.1 PBS and 0.5 PBS, and 2-liter roller bottle generated PEC-01 d15.
Figure 9F:
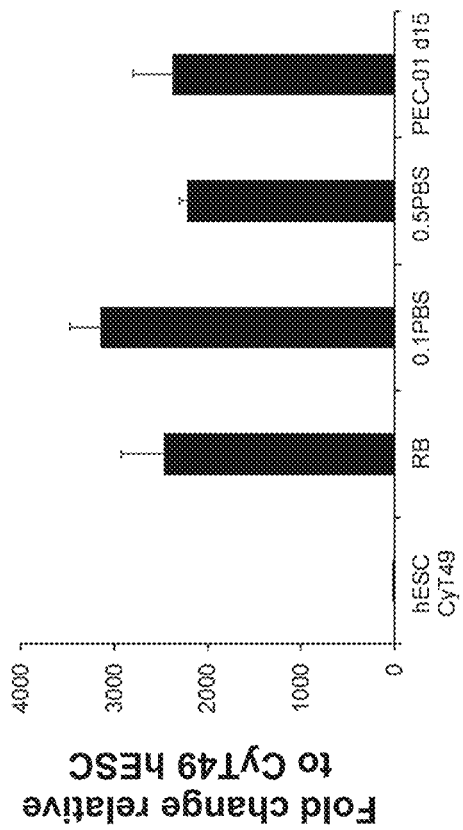
Figure 9H:
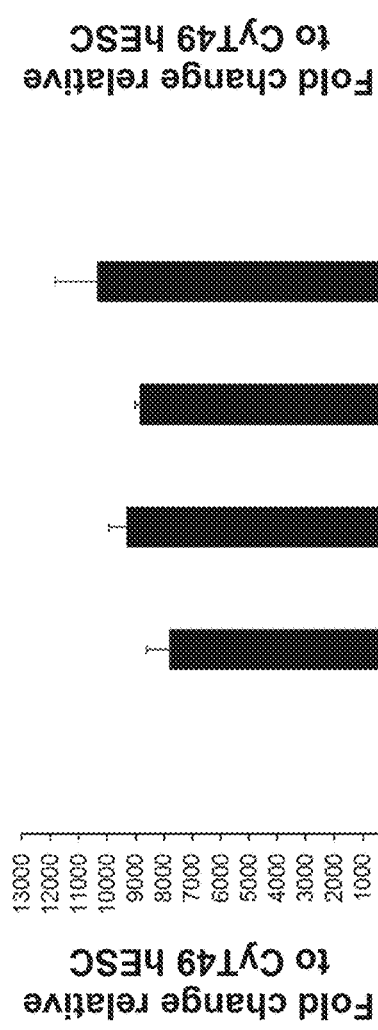
Figure 9I:
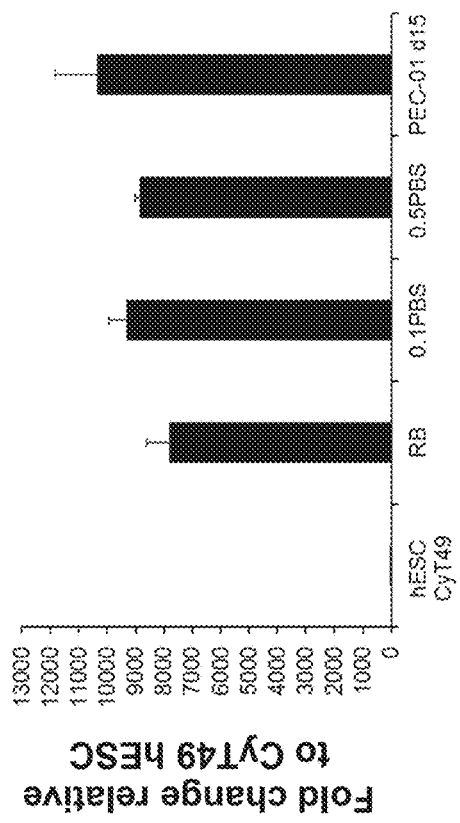
Figure 9K:
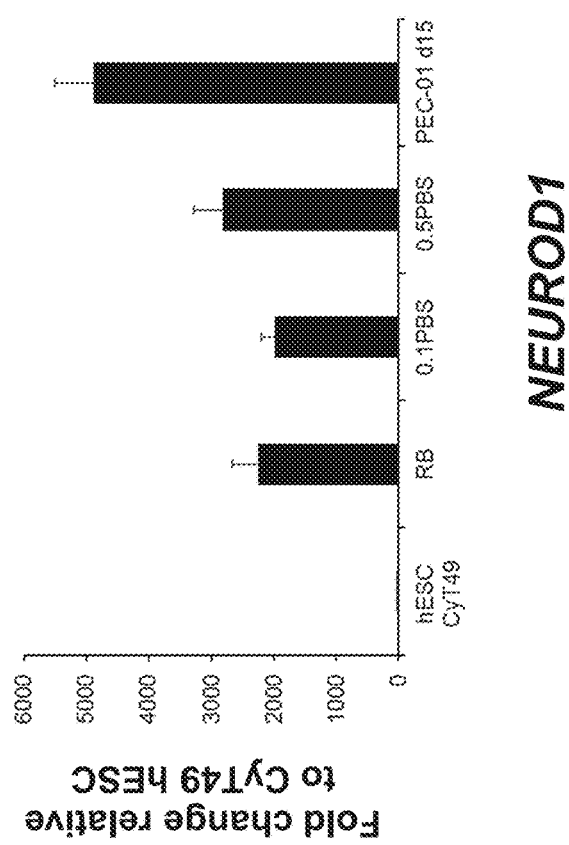
Figure 9J:
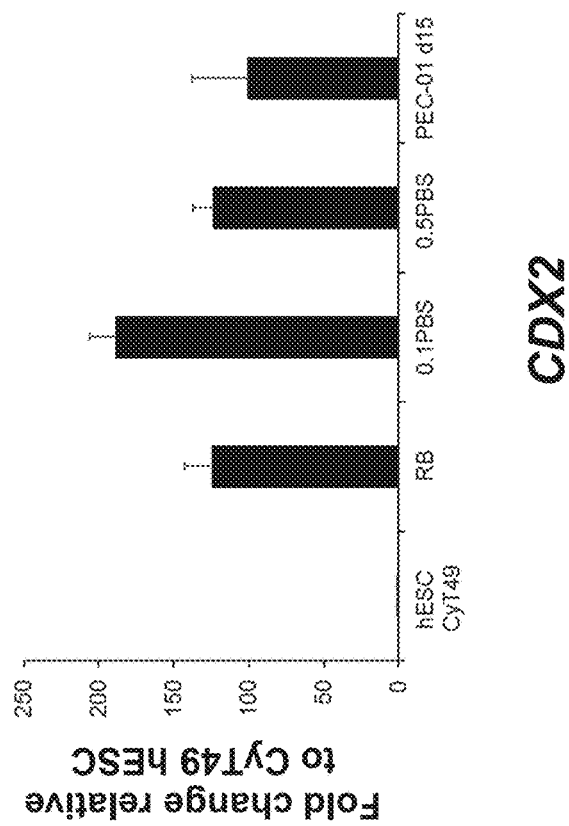
Figure 9M:
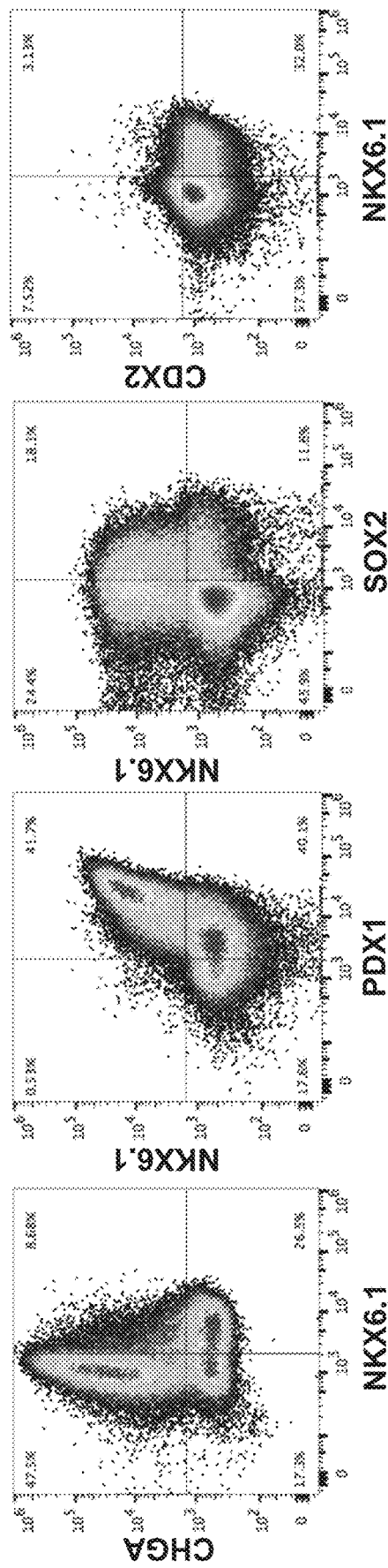
FIGS. 9A-9Q demonstrate the generation of pancreatic endoderm derived from CyT49 hESC in multiple types of suspension culture.
FIG. 9B shows the number of S4D3 cells generated relative to hESC input in millions of cells per ml.
FIG. 9C shows the S4D3 yields for 0.1 PBS Mini and 0.5 PBS Mini. For example, for the 0.5 PBS suspension culture format generated 4.08±0.854 cells per one hESC cell, markedly higher than PEC-01 d12 (2.23±0.090).
FIG. 9N-9P shows the strong protein co-localization of pancreatic endoderm markers (e.g. PDX1, NKX6.1), but not protein markers of alternative endoderm lineages (e.g. SOX2, CDX2) and markers for endocrine differentiation (e.g. CHGA) for S4D3 aggregates generated by the new protocol in 2-liter roller bottle (FIG. 9N), 0.1 PBS (FIG. 9O), and 0.5 PBS (FIG. 9P), relative to 2-liter roller bottle generated PEC-01 d12 aggregates (FIG. 9M), and PEC-01 d15 aggregates (FIG. 9Q).
Figure 9N:
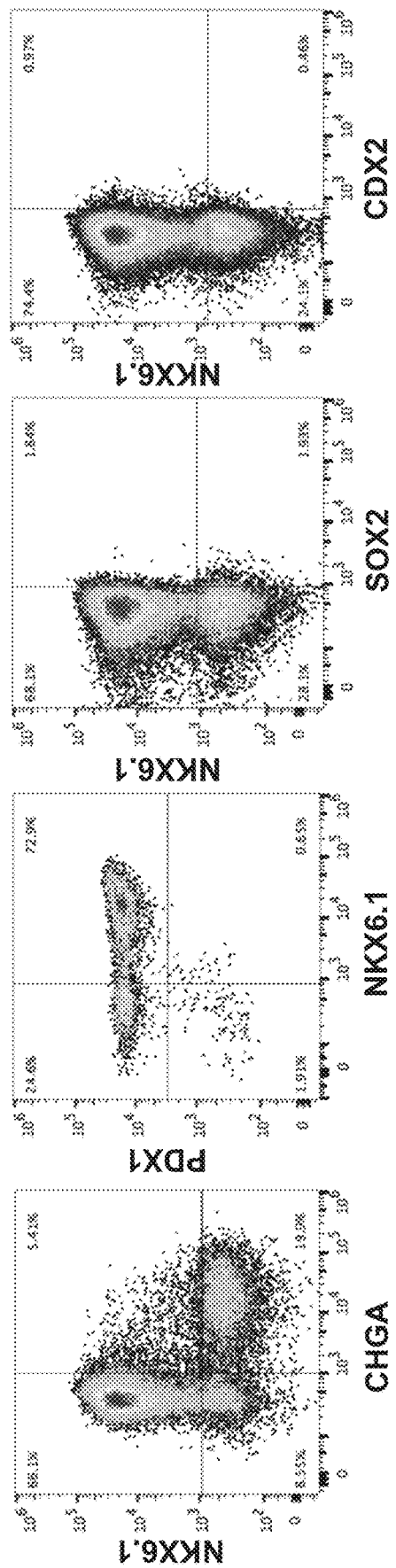
Figure 9O:
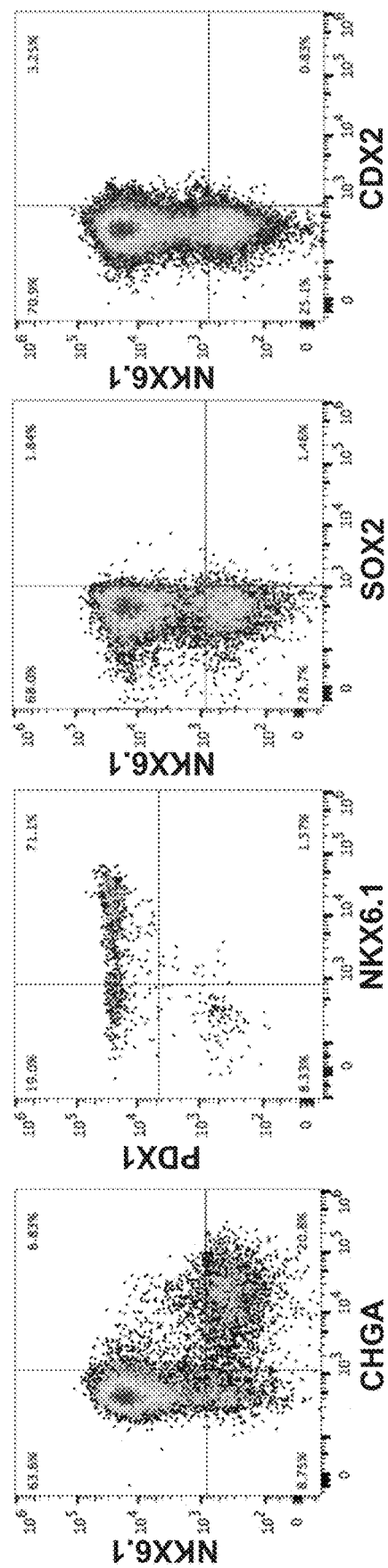
Figure 9P:
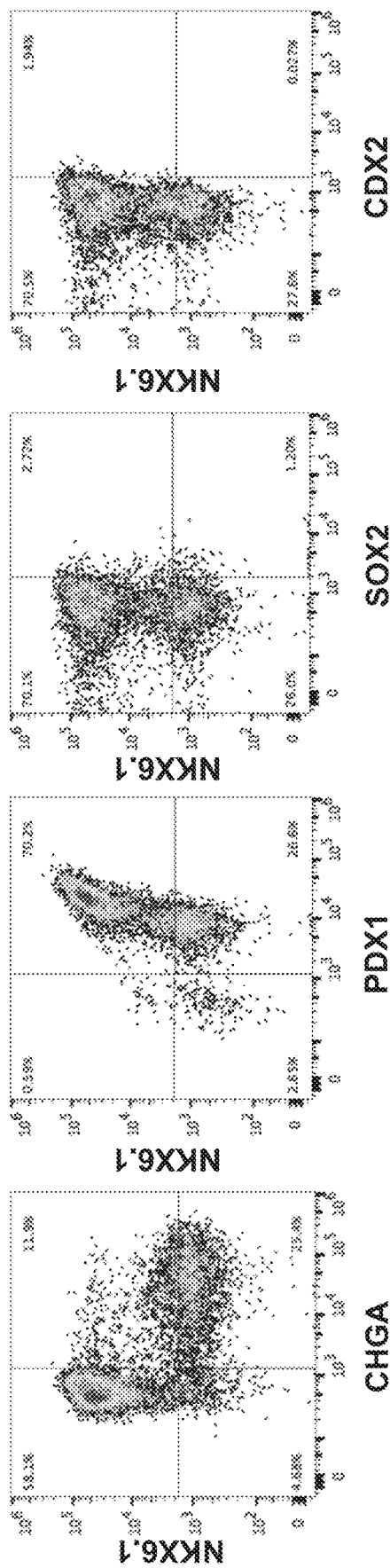
Figure 9Q:
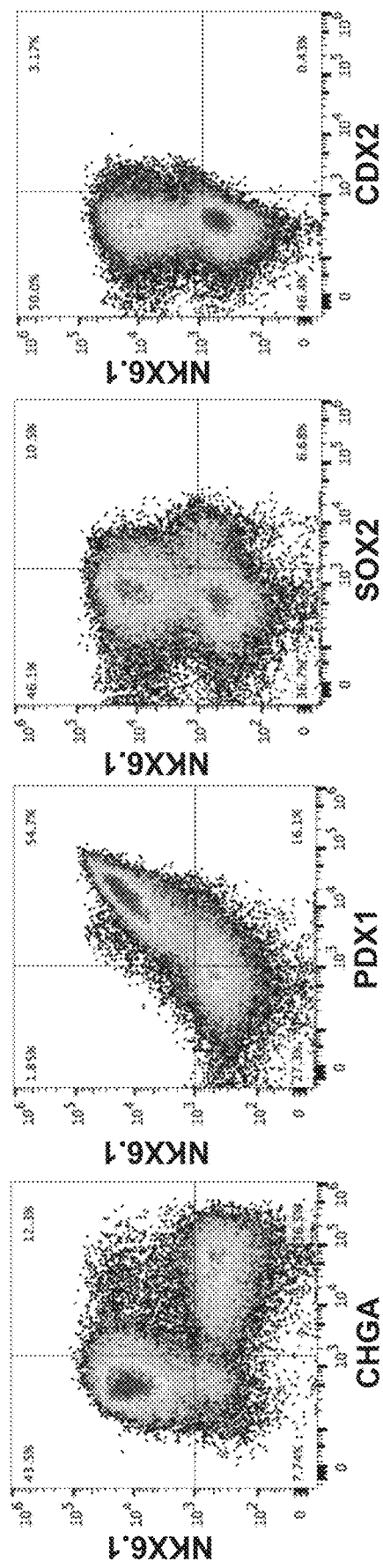

For FIGS. 9A-9Q the cultures were differentiated using the following protocol (depicted in FIG. 9A) in suspension culture format. During Stages 1 through 4 of the protocol, suspension cultures were maintained in either 2-liter roller bottles ("RB") at 31 rpm, 0.1 PBS Mini or 0.5 PBS Mini MagLift™ vertical wheel bioreactors (PBSBiotech, Camarillo, Ca) at 45 rpm. "0.1PBS" refers to the 100 ml Mini MagLift™ vertical wheel bioreactor, and "0.5PBS" refers to the 500 ml Mini MagLift™ vertical wheel bioreactor. CyT49 hESC aggregates were input at approximately 0.18-0.36 million cells per ml in 500 ml media volume of a 2-liter roller bottle, 100 ml media volume of a 0.1 PBS Mini, or 500 ml media volume of a 0.5 PBS Mini. Cell culture media was exchanged daily.

Stage 1 (2 Days):
Undifferentiated ES aggregates were cultured for one day in the following Stage 1 media: MCDB-131 medium containing 2.7 g/1000 ml sodium bicarbonate, and supplemented with 0.5% FAF-BSA, GlutaMAX™ in a 1:100 dilution ("1x concentration"), 4.5 mM D-glucose to obtain a final concentration of 10 mM of D-glucose, 100 ng/ml human Activin A, 50 ng/ml mouse Wnt3A (R and D Systems, Catalog No. 1324-WN), and ITS-X ("Insulin-Transferrin-Selenium-Ethanolamine"; ThermoFisher Scientific, Waltham, Massachusetts, Catalog No. 51500056) in a 1:10000 dilution. Cells were then cultured for an additional day in MCDB-131 medium containing 2.7 g/1000 ml sodium bicarbonate, and supplemented with 0.5% FAF-BSA, 1× concentration of GlutaMAX™, 4.5 mM D-glucose to obtain a concentration of 10 mM D-glucose, 100 ng/ml human Activin A, and ITS-X in a 1:10000 dilution.

Stage 2 (3 Days):
Aggregates were treated for two days with MCDB-131 medium containing 2.7 g/1000 ml sodium bicarbonate, and supplemented with 0.5% FAF-BSA, 1× GlutaMAX™, 4.5 mM D-glucose to obtain a concentration of 10 mM D-glucose, 0.25 mM ascorbic acid, and 50 ng/ml fibroblast growth factor 7 ("FGF7"; PeproTech, Catalog No. AF-100-19).

Stage 3 (2 Days):
Aggregates were treated for two days with BLAR001 custom medium containing 3.6 g/1000 ml sodium bicarbonate, and supplemented with a 1:200 dilution of ITS-X; 4.5 mM D-glucose to obtain a concentration of 10 mM D-glucose; 1× GlutaMAX™; 0.25% FAF-BSA; 25 ng/ml FGF7; 0.25 µM SANT-1 (N-[(3,5-dimethyl-1-phenyl-1H-pyrazol-4-yl)methylene]-4-(phenylmethyl)-1-piperazineamine); 1 µM retinoic acid ("RA"); 0.25 mM ascorbic acid; and 300 nM of the PKC activator ((2S, 5S-(E,E)-8-(5-(4-trifluoromethyl)phenyl-2,4,-pentadienoylamino)benzolactam ("TPB"); for two days.

Stage 4 (3 Days):
Aggregates were treated with BLAR001 medium containing 3.6 g/1000 ml sodium bicarbonate, and supplemented with a 1:200 dilution of ITS-X; 4.5 mM D-glucose to obtain a concentration of 10 mM D-glucose; 1× concentration of GlutaMAX™; 0.25% FAF-BSA; 0.25 µM SANT-1; 50 nM RA; 2 ng/ml FGF7; 0.25 mM ascorbic acid; and 300 nM TPB for three days.

U.S. Pat. Nos. 8,445,273; 8,895,300 incorporated herein by reference in their entireties describe PEC-01 ("Pancreatic endoderm cell 01") d15 generated by at least the protocol listed below. CyT49 hESC aggregates were input at 1.0 µl to 2.0 µl aggregate pellet volume ("APV") per ml. Stages 1 through 4 of the protocol below, were maintained as suspension cultures in 2-liter roller bottles in a 500 ml volume rotating at 31 rpm.

Stage 1 (2 Days; d1-d2):

Undifferentiated ES aggregates were treated for one day with RPMI1640 medium (Life Technologies, Catalog No. 21870-076), supplemented with 1× concentration of GlutaMAX™; 0.2% Fetal Bovine Serum ("FBS"; HyClone, Logan Utah, Catalog No. SH30070.03); 1× concentration of Penicillin-Streptomycin; 1:5000 dilution of ITS (Invitrogen, Waltham, Massachusetts, Catalog No. 41400); 100 ng/ml Activin A; and 50 ng/ml Wnt3A. Cells were then cultured for an additional day in RPMI1640 medium, supplemented with 1× concentration of GlutaMAX™; 0.2% Fetal Bovine Serum; 1× concentration of Penicillin-Streptomycin; 1:5000 dilution of ITS; 100 ng/ml Activin A; and 50 ng/ml Wnt3A.

Stage 2 (3 Days; d3-d5):

Aggregates were treated for one day with RPMI1640 medium, supplemented with 1× concentration of GlutaMAX™; 0.2% Fetal Bovine Serum; 1× concentration of Penicillin-Streptomycin; 1:1000 dilution of ITS; 25 ng/ml human FGF7; and 2.5 uM Transforming Growth Factor-beta inhibitor IV ("TGF-β"; EMD Bioscience, Billerica, Massachusetts, Catalog No. 616454). Cells were then cultured for an additional two days in RPMI1640 medium, supplemented with 1× concentration of GlutaMAX™; 0.2% Fetal Bovine Serum; 1× concentration of Penicillin-Streptomycin; 1:1000 dilution of ITS; and 25 ng/ml human FGF7.

Stage 3 (3 Days; d6-d8):

Aggregates were treated for three days with DMEM-HI Glucose medium (Invitrogen, Catalog No. 11960-051), supplemented with B-27 Supplement in a 1:50 dilution (Invitrogen, Catalog No. 17504-044); 1× concentration of Penicillin-Streptomycin; 1× concentration of GlutaMAX™; 1:1000 dilution of ITS; 3 nM TTNPB ("4-[(E)-2-(5,6,7,8-Tetrahydro-5,5,8,8-tetramethyl-2-naphthalenyl)-1-propenyl] benzoic acid"; Sigma-Aldrich, St. Louis, Missouri, Catalog No. T3757); 0.25 uM KAAD-Cyclopamine ("3-Keto-N-aminoethyl-N'-aminocaproyldihydrocinnamoyl Cyclopamine"; Toronto Research Chemicals, North York, Canada, Catalog No. K171000); and 50 ng/ml human Noggin (R and D Systems, Catalog No. 3344-NG).

Stage 4 (3 Days; d9-d12; d12 is Referred to as "PEC-01 d12"):

Aggregates were treated for three days with DMEM-HI Glucose medium, supplemented with B-27 Supplement in a 1:50 dilution; 1× concentration of Penicillin-Streptomycin; 1× concentration of GlutaMAX™; 50 ng/ml human epidermal growth factor ("EGF"; PeproTech, Catalog No. AF-100-15); 50 ng/ml FGF7; and 50 ng/ml human Noggin.

Cryopreservation at d12:

Aggregates were resuspended in DMEM-HI Glucose medium, supplemented with 1× concentration of GlutaMAX™; 15% concentration DMSO ("Dimethyl sulfoxide"; Origen Biomedical, Austin, Texas, Catalog No. CP-10); 60% concentration XF-free KSR; and 25 mM HEPES buffer solution ("N-2-hydroxyethylpiperazine-N-2-ethane sulfonic acid"; ThermoFisher Scientific, Catalog No. 15630080). The d12 aggregates were cryopreserved in a controlled rate freezer ("CRF"; Planer PLC, Shepperton Sunbury-on-Thames, United Kingdom, Catalog No. Kryo 560-16) using the following protocol: (1) start temperature −2.0 C; (2) −2.0 C/min to −9.0 C; (3) at −9.0 C for 10 minutes and manually initiate freezing; (4) −0.2 C/min to −40C; (5) −25C/min to −150C; (6) transferred to liquid nitrogen storage.

Post-Cryopreservation to PEC-01 (3 Days; d13-d15):

Aggregates were treated for three days with DMEM-HI Glucose medium, supplemented with B-27 Supplement in a 1:50 dilution; 1× concentration of Penicillin-Streptomycin; 1× concentration of GlutaMAX™; 50 ng/ml human epidermal growth factor ("EGF"; PeproTech, Catalog No. AF-100-15); 50 ng/ml FGF7; and 50 ng/ml human Noggin. On the first day only 10U/ml DNase I (Roche, Basel, Switzerland, Catalog No. 04536282001) is supplemented to the media.

Characterization of Differentiated Cells:

For quantification of gene expression utilizing 2-liter roller bottle, 0.1 PBS, or 0.5 PBS suspension culture methods, CyT49-hESC, Stage 4 day 3 ("54D3"), and PEC-01 d15 aggregates were harvested, as described in *Nature Biotechnology*, 2014, (32) 11, 1121-1133. Gene expression was assessed in cells using custom Taqman Arrays (Applied Biosystems, Foster City, California). Data were analyzed using Sequence Detection Software (Applied Biosystems, Foster City, California), and normalized using GAPDH as a housekeeping gene to undifferentiated CyT49-hESC using the ΔΔCt method. Primer details are outlined in Table XV.

TABLE XV

List of qRT-PCR primers.

| | Gene | Assay ID |
|---|---|---|
| 1 | PTF1A | Hs00603586_g1 |
| 2 | CDX2 | Hs00230919_m1 |
| 3 | SOX2 | Hs01053049_s1 |
| 4 | NKX6.1 | Hs00232355_m1 |
| 5 | PDX1 | Hs00236830_m1 |
| 6 | NEUROD1 | Hs00159598_m1 |
| 7 | CHGA | Hs00154441_m1 |
| 8 | GAPDH | Hs99999905_m1 |

For quantification of protein presence co-localization utilizing 2-liter roller bottle, 0.1 PBS, or 0.5 PBS suspension culture methods, CyT49-hESC, Stage 4 day 3 ("54D3"), and PEC-01 d15 aggregates were harvested and analyzed by fluorescence-activated flow cytometry ("FACS"). FACS staining was conducted as described in *Nature Biotechnology*, 2014 (32) 11, 1121-1133, and used the antibodies listed in Table XVI. Differentiated cells were incubated in Accumax (Innovative Cell Technologies, San Diego, California, Catalog No. AM105) for 20 minutes at room temperature, released into a single-cell suspension, after which they were washed twice with autoMACS Running Buffer (Bergisch, Germany, Miltenyl Biotec, Catalog No. 120-091-221), fixed in 4% Paraformaldehyde ("4% PFA"; Sigma-Aldrich, Catalog No. 158127) for 30 minutes at room temperature followed by two washes in the autoMACS Running buffer. Cells were then incubated with the appropriate antibodies (Table XVI) prior to analysis on the BD FACS Canto II using BD FACS Diva Software with at least 30,000 events being acquired. Non-viable cells were excluded during FACS analysis, and gating was determined by using isotype antibodies ("IgG").

TABLE XVI

List of antibodies used for FACS analysis.

| Antigen | Species | Source/Catalog Number | Dilution |
|---|---|---|---|
| Alexa Fluor 647 anti-NKX6.1 | Mouse | BD, Catalog No. 563338 | 1:3 |
| PE anti-PDX1 | Mouse | BD, Catalog No. 562161 | 1:2 |
| Alexa Fluor 405 anti-CHGA | Mouse | Novus Biologicals, Catalog No. NBP2-33198AF405 | 1:100 |
| PerCP-Cy™ 5.5 anti-SOX2 | Mouse | BD, Catalog No. 561506 | 1:2 |
| PE anti-CDX2 | Mouse | BD, Catalog No. 563428 | 1:4 |

For quantification of cell yields utilizing 2-liter roller bottle, 0.1 PBS, or 0.5 PBS suspension culture methods, CyT49-hESC and Stage 4 day 3 ("S4D3") aggregates were harvested, and counted by the Nucleocounter® NC-100 (Chemometec, Allerod, Denmark, Catalog No. NC-100).

FIG. 9A depicts how CyT49 hESC were differentiated utilizing a new protocol towards the pancreatic endoderm (e.g. S4D3). PEC-01 d12 and PEC-01 d15 are highlighted here as examples of prior art. Suspension culture methods were utilized based on their compatibility for commercial scale generation of insulin-producing cells via a pancreatic endoderm intermediate, namely 2-liter roller bottle, or the 0.1 PBS, or 0.5 PBS vertical wheel bioreactors. While the 2-liter roller bottle format is a useful tool for the scale-out of pancreatic endoderm cells, it is not ideal for the eventual commercial scale of insulin-producing cells. The PBS Biotech MagLift™ vertical wheel bioreactor system is an alternative scale-up system that would provide the ability to progressively improve insulin-producing cell production while increasing volume, and maintaining small/compact aggregate size over time. FIG. 9B demonstrates that, as expected, cell yields at S4D3 reflected a significant expansion of cell number relative to hESC input. The ratio of S4D3 cells to hESC input was consistent across all suspension culturing methods utilizing the new protocol; 4.30±0.782 for 2-liter roller bottle, 3.27±0.585 for 0.1PBS, and 4.08±0.854 for 0.5PBS, and markedly increased from prior art (2.23±0.090 PEC-01 d12 cell per hESC input). Furthermore, wedemonstrated in FIG. 9C that the disclosed differentiation protocol can be effectively scaled-up using the PBS MagLift™ vertical wheel bioreactor system. When the media volume was increased from 100 ml (0.1PBS) to 500 ml (0.5PBS) an approximately 6-fold increase in S4D3 yield (FIG. 9C) was observed. In addition, utilizing either the 0.1PBS (~150±33.2 microns) or 0.5PBS (~153±37.6 microns) suspension format resulted in uniformly smaller S4D3 aggregates relative to roller bottle based S4D3 (~274±92.5 microns), and PEC-01 d12 (~259±55.3 microns). Cryopreservation, thaw and further three-day culture of PEC-01 d12 was required to reduce PEC-01 aggregates size to the scale seen with 0.1PBS and 0.5PBS (PEC-01 d15; ~191±45.4 microns) (FIG. 9D-9E). It was demonstrated that a robust pancreatic endoderm phenotype was achieved utilizing the new CyT49 hESC-derived differentiation protocol across all suspension culture methods. NKX6.1 (FIG. 9F), PTF1A (FIG. 9G), PDX1 (FIG. 9H) were all significantly induced in 2-liter roller bottle, 0.1PBS, 0.5PBS methods, similarly to PEC-01 d15. Unlike the PEC-01 d15 differentiation protocol, which resulted in the heightened expression of SOX2 (alternative endoderm lineage; FIG. 9I), NEUROD1 (early endocrine differentiation; FIG. 9K), and CHGA (early endocrine differentiation; FIG. 9L), the new differentiation protocol reduced these non-pancreatic endoderm markers in all suspension culture methods tested in CyT49. Indeed, such an enrichment of non-pancreatic endoderm, decreases the efficiency of pancreatic endoderm production as assessed on the protein-level. Relative to PEC-01 d12 (~38.0%; FIG. 9M), the protein co-localization between PDX1 and NKX6.1 was enhanced across all new S4D3 suspension culture methods utilizing the new CyT49 hESC-derived differentiation protocol; 2-liter roller bottle ~64.6% (FIG. 9N), 0.1PBS ~48.9% (FIG. 9O), and 0.5PBS ~65.3% (FIG. 9P). Moreover, ~49% of PDX1+ NKX6.1±pancreatic endoderm observed in PEC-01 d12 also expressed SOX2+(FIG. 9M), unlike all new S4D3 suspension culture methods utilizing the new CyT49 hESC-derived differentiation protocol; 2-liter roller bottle ~2.0% (FIG. 9N), 0.1PBS ~10.0% (FIG. 9O), and 0.5PBS ~6.2% (FIG. 9P). The relatively low percentage of pancreatic endoderm seen in PEC-01 d12 was also reflected by the increased prevalence of early endocrine differentiation (~49.6%; FIG. 9M) relative to all new S4D3 suspension culture methods; 2-liter roller bottle ~26.9% (FIG. 9N), 0.1PBS ~26.6% (FIG. 9O), and 0.5PBS ~30.2% (FIG. 9P). Cryopreservation, thaw, and 3 days additional cell culture of PEC-01 d12 was required to slightly increase the co-localization of PDX1 and NKX6.1 (PEC-01 d15; ~47.5%; FIG. 9Q) by the reduction of SOX2 (~22.5%; FIG. 9Q) and CHGA (~42.5%; FIG. 9Q). The protein co-localization between NKX6.1 and CDX2 was low across all conditions tested (FIG. 9M-9Q), as mirrored by low CDX2 gene expression at S4D3 across all types of suspension culture (FIG. 9J).

Example 7

Generation of Insulin Producing Cells Derived from CyT49 hESC in Multiple Types of Suspension Culture The following example demonstrates the improved generation of pancreatic insulin-producing cells derived from the CyT49 human embryonic stem cell line ("hESC") utilizing a new differentiation protocol in multiple suspension culture formats (roller bottle, and both the 0.1PBS and 0.5PBS Biotech MagLift™ vertical wheel bioreactors). Table XVII lists the particular enhancements made to CyT49 hESC-derived insulin-producing cells. While, similar in duration to PEC-01-derived and PEC-01-similar-derived insulin producing cells (prior art is *Stem Cells Transl Med,* 2015 (10) 4, 1214-1222), the new differentiation protocol used to produce insulin-positives cells from CyT49 hESC exhibit the enhanced production of mono-hormonal insulin-producing cells ($INS^+$ only), via a significant reduction of poly-hormonal insulin-producing cells (both $INS^+$ $GCG^+$), and the protein presence of PDX1, NKX6.1, CHGA, MAFA in mono-hormonal insulin-producing cells. The lack of GCG-presence, and induction of NKX6.1, MAFA-presence in mono-hormonal insulin-positive cells is a requirement for eventual acquisition of human-islet-similar functionality (Examples 2-5). Moreover, the new CyT49 hESC-derived pancreatic insulin-producing cell protocol exhibits, for the first time, scale-up ability in a bioreactor, which is better able to handle, than scale-out by roller bottle, the eventual commercial cell manufacturing of insulin-producing cells (Example 7).

TABLE XVII

Improvements to generation of insulin-producing cells.

| | PEC-01-similar derived insulin-producing cells (CyT49) | H1 hESC-derived (Example 2-4) | New CyT49 hESC-derived (Example 7) |
|---|---|---|---|
| Protocol duration | 12-21 days (Stage 7) | 17 days (Stage 7) | 17-25 days (Stage 7) |
| Prevalence of total INS+ cells | ~45% | ~50% | ~50% |
| Prevalence of INS+ GCG+ cells | Intermediate; ~15% | Low; ~4% | Low; ~6.6% |
| MAFA presence in INS+ NKX6.1+ cells? | Not assessed but very low gene expression | Yes | Yes |
| Format | Rotating 6-well plates | bioreactor (Current disclosure) | Roller bottle, bioreactor (Current disclosure) |

Table XVIII outlines major adjustments made to the differentiation protocol for generation of improved CyT49 hESC-derived pancreatic endoderm. Major differences include small molecules and base mediums used. Abbreviations include: Nic—Nicotinamide; MG—Matrigel; GSI—gamma-secretase inhibitor; ROCKi—Rho-associated protein kinase inhibitor.

TABLE VIII hESC-derived differentiation protocol to insulin-producing cells.

| Stage | Stage 5 | Stage 6 | Stage 7 |
|---|---|---|---|
| PEC-01-derived insulin-producing cells (CyT49) (Stem Cell Trans Med, 2015) | Noggin, KGF, EGF, GSI, ROCKi, B-27; DMEM/HI Glucose | Nic, ROCKi, B-27; CMRL1066 | Nic, MG, ROCKi, T3, Nic, B-27; CMRL1066 |
| H1 hESC-derived (Example 2-4) | SANT, RA, LDN, ALK5 inh, T3, Heparin; BLAR001 | LDN, ALK5 inh, T3, XX, Heparin; BLAR001 | T3, Heparin, NAC, Formulation I; BLAR001 |
| New CyT49 hESC-derived (Example 7) | SANT, RA, LDN, ALK5 inh, T3, Heparin; BLAR001 | LDN, ALK5 inh, T3, XX, Heparin; BLAR001 | T3, Heparin, NAC, Formulation I; BLAR001 |

Cells of the human embryonic stem cell line CyT49 ("CyT49-hESC"; NIH registration 0041) at passage 27 of working cell bank 4A ("WCB4A") were seeded and maintained as described in Example 6. Also, CyT49 hESC aggregation, and differentiation through Stages 1-4 was performed as described in Example 6.

Figure 10A:
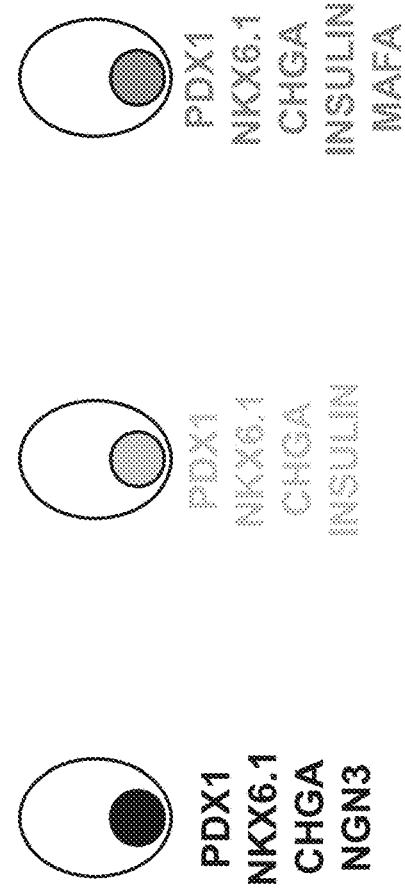
FIGS. 10A-10AB demonstrate the generation of insulin producing cells derived from CyT49 hESC in multiple types of suspension culture.

For FIGS. 10A-10AB, the cultures were further differentiated during Stages 5-7 using the following protocol (depicted in FIG. 10A) in suspension culture format. During Stages 5 through 7 of the protocol, suspension cultures were maintained in either roller bottles ("RB") at 31 rpm, 0.1 PBS Mini or 0.5 PBS Mini MagLift™ vertical wheel bioreactors at 45 rpm. "0.1PBS" refers to the 100 ml Mini MagLift™ vertical wheel bioreactor, and "0.5PBS" refers to the 500 ml Mini MagLift™ vertical wheel bioreactor. Note, that the Stage 7 differentiation protocol is referred to as basal conditioning, as the cocktail for inducing functionality of the insulin-producing cells is not included and is subject of another disclosure. During Stage 5-6, media exchanges occurred daily, while at Stage 7, media was exchanged every other day.

Stage 5 (3 Days):
S4D3 CyT49 (Example 6 new CyT49 hESC-derived protocol) or PEC-01 d15 derived aggregates were treated with BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM $ZnSO_4$; 0.25 µM SANT-1; 50 nM RA; 100 nM LDN-HCl; 1 µM of T3; and 10 µM of ALK5 inhibitor II.

Stage 6 (7 Days):
Aggregates were treated in BLAR001 medium containing 2.7 g/1000 ml sodium bicarbonate, supplemented with a 1:200 dilution of ITS-X; 14.5 mM D-glucose to achieve a final concentration of 20 mM D-glucose; 1× GlutaMAX™; 2% FAF-BSA; 10 µg/ml of heparin ("H"); 10 µM $ZnSO_4$; 100 nM LDN-HCl; 1 µM of T3; 10 µM of ALK5 inhibitor II, and 100 nM of gamma secretase inhibitor XX. S5D3 aggregates in 0.5 PBS suspension culture were transferred to 0.1 PBS suspension culture for Stages 6-7.

Stage 7 (7 to 23 Days):
Aggregates were treated in BLAR001 medium containing 2.7 g/1000 ml sodium bicarbonate, and supplemented with a 1:200 dilution of ITS-X; 1× GlutaMAX™; 2% FAF-BSA; 10 µg/ml of heparin ("H"), 10 nM of T3 ("low T3"); 1 mM NAC"); and the following components which constitute Formulation I ("FI") 1:200 dilution of RPMI vitamin supplement; 1:200 dilution of MEM non-essential amino acid supplement; 1:2000 dilution of chemically defined lipid concentrate; 1:200 dilution of sodium pyruvate; 1:2000 dilution of trace elements A; 1:2000 dilution of trace elements B.

Characterization of Differentiated Cells:
For quantification of gene expression utilizing roller bottle, 0.1 PBS, or 0.5 PBS suspension culture methods, CyT49-hESC, Stage 4 day 3 ("54D3"), Stage 5 day 3 ("S5D3"), Stage 6 day 7 ("56D7"), and Stage 7 day 7 ("57D7") aggregates were harvested, as described in Nature Biotechnology, 2014, (32) 11, 1121-1133, and Example 1. Primer details are outlined in Table XIX.

TABLE XIX

List of qRT-PCR primers.

| | Gene | Assay ID |
|---|---|---|
| 1 | NGN3 | Hs00360700_g1 |
| 2 | INSULIN | Hs00355773_m1 |
| 3 | MAFA | Hs01651425_s1 |
| 4 | NKX6.1 | Hs00232355_m1 |

TABLE XIX-continued

List of qRT-PCR primers.

| | Gene | Assay ID |
|---|---|---|
| 5 | PDX1 | Hs00236830_m1 |
| 6 | NEUROD1 | Hs00159598_m1 |
| 7 | CHGA | Hs00154441_m1 |
| 8 | GAPDH | Hs99999905_m1 |

For quantification of protein presence co-localization utilizing roller bottle, 0.1 PBS, or 0.5 PBS suspension culture methods CyT49-hESC, Stage 5 day 3 ("S5D3"), Stage 6 day 7 ("56D7"), Stage 7 day 13 ("S7D13"), and Stage 7 day 14 ("S7D14") aggregates were harvested and analyzed by fluorescence-activated flow cytometry ("FACS") as described in Example 1. List of antibodies used for FACS analysis are indicated in Table XX.

TABLE XX

List of antibodies used for FACS analysis.

| Antigen | Species | Source/Catalog Number | Dilution |
|---|---|---|---|
| Alexa Fluor 647 anti-NKX6.1 | Mouse | BD, Catalog No. 563338 | 1:3 |
| anti-PAX4 (unconjugated) | Goat | R and D Systems, Catalog No. AF2614 | 1:40 |
| Alexa Fluor 405 anti-CHGA | Mouse | Novus Biologicals, Catalog No. NBP2-33198AF405 | 1:100 |
| Alexa Fluor 488 anti-INSULIN | Mouse | Novus Biologicals, Catalog No. NBP2-34738AF488 | 1:10 |
| BV421 anti-GLUCAGON | Mouse | BD, Catalog No. 565891 | 1:10 |
| Alexa Fluor 488 Anti-goat IgG | Goat | Jackson Laboratories, Catalog No. 705-546-147 | 1:400 |

For quantification of cell yields utilizing roller bottle, 0.1 PBS, or 0.5 PBS suspension culture methods, CyT49-hESC, and Stage 6 day 7 ("56D7") aggregates were harvested, and counted by the Nucleocounter® NC-100 (Chemometec, Allerod, Denmark, Catalog No. NC-100).

For quantification of protein co-localization utilizing roller bottle, 0.1 PBS, or 0.5 PBS suspension culture methods Stage 6 day 7 ("56D7"), Stage 7 day 16 ("S7D16"), and Stage 7 day 23 ("57D23") aggregates were harvested and analyzed by immunofluorescence ("IF"). CyT49-hESC-derived aggregates were prepared as described in both *Nature Biotechnology*, 2014, (32) 11, 1121-1133 and in previous examples, and using the antibodies listed in Table XXI herein.

TABLE XXI

List of antibodies used for IF analysis.

| Antigen | Species | Source | Dilution |
|---|---|---|---|
| INSULIN | Mouse | Cell Signaling (Catalog No. 8138BF) | 1:250 |
| MAFA | Rabbit | Life Span Biosciences (Catalog No. LP9872) | 1:100 (Antigen retrieval) |
| SYNAPTOPHYSIN | Rabbit | Novus Biologicals (Catalog No. NB120-16659) | 1:50 |
| NKX6.1 | Rabbit | Life Span Biosciences (Catalog No. LP9878) | 1:1000 |

Figure 10D:
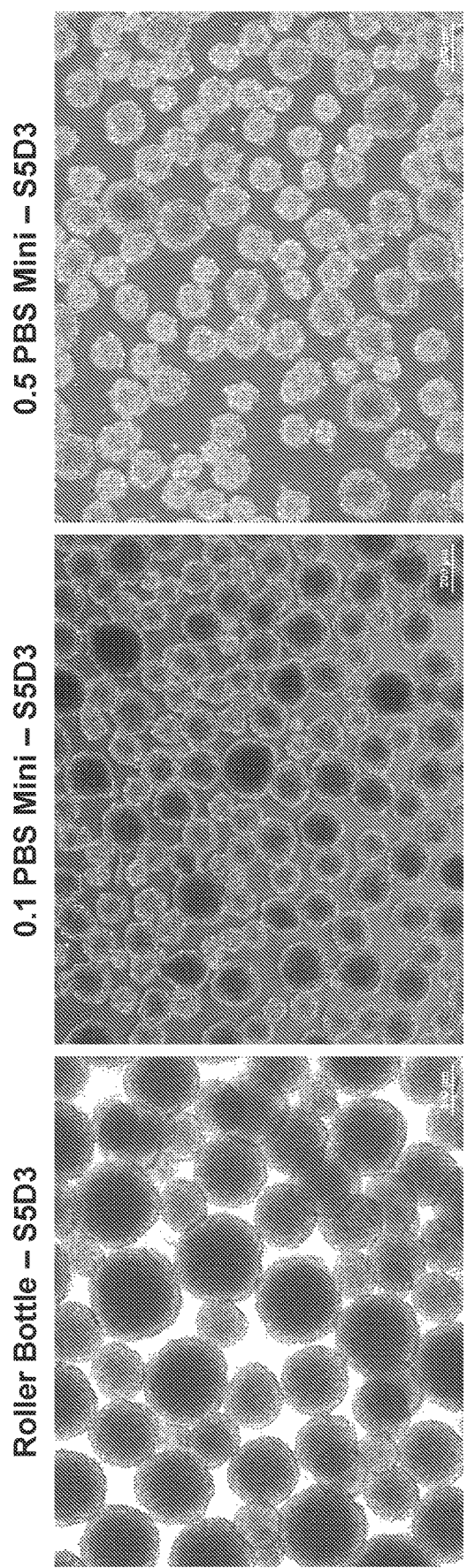
FIG. 10D depicts phase-contrast images of S5D3 aggregates from 2-liter roller bottle (FIG. 10D left), 0.1 PBS (FIG. 10D middle), and 0.5 PBS (FIG. 10D right) suspension formats.
Figure 10E:
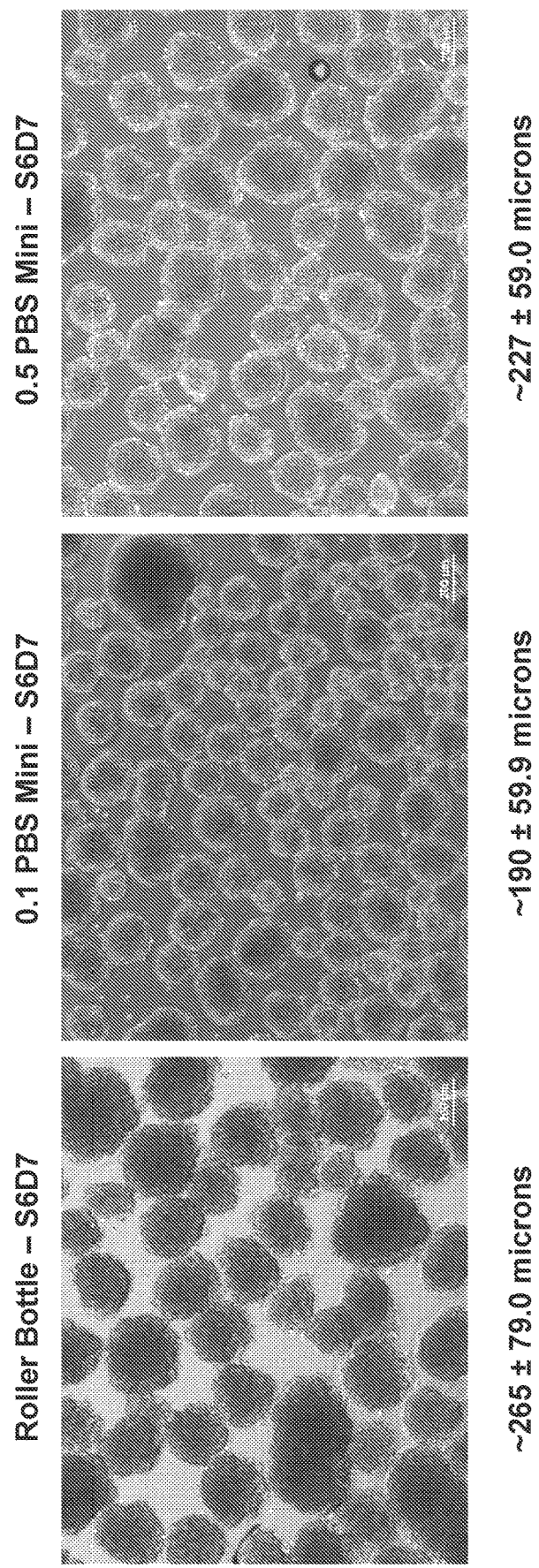
FIG. 10E depicts phase-contrast images of S6D7 aggregates from 2-liter roller bottle (FIG. 10E left), 0.1 PBS (FIG. 10E middle), and 0.5 PBS (FIG. 10E right) suspension formats with aggregate diameter indicated below each picture.
Figure 10F:
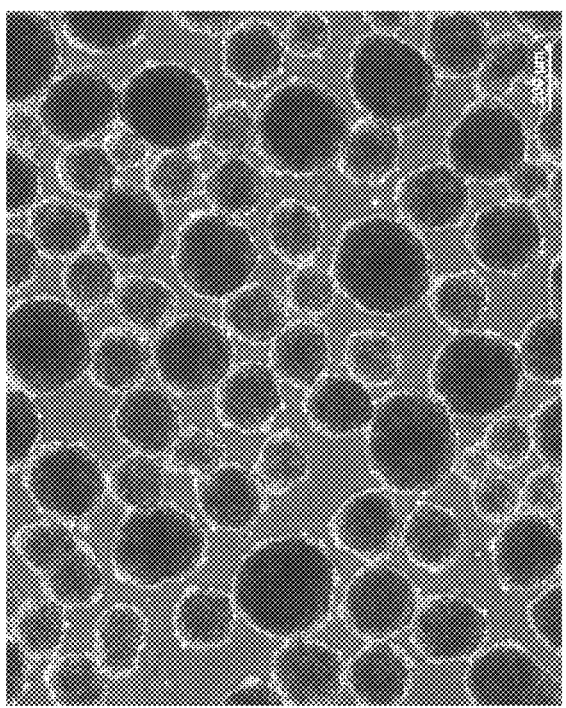
FIG. 10F depicts phase-contrast images of S7D13 aggregates from 2-liter roller bottle (FIG. 10F left), and 0.1 PBS (FIG. 10F right) suspension formats. Suspension culture by 0.1 PBS and 0.5 PBS maintains tight aggregate architecture through Stage 7. Conversely, Stage 6-7 aggregates loosen to form sheets of cells in 2-liter roller bottle suspension culture.
Figure 10F:
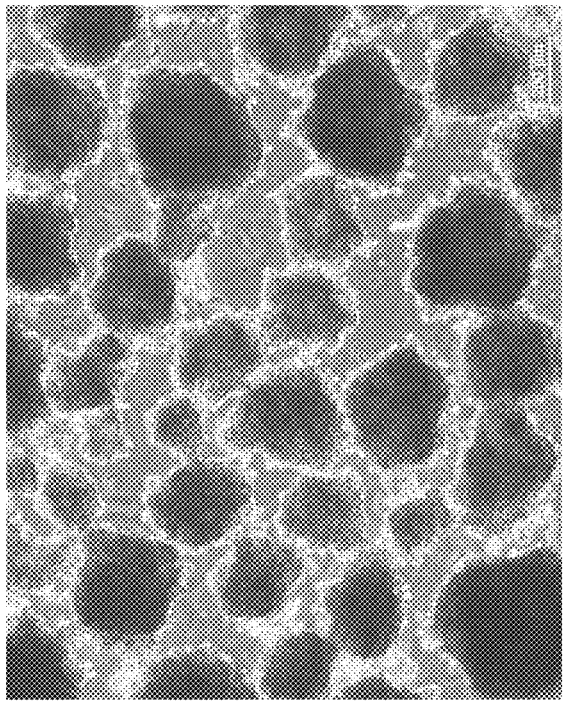
Figure 10O:
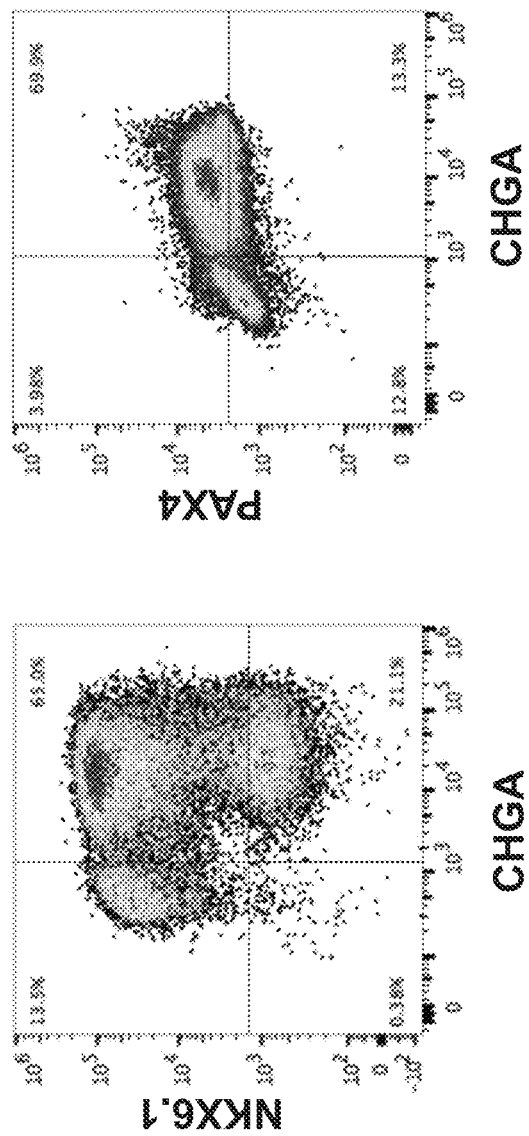
Figure 10P:
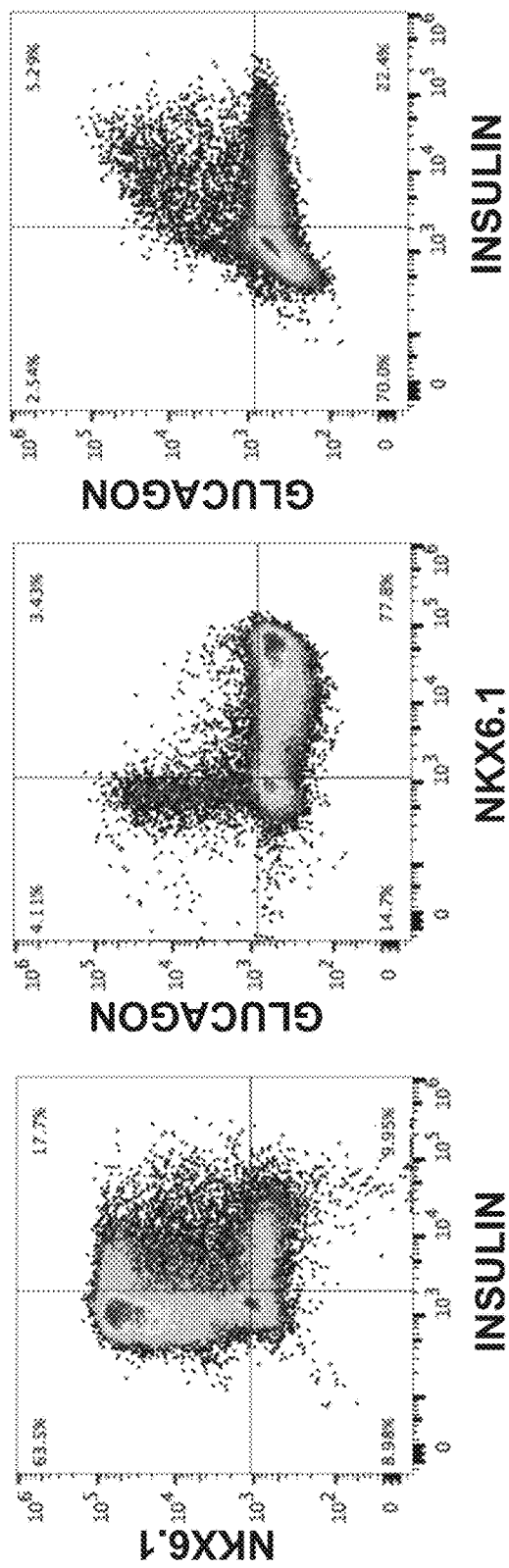
Figure 10Q:
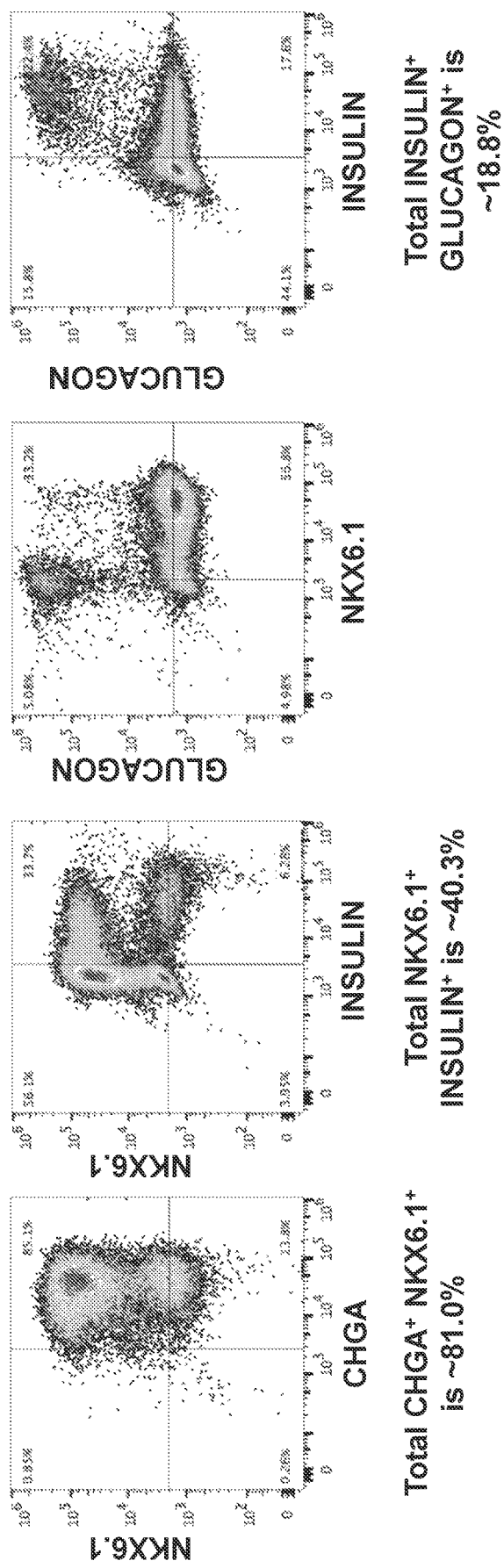
Figure 10R:
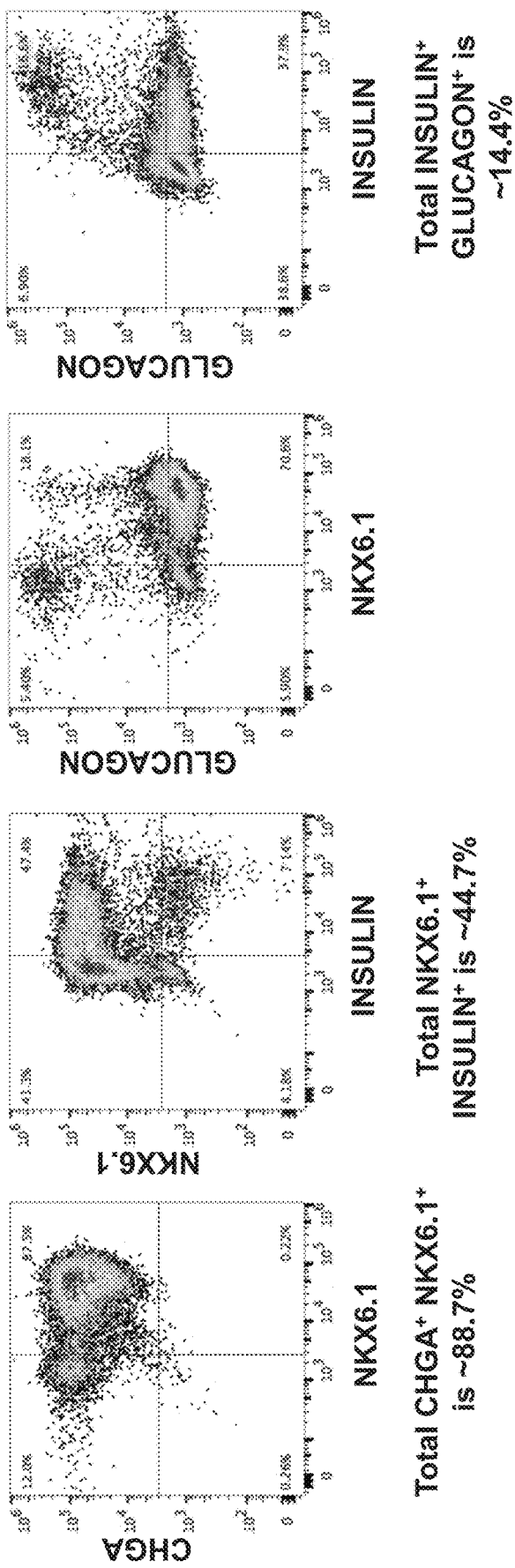
Figure 10S:
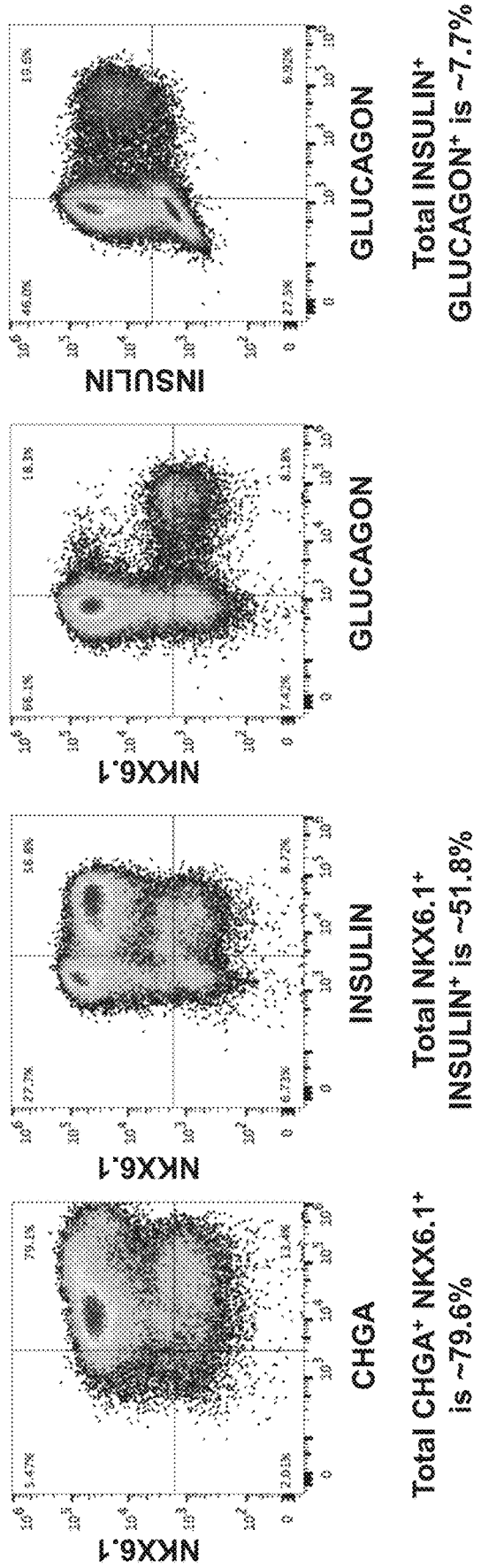
Figure 10U:
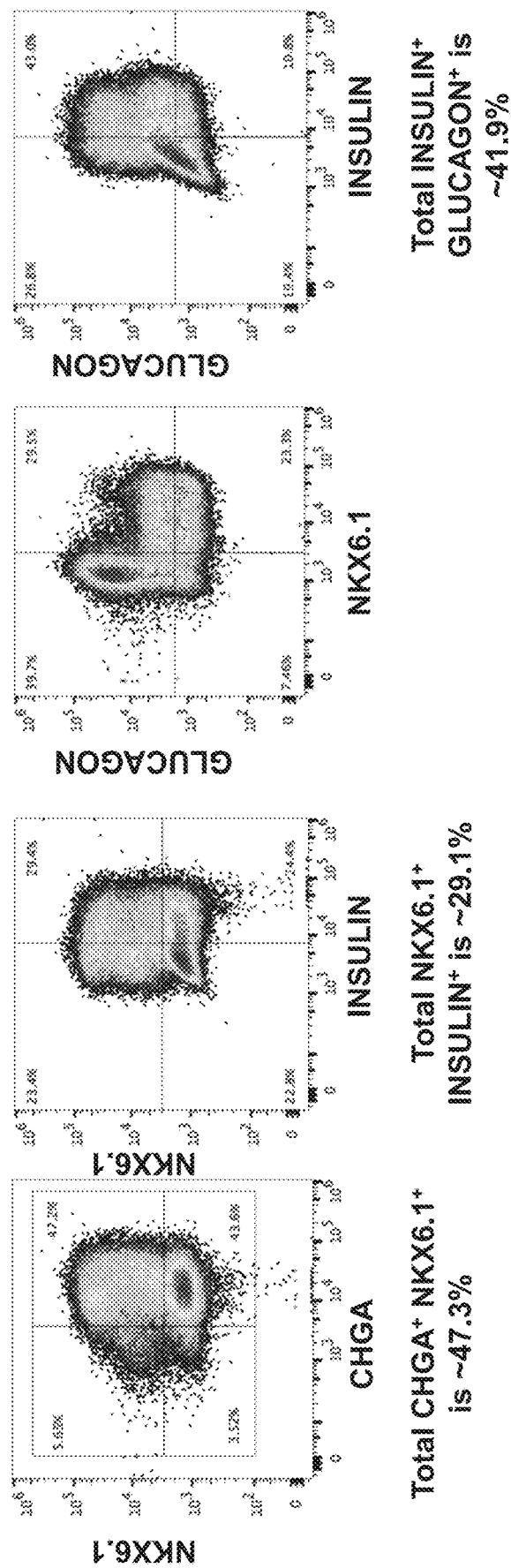
FIG. 10U shows the prevelance of NKX6.1 cells co-expressing CHGA, INSULIN or GLUCAGON as well as the prevelance of INSULIN and GLUCAON co-expressing cells for PEC-01-derived S6D7 cells.
Figure 10V:
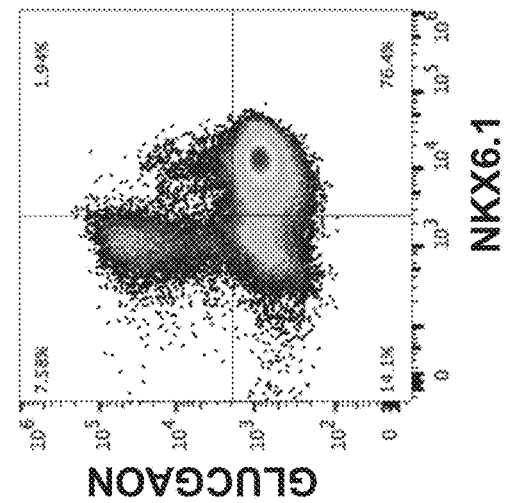
FIG. 10V shows the co-localization of GLUCAGON and NKX6.1 for: PEC-01-derived S6D7; 0.1PBS S7D14 and roller bottle (RB) S7D13.
Figure 10V:
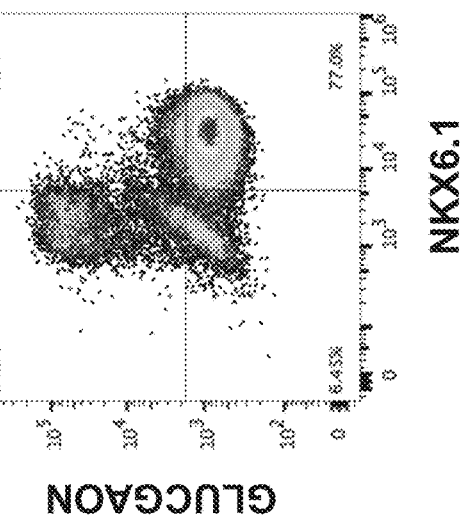
Figure 10V:
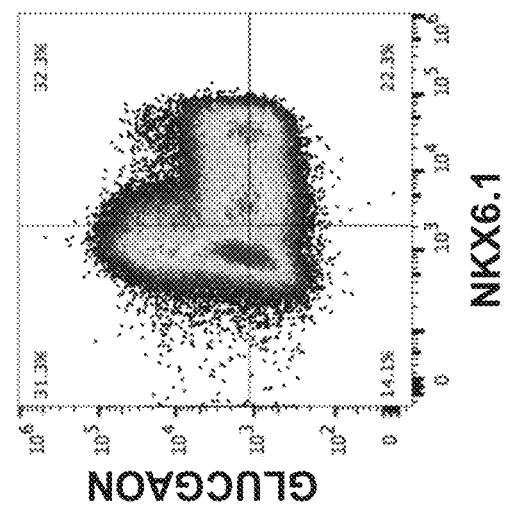
Figure 10W:
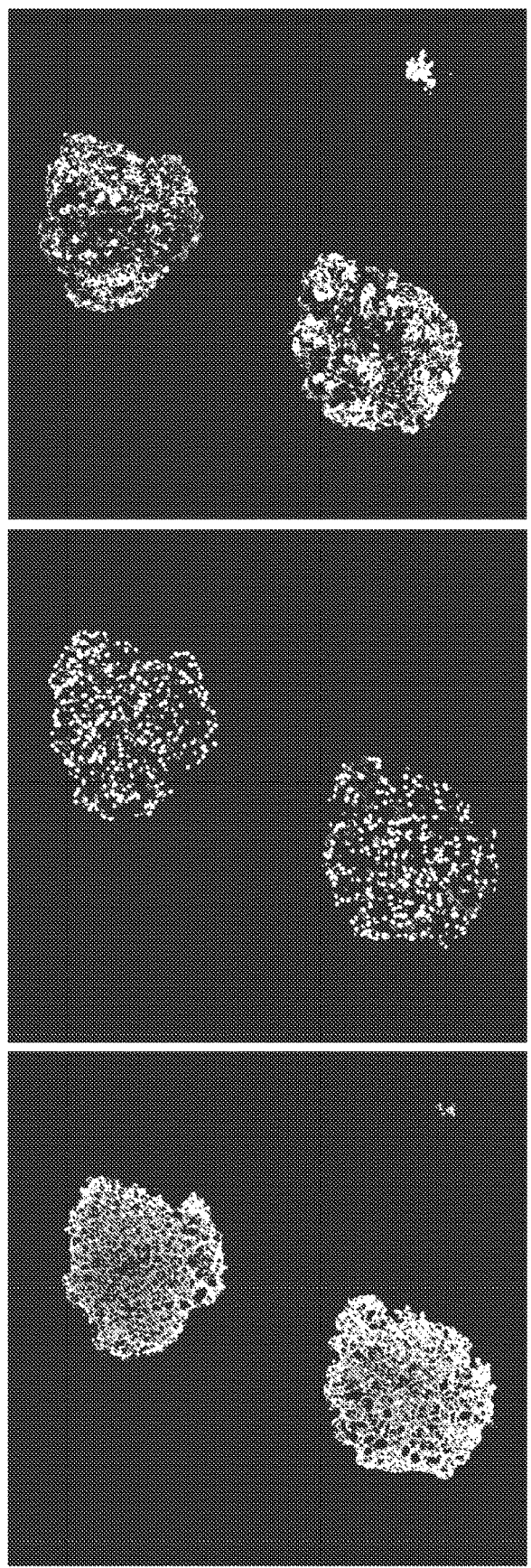
Figure 10X:
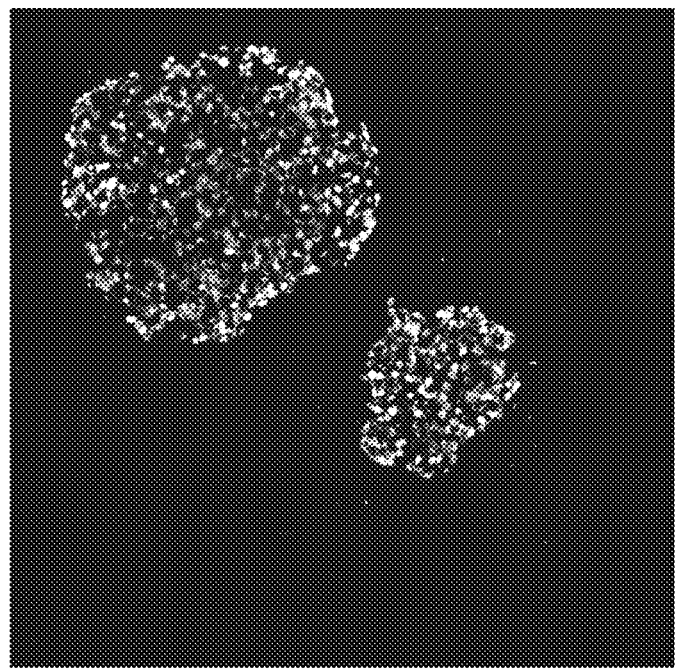
Figure 10X:
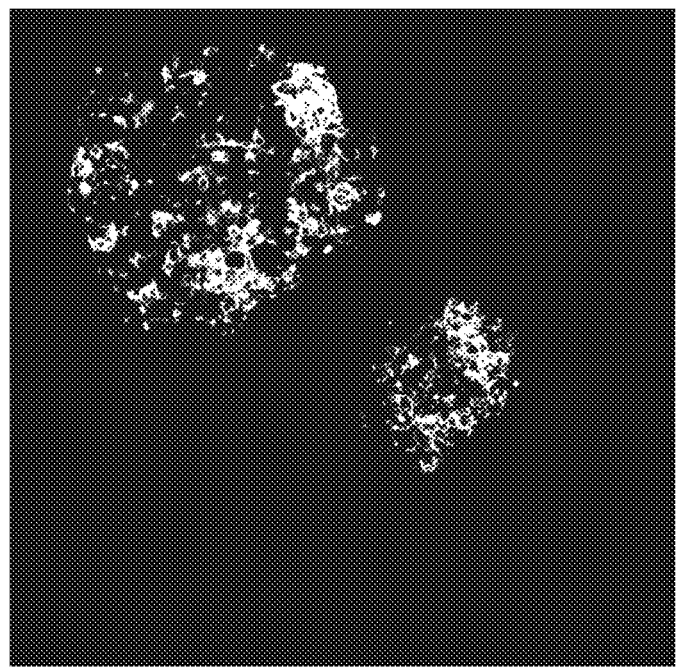
Figure 10Y:
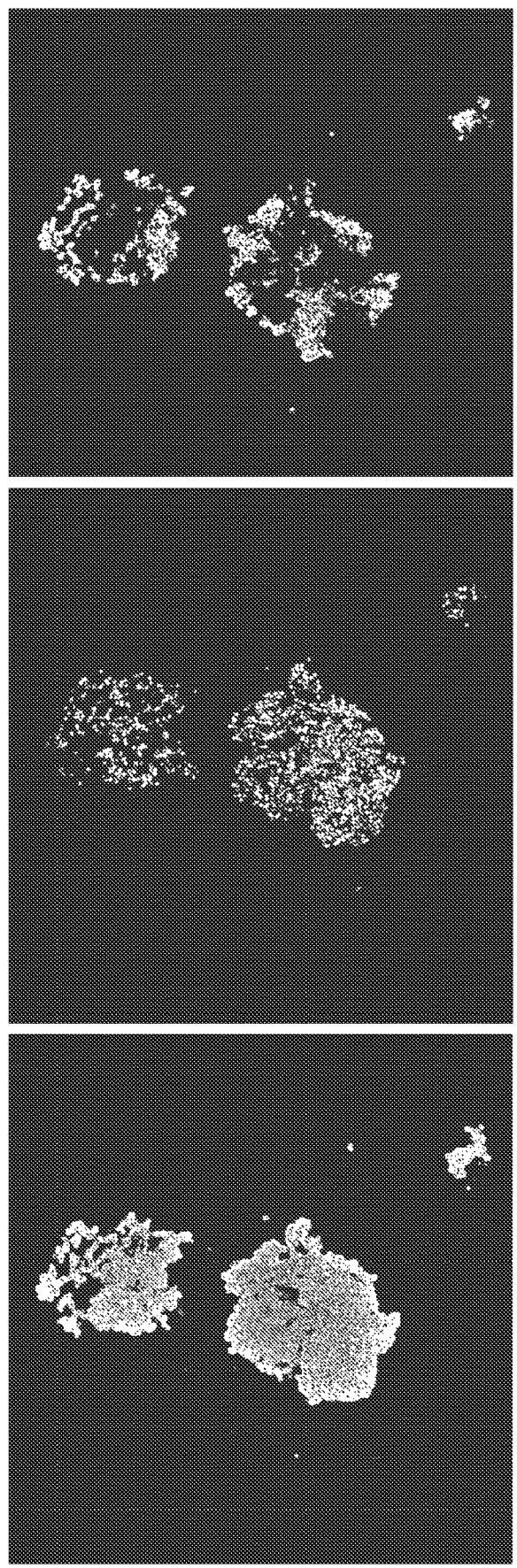
Figure 10Z:
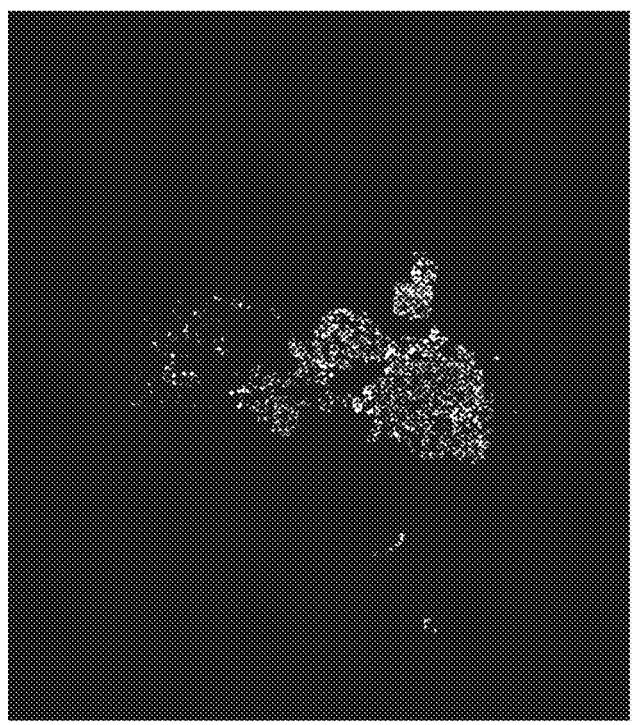
Figure 10Z:
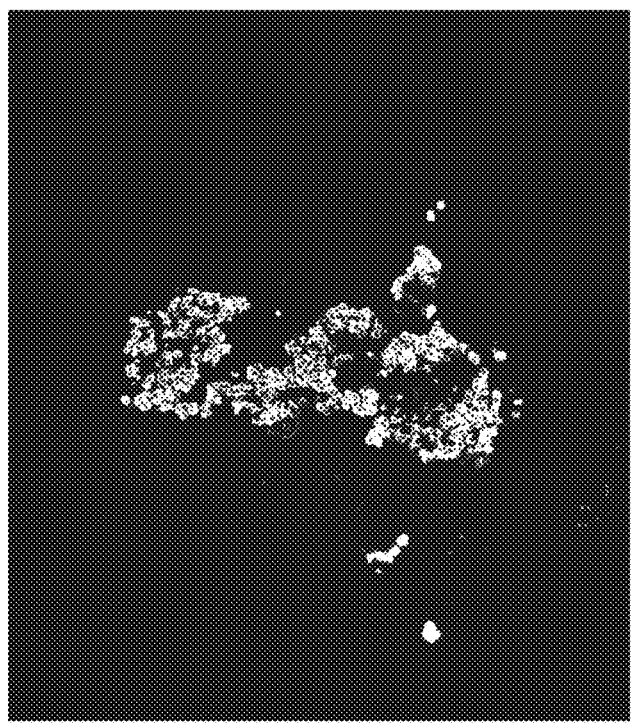
Figure 10A:
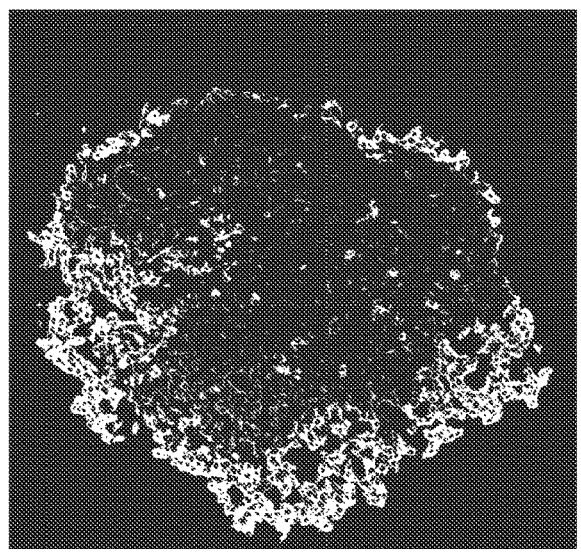
Figure 10A:
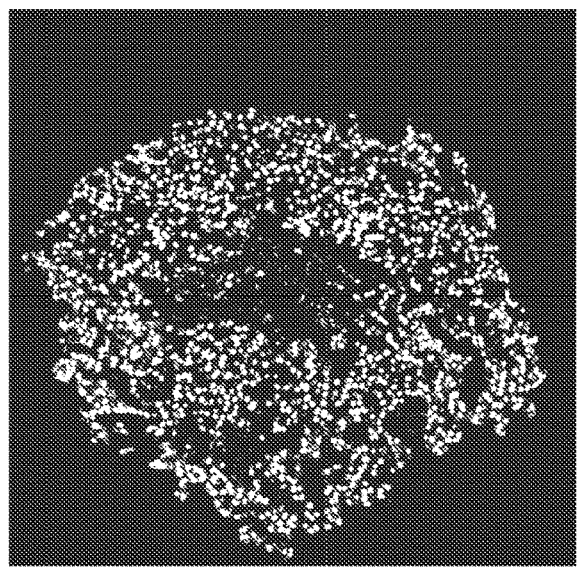
Figure 10A:
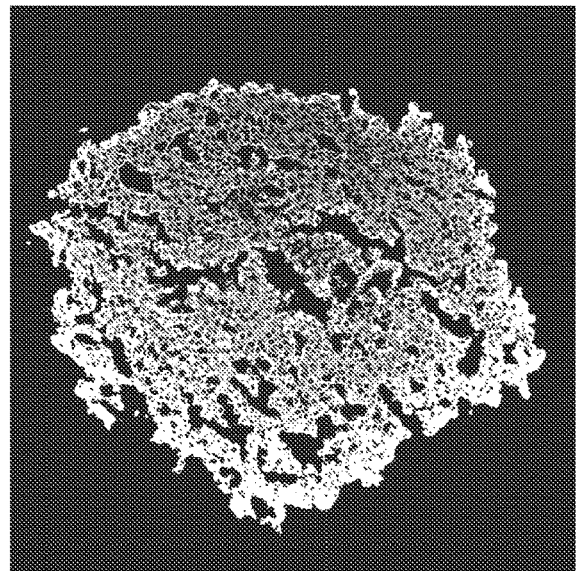
Figure 10A:
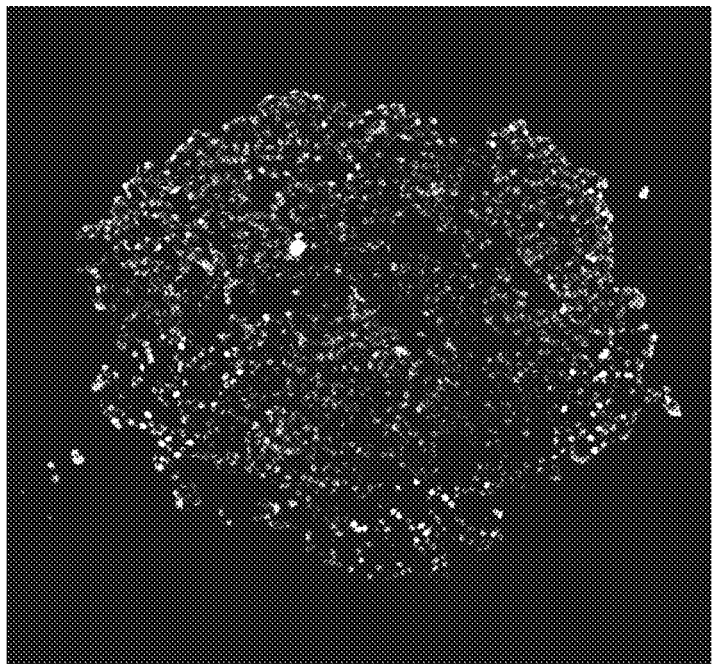
Figure 10A:
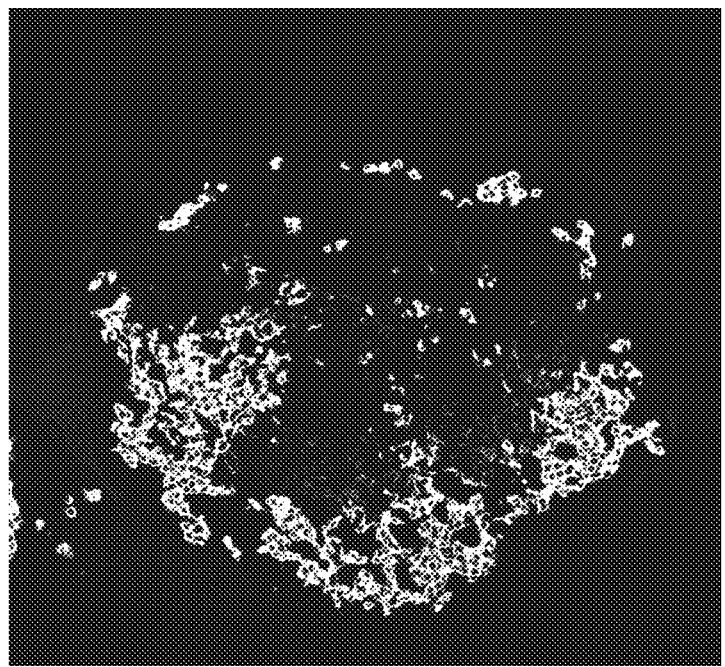

FIG. 10A depicts the new protocol used to differentiate S4D3 CyT49-derived hESC through Stages 5-7 towards an insulin-producing cell. Specifically, the insulin-producing cells derived here exhibited the co-expression and protein presence of PDX1, NKX6.1, CHGA, INSULIN and MAFA, but not GLUCAGON. FIG. 10B demonstrates that cell yields at S6D7 were approximately equal to the initial hESC input for 2-liter roller bottle ("RB") (0.95±0.31 S6D7-to-hESC input) and 0.1 PBS (0.92±0.23 S6D7-to-hESC input) suspension culture methods. Strikingly, suspension culturing using the 0.5 PBS format exhibited the highest cell yields at S6D7; for one hESC cell input 2.4±0.169 S6D7 cells were generated. Moreover, it was demonstrated (see FIG. 10C) that the Stages 5-7 differentiation protocol can be effectively scaled-up using the MagLift™ vertical wheel bioreactor system. When the media volume was increased from 100 ml (0.1 PBS) to 500 ml (0.5 PBS) an approximately 7.5-fold increase in S6D7 yield (FIG. 10C) was observed. In addition, utilizing either the 0.1 PBS or 0.5 PBS suspension format resulted in uniformly smaller S5D3 (FIG. 10D), S6D7 (FIG. 10E) and S7D13-S7D14 (FIG. 10F) aggregates relative to 2-liter roller bottle based aggregates. Briefly, S6D7 aggregates suspension cultured with the disclosed protocol using roller bottles exhibited the following diameters; RB 265±79.0 microns (FIG. 10E left), 0.1PBS~190±59.9 microns (FIG. 10E middle), and 0.5PBS 227±59.0 microns (FIG. 10E right). Also, utilizing the PBS Mini MagLift™ vertical wheel bioreactors maintained tight aggregate size, and architecture through S7D14 (FIG. 10F), required for human-islet level functionality (Example 7). Conversely, S7D13 aggregates in 2-liter roller bottle suspension eventually lost their tight aggregate architecture, and formed loose cellular sheets (FIG. 10F). It was demonstrated that all suspension culture methods using the new protocol induced a robust pancreatic insulin-producing cell gene signature; RB, 0.1 PBS and 0.5 PBS induce the maintain/increase the expression of beta-cell transcription factors PDX1 (FIG. 10G), NKX6.1 (FIG. 10H); endocrine markers/transcription factors CHGA (FIG. 10I), NEUROD1 (FIG. 10J), NGN3 (FIG. 10K); beta-cell hormone INSULIN (FIG. 10L); and early beta-cell maturation transcription factor MAFA (FIG. 10M). Conversely, when PEC-01 d15 aggregates were differentiated to insulin-producing cells using the new differentiation protocol in 2-liter roller bottles ("PEC-01-derived"), a significant induction of GLUCAGON together with INSULIN expression (FIG. 10L, 10N) was observed. Indeed, protein presence analysis demonstrated that, as described previously in *Nature Biotechnology*, 2014, (32) 11, 1121-1133, the new differentiation protocol induced robust pancreatic endocrine pre-cursors (Stage 5) leading to production of mono-hormonal, insulin producing cells (Stages 6-7) in the CyT49 hESC line. FIG. 10O showed that by S5D3 approximately 54.1% of aggregates cultured in 0.5PBS were CHGA$^+$ NKX6.1$^+$ (increased from ~1% CHGA$^+$ NKX6.1$^+$ at S4D3 for all suspension formats; FIG. 9N-9P), a result of the high rate of endocrine differentiation—indicated by enrichment for PAX4$^+$ CHGA$^+$ cells at S5D3. PAX4 is a direct target gene of NGN3, the driver of endocrine differentiation in the pancreas. By S7D13-S7D14 the total number of NKX6.1$^+$ INSULIN$^+$ cells increased dramatically in all suspension formats; from approximately 15.4% at S5D3 (FIG. 10P) to ~40.3% in RB at S6D7 (FIG. 10Q); ~44.7% in 0.1PBS at S6D7 (FIG. 10R); ~51.8% in RB at S7D13 (FIG. 10S); and ~48.9% in 0.1PBS at S7D14 (FIG. 10T). Similarly, by S7D13-S7D13 the percentage of NKX6.1$^+$ CHGA$^+$ cells increased from −1% at S4D3 (FIG. 9N-9P) to ~81.0% in RB at S6D7 (FIG. 10Q); ~88.7% in 0.1PBS at S6D7 (FIG. 10R); ~79.6% in RB at S7D13 (FIG. 10S); and ~80.9% in 0.1PBS at S7D14 (FIG. 10T). It was demonstrated that the majority of NKX6.1±INSULIN+ cells produced by the new protocol at Stage 7 were mono-hormonal, and were not enriched for the alpha-cell hormone GLUCAGON; ~18.8% INSULIN+ GLUCAGON+ in RB at S6D7 (FIG. 10Q); ~14.4% in 0.1PBS at S6D7 (FIG. 10R); ~7.7% in RB at S7D13 (FIG. 10S); and ~6.5% in 0.1PBS at S7D14 (FIG. 10T). Moreover, it was demonstrated that the poly-hormonal cells constituted only a small fraction of total cells by Stage 7 (FIG. 10S-10T), likely originating from the CHGA+ NKX6.1− population, inherently higher in number in the CyT49-derived S4D3 cells relative to H1-derived S4D3 cells (Example 3). Strikingly, PEC-01-derived aggregates in 2-liter roller bottles at S6D7 exhibited ~41.9% co-localization between INSULIN and GLUCAGON. In all conditions tested, the GLUCGAON+ INSULIN+ cells were not NKX6.1±, as shown for PEC-01-derived aggregates in 2-liter roller bottle at S6D7, and new protocol S4D3-derived 0.1PBS at S7D14, 2-liter roller bottle at S7D13 (FIG. 10y). The robust induction of insulin-producing endocrine cells was mirrored in the IF-analysis. Aggregates whether cultured in either RB or 0.1 PBS formats showed a great enrichment for SYNAPTOPHYSIN+ NKX6.1+ INSULIN+ cells at both S6D7 (0.1 PBS—FIG. 10W) and S7D16-D23 (RB—FIG. 10AA; 0.1 PBS—FIG. 10Y). Furthermore, the early maturation transcription factor MAFA was already induced in 0.1 PBS at S6D7 (FIG. 10X), and became co-present with INSULIN-positive cells at Stage 7 in RB at S7D23 (FIG. 10AB), and 0.1 PBS at S7D16 (FIG. 10Z).

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

We claim:

1. A method of producing functional beta cells, comprising:
    culturing pancreatic immature beta cells in a medium comprising:
    a) an effective amount of T3 or T4; and
    b) an effective amount of 5-Azacytidine (AZT), 3-Deazaneplanocin A (DEZA), or a combination thereof,
    thereby producing functional beta cells that express insulin, wherein the functional beta cells consume oxygen in response to glucose simulation at a higher rate than functional beta cells produced in the absence of the medium.

2. The method of claim 1, wherein the functional beta cells exhibit glucose stimulated insulin secretion.

3. The method of claim 2, wherein the functional beta cells exhibit glucose dependent mitochondrial respiration.

4. The method of claim 2, wherein the glucose-stimulated insulin secretion comprises a bi-phasic insulin secretion in response to glucose stimulation.

5. The method of claim 1, wherein the functional beta cells express PDX1, NKX6.1, MAFA, UCN3 and SLC2A1.

6. A method of producing functional beta cells, comprising:
    culturing pancreatic immature beta cells in a medium comprising:
    a) an effective amount of T3 or T4; and
    b) an effective amount of 5-Azacytidine (AZT), 3-Deazaneplanocin A (DEZA), or a combination thereof,
    and wherein the medium does not comprise an ALK5 inhibitor, thereby producing functional beta cells that express insulin.

7. The method of claim 1, wherein the immature beta cells are cultured at the air-liquid interface.

8. The method of claim 1, wherein the immature beta cells are cultured in suspension culture.

9. The method of claim 4, wherein a first phase of the bi-phasic insulin secretion has a four-fold increase to an eight-fold increase over baseline secretion of insulin from the functional beta cells.

10. The method of claim 1, wherein the medium comprises the effective amount of DEZA.

11. The method of claim 1, wherein the medium comprises the effective amount of AZT.

12. The method of claim 1, wherein the medium comprises the effective amount of T3.

13. The method of claim 1, wherein the medium comprises the effective amount of T4.

14. The method of claim 6, wherein the immature beta cells are cultured at the air-liquid interface.

15. The method of claim 6, wherein the immature beta cells are cultured in suspension culture.

16. The method of claim 6, wherein the medium comprises the effective amount of DEZA.

17. The method of claim 6, wherein the medium comprises the effective amount of AZT.

18. The method of claim 6, wherein the medium comprises the effective amount of T3.

19. The method of claim 6, wherein the medium comprises the effective amount of T4.

* * * * *

UNITED STATES PATENT AND TRADEMARK OFFICE
CERTIFICATE OF CORRECTION

PATENT NO. : 11,952,591 B2
APPLICATION NO. : 16/817413
DATED : April 9, 2024
INVENTOR(S) : Rieck et al.

Page 1 of 1

It is certified that error appears in the above-identified patent and that said Letters Patent is hereby corrected as shown below:

In the Claims

Claim 1:
Column 130, Line 1, "simulation" should read -- stimulation --

Signed and Sealed this
Thirty-first Day of December, 2024

Derrick Brent
*Acting Director of the United States Patent and Trademark Office*